(12) United States Patent
Kepinski et al.

(10) Patent No.: US 9,809,828 B2
(45) Date of Patent: Nov. 7, 2017

(54) MODIFIED PLANT CELL

(71) Applicant: University of Leeds, Leeds (GB)

(72) Inventors: Stefan Kepinski, Leeds (GB); Martin Kieffer, Leeds (GB); Suruchi Roychoudhry, Leeds (GB)

(73) Assignee: University of Leeds, Leeds (GB)

( * ) Notice: Subject to any disclaimer, the term of this patent is extended or adjusted under 35 U.S.C. 154(b) by 673 days.

(21) Appl. No.: 14/103,737

(22) Filed: Dec. 11, 2013

(65) Prior Publication Data

US 2015/0247158 A1    Sep. 3, 2015

(51) Int. Cl.
*C12N 15/82*    (2006.01)

(52) U.S. Cl.
CPC ................ *C12N 15/8294* (2013.01)

(58) Field of Classification Search
None
See application file for complete search history.

(56) References Cited

U.S. PATENT DOCUMENTS 6,388,173 B2 *    5/2002    Benfey ............... C07K 14/415
                                                                435/419

OTHER PUBLICATIONS

Roychoudhry et al, Current Biology, Aug. 5, 2013, vol. 23, pp. 1497-1504.*
Weijers et al, Developmental Cell, Feb. 2006, vol. 10, pp. 265-270.*
Hamann et al, Genes and Development, Jul. 1, 2002, Vo. 16, No. 13, pp. 1610-1615.*

* cited by examiner

*Primary Examiner* — Eileen O Hara
(74) *Attorney, Agent, or Firm* — Morgan, Lewis & Bockius LLP

(57) ABSTRACT

We describe a plant cell which is modified by the inclusion of a nucleic acid molecule that encodes a regulator of auxin signalling and which is adapted for expression in a gravity sensing cell.

16 Claims, 101 Drawing Sheets

FIG. 1A (truncated ARF5)

(SEQ ID: 1)

ATGATGGCTTCATTGTCTTGTGTTGAAGACAAGATGAAAACAAGTTGTTTGGTTA
ATGGTGGAGGAACTATAACAACAACAACATCTCAATCTACCTTGCTTGAAGAGA
TGAAGCTGTTGAAAGACCAGTCAGGTACAAGAAAGCCGGTAATAAACTCGGAGC
TATGGCACGCTTGTGCAGGCCCTTTGGTGTGTCTCCCTCAAGTTGGGAGCTTAGT
GTATTACTTCTCACAAGGTCATAGCGAGCAGGTTGCTGTTTCAACCAGAAGATCA
GCAACAACACAAGTTCCTAATTATCCGAACCTTCCATCTCAGTTGATGTGTCAAG
TCCATAATGTTACTCTTCATGCTGACAAAGACAGTGACGAAATCTATGCTCAGAT
GAGTCTTCAACCTGTTCACTCTGAGAGAGATGTGTTCCCTGTACCAGACTTTGGA
ATGCTGAGAGGAAGTAAGCACCCGACTGAGTTTTTCTGCAAAACACTTACTGCAA
GTGACACAAGCACACATGGAGGTTTCTCAGTGCCACGTAGAGCTGCAGAGAAGC
TATTTCCACCATTGGACTACTCAGCACAGCCGCCAACGCAAGAGCTTGTAGTTCG
AGATCTTCATGAGAATACTTGGACATTTCGCCATATCTACCGAGGGCAACCAAAG
AGACATCTCCTAACTACAGGATGGAGTTTGTTCGTTGGATCGAAGAGATTGAGAG
CTGGGGATTCTGTTTTGTTCATCAGGGATGAGAAGTCACAACTTATGGTCGGTGT
TAGGCGTGCCAATCGCCAACAAACAGCACTTCCTTCATCAGTTCTCTCAGCGGAT
AGTATGCACATCGGTGTTCTTGCTGCTGCTGCTCACGCAACCGCCAACCGTACTC
CTTTTTTGATATTCTATAATCCAAGAGCTTGTCCAGCAGAGTTCGTGATCCCTCTA
GCTAAGTACCGTAAGGCGATATGCGGGTCTCAGCTCTCAGTTGGTATGAGATTTG
GAATGATGTTTGAAACTGAAGATTCCGGGAAACGAAGGTACATGGGAACTATTG
TTGGAATCAGCGATTTGGATCCGTTGAGATGGCCTGGTTCTAAGTGGCGTAACCT
TCAGGTAGAATGGGATGAGCCTGGATGTAATGATAAACCTACTCGGGTCAGTCC
ATGGGATATCGAAACACCTGAAAGTCTCTTCATTTTTCCTTCTCTGACCTCAGGAC
TCAAACGTCAGCTCCATCCATCTTACTTTGCTGGTGAAACTGAATGGGGTAGCTT
GATAAAACGGCCACTTATACGTGTTCCTGATTCCGCGAATGGGATTATGCCATAT
GCATCTTTCCCTAGTATGGCTTCGGAGCAGCTTATGAAAATGATGATGAGGCCTC
ACAACAACCAAAATGTACCATCTTTCATGTCTGAGATGCAGCAGAATATTGTAAT
GGGGAATGGAGGTTTGCTAGGAGATATGAAGATGCAGCAACCCCTGATGATGAA
CCAGAAATCTGAGATGGTGCAGCCACAAAACAAGCTAACAGTGAACCCATCTGC
TTCTAATACGAGTGGCCAAGAACAGAATCTTTCACAGAGTATGAGTGCTCCTGCT
AAACCTGAGAACTCTACACTCTCTGGTTGCAGCTCTGGTAGAGTCCAACATGGAC

FIG. 1B (truncated ARF5)

TTGAGCAGTCAATGGAACAGGCAAGCCAGGTTACTACATCCACAGTGTGTAATG
AGGAAAAGGTTAATCAGCTACTTCAGAAACCGGGTGCTTCGTCGCCTGTACAAG
CTGATCAATGTCTTGACATTACTCATCAGATTTACCAACCACAGTCTGATCCAAT
AAATGGATTCTCTTTCCTGGAAACTGATGAGCTGACATCACAAGTCTCTTCCTTCC
AGTCTCTTGCCGGATCATACAAGCAACCATTCATTCTATCCTCCCAGGATTCTTCA
GCTGTTGTGTTACCGGATTCCACAAACTCACCGCTGTTTCATGATGTGTGGGACA
CTCAGTTGAACGGTCTCAAGTTTGACCAGTTCAGTCCCTTGATGCAGCAGGACCT
TTATGCTAGTCAGAATATCTGTATGAGTAATAGCACAACCAGTAACATTCTAGAT
CCTCCACTCTCAAACACAGTCCTTGATGACTTCTGTGCCATCAAAGACACTGATT
TCCAGAACCACCCTTCTGGTTGTTTGGTTGGAAACAACAACACTAGCTTTGCTCA
AGATGTCCAGTCGCAGATCACATCAGCTAGCTTTGCAGACTCACAGGCCTTCTCT
CGCCAAGATTTTCCAGATAATTCTGGAGGCACTGGTACATCTTCAAGCAATGTTG
ATTTTGATGATTGTAGTCTGCGGCAAAATAGTAAAGGCTCATCATGGCAGAAAAT
TGCGACACCCCGCTAA

FIG. 1C (truncated ARF 6)

(SEQ ID: 2)

ATGAGATTATCTTCAGCTGGGTTTAATCCTCAACCTCATGAAGTTACAGGAGAGA
AAAGAGTTCTTAATTCTGAGCTCTGGCATGCTTGTGCTGGTCCTCTTGTCTCACTA
CCTCCTGTTGGAAGCAGAGTTGTGTATTTTCCTCAAGGTCACAGTGAACAGGTTG
CTGCTTCGACCAACAAAGAAGTAGATGCTCATATACCAAATTATCCGAGCTTGCA
TCCGCAGCTTATCTGTCAGCTTCATAATGTTACAATGCATGCTGATGTGGAGACT
GATGAAGTCTATGCACAGATGACTTTGCAACCGTTGAATGCGCAAGAGCAAAAA
GATCCTTACCTTCCCGCGGAATTAGGTGTCCCAAGTAGACAGCCTACAAACTATT
TCTGTAAAACTCTGACTGCTAGTGATACAAGCACTCACGGAGGTTTTTCTGTACC
TCGCCGAGCTGCTGAGAAAGTTTTCCCTCCCTTGGATTACTCGCAGCAGCCACCA
GCTCAAGAGTTAATGGCGAGGGATCTGCATGATAATGAATGGAAGTTCAGGCAT
ATTTTCCGAGGCCAACCAAAGAGACATCTCCTTACCACGGGTTGGAGCGTATTTG
TGAGTGCTAAAAGGCTTGTTGCTGGTGACTCTGTTCTTTTCATCTGGAACGATAA
GAATCAATTACTTCTTGGTATAAGACGAGCCAACCGACCACAAACTGTCATGCCT
TCATCTGTTTTGTCAAGTGACAGTATGCATTTAGGCCTTCTTGCTGCAGCAGCTCA
TGCTGCCGCTACAAACAGCCGATTCACCATCTTCTATAACCCGAGGGCGAGTCCA
TCAGAGTTTGTTATACCCCTGGCTAAGTATGTGAAAGCGGTTTATCACACTCGCG
TCTCTGTTGGTATGCGGTTTAGGATGCTGTTTGAAACTGAAGAATCTAGTGTTCGT
CGGTACATGGGTACAATAACTGGCATTTGTGATCTAGATCCTACTCGTTGGGCTA
ATTCGCATTGGCGATCTGTCAAGGTTGGGTGGGACGAATCTACTGCAGGAGAGA
GACAGCCAAGGGTTTCATTGTGGGAGATTGAGCCTTTAACAACATTCCCTATGTA
TCCATCTCCTTTTCCTCTCAGGCTTAAACGGCCGTGGCCTCCTGGTCTCCCATCTT
TCCATGGCCTTAAAGAAGATGATATGGGTATGAGTATGAGTTCACCGCTTATGTG
GGATCGAGGACTCCAATCTCTAAACTTTCAAGGTATGGGAGTAAACCCGTGGAT
GCAGCCGAGACTTGATACGTCGGGCTTGCTTGGTATGCAAAATGATGTGTACCAA
GCAATGGCTGCAGCTGCCCTTCAAGACATGAGAGGCATTGATCCTGCAAAAGCT
GCTGCTTCACTTCTTCAGTTCCAAAATTCGCCGGGGTTCTCAATGCAATCTCCGTC
CTTAGTGCAGCCGCAGATGCTGCAGCAGCAACTCTCTCAGCAGCAGCAACAACT
CTCTCAGCAGCAGCAGCAGCAGCAACAGCTCTCCCAACAGCAGCAGCAACAGCT
CTCTCAACAGCAGCAGCAGCAGCTCTCTCAACAGCAGCAGCAACAACTCTCTCA
GCAGCAGCAGCAACAGGCGTATCTTGGCGTTCCTGAAACCCACCAGCCTCAGTCT
CAGGCTCAATCACAGTCAAACAATCATCTTTCTCAGCAGCAGCAGCAAGTAGTG

FIG. 1D (truncated ARF 6)

GATAATCATAATCCGTCTGCGTCCAGTGCTGCTGTTGTTTCCGCTATGTCTCAATT
TGGTTCTGCTTCTCAGCCCAACACGTCACCACTCCAGTCCATGACCTCTCTGTGTC
ATCAGCAAAGCTTCTCCGATACCAACGGAGGAAACAATCCTATTTCTCCACTTCA
CACTCTTCTCAGTAACTTCTCTCAAGACGAATCTTCTCAACTGCTCCACCTCACTA
GAACAAACTCTGCAATGACTTCATCCGGTTGGCCATCAAAGCGTCCTGCAGTTGA
TTCATCGTTCCAGCACTCTGGAGCCGGTAATAATAACACTCAATCCGTATTGGAG
CAACTGGGACAGTCCCACACAAGCAACGTTCCTCCAAACGCTGTCTCGTTGCCTC
CATTTCCCGGTGGTAGAGAGTGCTCGATCGAGCAAGAAGGAAGCGCCTCAGACC
CGCATAGCCATCTTCTCTTTGGAGTCAATATAGATTCATCTTCTCTTTTGATGCCG
AACGGAATGTCAAACCTTAGAAGCATTGGTATTGAAGGTGGTGACTCCACGACTT
TACCCTTCACATCATCTAATTTCAACAATGATTTCTCGGGTAATCTTGCAATGACA
ACACCTTCTAGTTGCATAGATGAATCGGGTTTTCTACAATCCTCAGAAAACCTCG
GTTCCGAGAACCCACAATAA

FIG. 1E (truncated ARF7)

(SEQ ID: 3)

ATGAAAGCTCCTTCATCAAATGGAGTTTCTCCTAATCCTGTTGAAGGAGAAAGGA
GAAATATAAACTCAGAGCTATGGCACGCTTGTGCTGGGCCATTGATTTCGTTGCC
TCCAGCAGGAAGTCTTGTTGTTTACTTCCCTCAAGGTCACAGTGAGCAAGTCGCG
GCTTCAATGCAGAAGCAGACTGATTTCATACCAAGTTACCCGAATCTTCCTTCCA
AGCTCATATGCATGCTCCACAATGTTACACTGAATGCTGATCCTGAGACGGATGA
GGTCTATGCGCAGATGACTCTTCAGCCAGTAAACAAATATGACAGAGATGCATT
GCTTGCTTCTGACATGGGTCTTAAGCTAAACAGACAACCTAATGAATTTTTCTGC
AAAACCCTCACGGCGAGTGACACAAGTACTCACGGTGGATTTTCTGTACCCCGAC
GAGCTGCTGAGAAAATCTTTCCTGCTCTGGATTTCTCGATGCAACCACCTTGTCA
GGAGCTTGTTGCTAAGGATATTCATGACAACACATGGACTTTCAGACATATTTAT
CGAGGTCAACCAAAAAGGCACTTGCTAACTACAGGCTGGAGTGTGTTTGTCAGC
ACGAAAAGGCTCTTTGCTGGAGACTCTGTTCTTTTTATAAGAGATGGAAAGGCGC
AACTTCTGTTGGGGATAAGACGTGCAAATAGACAACAGCCTGCACTTTCTTCATC
TGTAATATCAAGTGATAGCATGCACATCGGAGTTCTTGCAGCTGCAGCTCATGCT
AATGCTAATAACAGTCCTTTCACCATTTTCTACAACCCGAGGTGGGCTGCTCCTG
CTGAGTTTGTGGTTCCTTTAGCCAAGTATACCAAAGCGATGTACGCTCAAGTTTC
CCTCGGTATGCGGTTTAGAATGATATTTGAGACTGAAGAATGTGGAGTTCGTCGG
TATATGGGTACAGTTACCGGTATCAGTGATCTTGATCCAGTGAGATGGAAAAACT
CTCAGTGGCGGAATCTTCAGATTGGATGGGATGAGTCAGCTGCTGGTGATAGGCC
CAGTCGAGTTTCAGTTTGGGACATTGAACCGGTTTTAACTCCTTTCTACATATGTC
CTCCTCCATTTTTCCGACCTCGCTTTTCTGGACAACCTGGAATGCCAGATGATGAG
ACTGACATGGAGTCTGCACTGAAGAGAGCAATGCCATGGCTTGATAATAGCTTA
GAGATGAAAGACCCTTCGAGTACTATCTTTCCTGGTCTGAGTTTAGTTCAGTGGA
TGAATATGCAGCAGCAGAACGGCCAGCTACCCTCTGCTGCTGCACAGCCAGGTTT
CTTCCCATCAATGCTTTCGCCAACCGCGGCGCTGCACAACAATCTTGGCGGCACT
GATGATCCCTCCAAGTTACTGAGCTTTCAGACGCCGCACGGGGGGATTTCCTCCT
CAAATCTCCAATTTAACAAACAGAATCAGCAAGCCCCAATGTCTCAGTTGCCTCA
GCCACCAACTACGTTGTCCCAACAACAGCAGCTGCAGCAATTGTTGCACTCCTCT
TTGAACCATCAACAACAGCAATCGCAGTCTCAACAACAGCAACAACAACAACAG
TTGCTGCAGCAGCAACAACAATTGCAGTCTCAACAACACAGCAACAACAATCAA
TCGCAGTCTCAGCAACAACAACAATTGCTCCAGCAGCAACAACAACAACAACTG

FIG. 1F (truncated ARF7)

CAGCAACAACATCAACAACCGTTACAGCAACAGACTCAGCAGCAGCAGCTAAGA
ACACAGCCATTGCAATCTCACTCGCATCCACAGCCACAACAGTTACAACAACATA
AGTTGCAGCAACTTCAGGTTCCACAGAATCAGCTTTACAATGGTCAACAAGCAGC
GCAGCAGCATCAGTCGCAACAAGCATCTACACATCATTTGCAACCACAATTAGTT
TCGGGATCAATGGCAAGCAGTGTCATCACGCCTCCGTCCAGCTCCCTTAATCAAA
GCTTTCAACAGCAACAACAACAGTCTAAGCAACTTCAACAAGCACATCACCATTT
AGGTGCTAGCACTAGCCAGAGTAGTGTAATTGAAACCAGCAAGTCTTCATCCAAT
CTGATGTCCGCACCGCCGCAAGAGACACAGTTTTCACGACAAGTAGAACAGCAG
CAGCCTCCTGGTCTCAACGGGCAGAATCAGCAAACACTTTTGCAGCAGAAAGCT
CACCAGGCACAGGCCCAACAGATATTCCAGCAGAGTCTCTTGGAACAGCCGCAT
ATACAGTTTCAGCTGTTACAGAGATTACAACAGCAACAGCAGCAGCAATTTCTTT
CGCCGCAGTCTCAGTTACCACACCATCAATTGCAAAGCCAGCAGTTGCAACAGCT
GCCTACTCTCTCAAGGTCATCAGTTTCCGTCATCTTGCACTAACAATGGCTTAT
CGACGTTGCAACCACCTCAAATGCTGGTGAGCCGACCTCAGGAAAAACAAAACC
CACCGGTTGGGGGAGGGGTCAAAGCTTATTCAGGCATCACAGATGGAGGAGATG
CACCTTCCTCTTCAACGTCGCCTTCCACCAACAACTGTCAGATCTCTTCTTCAGGC
TTTCTCAACAGAAGCCAAAGCGGGCCAGCGATCTTGATACCTGATGCAGCGATTG
ATATGTCTGGTAATCTTGTTCAGGATCTTTACAGCAAATCCGATATGCGGCTAAA
ACAAGAACTCGTGGGTCAGCAAAAGTCCAAAGCTAGTTTAACAGATCATCAACT
AGAAGCATCTGCCTCTGGAACTTCTTACGGTTTAGATGGAGGCGAAAACAACAG
ACAACAAAATTTCTTGGCTCCAACTTTTGGCCTTGACGGTGATTCCAGGAACAGC
TTGCTCGGTGGAGCTAATGTTGATAATGGCTTTGTGCCTGACACGCTACTCTCGA
GGGGATATGACTCCCAGAAAGATCTTCAGAACATGCTTTCAAACTATGGAGGAG
TGACAAATGACATTGGTACAGAGATGTCTACTTCAGCTGTAAGAACTCAATCTTT
TGGTGTCCCCAATGTGCCCGCCATTTCGAACGATCTAGCTGTCAACGATGCTGGA
GTTCTTGGTGGTGGATTGTGGCCAGCTCAGACTCAGCGATAA

FIG. 1G (truncated ARF 8)

(SEQ ID: 4)

ATGAAGCTGTCAACATCTGGATTGGGTCAACAGGGTCATGAAGGAGAGAAGTGT
CTGAATTCTGAGCTATGGCATGCTTGTGCTGGACCATTAGTCTCTCTTCCATCATC
TGGTAGTCGAGTTGTTTACTTTCCACAGGGTCACAGTGAACAGGTAGCTGCTACA
ACTAATAAGGAAGTTGATGGTCACATACCCAATTACCCAAGCCTACCACCACAAT
TGATATGCCAGCTCCATAATGTTACAATGCATGCAGATGTTGAGACGGATGAAGT
CTATGCTCAAATGACACTTCAACCATTGACACCGGAGGAGCAGAAGGAAACATT
TGTACCGATTGAGTTGGGGATACCGAGTAAGCAACCTAGTAATTATTTTTGTAAG
ACTCTCACAGCTAGTGATACCAGTACACATGGAGGGTTTTCTGTTCCTAGACGTG
CTGCTGAGAAAGTGTTTCCTCCATTGGATTACACACTGCAGCCACCAGCTCAAGA
ACTGATTGCAAGGGATCTCCATGATGTTGAATGGAAGTTTAGGCATATCTTTCGG
GGACAGCCCAAACGGCATCTCCTAACTACTGGATGGAGTGTCTTTGTCAGTGCCA
AGCGACTAGTAGCTGGAGATTCTGTCATTTTCATCAGGAATGAAAAGAATCAACT
CTTTTTGGGAATTCGTCATGCCACTCGGCCGCAGACTATTGTACCATCATCTGTTT
TATCTAGTGATAGCATGCATATTGGACTCCTTGCTGCTGCTGCACATGCTTCTGCA
ACTAATAGCTGTTTCACTGTTTTCTTTCATCCAAGGGCTAGCCAATCTGAGTTTGT
GATACAACTTTCCAAGTACATTAAAGCCGTTTTTCACACGCGTATTTCAGTTGGG
ATGCGCTTTCGCATGCTCTTCGAGACAGAAGAGTCGAGTGTCCGCAGGTACATGG
GTACTATAACTGGTATTAGTGATCTAGATTCTGTTCGTTGGCCAAACTCTCATTGG
CGATCTGTGAAGGTTGGTTGGGATGAATCGACTGCAGGGGAGAGACAGCCAAGG
GTTTCTTTATGGGAGATTGAGCCTCTGACTACCTTTCCTATGTATCCATCTCTTTT
CCTCTCAGACTAAAACGTCCATGGCATGCTGGCACATCATCTTTGCCTGATGGAA
GGGGTGATTTGGGAAGTGGTCTAACATGGCTAAGAGGGGGAGGTGGAGAGCAGC
AAGGTTTGCTTCCTCTAAATTATCCATCTGTTGGTTTGTTTCCATGGATGCAACAA
AGGCTGGATCTCAGTCAAATGGGGACTGATAATAATCAGCAATACCAAGCAATG
TTAGCTGCTGGGTTGCAGAACATCGGCGGTGGAGATCCTTTAAGACAGCAGTTTG
TACAGCTGCAAGAGCCTCACCACCAATATCTTCAACAATCAGCTTCCCATAATTC
TGATTTGATGCTTCAGCAGCAACAGCAGCAACAAGCGTCACGCCATCTCATGCAT
GCTCAAACACAGATTATGAGTGAGAATCTTCCGCAGCAGAATATGCGACAAGAA
GTTAGTAACCAACCAGCTGGACAGCAGCAACAGCTACAGCAACCGGACCAAAAT
GCATATCTTAATGCTTTCAAAATGCAAAATGGCCATCTTCAACAGTGGCAGCAGC
AATCAGAGATGCCATCTCCCTCGTTCATGAAGTCAGATTTTACTGACTCAAGCAA

FIG. 1H (truncated ARF 8)

CAAATTTGCAACAACTGCTAGTCCGGCTTCTGGAGATGGCAATCTTTTGAATTTTT
CTATAACCGGTCAGTCTGTACTCCCTGAGCAGTTAACAACAGAGGGCTGGTCTCC
AAAAGCATCCAACACTTTTTCTGAACCGTTGTCACTTCCACAAGCCTATCCTGGG
AAGAGTCTTGCTCTAGAACCCGGAAATCCGCAGAATCCCTCTCTTTTCGGTGTTG
ATCCCGACTCTGGACTCTTCCTCCCCAGTACGGTTCCCCGCTTTGCTTCTTCATCA
GGAGATGCTGAAGCTTCCCCTATGTCACTAACAGATTCAGGATTTCAGAATTCCT
TATATAGCTGCATGCAAGACACAACTCATGAGTTATTGCATGGAGCTGGACAGAT
TAACTCGTCCAACCAATAA

FIG. 1I (truncated ARF 19)

(SEQ ID: 5)

ATGAAAGCTCCATCAAATGGATTTCTTCCAAGTTCCAACGAAGGAGAGAAGAAG
CCAATCAATTCTCAACTATGGCACGCTTGTGCAGGGCCTTTAGTTTCATTACCTCC
TGTGGGAAGTCTTGTGGTTTACTTCCCTCAAGGACACAGCGAGCAAGTTGCAGCA
TCGATGCAGAAGCAAACAGATTTTATACCAAATTACCCAAATCTTCCTTCTAAGC
TGATTTGCTTGCTTCACAGTGTTACATTACATGCTGATACCGAAACAGATGAAGT
CTATGCACAAATGACTCTTCAACCTGTGAATAAGTATGATAGAAGCATTGCTA
GCTTCTGATATGGGCTTGAAGCTAAACAGACAACCTACTGAGTTTTTTGCAAGA
CTCTTACTGCAAGTGACACAAGCACTCATGGTGGATTCTCTGTACCGCGTCGTGC
AGCTGAGAAAATATTCCCTCCTCTTGATTTCTCGATGCAACCGCCTGCGCAAGAG
ATTGTAGCTAAAGATTTACATGATACTACATGGACTTTCAGACATATCTATCGAG
GCCAACCAAAAGACACTTGCTTACCACAGGTTGGAGCGTTTTGTTAGCACAAA
GAGACTATTTGCGGGTGATTCAGTTTTGTTTGTAAGAGATGAGAAATCACAGCTG
ATGTTGGGTATAAGACGTGCAAATAGACAAACTCCGACTCTTTCCTCATCGGTCA
TATCCAGCGACAGTATGCACATTGGGATACTTGCAGCTGCAGCTCATGCTAATGC
CAATAGTAGCCCTTTTACCATCTTCTTCAATCCAAGGGCAAGTCCTTCAGAGTTTG
TAGTTCCTTTAGCCAAATACAACAAAGCCTTATACGCTCAAGTATCTCTAGGAAT
GAGATTCCGGATGATGTTTGAGACTGAGGATTGTGGGGTTCGTAGATATATGGGT
ACAGTCACAGGTATTAGTGATCTTGACCCTGTAAGATGGAAAGGCTCACAATGG
CGTAATCTTCAGGTAGGATGGGATGAATCAACAGCTGGAGATAGGCCAAGCCGA
GTATCCATATGGGAAATCGAACCCGTCATAACTCCTTTTTACATATGTCCTCCTCC
ATTTTTCAGACCTAAGTACCCGAGGCAACCCGGGATGCCAGATGATGAGTTAGA
CATGGAAAATGCTTTCAAAAGAGCAATGCCTTGGATGGGAGAAGACTTTGGGAT
GAAGGACGCACAGAGTTCGATGTTCCCTGGTTTAAGTCTAGTTCAATGGATGAGT
ATGCAGCAAAACAATCCATTGTCAGGTTCTGCTACTCCTCAGCTCCCGTCCGCGC
TCTCATCTTTTAACCTACCAAACAATTTTGCTTCCAACGACCCTTCCAAGCTGTTG
AACTTCCAATCCCCAAACCTCTCTTCCGCAAATTCCCAATTCAACAAACCGAACA
CGGTTAACCATATCAGCCAACAGATGCAAGCACAACCAGCCATGGTGAAATCTC
AACAACAACAACAACAACAACAACAACACCAACACCAACAACAACAACTG
CAACAACAACAACAACTACAGATGTCACAGCAACAGGTGCAGCAACAAGGGATT
TATAACAATGGTACGATTGCTGTTGCTAACCAAGTCTCTTGTCAAAGTCCAAACC
AACCTACTGGATTCTCTCAGTCTCAGCTTCAGCAGCAGTCAATGCTCCCTACTGG

FIG. 1J (truncated ARF 19)

TGCTAAAATGACACACCAGAACATAAATTCTATGGGGAATAAAGGCTTGTCTCA
AATGACATCGTTTGCGCAAGAAATGCAGTTTCAGCAGCAACTGGAAATGCATAA
CAGTAGCCAGTTATTAAGAAACCAGCAAGAACAGTCCTCTCTCCATTCATTACAA
CAAAATCTGTCCCAAAATCCTCAGCAACTCCAAATGCAACAACAATCATCAAAA
CCAAGTCCTTCACAACAGCTTCAGTTGCAGCTACTGCAGAAGCTACAGCAGCAGC
AACAGCAGCAGTCGATTCCTCCAGTAAGCTCATCCTTACAGCCACAATTATCAGC
GTTGCAGCAGACACAAAGCCATCAATTGCAACAACTTCTGTCGTCTCAAAATCAA
CAGCCCTTGGCACATGGTAATAACAGCTTCCCAGCTTCAACTTTCATGCAGCCTC
CACAGATTCAGGTGAGTCCTCAGCAGCAAGGACAGATGAGTAACAAAAATCTTG
TAGCCGCTGGAAGATCACATTCTGGCCACACAGATGGAGAAGCTCCTTCTTGTTC
AACCTCACCTTCCGCCAATAACACGGGACATGATAATGTTTCACCGACAAATTTC
CTGAGCAGAAATCAACAGCAAGGACAAGCTGCATCTGTATCTGCATCTGATTCA
GTCTTTGAGCGCGCAAGCAATCCGGTCCAAGAGCTTTATACAAAAACTGAGAGC
CGGATCAGTCAAGGCATGATGAATATGAAGAGTGCTGGTGAACATTTCAGATTT
AAAAGCGCGGTAACAGATCAAATCGATGTATCCACAGCGGGAACGACGTACTGT
CCTGATGTTGTTGGCCCTGTACAGCAGCAACAAACTTTCCCACTACCATCATTTG
GTTTTGATGGAGACTGCCAATCTCATCATCCAAGAAACAACTTAGCTTTCCCTGG
TAATCTCGAAGCCGTAACTTCTGATCCACTCTATTCTCAAAAGGACTTTCAAAAC
TTGGTTCCCAACTATGGCAACACACCAAGAGACATTGAGACGGAGCTGTCCAGT
GCTGCAATCAGTTCTCAGTCATTTGGTATTCCCAGCATTCCCTTTAAGCCCGGATG
TTCAAATGAGGTTGGCGGCATCAATGATTCAGGAATCATGAATGGTGGAGGACT
GTGGCCCAATCAGACTCAACGATAA

FIG. 1K (ARF5)

(SEQ ID: 6)

ATGATGGCTTCATTGTCTTGTGTTGAAGACAAGATGAAAACAAGTTGTTTGGTTA
ATGGTGGAGGAACTATAACAACAACAACATCTCAATCTACCTTGCTTGAAGAGA
TGAAGCTGTTGAAAGACCAGTCAGGTACAAGAAAGCCGGTAATAAACTCGGAGC
TATGGCACGCTTGTGCAGGCCCTTTGGTGTGTCTCCCTCAAGTTGGGAGCTTAGT
GTATTACTTCTCACAAGGTCATAGCGAGCAGGTTGCTGTTTCAACCAGAAGATCA
GCAACAACACAAGTTCCTAATTATCCGAACCTTCCATCTCAGTTGATGTGTCAAG
TCCATAATGTTACTCTTCATGCTGACAAAGACAGTGACGAAATCTATGCTCAGAT
GAGTCTTCAACCTGTTCACTCTGAGAGATGTGTTCCCTGTACCAGACTTTGGA
ATGCTGAGAGGAAGTAAGCACCCGACTGAGTTTTTCTGCAAAACACTTACTGCAA
GTGACACAAGCACACATGGAGGTTTCTCAGTGCCACGTAGAGCTGCAGAGAAGC
TATTTCCACCATTGGACTACTCAGCACAGCCGCCAACGCAAGAGCTTGTAGTTCG
AGATCTTCATGAGAATACTTGGACATTTCGCCATATCTACCGAGGGCAACCAAAG
AGACATCTCCTAACTACAGGATGGAGTTTGTTCGTTGGATCGAAGAGATTGAGAG
CTGGGGATTCTGTTTTGTTCATCAGGGATGAGAAGTCACAACTTATGGTCGGTGT
TAGGCGTGCCAATCGCCAACAAACAGCACTTCCTTCATCAGTTCTCTCAGCGGAT
AGTATGCACATCGGTGTTCTTGCTGCTGCTGCTCACGCAACCGCCAACCGTACTC
CTTTTTTGATATTCTATAATCCAAGAGCTTGTCCAGCAGAGTTCGTGATCCCTCTA
GCTAAGTACCGTAAGGCGATATGCGGGTCTCAGCTCTCAGTTGGTATGAGATTTG
GAATGATGTTTGAAACTGAAGATTCCGGGAAACGAAGGTACATGGGAACTATTG
TTGGAATCAGCGATTTGGATCCGTTGAGATGGCCTGGTTCTAAGTGGCGTAACCT
TCAGGTAGAATGGGATGAGCCTGGATGTAATGATAAACCTACTCGGGTCAGTCC
ATGGGATATCGAAACACCTGAAAGTCTCTTCATTTTTCCTTCTCTGACCTCAGGAC
TCAAACGTCAGCTCCATCCATCTTACTTTGCTGGTGAAACTGAATGGGGTAGCTT
GATAAAACGGCCACTTATACGTGTTCCTGATTCCGCGAATGGGATTATGCCATAT
GCATCTTTCCCTAGTATGGCTTCGGAGCAGCTTATGAAAATGATGATGAGGCCTC
ACAACAACCAAAATGTACCATCTTTCATGTCTGAGATGCAGCAGAATATTGTAAT
GGGGAATGGAGGTTTGCTAGGAGATATGAAGATGCAGCAACCCCTGATGATGAA
CCAGAAATCTGAGATGGTGCAGCCACAAAACAAGCTAACAGTGAACCCATCTGC
TTCTAATACGAGTGGCCAAGAACAGAATCTTTCACAGAGTATGAGTGCTCCTGCT
AAACCTGAGAACTCTACACTCTCTGGTTGCAGCTCTGGTAGAGTCCAACATGGAC
TTGAGCAGTCAATGGAACAGGCAAGCCAGGTTACTACATCCACAGTGTGTAATG

FIG. 1L (ARF5)

AGGAAAAGGTTAATCAGCTACTTCAGAAACCGGGTGCTTCGTCGCCTGTACAAG
CTGATCAATGTCTTGACATTACTCATCAGATTTACCAACCACAGTCTGATCCAAT
AAATGGATTCTCTTTCCTGGAAACTGATGAGCTGACATCACAAGTCTCTTCCTTCC
AGTCTCTTGCCGGATCATACAAGCAACCATTCATTCTATCCTCCCAGGATTCTTCA
GCTGTTGTGTTACCGGATTCCACAAACTCACCGCTGTTTCATGATGTGTGGGACA
CTCAGTTGAACGGTCTCAAGTTTGACCAGTTCAGTCCCTTGATGCAGCAGGACCT
TTATGCTAGTCAGAATATCTGTATGAGTAATAGCACAACCAGTAACATTCTAGAT
CCTCCACTCTCAAACACAGTCCTTGATGACTTCTGTGCCATCAAAGACACTGATT
TCCAGAACCACCCTTCTGGTTGTTTGGTTGGAAACAACAACACTAGCTTTGCTCA
AGATGTCCAGTCGCAGATCACATCAGCTAGCTTTGCAGACTCACAGGCCTTCTCT
CGCCAAGATTTTCCAGATAATTCTGGAGGCACTGGTACATCTTCAAGCAATGTTG
ATTTTGATGATTGTAGTCTGCGGCAAAATAGTAAAGGCTCATCATGGCAGAAAAT
TGCGACACCCCGCGTCCGAACCTACACTAAGGTTCAAAAAACCGGGTCAGTCGG
GAGATCAATTGATGTCACAAGCTTTAAAGACTACGAGGAGCTAAAATCTGCTATC
GAATGCATGTTTGGATTGGAAGGACTACTAACTCACCCACAAAGCTCGGGTTGG
AAGCTTGTATATGTTGATTATGAGAGTGATGTTCTGCTTGTAGGAGATGATCCAT
GGGAAGAGTTTGTGGGATGCGTAAGGTGCATAAGGATATTGTCGCCAACTGAGG
TCCAGCAGATGAGTGAAGAAGGGATGAAGCTTTTGAACAGCGCAGGCATTAACG
ATCTTAAGACTTCTGTTTCATAA

FIG. 1M (ARF6)

(SEQ ID: 7)

CTTCTTCTTCTGATTCTCATTTCAAATAAGAGAGAGAGAGAGAGAAGTAAGTAAA
ACTTTAGCAGAGAGAAGAATAAACAAATAATTATAGCACCGTCACGTCGCCGCC
GTATTTCGTTACCGGAAAAAAAAAATCATTCTTCAACATAAAAATAAAAACAGT
CTCTTTCTTTCTATCTTTGTCTATCTTTGATTATTCTCTGTGTACCCATGTTCTGCA
ACAGTTGAGCAAGTGCATGCCCCATATCTCTCTGTTTCTCATTTCCCGATCTTTGC
ATTAATCATATACTTCGCCTGAGATCTCGATTAAGCCAGCTTATAGAAGAAGAAA
CGGCACCAGCTTCTGTCGTTTTAGTTAGCTCGAGATCTGTGTTTCTTTTTTTCTTGG
CTTCTGAGCTTTTGGCGGTGGTGGGTTTTTCTGGAGAAACCCAAACGACTATCAA
AGTTTTGTTTTTTACAATTTTAAGTGGGAGTTATGAGTGGGGTGGATTAAGTAAG
TTACAAGTATGAAGGAGTTGAAGATTCGAAGAAGCGGGTTTTTAGATTTGGTTGG
TGAATGGGTGGGAGGTGGAGGGAAACAGTTAAAAAAGTTATGCTTTTAGTGTCT
CTTCTTCATAATTACATTTGGGCATCTTGAAATCTTTGGATCTTTGAAGAAACAAA
GTTGTGTTTTTTTTTTGTTCTTTGTTGTTTGCTTTTTAAGTTAGAATAAAAAATGA
GATTATCTTCAGCTGGGTTTAATCCTCAACCTCATGAAGTTACAGGAGAGAAAAG
AGTTCTTAATTCTGAGCTCTGGCATGCTTGTGCTGGTCCTCTTGTCTCACTACCTC
CTGTTGGAAGCAGAGTTGTGTATTTTCCTCAAGGTCACAGTGAACAGGTTGCTGC
TTCGACCAACAAAGAAGTAGATGCTCATATACCAAATTATCCGAGCTTGCATCCG
CAGCTTATCTGTCAGCTTCATAATGTTACAATGCATGCTGATGTGGAGACTGATG
AAGTCTATGCACAGATGACTTTGCAACCGTTGAATGCGCAAGAGCAAAAAGATC
CTTACCTTCCCGCGGAATTAGGTGTCCCAAGTAGACAGCCTACAAACTATTTCTG
TAAAACTCTGACTGCTAGTGATACAAGCACTCACGGAGGTTTTTCTGTACCTCGC
CGAGCTGCTGAGAAAGTTTTCCCTCCCTTGGATTACTCGCAGCAGCCACCAGCTC
AAGAGTTAATGGCGAGGGATCTGCATGATAATGAATGGAAGTTCAGGCATATTT
TCCGAGGCCAACCAAAGAGACATCTCCTTACCACGGGTTGGAGCGTATTTGTGAG
TGCTAAAAGGCTTGTTGCTGGTGACTCTGTTCTTTTCATCTGGAACGATAAGAAT
CAATTACTTCTTGGTATAAGACGAGCCAACCGACCACAAACTGTCATGCCTTCAT
CTGTTTTGTCAAGTGACAGTATGCATTTAGGCCTTCTTGCTGCAGCAGCTCATGCT
GCCGCTACAAACAGCCGATTCACCATCTTCTATAACCCGAGGGCGAGTCCATCAG
AGTTTGTTATACCCCTGGCTAAGTATGTGAAAGCGGTTTATCACACTCGCGTCTCT
GTTGGTATGCGGTTTAGGATGCTGTTTGAAACTGAAGAATCTAGTGTTCGTCGGT

FIG. 1N (ARF6)

ACATGGGTACAATAACTGGCATTTGTGATCTAGATCCTACTCGTTGGGCTAATTC
GCATTGGCGATCTGTCAAGGTTGGGTGGGACGAATCTACTGCAGGAGAGAGACA
GCCAAGGGTTTCATTGTGGGAGATTGAGCCTTTAACAACATTCCCTATGTATCCA
TCTCCTTTTCCTCTCAGGCTTAAACGGCCGTGGCCTCCTGGTCTCCCATCTTTCCA
TGGCCTTAAAGAAGATGATATGGGTATGAGTATGAGTTCACCGCTTATGTGGGAT
CGAGGACTCCAATCTCTAAACTTTCAAGGTATGGGAGTAAACCCGTGGATGCAG
CCGAGACTTGATACGTCGGGCTTGCTTGGTATGCAAAATGATGTGTACCAAGCAA
TGGCTGCAGCTGCCCTTCAAGACATGAGAGGCATTGATCCTGCAAAAGCTGCTGC
TTCACTTCTTCAGTTCCAAAATTCGCCGGGGTTCTCAATGCAATCTCCGTCCTTAG
TGCAGCCGCAGATGCTGCAGCAGCAACTCTCTCAGCAGCAGCAACAACTCTCTCA
GCAGCAGCAGCAGCAGCAACAGCTCTCCAACAGCAGCAGCAACAGCTCTCTCA
ACAGCAGCAGCAGCAGCTCTCTCAACAGCAGCAGCAACAACTCTCTCAGCAGCA
GCAGCAACAGGCGTATCTTGGCGTTCCTGAAACCCACCAGCCTCAGTCTCAGGCT
CAATCACAGTCAAACAATCATCTTTCTCAGCAGCAGCAGCAAGTAGTGGATAATC
ATAATCCGTCTGCGTCCAGTGCTGCTGTTGTTTCCGCTATGTCTCAATTTGGTTCT
GCTTCTCAGCCCAACACGTCACCACTCCAGTCCATGACCTCTCTGTGTCATCAGC
AAAGCTTCTCCGATACCAACGGAGGAAACAATCCTATTTCTCCACTTCACACTCT
TCTCAGTAACTTCTCTCAAGACGAATCTTCTCAACTGCTCCACCTCACTAGAACA
AACTCTGCAATGACTTCATCCGGTTGGCCATCAAAGCGTCCTGCAGTTGATTCAT
CGTTCCAGCACTCTGGAGCCGGTAATAATAACACTCAATCCGTATTGGAGCAACT
GGGACAGTCCCACACAAGCAACGTTCCTCCAAACGCTGTCTCGTTGCCTCCATTT
CCCGGTGGTAGAGAGTGCTCGATCGAGCAAGAAGGAAGCGCCTCAGACCCGCAT
AGCCATCTTCTCTTTGGAGTCAATATAGATTCATCTTCTCTTTTGATGCCGAACGG
AATGTCAAACCTTAGAAGCATTGGTATTGAAGGTGGTGACTCCACGACTTTACCC
TTCACATCATCTAATTTCAACAATGATTTCTCGGGTAATCTTGCAATGACAACAC
CTTCTAGTTGCATAGATGAATCGGGTTTTCTACAATCCTCAGAAAACCTCGGTTC
CGAGAACCCACAATCTAACACCTTTGTGAAGGTGTACAAGTCAGGGTCTTTTGGA
AGATCGTTAGATATATCAAAGTTTAGCAGCTACCACGAGCTGCGAAGCGAGCTT
GCTCGCATGTTTGGCCTCGAAGGCCAATTAGAAGACCCTGTGAGATCAGGCTGGC
AGCTTGTATTTGTTGACCGAGAGAACGACGTTCTTCTCCTCGGCGATGACCCTTG
GCCGGAGTTTGTGAGCAGCGTGTGGTGCATTAAGATACTGTCACCACAAGAAGT
GCAACAAATGGGAAAAGAGGCCTTGAGCTTCTCAACTCCGCGCCATCTTCCAA

FIG. 1O (ARF6)

CAATGTCGATAAGCTCCCGAGCAACGGGAACTGTGACGACTTTGGGAACCGGTC
AGACCCGAGGAATCTCGGTAACGGTATCGCATCAGTTGGGGGTTCATTCAACTAC
TAGAAGTAGATGGAAACCTCCCTTTTTATTCAAGTTAAGTTTCAATCTTATAAATT
AGTAGTGAGATCATCTTAGTTTAATTACTAGCAAAAATCTCTCTTTATTACTTATA
AAAAAGGGAGATTTGCCTTTGCCTTTGATGGAAACAAAAACTATATAATCCCTCT
GTCGACTCGTAATACTGTAATTATAAGATCTTTTGGTCTTTTTCTTATATGAATAT
TTTTACTGAACTCTATATATGTCACTTTCCTTACTCATTCTTCAATCAATATGATA
GTGAAGGGTTATTTTGGAGTTACATT

FIG. 1P (ARF 7)

(SEQ ID: 8)

ATGAAAGCTCCTTCATCAAATGGAGTTTCTCCTAATCCTGTTGAAGGAGAAAGGA
GAAATATAAACTCAGAGCTATGGCACGCTTGTGCTGGGCCATTGATTTCGTTGCC
TCCAGCAGGAAGTCTTGTTGTTTACTTCCCTCAAGGTCACAGTGAGCAAGTCGCG
GCTTCAATGCAGAAGCAGACTGATTTCATACCAAGTTACCCGAATCTTCCTTCCA
AGCTCATATGCATGCTCCACAATGTTACACTGAATGCTGATCCTGAGACGGATGA
GGTCTATGCGCAGATGACTCTTCAGCCAGTAAACAAATATGACAGAGATGCATT
GCTTGCTTCTGACATGGGTCTTAAGCTAAACAGACAACCTAATGAATTTTTCTGC
AAAACCCTCACGGCGAGTGACACAAGTACTCACGGTGGATTTTCTGTACCCCGAC
GAGCTGCTGAGAAAATCTTTCCTGCTCTGGATTTCTCGATGCAACCACCTTGTCA
GGAGCTTGTTGCTAAGGATATTCATGACAACACATGGACTTTCAGACATATTTAT
CGAGGTCAACCAAAAAGGCACTTGCTAACTACAGGCTGGAGTGTGTTTGTCAGC
ACGAAAAGGCTCTTTGCTGGAGACTCTGTTCTTTTTATAAGAGATGGAAAGGCGC
AACTTCTGTTGGGGATAAGACGTGCAAATAGACAACAGCCTGCACTTTCTTCATC
TGTAATATCAAGTGATAGCATGCACATCGGAGTTCTTGCAGCTGCAGCTCATGCT
AATGCTAATAACAGTCCTTTCACCATTTTCTACAACCCGAGGTGGGCTGCTCCTG
CTGAGTTTGTGGTTCCTTTAGCCAAGTATACCAAAGCGATGTACGCTCAAGTTTC
CCTCGGTATGCGGTTTAGAATGATATTTGAGACTGAAGAATGTGGAGTTCGTCGG
TATATGGGTACAGTTACCGGTATCAGTGATCTTGATCCAGTGAGATGGAAAAACT
CTCAGTGGCGGAATCTTCAGATTGGATGGGATGAGTCAGCTGCTGGTGATAGGCC
CAGTCGAGTTTCAGTTTGGGACATTGAACCGGTTTTAACTCCTTTCTACATATGTC
CTCCTCCATTTTTCCGACCTCGCTTTTCTGGACAACCTGGA
ATGCCAGATGATGAGACTGACATGGAGTCTGCACTGAAGAGAGCAATGCCATGG
CTTGATAATAGCTTAGAGATGAAAGACCCTTCGAGTACTATCTTTCCTGGTCTGA
GTTTAGTTCAGTGGATGAATATGCAGCAGCAGAACGGCCAGCTACCCTCTGCTGC
TGCACAGCCAGGTTTCTTCCCATCAATGCTTTCGCCAACCGCGGCGCTGCACAAC
AATCTTGGCGGCACTGATGATCCCTCCAAGTTACTGAGCTTTCAGACGCCGCACG
GGGGGATTTCCTCCTCAAATCTCCAATTTAACAAACAGAATCAGCAAGCCCCAAT
GTCTCAGTTGCCTCAGCCACCAACTACGTTGTCCCAACAACAGCAGCTGCAGCAA
TTGTTGCACTCCTCTTTGAACCATCAACAACAGCAATCGCAGTCTCAACAACAGC
AACAACAACAACAGTTGCTGCAGCAGCAACAACAATTGCAGTCTCAACAACACA
GCAACAACAATCAATCGCAGTCTCAGCAACAACAACAATTGCTCCAGCAGCAAC

FIG. 1Q (ARF 7)

AACAACAACAACTGCAGCAACAACATCAACAACCGTTACAGCAACAGACTCAGC
AGCAGCAGCTAAGAACACAGCCATTGCAATCTCACTCGCATCCACAGCCACAAC
AGTTACAACAACATAAGTTGCAGCAACTTCAGGTTCCACAGAATCAGCTTTACAA
TGGTCAACAAGCAGCGCAGCAGCATCAGTCGCAACAAGCATCTACACATCATTT
GCAACCACAATTAGTTTCGGGATCAATGGCAAGCAGTGTCATCACGCCTCCGTCC
AGCTCCCTTAATCAAAGCTTTCAACAGCAACAACAACAGTCTAAGCAACTTCAAC
AAGCACATCACCATTTAGGTGCTAGCACTAGCCAGAGTAGTGTAATTGAAACCA
GCAAGTCTTCATCCAATCTGATGTCCGCACCGCCGCAAGAGACACAGTTTTCACG
ACAAGTAGAACAGCAGCAGCCTCCTGGTCTCAACGGGCAGAATCAGCAAACACT
TTTGCAGCAGAAAGCTCACCAGGCACAGGCCCAACAGATATTCCAGCAGAGTCT
CTTGGAACAGCCGCATATACAGTTTCAGCTGTTACAGAGATTACAACAGCAACA
GCAGCAGCAATTTCTTTCGCCGCAGTCTCAGTTACCACACCATCAATTGCAAAGC
CAGCAGTTGCAACAGCTGCCTACTCTCTCTCAAGGTCATCAGTTTCCGTCATCTTG
CACTAACAATGGCTTATCGACGTTGCAACCACCTCAAATGCTGGTGAGCCGACCT
CAGGAAAAACAAAACCCACCGGTTGGGGGAGGGGTCAAAGCTTATTCAGGCATC
ACAGATGGAGGAGATGCACCTTCCTCTTCAACGTCGCCTTCCACCAACAACTGTC
AGATCTCTTCTTCAGGCTTTCTCAACAGAAGCCAAAGCGGGCCAGCGATCTTGAT
ACCTGATGCAGCGATTGATATGTCTGGTAATCTTGTTCAGGATCTTTACAGCAAA
TCCGATATGCGGCTAAAACAAGAACTCGTGGGTCAGCAAAAGTCCAAAGCTAGT
TTAACAGATCATCAACTAGAAGCATCTGCCTCTGGAACTTCTTACGGTTTAGATG
GAGGCGAAAACAACAGACAACAAAATTTCTTGGCTCCAACTTTTGGCCTTGACG
GTGATTCCAGGAACAGCTTGCTCGGTGGAGCTAATGTTGATAATGGCTTTGTGCC
TGACACGCTACTCTCGAGGGGATATGACTCCCAGAAAGATCTTCAGAACATGCTT
TCAAACTATGGAGGAGTGACAAATGACATTGGTACAGAGATGTCTACTTCAGCT
GTAAGAACTCAATCTTTTGGTGTCCCCAATGTGCCCGCCATTTCGAACGATCTAG
CTGTCAACGATGCTGGAGTTCTTGGTGGTGGATTGTGGCCAGCTCAGACTCAGCG
AATGCGAACTTATACAAAGGTGCAAAAACGAGGCTCAGTGGGGAGATCAATAGA
CGTCAACCGTTACAGAGGTTACGATGAGCTGAGGCATGATCTAGCGCGCATGTTT
GGGATCGAAGGACAGCTCGAAGATCCTCAAACATCTGACTGGAAACTTGTTTAT
GTCGATCATGAAAATGACATCCTCCTCGTCGGCGATGATCCATGGGAAGAATTCG
TAAACTGTGTTCAGAGCATTAAGATCCTTTCATCAGCTGAGGTTCAGCAGATGAG
CTTAGACGGGAACTTTGCCGGTGTACCAGTTACTAATCAAGCTTGTAGTGGCGGT

FIG. 1R (ARF 7)

GACAGTGGCAATGCTTGGAGAGGTCATTATGATGATAACTCAGCCACTTCGTTTA
ACCGGTGA

FIG. 1S (ARF 8)

(SEQ ID: 9)

ATGAAGCTGTCAACATCTGGATTGGGTCAACAGGGTCATGAAGGAGAGAAGTGT
CTGAATTCTGAGCTATGGCATGCTTGTGCTGGACCATTAGTCTCTCTTCCATCATC
TGGTAGTCGAGTTGTTTACTTTCCACAGGGTCACAGTGAACAGGTAGCTGCTACA
ACTAATAAGGAAGTTGATGGTCACATACCCAATTACCCAAGCCTACCACCACAAT
TGATATGCCAGCTCCATAATGTTACAATGCATGCAGATGTTGAGACGGATGAAGT
CTATGCTCAAATGACACTTCAACCATTGACACCGGAGGAGCAGAAGGAAACATT
TGTACCGATTGAGTTGGGGATACCGAGTAAGCAACCTAGTAATTATTTTTGTAAG
ACTCTCACAGCTAGTGATACCAGTACACATGGAGGGTTTTCTGTTCCTAGACGTG
CTGCTGAGAAAGTGTTTCCTCCATTGGATTACACACTGCAGCCACCAGCTCAAGA
ACTGATTGCAAGGGATCTCCATGATGTTGAATGGAAGTTTAGGCATATCTTTCGG
GGACAGCCCAAACGGCATCTCCTAACTACTGGATGGAGTGTCTTTGTCAGTGCCA
AGCGACTAGTAGCTGGAGATTCTGTCATTTTCATCAGGAATGAAAAGAATCAACT
CTTTTTGGGAATTCGTCATGCCACTCGGCCGCAGACTATTGTACCATCATCTGTTT
TATCTAGTGATAGCATGCATATTGGACTCCTTGCTGCTGCTGCACATGCTTCTGCA
ACTAATAGCTGTTTCACTGTTTTCTTTCATCCAAGGGCTAGCCAATCTGAGTTTGT
GATACAACTTTCCAAGTACATTAAAGCCGTTTTTCACACGCGTATTTCAGTTGGG
ATGCGCTTTCGCATGCTCTTCGAGACAGAAGAGTCGAGTGTCCGCAGGTACATGG
GTACTATAACTGGTATTAGTGATCTAGATTCTGTTCGTTGGCCAAACTCTCATTGG
CGATCTGTGAAGGTTGGTTGGGATGAATCGACTGCAGGGGAGAGACAGCCAAGG
GTTTCTTTATGGGAGATTGAGCCTCTGACTACCTTTCCTATGTATCCATCTCTTTT
CCTCTCAGACTAAAACGTCCATGGCATGCTGGCACATCATCTTTGCCTGATGGAA
GGGGTGATTTGGGAAGTGGTCTAACATGGCTAAGAGGGGGAGGTGGAGAGCAGC
AAGGTTTGCTTCCTCTAAATTATCCATCTGTTGGTTTGTTTCCATGGATGCAACAA
AGGCTGGATCTCAGTCAAATGGGGACTGATAATAATCAGCAATACCAAGCAATG
TTAGCTGCTGGGTTGCAGAACATCGGCGGTGGAGATCCTTTAAGACAGCAGTTTG
TACAGCTGCAAGAGCCTCACCACCAATATCTTCAACAATCAGCTTCCCATAATTC
TGATTTGATGCTTCAGCAGCAACAGCAGCAACAAGCGTCACGCCATCTCATGCAT
GCTCAAACACAGATTATGAGTGAGAATCTTCCGCAGCAGAATATGCGACAAGAA
GTTAGTAACCAACCAGCTGGACAGCAGCAACAGCTACAGCAACCGGACCAAAAT
GCATATCTTAATGCTTTCAAAATGCAAAATGGCCATCTTCAACAGTGGCAGCAGC
AATCAGAGATGCCATCTCCCTCGTTCATGAAGTCAGATTTTACTGACTCAAGCAA

FIG. 1T (ARF 8)

CAAATTTGCAACAACTGCTAGTCCGGCTTCTGGAGATGGCAATCTTTTGAATTTTT
CTATAACCGGTCAGTCTGTACTCCCTGAGCAGTTAACAACAGAGGGCTGGTCTCC
AAAAGCATCCAACACTTTTTCTGAACCGTTGTCACTTCCACAAGCCTATCCTGGG
AAGAGTCTTGCTCTAGAACCCGGAAATCCGCAGAATCCCTCTCTTTTCGGTGTTG
ATCCCGACTCTGGACTCTTCCTCCCCAGTACGGTTCCCCGCTTTGCTTCTTCATCA
GGAGATGCTGAAGCTTCCCCTATGTCACTAACAGATTCAGGATTTCAGAATTCCT
TATATAGCTGCATGCAAGACACAACTCATGAGTTATTGCATGGAGCTGGACAGAT
TAACTCGTCCAACCAAACCAAGAACTTTGTAAAGGTTTATAAATCTGGTTCGGTT
GGGCGTTCATTAGACATCTCCCGATTCAGCAGCTACCACGAGCTGCGAGAAGAG
TTAGGGAAGATGTTTGCTATCGAAGGGTTGTTGGAAGACCCCCTTAGATCAGGCT
GGCAGCTTGTATTCGTTGACAAGGAAAATGATATTCTTCTCCTTGGTGATGACCC
ATGGGAGTCATTTGTGAATAACGTTTGGTACATAAAGATACTATCACCAGAAGAT
GTGCATCAAATGGGAGATCATGGAGAAGGCAGTGGTGGGTTATTCCCGCAAAAC
CCGACCCATCTCTAG

FIG. 1U (ARF 19)

(SEQ ID: 10)

ATGAAAGCTCCATCAAATGGATTTCTTCCAAGTTCCAACGAAGGAGAGAAGAAG
CCAATCAATTCTCAACTATGGCACGCTTGTGCAGGGCCTTTAGTTTCATTACCTCC
TGTGGGAAGTCTTGTGGTTTACTTCCCTCAAGGACACAGCGAGCAAGTTGCAGCA
TCGATGCAGAAGCAAACAGATTTTATACCAAATTACCCAAATCTTCCTTCTAAGC
TGATTTGCTTGCTTCACAGTGTTACATTACATGCTGATACCGAAACAGATGAAGT
CTATGCACAAATGACTCTTCAACCTGTGAATAAGTATGATAGAAGCATTGCTA
GCTTCTGATATGGGCTTGAAGCTAAACAGACAACCTACTGAGTTTTTTGCAAGA
CTCTTACTGCAAGTGACACAAGCACTCATGGTGGATTCTCTGTACCGCGTCGTGC
AGCTGAGAAAATATTCCCTCCTCTTGATTTCTCGATGCAACCGCCTGCGCAAGAG
ATTGTAGCTAAAGATTTACATGATACTACATGGACTTTCAGACATATCTATCGAG
GCCAACCAAAAAGACACTTGCTTACCACAGGTTGGAGCGTTTTGTTAGCACAAA
GAGACTATTTGCGGGTGATTCAGTTTTGTTTGTAAGAGATGAGAAATCACAGCTG
ATGTTGGGTATAAGACGTGCAAATAGACAAACTCCGACTCTTTCCTCATCGGTCA
TATCCAGCGACAGTATGCACATTGGGATACTTGCAGCTGCAGCTCATGCTAATGC
CAATAGTAGCCCTTTTACCATCTTCTTCAATCCAAGGGCAAGTCCTTCAGAGTTTG
TAGTTCCTTTAGCCAAATACAACAAAGCCTTATACGCTCAAGTATCTCTAGGAAT
GAGATTCCGGATGATGTTTGAGACTGAGGATTGTGGGGTTCGTAGATATATGGGT
ACAGTCACAGGTATTAGTGATCTTGACCCTGTAAGATGGAAAGGCTCACAATGG
CGTAATCTTCAGGTAGGATGGGATGAATCAACAGCTGGAGATAGGCCAAGCCGA
GTATCCATATGGGAAATCGAACCCGTCATAACTCCTTTTTACATATGTCCTCCTCC
ATTTTTCAGACCTAAGTACCCGAGGCAACCCGGGATGCCAGATGATGAGTTAGA
CATGGAAAATGCTTTCAAAAGAGCAATGCCTTGGATGGGAGAAGACTTTGGGAT
GAAGGACGCACAGAGTTCGATGTTCCCTGGTTTAAGTCTAGTTCAATGGATGAGT
ATGCAGCAAAACAATCCATTGTCAGGTTCTGCTACTCCTCAGCTCCCGTCCGCGC
TCTCATCTTTTAACCTACCAAACAATTTTGCTTCCAACGACCCTTCCAAGCTGTTG
AACTTCCAATCCCCAAACCTCTCTTCCGCAAATTCCCAATTCAACAAACCGAACA
CGGTTAACCATATCAGCCAACAGATGCAAGCACAACCAGCCATGGTGAAATCTC
AACAACAACAACAACAACAACAACAACACCAACACCAACAACAACAACTG
CAACAACAACAACAACTACAGATGTCACAGCAACAGGTGCAGCAACAAGGGATT
TATAACAATGGTACGATTGCTGTTGCTAACCAAGTCTCTTGTCAAAGTCCAAACC
AACCTACTGGATTCTCTCAGTCTCAGCTTCAGCAGCAGTCAATGCTCCCTACTGG

FIG. 1V (ARF 19)

TGCTAAAATGACACACCAGAACATAAATTCTATGGGGAATAAAGGCTTGTCTCA
AATGACATCGTTTGCGCAAGAAATGCAGTTTCAGCAGCAACTGGAAATGCATAA
CAGTAGCCAGTTATTAAGAAACCAGCAAGAACAGTCCTCTCTCCATTCATTACAA
CAAAATCTGTCCCAAAATCCTCAGCAACTCCAAATGCAACAACAATCATCAAAA
CCAAGTCCTTCACAACAGCTTCAGTTGCAGCTACTGCAGAAGCTACAGCAGCAGC
AACAGCAGCAGTCGATTCCTCCAGTAAGCTCATCCTTACAGCCACAATTATCAGC
GTTGCAGCAGACACAAAGCCATCAATTGCAACAACTTCTGTCGTCTCAAAATCAA
CAGCCCTTGGCACATGGTAATAACAGCTTCCCAGCTTCAACTTTCATGCAGCCTC
CACAGATTCAGGTGAGTCCTCAGCAGCAAGGACAGATGAGTAACAAAAATCTTG
TAGCCGCTGGAAGATCACATTCTGGCCACACAGATGGAGAAGCTCCTTCTTGTTC
AACCTCACCTTCCGCCAATAACACGGGACATGATAATGTTTCACCGACAAATTTC
CTGAGCAGAAATCAACAGCAAGGACAAGCTGCATCTGTATCTGCATCTGATTCA
GTCTTTGAGCGCGCAAGCAATCCGGTCCAAGAGCTTTATACAAAAACTGAGAGC
CGGATCAGTCAAGGCATGATGAATATGAAGAGTGCTGGTGAACATTTCAGATTT
AAAAGCGCGGTAACAGATCAAATCGATGTATCCACAGCGGGAACGACGTACTGT
CCTGATGTTGTTGGCCCTGTACAGCAGCAACAAACTTTCCCACTACCATCATTTG
GTTTTGATGGAGACTGCCAATCTCATCATCCAAGAAACAACTTAGCTTTCCCTGG
TAATCTCGAAGCCGTAACTTCTGATCCACTCTATTCTCAAAAGGACTTTCAAAAC
TTGGTTCCCAACTATGGCAACACACCAAGAGACATTGAGACGGAGCTGTCCAGT
GCTGCAATCAGTTCTCAGTCATTTGGTATTCCCAGCATTCCCTTTAAGCCCGGATG
TTCAAATGAGGTTGGCGGCATCAATGATTCAGGAATCATGAATGGTGGAGGACT
GTGGCCCAATCAGACTCAACGAATGCGAACATATACAAAGGTTCAAAAACGAGG
GTCAGTAGGTAGATCAATAGATGTTACCCGTTATAGCGGCTATGATGAACTTAGG
CATGACTTAGCGAGAATGTTTGGCATCGAAGGACAGCTCGAAGATCCGCTAACC
TCTGATTGGAAACTCGTCTACACCGATCACGAAAACGATATTTTACTAGTTGGTG
ATGATCCTTGGGAAGAGTTTGTGAACTGCGTGCAGAACATAAAGATACTATCATC
AGTAGAAGTTCAGCAAATGAGCTTAGACGGAGATCTTGCAGCTATCCCAACCAC
AAACCAAGCCTGCAGCGAAACAGACAGCGGAAATGCTTGGAAAGTACACTATGA
AGACACTTCTGCTGCAGCTTCTTTCAACAGATAG

FIG. 2A (IAA1)

(SEQ ID: 11)

ATGGAAGTCACCAATGGGCTTAACCTTAAGGACACAGAGCTTCGTTTGGGATTAC
CCGGAGCACAAGAAGAACAACAACTAGAACTTTCTTGCGTCAGAAGCAACAACA
AGCGCAAGAACAACGACTCAACAGAAGAATCTGCTCCTCCTCCTGCAAAAACAC
AAATCGTTGGATGGCCTCCAGTGAGATCTAACCGTAAGAACAACAACAACAAAA
ACGTGAGTTATGTGAAAGTGAGTATGGACGGAGCTCCATATCTCCGTAAGATAG
ATCTCAAGATGTACAAAAACTATCCAGAGCTTCTCAAAGCACTAGAGAACATGTT
CAAGTTCACAGTAGGTGAATATTCCGAGAGAGAAGGCTACAAAGGATCTGGATT
TGTACCTACTTATGAAGACAAAGATGGAGATTGGATGTTGGTCGGTGATGTTCCA
TGGGACATGTTCTCTTCATCTTGTCAAAAACTCAGAATCATGAAAGGATCCGAAG
CTCCTACTGCCTTATGA

FIG. 2B (IAA2)

(SEQ ID: 12)

ATGGCGTACGAGAAAGTCAACGAGCTTAACCTTAAGGACACAGAGCTATGTCTT
GGATTACCCGGAAGAACAGAGAAGATCAAAGAAGAACAAGAGGTTTCTTGCGTT
AAAAGTAACAACAAGCGTCTATTTGAGGAAACTCGTGATGAAGAAGAATCTACA
CCTCCTACCAAAACTCAAATCGTTGGTTGGCCACCAGTGAGATCTTCCCGTAAGA
ACAACAACAGTGTGAGCTACGTGAAAGTGAGTATGGACGGAGCTCCTTACCTTC
GCAAGATCGATCTCAAGACATACAAAAACTACCCCGAGCTTCTCAAAGCGTTAG
AGAATATGTTCAAAGTCATGATTGGTGAATATTGTGAGAGAGAAGGATACAAAG
GATCTGGATTTGTACCAACATACGAAGATAAAGATGGTGACTGGATGTTGGTTGG
TGATGTTCCATGGGACATGTTCTCTTCTTCTTGTAAGAGACTCAGAATCATGAAG
GGATCCGACGCTCCTGCTCTAGACTCTTCCTTATGA

FIG. 2C (IAA3)

(SEQ ID: 13)

ATGGATGAGTTTGTTAACCTCAAGGAAACAGAGCTGAGGCTGGGATTACCGGGA
ACAGATAATGTATGTGAAGCAAAAGAGAGAGTTTCTTGCTGTAATAACAACAAT
AAGAGAGTACTATCAACTGATACTGAGAAGGAGATTGAATCATCATCAAGGAAA
ACTGAAACATCCCCTCCTCGAAAGGCTCAGATTGTTGGATGGCCACCAGTTAGAT
CTTACAGGAAGAACAACATTCAGAGTAAGAAGAATGAATCTGAGCATGAGGGTC
AAGGAATCTATGTGAAAGTAAGTATGGATGGTGCACCATACTTGAGGAAAATAG
ATCTGAGTTGTTACAAAGGATACTCAGAGTTGCTTAAAGCTTTAGAAGTGATGTT
CAAATTCTCTGTGGGAGAGTACTTTGAGAGAGATGGATATAAAGGTTCAGACTTT
GTGCCTACTTATGAAGACAAAGATGGTGATTGGATGCTCATTGGTGATGTTCCAT
GGGAGATGTTCATATGTACGTGCAAGAGACTAAGGATCATGAAAGGATCAGAAG
CCAAAGGTTTAGGCTGTGGTGTATGA

FIG. 2D (IAA4)

(SEQ ID: 14)

ATGGAAAAAGTTGATGTTTATGATGAGCTTGTTAACCTAAAGGCAACAGAGCTG
AGATTGGGATTACCAGGGACAGAAGAAACTGTTTCTTGTGGAAAAAGCAACAAA
AGAGTTTTACCTGAAGCTACTGAGAAAGAGATTGAATCCACTGGAAAAACTGAA
ACCGCTTCTCCTCCAAAGGCTCAGATTGTTGGATGGCCACCAGTTAGATCTTACA
GAAAGAACAATGTTCAGACAAAGAAGAGTGAATCTGAAGGTCAAGGAAACTAT
GTGAAAGTAAGTATGGATGGTGCTCCATATCTAAGGAAGATAGATCTAACGATG
TATAAACAATATCCAGAGTTGATGAAATCACTTGAAAACATGTTTAAATTCTCTG
TGGGAGAATATTTTGAGAGAGAAGGATATAAAGGCTCAGACTTTGTACCTACTTA
TGAAGACAAAGATGGTGATTGGATGCTTGTTGGTGATGTTCCTTGGGAGATGTTT
GTTTCGTCTTGTAAGAGGCTAAGGATCATGAAAGGATCTGAAGTTAAAGGTTTAG
GTTGTGGTGGTCTTTAA

FIG. 2E (IAA5)

(SEQ ID: 15)

ATGGCGAATGAGAGTAATAATCTTGGACTCGAAATCACCGAACTACGGCTAGGT
CTTCCCGGAGATATCGTCGTCTCCGGTGAGTCCATCTCCGGGAAGAAGAGGGCTT
CTCCGGAAGTAGAGATTGATTTGAAATGTGAACCGGCGAAAAAGAGTCAAGTTG
TGGGTTGGCCACCGGTTTGTTCGTACCGGAGAAAGAACAGTCTCGAACGGACCA
AAAGTTCGTACGTGAAAGTGAGTGTAGATGGAGCTGCATTTTTAAGGAAGATTG
ATTTGGAAATGTACAAATGTTACCAAGATCTTGCTTCCGCTCTGCAAATTCTGTTC
GGATGCTATATCAATTTTGATGATACGTTGAAGGAAAGTGAATGTGTACCAATAT
ATGAAGACAAAGATGGAGATTGGATGCTTGCTGGAGATGTTCCTTGGGAAATGT
TCCTTGGATCGTGCAAGAGGTTAAGGATTATGAAGAGATCATGTAACAGAGGAT
GA

FIG. 2F (IAA6)

(SEQ ID: 16)

ATGGCAAAGGAAGGTCTAGCACTCGAGATCACAGAGCTTCGATTGGGTCTTCCA
GGAGATAATTATAGCGAAATATCAGTATGCGGATCGAGTAAGAAGAAGAAGAG
GGTGCTCTCGGATATGATGACCTCATCAGCGTTAGATACTGAGAATGAAAACAG
CGTCGTTTCATCAGTTGAAGATGAATCACTGCCGGTTGTGAAGAGTCAAGCGGTG
GGATGGCCACCTGTGTGTTCTTACAGGAGAAAGAAGAACAATGAGGAAGCATCG
AAAGCTATAGGCTACGTGAAAGTGAGCATGGATGGTGTGCCATACATGAGGAAG
ATTGACCTTGGTTCGAGCAACAGTTATATTAATCTAGTCACGGTTCTTGAGAATC
TCTTCGGCTGTCTTGGCATAGGAGTGGCGAAGGAGGGTAAGAAGTGTGAATACA
TTATTATATACGAAGACAAGGATAGAGACTGGATGCTCGTCGGAGATGTACCTTG
GCAGATGTTTAAAGAATCATGCAAGAGGCTGAGGATCGTGAAGAGATCAGATGC
AACTGGTTTTGGTCTCCAGCAAGATTAA

FIG. 2G (IAA7)

(SEQ ID: 17)

ATGATCGGCCAACTTATGAACCTCAAGGCCACGGAGCTCTGTCTCGGCCTCCCCG
GCGGCGCTGAAGCAGTTGAGAGTCCTGCCAAATCGGCGGTGGGAAGCAAGAGAG
GCTTCTCCGAAACCGTTGATCTCATGCTCAATCTTCAATCTAACAAAGAAGGCTC
CGTTGATCTCAAAAACGTTTCTGCTGTTCCCAAGGAGAAGACTACCCTTAAAGAT
CCTTCTAAGCCTCCTGCTAAAGCACAAGTGGTGGGATGGCCACCTGTGAGGAACT
ACAGGAAGAACATGATGACTCAGCAGAAGACCAGTAGTGGTGCGGAGGAGGCC
AGCAGTGAGAAGGCCGGGAACTTTGGTGGAGGAGCAGCCGGAGCCGGCTTGGTG
AAGGTCTCCATGGACGGTGCTCCATATCTGAGGAAAGTTGACCTCAAGATGTACA
AAAGCTACCAGGATCTTTCTGATGCATTGGCCAAAATGTTCAGCTCCTTTACTAT
GGGAAACTATGGAGCACAAGGAATGATAGATTTCATGAACGAGAGCAAGCTAAT
GAATCTGCTGAATAGCTCTGAGTATGTGCCAAGCTACGAGGACAAAGATGGTGA
CTGGATGCTCGTTGGCGATGTCCATGGGAAATGTTTGTCGAGTCTTGCAAACGT
TTGCGCATTATGAAGGGATCTGAAGCAGTTGGACTTGCTCCGAGAGCAATGGAG
AAGTACTGCAAGAACAGATCTTGA

FIG. 2H (IAA8)

(SEQ ID: 18)

ATGAGTTCTGGGAACGATAAGATAAAACAAGTCCTGCATATTGAAGATCTGATG
TCTTATCGATTGCTAAGTGTGGATAAGGATGAACTGGTTACGTCACCTTGTTTGA
AAGAACGTAACTACTTGGGTCTCTCTGATTGTTCCTCTGTTGATAGCTCAACTATT
CCCAATGTTGTTGGGAAGAGCAATCTCAATTTCAAAGCTACTGAACTGAGGCTAG
GTCTTCCTGAGTCTCAATCTCCTGAGAGAGAGACTGATTTCGGTTTGCTGAGTCC
GAGAACACCCGATGAGAAGCTTCTCTTCCCGTTGCTACCTTCTAAAGACAATGGT
TCTGCTACTACAGGGCATAAGAATGTTGTTTCTGGTAACAAGAGAGGATTTGCTG
ACACTTGGGATGAGTTTTCGGGTGTGAAAGGATCTGTTAGACCTGGAGGAGGAA
TCAACATGATGTTGTCGCCGAAAGTTAAGGATGTCTCGAAGAGTATTCAAGAAG
AAAGATCTCATGCTAAGGGTGGCTTGAACAATGCACCAGCTGCCAAGGCACAGG
TTGTTGGTTGGCCTCCAATCAGATCATACCGGAAGAATACAATGGCTTCTTCTAC
TTCGAAGAACACTGATGAGGTTGATGGGAAACCTGGTCTTGGTGTTCTGTTTGTG
AAGGTGAGCATGGATGGTGCTCCGTATCTGAGAAAGGTCGACTTGAGAACTTAC
ACTTCCTATCAACAGTTGTCTTCTGCACTTGAGAAAATGTTCAGCTGCTTCACCCT
TGGTCAATGTGGTCTTCATGGTGCTCAAGGGAGGGAAAGAATGAGCGAGATTAA
ACTGAAGGATCTTCTTCATGGATCAGAATTTGTGCTTACTTATGAAGATAAAGAC
GGTGATTGGATGCTTGTTGGCGATGTTCCATGGGAGATATTTACTGAAACATGCC
AGAAACTGAAGATCATGAAGGGTTCTGATTCTATTGGCTTAGCTCCAGGTGCAGT
GGAGAAATCGAAGAACAAAGAGCGGGTTTGA

FIG. 2I (IAA9)

(SEQ ID: 19)

ATGTCCCCGGAAGAGGAGCTACAGAGCAATGTATCGGTGGCTAGTTCTTCACCTA
CTAGCAATTGCATCTCCAGGAACACTCTAGGAGGACTTAAAGAGCATAACTACTT
GGGTCTCTCTGATTGTTCTTCTGTTGGAAGCTCTACTCTCTCTCCCCTTGCTGAAG
ATGACAAAGCTACTATCAGCCTCAAGGCTACGGAGCTGACACTTGGTCTTCCTGG
ATCACAATCTCCTGCGAGAGACACAGAGCTTAACCTTTTGAGCCCAGCAAAGCTA
GATGAGAAGCCATTCTTTCCTTTGCTTCCTTCTAAAGATGAGATATGCTCCTCCTC
GCAAAAGAACAATGCATCGGGAAACAAAAGAGGCTTTTCTGACACAATGGATCA
GTTTGCTGAAGCTAAAAGTTCAGTGTATACTGAGAAAAACTGGATGTTCCCTGAA
GCAGCAGCCACCCAGTCTGTAACAAAGAAAGATGTGCCACAAAACATACCCAAA
GGACAGTCTAGCACTACAAACAATAGCTCTAGTCCACCTGCAGCCAAGGCACAA
ATTGTCGGTTGGCCTCCAGTGAGATCCTACAGGAAGAACACATTGGCCACTACTT
GTAAGAACAGTGACGAAGTTGATGGGAGGCCAGGTTCTGGGGCTCTCTTCGTGA
AGGTCAGTATGGATGGTGCTCCTTATCTGAGGAAAGTTGACCTGAGGAGCTACAC
TAACTACGGGGAGCTTTCTTCAGCCTTGGAGAAAATGTTCACCACTTTCACTCTT
GGTCAATGTGGATCTAATGGAGCTGCTGGGAAGGATATGCTTAGTGAGACCAAG
CTCAAGGATCTTTTGAATGGAAAAGACTATGTGCTCACTTATGAGGATAAGGATG
GTGACTGGATGCTTGTTGGAGATGTTCCGTGGGAGATGTTTATTGATGTCTGCAA
GAAGCTGAAGATAATGAAAGGGTGTGATGCTATTGGGTTAGCTGCAGCTCCGAG
AGCAATGGAGAAATCGAAGATGAGAGCTTAA

FIG. 2J (IAA10)

(SEQ ID: 20)

ATGAATGGTTTGCAAGAAGTTTGTTCGTCAAGTGGGTCGGTGATGATCGGACTAC
CAGCTGAAGAAGACGAAAACGCCGCACATTCGTCGGAGGATTCATCTTGCCCCG
ACGAGTCAGTGTCAGAGACAGAGCTCGACCTAGCTTTGGGTCTTAGCATTGGTCG
TCGGAAGGTTCGATCGTCTTTGTCTTCCTCGTCTTCTTCTCTGACCAGGGAAAGTG
GGACCAAACGCTCTGCTGATTCTTCTCCGGCTGCCGCCTCAAACGCAACCAGACA
AGTTGCTGTAGGTTGGCCGCCTCTACGGACTTACAGAATCAACAGTTTGGTCAAT
CAAGCAAAGTCTTTAGCTACGGAAGGCGGCTTGAGTTCTGGCATTCAAAAGGAG
ACTACAAAAAGTGTAGTGGTTGCTGCTAAGAACGATGATGCTTGCTTTATCAAAT
CGTCCAGGACTTCTATGCTTGTGAAGGTGACAATGGACGGAGTTATAATTGGAAG
GAAGGTTGATCTCAATGCTCTGGATTCTTATGCAGCCTTAGAGAAAACTTTGGAT
CTAATGTTTTTCCAGATTCCTTCTCCTGTAACAAGATCCAACACACAAGGATACA
AGACAATTAAGGAAACATGTACTTCGAAATTACTGGATGGCTCATCGGAATATAT
CATAACATATCAAGATAAAGACGGAGATTGGATGCTTGTAGGAGATGTTCCTTG
GCAGATGTTCCTCGGGTCTGTGACAAGACTGAGAATCATGAAGACATCAATTGG
AGCTGGAGTAGGTAAGTAG

FIG. 2K (IAA11)

(SEQ ID: 21)

ATGGAAGGCGGTTCCGCTAGTGGATCGGCTTCGGCTTTGTCAAACGATGAAAATC
TCGTCGTTTCTTGTGAGGATTCTTCTTCTCCTATAGGGAATGAGCTTGAGCTTGGT
CTTACGTTGAGCCTTGGTCGCAAAGGGTATCGAGATTGTAGGGTTTACGCTGATG
ATTCTTCTTCTTCATCATCTTCTTCTCTGAGCAGAGCTAGCGTAATTGCTGGG
ATCAAGAGGACAGCTGATTCCATGGCTGCAACTAGTGGGCAAGTTGTGGGATGG
CCACCAATAAGGACTTACAGAATGAACAGTATGGTTAACCAAGCTAAGGCTTCA
GCCACTGAAGATCCGAACTTGGAGATAAGTCAAGCCGTAAACAAGAATAGAAGT
GATTCAACAAAGATGAGAAATTCCATGTTTGTTAAGGTGACTATGGATGGCATTC
CTATTGGAAGGAAAATCGATCTGAATGCTCATAAATGCTATGAATCATTGTCAAA
CACTCTAGAGGAAATGTTTCTGAAACCTAAATTAGGTTCACGCACACTAGAAACC
GATGGTCACATGGAAACACCGGTCAAGATACTACCAGATGGGTCTTCCGGATTA
GTACTAACGTATGAAGACAAGGAAGGAGATTGGATGCTTGTTGGCGATGTTCCG
TGGGGGATGTTTATTGGTTCAGTGAGAAGGCTCCGGATAATGAAAACATCGGAG
GCTACTGGTAAAGATGATATTATGAAGCAAATAATAATCTACGAAGAACCCTTTA
TGTTTGAAGCAGTAATAAGACAGATCACAGATCAAAGAGAAGACAAAACATTG
TAAGAAGCTTCTTCTTCTTCTCCCCTTTACAGTTTCTTTTTGGCTCTGCCATTT
TTCTTTTAGTTAGTTATATGTTCTCTTTGTAA

FIG. 2L (IAA12)

(SEQ ID: 22)

ATGCGTGGTGTGTCAGAATTGGAGGTGGGGAAGAGTAATCTTCCGGCGGAGAGT
GAGCTGGAATTGGGATTAGGGCTCAGCCTCGGTGGTGGCGCGTGGAAAGAGCGT
GGGAGGATTCTTACTGCTAAGGATTTTCCTTCCGTTGGGTCTAAACGCTCTGCTG
AATCTTCCTCTCACCAAGGAGCTTCTCCTCCTCGTTCAAGTCAAGTGGTAGGATG
GCCACCAATTGGGTTACACAGGATGAACAGTTTGGTTAATAACCAAGCTATGAA
GGCAGCAAGAGCGGAAGAAGGAGACGGGGAGAAGAAAGTTGTGAAGAATGATG
AGCTCAAAGATGTGTCAATGAAGGTGAATCCGAAAGTTCAGGGCTTAGGGTTTG
TTAAGGTGAATATGGATGGAGTTGGTATAGGCAGAAAAGTGGATATGAGAGCTC
ATTCGTCTTACGAAAACTTGGCTCAGACGCTTGAGGAAATGTTCTTTGGAATGAC
AGGTACTACTTGTCGAGAAAAGGTTAAACCTTTAAGGCTTTTAGATGGATCATCA
GACTTTGTACTCACTTATGAAGATAAGGAAGGGGATTGGATGCTTGTTGGAGATG
TTCCATGGAGAATGTTTATCAACTCGGTGAAAAGGCTTCGGATCATGGGAACCTC
AGAAGCTAGTGGACTAGCTCCAAGACGTCAAGAGCAGAAGGATAGACAAAGAA
ACAACCCTGTTTAG

FIG. 2M (IAA13)

(SEQ ID: 23)

ATGATTACTGAACTTGAGATGGGGAAAGGTGAGAGTGAGCTTGAGCTTGGTCTA
GGGCTGAGTCTTGGCGGTGGAACGGCGGCCAAGATTGGTAAATCAGGTGGTGGT
GGCGCGTGGGGAGAGCGTGGAAGGCTTTTGACGGCTAAGGATTTTCCTTCTGTTG
GTTCTAAACGTGCTGCTGATTCTGCTTCTCATGCTGGTTCATCTCCTCCTCGTTCA
AGCAGTCAAGTTGTTGGATGGCCTCCTATAGGGTCACACAGGATGAACAGTTTGG
TTAATAACCAAGCTACAAAGTCAGCAAGAGAAGAAGAAGAAGCTGGTAAGAAG
AAAGTGAAAGATGATGAACCTAAAGATGTGACAAAGAAAGTGAATGGGAAAGT
ACAAGTTGGATTTATTAAGGTGAACATGGATGGAGTTGCTATAGGAAGAAAAGT
GGATTTGAATGCTCATTCTTCTTACGAGAATTTGGCGCAAACATTGGAAGATATG
TTCTTTCGCACTAATCCGGGTACTGTCGGGTTAACCAGTCAGTTCACTAAACCGTT
GAGGCTTTTAGATGGATCGTCTGAGTTTGTACTTACTTATGAAGATAAGGAAGGA
GATTGGATGCTTGTTGGTGATGTTCCATGGAGAATGTTCATCAACTCGGTGAAAA
GGCTACGTGTGATGAAAACCTCTGAAGCTAATGGACTCGCTGCACGAAATCAAG
AACCAAACGAGAGACAGCGAAAGCAGCCGGTTTAG

FIG. 2N (IAA14)

(SEQ ID: 24)

ATGAACCTTAAGGAGACGGAGCTTTGTCTTGGCCTCCCCGGAGGCACTGAAACC
GTTGAAAGTCCGGCCAAGTCGGGTGTTGGGAACAAGAGAGGCTTCTCCGAGACC
GTTGATCTCAAACTTAATCTTCAATCTAACAAACAAGGACATGTGGATCTCAACA
CTAATGGAGCTCCCAAGGAGAAGACCTTCCTTAAAGACCCTTCTAAGCCTCCTGC
TAAAGCACAAGTGGTGGGTTGGCCACCGGTGAGGAACTACCGGAAAAATGTTAT
GGCTAATCAGAAGAGCGGCGAAGCAGAGGAGGCAATGAGTAGTGGTGGAGGAA
CCGTCGCCTTTGTGAAGGTTTCCATGGATGGAGCTCCTTATCTTCGGAAGGTTGA
CCTCAAGATGTACACCAGCTACAAGGATCTCTCTGATGCCTTGGCCAAAATGTTC
AGCTCCTTTACCATGGGGAGTTATGGAGCACAAGGGATGATAGATTTCATGAAC
GAGAGTAAAGTGATGGATCTGTTGAACAGTTCTGAGTATGTTCCAAGCTACGAG
GACAAAGATGGTGACTGGATGCTCGTTGGTGATGTCCCCTGGCCGATGTTTGTCG
AGTCATGCAAACGTTTGCGCATAATGAAAGGATCCGAAGCAATTGGACTTGCTCC
AAGAGCAATGGAGAAGTTCAAGAACAGATCATGA

FIG. 2O (IAA15)

(SEQ ID: 25)

ATGTCACCGGAGGAATACGTTAGGGTTTGGCCGGATTCCGGTGATCTTGGAGGA
ACTGAGCTGACCCTAGCTTTGCCTGGCACTCCGACAAATGCATCGGAAGGTCCAA
AAAAGTTCGGGAACAAACGTAGATTCCTCGAGACCGTTGATTTAAAACTCGGGG
AAGCACACGAGAACAATTATATCTCAAGCATGGTCACTAATGACCAGTTGGTGG
GCTGGCCGCCGGTAGCGACAGCGAGGAAAACAGTGAGGCGGAAATACGTGAAA
GTGGCGTTGGATGGTGCGGCCTATCTCAGAAAGGTTGATCTTGGGATGTACGATT
GCTATGGACAGCTTTTCACCGCTCTAGAAAACATGTTTCAGGGGATAATAACAAT
ATGTAGAGTGACAGAGTTGGAGAGGAAGGGAGAGTTTGTTGCTACTTACGAGGA
TAAGGACGGTGACTTGATGTTAGTCGGAGATGTGCCGTGGATGATGTTTGTGGAA
TCTTGCAAACGTATGAGGTTAATGAAAACCGGAGATGCTATTGGATTATAG

FIG. 2P (IAA16)

(SEQ ID: 26)

ATGATTAATTTTGAGGCCACGGAGCTGAGATTAGGGCTACCGGGTGGGAATCAC
GGAGGAGAAATGGCTGGAAAAAATAATGGTAAAAGAGGATTTTCTGAGACTGTT
GATCTCAAACTGAATCTTTCATCGACGGCTATGGATTCAGTTTCCAAAGTCGATT
TAGAGAATATGAAGGAGAAGGTCGTAAAACCACCAGCCAAGGCACAAGTTGTGG
GATGGCCACCGGTACGATCTTTCCGCAAGAACGTCATGTCCGGCCAAAAACCGA
CCACCGGAGATGCCACCGAAGGAAACGATAAGACTTCTGGCAGCAGTGGAGCCA
CCTCATCCGCCTCCGCATGTGCCACCGTGGCTTATGTGAAGGTTAGCATGGACGG
TGCACCGTACCTACGGAAAATTGACTTGAAACTCTACAAAACTTACCAAGATCTC
TCCAACGCCTTAAGCAAAATGTTTAGCTCTTTTACCATAGGCAACTATGGACCAC
AAGGAATGAAAGATTTCATGAATGAGAGTAAATTGATCGATCTTCTAAACGGAT
CAGATTATGTTCCAACATATGAAGATAAAGATGGCGACTGGATGCTTGTAGGAG
ACGTACCGTGGGAGATGTTTGTTGATTCATGCAAACGTATACGAATAATGAAGG
GATCAGAAGCAATCGGACTTGCTCCAAGGGCATTAGAAAAGTGCAAGAACAGAA
GTTGA

FIG. 2Q (IAA17)

(SEQ ID: 27)

ATGATGGGCAGTGTCGAGCTGAATCTGAGGGAGACTGAGCTGTGTCTTGGTCTTC
CCGGTGGAGATACAGTGGCTCCGGTAACCGGAAACAAGAGAGGGTTCTCAGAGA
CGGTTGATCTGAAGCTAAATCTGAATAATGAGCCTGCAAACAAGGAAGGATCTA
CGACTCATGACGTCGTGACTTTTGATTCCAAGGAGAAGAGTGCTTGTCCTAAAGA
TCCAGCCAAACCTCCGGCCAAGGCACAAGTTGTGGGATGGCCACCGGTGAGATC
ATACCGGAAGAACGTGATGGTTTCCTGCCAAAAATCAAGCGGTGGCCCGGAGGC
GGCGGCGTTCGTGAAGGTATCAATGGACGGAGCACCGTACTTGAGGAAAATCGA
TTTGAGGATGTATAAAAGCTACGATGAGCTTTCTAATGCTTTGTCCAACATGTTC
AGCTCTTTTACCATGGGCAAACATGGAGGAGAAGAAGGAATGATAGACTTCATG
AATGAGAGGAAATTGATGGATTTGGTGAATAGCTGGGACTATGTTCCCTCTTATG
AAGACAAAGACGGTGATTGGATGCTCGTCGGCGACGTTCCTTGGCCAATGTTCGT
CGATACATGCAAGCGTTTACGTCTCATGAAAGGATCGGATGCCATTGGTCTCGCT
CCGAGGGCGATGGAGAAGTGCAAGAGCAGAGCTTGA

FIG. 2R (IAA18)

(SEQ ID: 28)

ATGGAGGGTTATTCAAGAAACGGTGAAATCTCTCCGAAGCTGCTTGACTTGATGA
TTCCACAAGAGAGAAGAAATTGGTTTCACGATGAGAAAAACTCTGTTTTCAAAA
CAGAGGAGAAGAAGCTTGAGCTAAAGCTTGGACCACCTGGTGAAGAAGATGATG
ATGAATCGATGATAAGACACATGAAGAAGAACCAAAAGACAAATCTATCCTCT
CTCTCGCTGGCAAATACTTCTCTCCTTCTTCCACCAAAACCACATCCCATAAAAG
AACTGCTCCTGGTCCAGTGGTGGGATGGCCTCCGGTTCGATCCTTCAGGAAGAAT
TTAGCTAGTGGAAGTTCTTCAAAGCTTGGAAATGACTCAACCACCTCCAATGGTG
TTACCCTCAAGAACCAAAAGTGTGATGCTGCTGCTAAGACAACAGAACCAAAGA
GACAAGGAGGCATGTTTGTGAAGATCAACATGTATGGTGTTCCCATTGGTCGTAA
AGTTGATCTCAGTGCTCATAATAGCTATGAGCAGTTATCTTTCACAGTTGACAAG
CTCTTCAGAGGTCTTCTTGCAGCTCAAAGAGACTTTCCATCATCCATAGAAGATG
AAAAACCAATCACTGGATTATTAGATGGGAATGGAGAATATACTCTTACATATG
AAGACAATGAAGGAGACAAGATGCTTGTAGGAGATGTTCCATGGCAAATGTTTG
TGTCTTCGGTGAAGAGGCTGCGTGTGATTAAAACTTCTGAGATTTCTTCAGCATT
AACATATGGAAATGGTAAGCAAGAGAAAATGAGAAGATGA

FIG. 2S (IAA19)

(SEQ ID: 29)

AAGAGAAGTGTAGGAGAAGAAAGTTCTCATTTCATAATTGTATCAAATTGTGAG
AGGAAAAAAAGAAGTTCAAGAAATGGAGAAGGAAGGACTCGGGCTTGAGATAA
CGGAGCTGAGATTGGGGCTTCCGGGGAGAGATGTGGCAGAGAAGATGATGAAG
AAGAGAGCTTTCACGGAGATGAATATGACGTCGTCGGGTAGTAATAGTGATCAA
TGTGAAAGCGGCGTCGTTTCATCTGGTGGTGACGCTGAGAAGGTTAATGATTCGC
CGGCGGCGAAAAGCCAGGTGGTGGGGTGGCCACCGGTTTGTTCTTACCGGAAGA
AAAACAGCTGTAAGGAAGCTTCGACCACGAAAGTGGGGTTAGGGTATGTGAAAG
TGAGCATGGATGGTGTGCCTTATTTGAGGAAGATGGATCTTGGTTCGAGCCAAGG
CTATGATGATCTAGCCTTTGCTCTTGATAAGCTCTTCGGTTTCCGTGGCATCGGTG
TGGCCTTGAAAGATGGTGACAACTGCGAATACGTTACCATATACGAAGACAAAG
ATGGAGACTGGATGCTCGCCGGTGATGTACCTTGGGGGATGTTTCTAGAGTCATG
CAAGAGGTTGAGAATAATGAAAAGATCGGATGCTACCGGGTTTGGGCTGCAGCC
TAGAGGAGTAGACGAGTGATGATGACTTGAACAAGAAGCAAGGAGCTGGTTCAT
TAATTTAATCTTAAACTTGATCATCAAGATCCTTTAGAACATTTTTCCTATTCATG
TTATATAAATATATATGTTATAGTATATTATTTTGCAACAAAATTTCATGTTATGG
TTTTGCATAATTATCTTCAGAAAGACAGCTATATATATATACACTACTTGTTTCTT
GAGTGTTGAGTTAAAACATTAATCTGTTTCAAAATTTATTGTTATTTCGGATCTAT
ATATGTGTGTAGAAACATATGTAATAAGTATCCATTATT

FIG. 2T (IAA20)

(SEQ ID: 30)

ATGGGAAGAGGGAGAAGTTCATCGTCTTCTTCAATAGAGAGTAGCAGCAAGAGC
AACCCATTCGGTGCTTCGTCAAGTACTCGAAACCTAAGCACGGACCTGAGACTCG
GACTCAGCTTCGGGACATCCTCAGGGACTCAATATTTCAACGGTGGCTATGGGTA
CTCCGTTGCAGCTCCGGCGGTAGAGGATGCGGAATATGTGGCGGCTGTGGAGGA
GGAAGAAGAGAATGAGTGTAACAGTGTAGGGAGCTTTTACGTGAAAGTGAACAT
GGAAGGAGTTCCAATTGGAAGAAAGATCGATCTAATGTCTCTTAATGGCTACCGC
GACTTGATCAGAACCCTTGATTTCATGTTCAACGCATCCATTCTCTGGGCTGAAG
AAGAAGACATGTGCAATGAGAAGAGTCACGTGCTAACGTACGCAGATAAGGAA
GGTGACTGGATGATGGTTGGAGATGTTCCTTGGGAGATGTTCTTGTCTACTGTGA
GAAGACTGAAGATTTCAAGAGCTAATTACCACTACTGA

FIG. 2U (IAA21)

(SEQ ID: 31)

ATGGAAGGTTGTCCAAGAAACAGAGAAATCGGTCCAAAACTTCTTGATTTGATTC
CACAAGGAAGGAAATGGTACCAAGAAGACAAGAACAACACAGATCAGGAGAAG
AAACTTGAGCTAAGGCTTGGACCACCCGGTGGTGATGAAGAAGATCATTCAGCA
ATCAAGAAGAAGAACACAGAGATAAGAAACATCAAGAAGGAAACAGAAGACAA
ATCTTTCCACTGTTTTAATGGCAATCACTTCTCTCCTTCCAACAAAACCACTTCTG
TTCCTCACATCTCACAGAAAAGAACTGCTCCTGGTCCAGTGGTGGGTTGGCCTCC
GGTTCGTTCGTTCAGAAAGAATCTAGCGAGCACAAGCTCTTCAAAGCTAGGTAAC
GAATCCTCTCATGGAGGTCAAATCAACAAGAGTGATGATGGTGAAAAACAAGTT
GAAACCAAGAAGGAAGGAATGTTTGTCAAGATCAACATGGATGGTGTTCCTATT
GGTCGTAAAGTTGATCTCAATGCTTACAACAGCTACGACAGCTCTCTTTTGTCG
TTGACAAACTCTTCAGAGGTCTACTCGCAGCTCAAAGAGATATCTCTGATGGTCA
AGGAGAAGAGAAACCTATCATTGGATTATTAGATGGGAAGGAGAATTTACTTT
AACCTATGAAGACAATGAAGGGGACAAGATGCTTGTTGGGGATGTTCCATGGCA
AATGTTTGTTTCATCTGTGAAGAGACTGCGTGTGATTAAAGCTCTGAGATTTCA
TCTGCCTTGACATTTGGATGCAGTAAGCAAGAGAAGATGATGCACTGA

FIG. 2V (IAA22)

(SEQ ID: 32)

ATGTCTGTATCTGTAGCAGCAGAGCATGATTACATAGGTTTGTCAGAGTTTCCAA
CCATGGAAGCAACAACAATGTCTGACAAAACCAAAACCAGAGACAATAACAAC
GGTCTCAATTTCAAGGCTACCGAGTTAAGACTCGGTTTACCCGGTTCTGAGTCGC
CGGAGCGAGTCGACTCAAGATTCTTGGCTCTCAACAAGAGTAGCTGTCCCGTGTC
AGGTGCCAAAAGGGTGTTCTCCGACGCTATTAACGACTCTAACAAATGGGTCTTC
TCTCCTGGATCCACTACTGCTACTGGTGATGTCGGCTCGGGTTCTGGTCCCCGTAC
CTCCGTCGTTAAAGATGGAAAGTCGACAACTTTCACTAAACCGGCTGTTCCGGTT
AAGGAGAAGAAGAGCTCTGCTACAGCTCCAGCTTCAAAAGCACAAGTGGTGGGA
TGGCCACCAATAAGATCATTCAGGAAGAACTCAATGGCTTCTTCTCAATCTCAGA
AACCTGGTAATAACTCAGAGACTGAAGAAGCAGAAGCTAAGTCTGGACCAGAAC
AACCTTGCTTGTATGTCAAAGTGAGTATGGAAGGTGCTCCTTACTTGAGGAAAAT
CGATCTCAAGACTTACAAAAGCTACCTTGAGCTCTCTTCTGCTCTTGAGAAGATG
TTCAGTTGCTTCACCATTGGTCAGTTTGGTTCTCATGGAGGGTGTGGCAGAGATG
GGTTAAACGAGAGTCGCTTGACTGATCTCTTGCGTGGTTCTGAGTATGTTGTAAC
CTATGAAGATAAAGACAGTGACTGGATGCTGGTCGGAGATGTCCCTTGGGAAAT
GTTTATATGCTCCTGCAAGAAGCTGAGAATCATGAAGAGCTCTGAGGCTATCGGC
TTAGCTCCAAGGGTGATGGAGAAGTGCAGAAGCAGGAACTAG

FIG. 2W (IAA23)

(SEQ ID: 33)

ATGGAAGAAGAAAAGAGATTGGAGCTAAGGCTAGCTCCTCCTTGTCACCAATTC
ACTTCCAACAACAACATCAATGGATCTAAACAAAAAAGCTCGACCAAAGAAACA
TCATTCCTTTCCAATAACAGGGTTGAGGTAGCTCCAGTGGTGGGATGGCCGCCGG
TGAGATCATCCCGGAGAAACCTAACGGCACAACTAAAGGAGGAGATGAAGAAG
AAGGAGAGTGATGAAGAGAAGGAATTGTACGTTAAGATCAACATGGAAGGAGTT
CCAATAGGAAGAAAAGTCAACCTTTCAGCTTATAACAACTACCAACAGCTTTCAC
ATGCCGTTGACCAACTCTTCTCTAAGAAAGATTCGTGGGATCTAAACAGACAATA
CACTTTGGTCTACGAAGACACTGAAGGAGATAAAGTTCTGGTCGGGGATGTTCCT
TGGGAGATGTTTGTATCTACTGTAAAGAGGTTGCATGTTTTAAAGACCTCCCACG
CCTTCTCACTCTCACCTAGAAAACATGGCAAGGAATAG

FIG. 2X (IAA24)

(SEQ ID: 34)

ATGGAGTTGGATCTTGGTCTATCTCTTTCACCTCATAAATCTTCCAAGTTAGGGTT
TAACTTTGACCTCAACAAGCATTGTGCGATCGAGGGTGCTGCGTCTTGTTTGGGT
ACCGAAAAACTGCGTTTTGAGGCGACGTTTGGGTTAGGGAATGTGGAGGAAAAT
TGTTATATGCCAAAACAGCGTTTGTTTGCCTTGAATGGCCAGCCCAACGAGGAAG
ACGAAGATCCTCTGGAATCCGAGTCTTCAATAGTTTACGATGATGAGGAGGAAA
ATAGCGAAGTTGTTGGATGGCCACCAGTAAAAACATGTATGATAAAGTATGGTA
GTTATCATCATCGTCATATTCGTAATCACCATCATTGCCCGTATCATCATCGTGGT
AGGAGGATCACGGCGATGAACAACAACATATCTAATCCAACAACGGCTACTGTG
GGATCATCATCTTCTTCGTCAATATCATCAAGATCATCAATGTATGTTAAGGTTA
AGATGGATGGTGTGGCAATAGCAAGAAAAGTGGATATCAAGCTTTTTAACTCTTA
CGAGTCCCTCACTAACTCCTTGATCACTATGTTTACCGAATATGAAGATTGCGAC
AGAGAAGATACAAATTATACATTCACCTTCCAAGGGAAAGAGGGTGACTGGCTA
CTTCGAGGGGATGTTACATGGAAGATCTTTGCGGAATCTGTTCATCGGATATCAA
TAATTAGAGATCGACCGTGTGCATATACAAGATGTTTGTTTTAA

FIG. 2Y (IAA25)

(SEQ ID: 35)

ATGGGAAGAGGGAGAAGCTCATCGTCTTCATCGATAGAGAGCAGCTGCAAAAGC
AACCCATTTGGTGTGTCTTCGAGTAATACTCGGAACCTAAGCACGGACCTGAGAC
TCGGGCTCAGCTTCGGATCATCTTCCGGACAATATTACAACGGTGGAGATAACCA
TGAATATGATGGAGTCGGTGCGGCAGAGGAAATGATGATCATGGAAGAAGAAG
AGCAAAACGAGTGTAATAGTGTCGGAAGCTTCTACGTGAAAGTGAACATGGAAG
GAGTTCCTATTGGGAGAAAGATCGATCTTTTATCTCTTAATGGATATCATGATTTG
ATCACAACTCTCGACTACATGTTCAATGCTTCAATCCTTTGGGCTGAAGAAGAAG
ATATGTGTAGTGAGAAGAGTCACGTGCTAACGTACGCAGACAAAGAAGGTGACT
GGATGATGGTTGGAGATGTTCCTTGGGAGATGTTCTTGTCTAGCGTGAGAAGACT
AAAGATCTCAAGAGCTTATCACTACTGA

FIG. 2Z (IAA26)

(SEQ ID: 36)

ATGGAGGTCTCTAACTCTTGTTCTTCATTTTCTTCATCCTCTGTCGACAGTACTAA
ACCTTCTCCTTCTGAATCTTCTGTTAATCTCTCCCTTAGTCTCACATTTCCTTCTAC
TTCTCCACAAAGAGAAGCAAGACAAGATTGGCCACCGATAAAGTCTAGATTAAG
AGATACACTAAAGGGTCGTCGTCTTCTTCGTCGTGGTGATGACACTTCTCTCTTTG
TTAAGGTTTATATGGAAGGTGTTCCCATTGGAAGAAAACTCGACCTTTGCGTATT
CTCAGGCTACGAGAGTCTATTAGAAATCTCTCTCACATGTTCGATACTTCAATC
ATCTGCGGTAATCGAGATCGAAAACATCATGTTTTGACATATGAAGACAAGGAT
GGAGATTGGATGATGGTCGGAGATATTCCATGGGATATGTTTCTTGAAACCGTGA
GAAGACTAAAGATCACGAGACCGGAGAGGTATTAA

FIG. 2AA (IAA27)

(SEQ ID: 37)

ATGGACCCAAACACACCTGCAGACTTCTTCAAAGGTTCTTCCAAGTTTCATACAT
ATTACTCACAGACCAAAAAGGGTGGTGGGGTAATCGATCTAGGCCTCAGCCTTA
GGACCATACAACATGAAACTTACCTCCCACCGGCGCGAATGATAGGTCTCGACG
GGTATGGAGAGCTCATAGACTGGTCGCAGCCCAGCTATAACAGCATTACACAGT
TGAAGAGTGAGGACACTGGACACCAAAGACTTGCCCAAGGATATTACAATAATG
AAGGAGAGAGCAGAGGAAAATATGCTTACGTAAAGGTAAATCTGGATGGCCTAG
TGGTAGGGCGCAAGGTTTGCCTTGTTGATCAAGGAGCTTACGCAACTCTTGCTCT
TCAGCTCAATGATATGTTTGGGATGCAGACCGTGTCGGGATTGAGGTTGTTCCAG
ACTGAGTCTGAGTTCTCTTTGGTCTACAGAGACAGAGAAGGCATTTGGAGGAATG
TTGGGGATGTTCCATGGAAGGAGTTTGTCGAAAGCGTGGATCGGATGCGAATCG
CAAGAAGAAACGATGCTCTTCTTCCCTTTTAA

FIG. 2BB (IAA28)

(SEQ ID: 38)

ATGAATAGTTTCGAGCCACAAAGCCAAGACTCTTTGCAAAGAAGGTTTCATCAA
GACAACAGCACCACACAACAACCTCGTGACACCACGACACCTTTCATACCCAAA
CCGGCTTCCAAAAACCATAATAATAGCAACTCCAGCTCTGGAGCGGCCGGGAGA
TCATTCCAAGGCTTTGGGCTTAACGTAGAGGACGATCTTGTTTCATCGGTGGTTC
CTCCGGTTACGGTTGTGCTAGAGGGACGTTCTATATGTCAACGCATAAGCCTAGA
CAAGCATGGGAGTTATCAGAGCTTGGCTTCGGCTCTAAGGCAAATGTTTGTCGAT
GGAGCTGATTCAACGGACGATCTTGATCTGTCAAACGCCATTCCTGGCCATCTTA
TTGCTTATGAAGACATGGAGAACGATCTCCTTCTTGCCGGAGATCTTACTTGGAA
GGACTTTGTTCGTGTAGCGAAGAGAATTCGAATCTTGCCGGTCAAGGGAAACAC
AAGACAAGTTAAAAGAAACGAGTGA

FIG. 2CC (IAA29)

(SEQ ID: 39)

ATGTATTGCAGCGATCCTCCCCATCCCTTGCACTTAGTGGCATCAGACAAACAAC
AAAAAGACCACAAACTGATCCTTTCCTGGAAGAAACCAACAATGGACTCAGACC
CACTCGGTGTTTTCCCAAATTCTCCCAAGTATCATCCATATTACTCGCAGACCACG
GAGTTTGGTGGCGTAATCGATTTAGGTCTCAGCCTGAGAACCATACAACATGAGA
TTTACCACTCATCTGGCCAAAGATATTGTAGTAATGAAGGATACAGACGGAAGT
GGGGTTATGTAAAGGTCACCATGGATGGTTTGGTGGTAGGTCGCAAGGTCTGTGT
TCTTGATCATGGAAGCTATTCAACTCTTGCTCATCAACTCGAGGACATGTTTGGG
ATGCAGAGTGTGTCGGGATTGAGGTTGTTCCAGATGGAGTCTGAGTTCTGTTTGG
TCTACAGAGACGAAGAAGGTCTGTGGAGAAATGCTGGGGATGTTCCATGGAATG
AGTTCATAGAAAGCGTGGAGCGGCTGAGAATCACAAGAAGAAACGATGCTGTAC
TTCCCTTTTAA

FIG. 2DD (BDL/IAA12)

(SEQ ID: 40)

ATGCGTGGTGTGTCAGAATTGGAGGTGGGGAAGAGTAATCTTCCGGCGGAGAGT
GAGCTGGAATTGGGATTAGGGCTCAGCCTCGGTGGTGGCGCGTGGAAAGAGCGT
GGGAGGATTCTTACTGCTAAGGATTTTCCTTCCGTTGGGTCTAAACGCTCTGCTG
AATCTTCCTCTCACCAAGGAGCTTCTCCTCCTCGTTCAAGTCAAGTGGTAGGATG
GCCACCAATTGGGTTACACAGGATGAACAGTTTGGTTAATAACCAAGCTATGAA
GGCAGCAAGAGCGGAAGAAGGAGACGGGGAGAAGAAAGTTGTGAAGAATGATG
AGCTCAAAGATGTGTCAATGAAGGTGAATCCGAAAGTTCAGGGCTTAGGGTTTG
TTAAGGTGAATATGGATGGAGTTGGTATAGGCAGAAAAGTGGATATGAGAGCTC
ATTCGTCTTACGAAAACTTGGCTCAGACGCTTGAGGAAATGTTCTTTGGAATGAC
AGGTACTACTTGTCGAGAAAAGGTTAAACCTTTAAGGCTTTTAGATGGATCATCA
GACTTTGTACTCACTTATGAAGATAAGGAAGGGGATTGGATGCTTGTTGGAGATG
TTCCATGGAGAATGTTTATCAACTCGGTGAAAAGGCTTCGGATCATGGGAACCTC
AGAAGCTAGTGGACTAGCTCCAAGACGTCAAGAGCAGAAGGATAGACAAAGAA
ACAACCCTGTTTAG

FIG. 2EE (AXR3/IAA17)

(SEQ ID: 41)

ATGATGGGCAGTGTCGAGCTGAATCTGAGGGAGACTGAGCTGTGTCTTGGTCTTC
CCGGTGGAGATACAGTGGCTCCGGTAACCGGAAACAAGAGAGGGTTCTCAGAGA
CGGTTGATCTGAAGCTAAATCTGAATAATGAGCCTGCAAACAAGGAAGGATCTA
CGACTCATGACGTCGTGACTTTTGATTCCAAGGAGAAGAGTGCTTGTCCTAAAGA
TCCAGCCAAACCTCCGGCCAAGGCACAAGTTGTGGGATGGCCACCGGTGAGATC
ATACCGGAAGAACGTGATGGTTTCCTGCCAAAAATCAAGCGGTGGCCCGGAGGC
GGCGGCGTTCGTGAAGGTATCAATGGACGGAGCACCGTACTTGAGGAAAATCGA
TTTGAGGATGTATAAAAGCTACGATGAGCTTTCTAATGCTTTGTCCAACATGTTC
AGCTCTTTTACCATGGGCAAACATGGAGGAGAAGAAGGAATGATAGACTTCATG
AATGAGAGGAAATTGATGGATTTGGTGAATAGCTGGGACTATGTTCCCTCTTATG
AAGACAAAGACGGTGATTGGATGCTCGTCGGCGACGTTCCTTGGCCAATGTTCGT
CGATACATGCAAGCGTTTACGTCTCATGAAAGGATCGGATGCCATTGGTCTCGCT
CCGAGGGCGATGGAGAAGTGCAAGAGCAGAGCTTGA

FIG. 3A (TIR1)

(SEQ ID: 42)

ATGCAGAAGCGAATAGCCTTGTCGTTTCCAGAAGAGGTACTAGAGCATGTGTTCT
CGTTTATTCAGCTGGATAAGGATAGGAACTCAGTCTCTCTGGTGTGCAAGTCATG
GTACGAGATCGAGCGGTGGTGCAGGAGGAAAGTCTTCATCGGGAACTGCTACGC
CGTGAGTCCAGCGACGGTGATTAGGAGGTTCCCGAAAGTGAGATCCGTGGAGCT
TAAAGGAAAACCTCACTTTGCTGACTTTAATTTGGTACCTGACGGATGGGGAGGT
TACGTGTATCCATGGATTGAGGCCATGTCTTCGTCTTACACGTGGCTTGAAGAGA
TAAGGCTGAAGAGGATGGTGGTCACCGACGATTGCTTGGAGCTCATAGCCAAGT
CTTTTAAGAATTTTAAGGTTCTTGTGCTTTCTTCCTGCGAAGGCTTCTCCACCGAT
GGTCTCGCTGCTATCGCTGCCACTTGCAGGAATCTGAAAGAGCTTGACTTACGAG
AGAGTGATGTTGACGACGTTAGTGGCCACTGGCTTAGCCATTTCCCAGATACATA
CACTTCTTTGGTATCACTCAATATATCTTGCTTAGCATCTGAGGTCAGTTTCTCTG
CTCTGGAAAGGCTGGTGACTAGGTGTCCCAATCTCAAGTCTCTCAAGCTTAACCG
AGCTGTTCCACTTGAAAAATTGGCTACTTTACTTCAAAGAGCACCTCAATTGGAG
GAATTGGGCACTGGTGGGTACACTGCAGAAGTGCGACCAGATGTTTACTCTGGTT
TATCTGTAGCGCTCTCTGGGTGCAAGGAATTGAGGTGCTTATCTGGATTTTGGGA
TGCTGTTCCTGCCTATCTTCCAGCAGTTTATTCGGTTTGCAGTCGGCTTACAACTT
TGAATCTGAGTTATGCAACAGTCCAGAGCTATGATCTTGTCAAGCTTCTTTGTCA
ATGCCCTAAACTGCAGCGCCTCTGGGTGCTTGACTACATCGAGGATGCTGGTCTT
GAGGTGCTTGCTTCAACCTGCAAGGACCTACGCGAGCTGAGAGTGTTTCCGTCCG
AGCCTTTTGTCATGGAACCAAATGTGGCATTGACGGAACAGGGGCTTGTCTCCGT
CTCCATGGGCTGTCCAAAACTCGAGTCGGTTCTCTACTTCTGCCGTCAAATGACC
AATGCTGCATTGATAACCATTGCTAGGAACCGTCCCAACATGACTCGCTTCCGTT
TGTGCATCATTGAGCCAAAAGCCCCAGACTATCTGACTCTAGAGCCACTGGATAT
TGGATTTGGAGCCATAGTAGAGCACTGCAAGGATCTCCGTCGCCTCTCTCTATCT
GGCCTCTTGACCGACAAGGTTTTTGAATACATTGGGACATATGCCAAGAAGATGG
AAATGCTCTCAGTGGCATTTGCAGGAGACAGTGACTTAGGCATGCATCATGTTTT
GTCCGGGTGCGATAGCTTGAGGAAACTAGAGATAAGGGACTGCCCGTTTGGAGA
CAAGGCGCTTTTGGCCAATGCTTCAAAGCTGGAGACAATGCGATCCCTTTGGATG
TCTTCTTGTTCCGTGAGTTTTGGAGCCTGCAAGTTACTAGGACAGAAGATGCCAA
AGCTGAATGTGGAAGTCATCGATGAACGGGGTGCACCGGACTCGAGACCAGAGA
GCTGCCCTGTTGAGAGAGTCTTCATATACCGAACAGTGGCTGGTCCTCGATTTGA

FIG. 3B (TIR1)

CATGCCTGGCTTCGTCTGGAACATGGACCAAGACTCAACAATGAGGTTTTCCAGG
CAAATCATTACTACTAACGGATTATAA

FIG. 3C (AFB1)

(SEQ ID: 43)

ATGGGTCTCCGATTCCCACCTAAGGTGTTGGAACATATCCTCTCCTTCATTGATTC
CAACGAGGACCGGAACTCTGTTTCTCTGGTCTGCAAGTCATGGTTTGAGACAGAA
CGGAAGACTAGGAAGCGAGTCTTTGTCGGAAACTGTTACGCGGTCAGTCCTGCTG
CGGTTACACGACGGTTCCCGGAGATGAGATCTTTGACTTTGAAGGGGAAGCCAC
ACTTCGCTGACTATAATCTCGTTCCTGATGGTTGGGGTGGTTATGCTTGGCCGTGG
ATTGAAGCTATGGCGGCGAAAAGTTCGTCTCTTGAAGAGATCAGAATGAAGAGG
ATGGTGGTGACTGATGAGTGCTTAGAGAAAATTGCTGCTTCGTTTAAGGATTTTA
AAGTCCTTGTGTTGACTTCTTGTGAAGGTTTCTCTACTGATGGTATCGCTGCTATT
GCAGCTACTTGCAGGAACTTGAGAGTGTTGGAACTACGAGAGTGTATTGTTGAA
GATTTAGGAGGAGATTGGCTTAGCTATTTTCCAGAGAGTTCAACTTCTTTGGTCTC
TCTTGACTTCTCTTGTTTAGATTCTGAGGTTAAAATCTCGGATTTAGAGCGTCTTG
TGAGCAGATCTCCAAACTTGAAGTCTTTGAAGTTGAATCCAGCTGTGACTCTAGA
TGGACTCGTTAGCTTACTTCGTTGTGCTCCACAACTGACTGAGCTCGGCACAGGT
TCTTTCGCAGCTCAATTGAAACCTGAAGCGTTTTCAAAGTTATCAGAAGCTTTTC
AAACTGTAAGCAACTTCAGAGCTTATCTGGTCTCTGGGATGTCCTCCCTGAATAT
CTTCCAGCTCTTTATTCTGTCTGTCCTGGTCTTACCTCGTTGAACTTGAGCTACGC
TACTGTCCGAATGCCTGATCTTGTTGAGCTTCTTAGGCGATGCTCGAAACTGCAG
AAGCTATGGGTGATGGACTTGATTGAGGACAAAGGTCTTGAAGCTGTTGCCTCAT
ATTGCAAGGAACTGCGAGAACTGAGGGTGTTTCCATCTGAGCCAGATCTTGATGC
AACCAACATACCTCTGACGGAACAAGGCCTGGTCTTTGTGTCTAAAGGCTGTCGA
AAGCTTGAGTCTGTTCTCTACTTCTGTGTCCAGTTCACAAACGCAGCTTTGTTTAC
CATAGCAAGAAAACGTCCGAATCTCAAGTGCTTCCGTCTCTGTGTGATAGAGCCA
TTTGCTCCTGATTACAAAACAAATGAGCCACTTGATAAAGGATTCAAAGCCATAG
CTGAGGGATGCAGGGATCTTCGACGGCTCTCCGTCTCTGGTCTTCTCTCTGACAA
GGCCTTCAAATACATTGGGAAACATGCCAAGAAGGTTAGGATGCTATCAATAGC
ATTTGCTGGGGACAGTGATTTGATGCTTCATCACTTGTTGTCGGGCTGTGAGAGT
TTAAAGAAGCTTGAGATACGAGACTGCCCTTTTGGAGACACTGCACTACTGGAGC
ACGCTGCCAAGCTAGAGACCATGCGATCCCTTTGGATGTCATCTTGCTTTGTAAG
TTTTGGTGCTTGCAAGCTTCTAAGTCAGAAAATGCCAAGGCTCAATGTCGAAGTC
ATTGATGAACATCCTCCAGAGTCAAGACCTGAGAGCTCTCCAGTTGAGAGGATAT
ACATATACAGAACAGTCGCAGGACCGAGAATGGATACGCCTGAATTTGTGTGGA

FIG. 3D (AFB1)

CGATACACAAGAATCCTGAGAATGGAGTTTCACATCTAGCCATAAAGTAA

FIG. 3E (AFB2)

(SEQ ID: 44)

ATGAATTATTTCCCAGATGAAGTAATAGAGCATGTATTCGACTTTGTAACATCTC
ACAAAGACAGGAATGCTATATCTCTTGTATGCAAATCATGGTACAAGATTGAAA
GATACAGTAGGCAAAAGGTTTTCATTGGAAACTGTTATGCCATTAATCCAGAGAG
GTTGCTTCGGAGATTCCCATGTCTAAAGTCTTTGACTTTGAAAGGAAAACCTCAT
TTTGCGGATTTCAATTTGGTTCCTCATGAATGGGGAGGTTTTGTGCTACCTTGGAT
TGAGGCTTTGGCTAGAAGCCGTGTAGGACTTGAAGAGCTTAGGTTGAAGAGGAT
GGTTGTTACTGATGAGAGTCTTGAGCTGCTTTCTCGTTCTTTTGTCAATTTTAAGT
CTTTGGTCCTTGTTAGCTGTGAAGGTTTTACCACTGATGGTCTTGCCTCTATTGCC
GCTAATTGCAGGCATCTTCGGGATCTTGATTTGCAAGAGAATGAAATCGATGATC
ATAGAGGTCAATGGTTAAGTTGTTTCCCAGACACTTGCACGACTCTTGTCACGCT
AAACTTTGCGTGCCTCGAAGGAGAAACTAATCTGGTTGCTCTAGAGAGGCTTGTT
GCTAGGTCTCCAAACCTAAAGAGTCTGAAGCTAAATCGTGCAGTACCGTTAGATG
CACTCGCAAGGTTAATGGCGTGTGCGCCGCAGATAGTTGACTTAGGAGTAGGGT
CTTATGAGAATGACCCAGATTCCGAGTCTTACTTGAAACTCATGGCTGTCATAAA
GAAATGCACCTCGTTGAGGAGTTTGTCGGGTTTTCTAGAGGCTGCTCCTCACTGT
CTCTCAGCTTTCCACCCAATATGTCATAACCTCACCTCCTTGAATCTTAGTTACGC
AGCTGAGATTCATGGTAGCCACCTTATTAAGCTTATTCAGCATTGCAAGAAACTT
CAGCGGTTATGGATTTTGGATAGTATAGGTGACAAAGGGCTTGAAGTTGTAGCTT
CTACATGTAAAGAGTTACAAGAGCTTAGGGTTTTTCCATCTGATTTACTCGGTGG
AGGCAACACAGCTGTGACCGAAGAAGGTCTAGTTGCCATCTCGGCAGGCTGCCC
TAAGCTCCACTCTATACTCTACTTCTGCCAACAAATGACAAACGCAGCTCTCGTA
ACCGTTGCCAAGAACTGTCCAAATTTCATCCGTTTCCGACTCTGCATCCTCGAGC
CAAACAAACCCGATCACGTCACATCTCAACCTCTAGACGAAGGCTTTGGAGCAA
TCGTCAAAGCCTGCAAGAGCCTGAGAAGGCTTTCTCTCTCAGGTCTCCTTACAGA
CCAAGTCTTCCTCTACATCGGAATGTACGCGAATCAGCTCGAGATGCTCTCCATA
GCCTTTGCAGGAGATACAGACAAAGGCATGCTATATGTGTTGAATGGTTGCAAA
AAGATGAAGAAACTAGAGATAAGGGATAGTCCGTTTGGGGACACGGCGCTTCTT
GCTGATGTGAGCAAGTATGAAACAATGCGATCCCTTTGGATGTCTTCATGTGAAG
TCACACTCAGTGGATGCAAAAGGCTCGCAGAGAAAGCGCCATGGCTCAATGTAG
AGATCATAAACGAGAATGATAATAACCGGATGGAAGAAAACGGACACGAGGGG

FIG. 3F (AFB2)

AGGCAGAAAGTGGATAAGTTGTATCTGTACCGGACTGTGGTTGGGACAAGAATG
GATGCGCCGCCATTTGTGTGGATTCTCTAA

FIG. 3G (AFB3)

(SEQ ID: 45)

ATGAATTATTTCCCAGACGAGGTTATAGAGCACGTGTTTGACTTCGTAGCTTCTC
ACAAAGACAGGAACTCGATATCTCTGGTCTGCAAATCATGGCACAAGATCGAGA
GGTTTAGTAGGAAGGAAGTGTTCATCGGAAACTGCTACGCGATTAACCCGGAGA
GGTTGATCAGGAGGTTTCCATGTCTCAAATCCTTAACTTTAAAAGGGAAGCCTCA
TTTTGCAGACTTCAACTTGGTTCCTCATGAATGGGGAGGTTTCGTGCATCCTTGGA
TTGAAGCTTTGGCTAGAAGCCGTGTGGGACTTGAGGAGCTGAGGTTGAAGCGGA
TGGTTGTAACAGATGAAAGCTTGGACCTTCTTTCACGTTCTTTTGCAAATTTCAAG
TCTTTGGTTCTTGTTAGCTGTGAAGGGTTTACCACTGATGGCTTAGCTTCCATTGC
CGCTAATTGCAGGCATCTTCGTGAGCTGGACTTGCAAGAGAATGAGATTGATGAT
CATAGAGGTCAATGGCTGAACTGTTTTCCAGATAGCTGCACTACTCTTATGTCGT
TGAATTTCGCTTGCCTTAAAGGAGAGACCAATGTTGCTGCTTTAGAAAGGCTTGT
TGCTAGGTCACCAAACCTGAAGAGCTTGAAGTTAAACCGTGCAGTACCGCTTGAC
GCACTCGCAAGGTTAATGAGTTGTGCGCCGCAGCTAGTGGACTTAGGAGTAGGG
TCTTATGAGAATGAGCCAGATCCTGAATCTTTTGCAAAACTCATGACTGCCATTA
AGAAATACACATCGTTAAGGAGCTTGTCTGGCTTTTAGAGGTTGCTCCACTCTG
CCTCCCAGCGTTCTACCCAATTTGCCAAAACCTTATCTCTTTGAACCTCAGCTATG
CAGCTGAAATCCAAGGCAACCACCTCATTAAGCTTATTCAGCTTTGCAAGAGACT
TCAACGATTATGGATATTGGATAGTATTGGTGACAAAGGACTTGCGGTTGTCGCT
GCCACATGTAAAGAGTTACAAGAGCTTAGAGTTTTTCCCTCTGATGTACATGGTG
AAGAAGATAACAACGCATCTGTGACTGAGGTTGGACTAGTCGCCATTTCCGCAG
GTTGCCCTAAACTTCATTCGATTCTGTACTTCTGCAAACAGATGACAAACGCAGC
GCTCATAGCCGTGGCCAAAAACTGTCCAAACTTCATCCGGTTCAGGCTATGCATT
CTCGAGCCACACAAACCTGACCACATTACATTTCAATCACTGGACGAGGGCTTTG
GTGCAATCGTACAAGCTTGCAAGGGTCTAAGACGGCTCTCTGTCTCCGGTCTCTT
AACCGATCAAGTCTTTCTCTACATCGGTATGTACGCGGAACAGCTCGAGATGCTT
TCGATAGCTTTTGCGGGGGACACTGACAAAGGAATGCTCTATGTGTTGAATGGAT
GCAAAAAAATGAGGAAGCTGGAGATAAGGGACAGTCCTTTTGGGAACGCTGCGC
TTCTTGCTGACGTGGGTAGGTACGAAACAATGCGATCCCTTTGGATGTCGTCTTG
TGAAGTAACACTCGGTGGCTGCAAGAGGCTCGCGCAGAATTCGCCACGGCTTAA
CGTAGAGATCATCAACGAGAATGAGAATAATGGGATGGAACAGAATGAAGAAG
ATGAAAGAGAGAAGGTTGATAAACTTTACC

FIG. 3H (AFB4)

(SEQ ID: 46)

ATGACAGAAGAAGATAGCTCAGCTAAAATGTCAGAGGATGTTGAGAAATATCTC
AACTTAAATCCACCTTGCTCCTCCTCCTCCTCTTCTTCCTCCGCCGCTACATTCAC
GAACAAGTCTCGAAATTTCAAATCTTCTCCCCCGCCGTGTCCAGATCATGTCCTT
GAGAACGTTTTAGAGAACGTGCTTCAGTTCCTCACTTCCAGATGCGATCGCAACG
CAGTCTCATTGGTCTGCAGATCGTGGTATCGCGTCGAGGCTCAGACTCGATTAGA
GGTTTTTATTGGAAACTGTTACTCGCTCTCTCCTGCTCGGCTTATTCACCGGTTCA
AGCGTGTTAGGTCTCTTGTGCTTAAAGGGAAACCTAGGTTTGCTGATTTTAATCTC
ATGCCTCCTAATTGGGGAGCTCAATTCTCTCCTTGGGTTGCTGCTACAGCTAAGG
CTTATCCTTGGCTCGAGAAGGTTCATTTGAAGCGTATGTTTGTTACGGATGATGA
TTTGGCTCTTCTTGCTGAGTCGTTTCCTGGGTTCAAAGAGCTTACTTTGGTCTGCT
GTGAAGGTTTTGGGACTAGTGGTATTGCTATTGTTGCTAACAAATGCAGGCAGCT
AAAGGTCCTTGATTTGATGGAGTCAGAAGTCACAGATGATGAGTTGGATTGGATT
TCTTGTTTTCCTGAGGGTGAAACTCATCTGGAGTCTTTGTCTTTTGACTGTGTTGA
ATCCCCTATCAATTTCAAGGCATTGGAGGAGCTCGTGGTTAGGTCACCATTCTTG
AAGAAACTTAGAACGAACAGGTTTGTTTCCCTTGAAGAGCTGCATCGACTAATGG
TTCGAGCGCCGCAGTTAACGAGTCTTGGGACGGGGTCATTTAGTCCAGACAATGT
GCCTCAGGGAGAACAACAACCGGATTATGCAGCTGCTTTTCGTGCTTGTAAATCC
ATAGTTTGTCTCTCAGGATTCAGGGAATTTAGACCGGAATACCTCCTAGCCATCT
CTTCAGTTTGTGCTAATCTCACCTCTCTTAACTTCAGTTATGCTAACATTTCTCCTC
ACATGCTCAAGCCCATCATAAGCAACTGTCACAATATCCGAGTCTTCTGGGCTCT
TGACTCGATACGTGATGAAGGACTACAGGCAGTGGCTGCCACATGCAAGGAGCT
CCGTGAGCTTCGGATTTTCCCTTTTGATCCTCGTGAAGACAGTGAAGGTCCTGTCT
CGGGAGTAGGCCTCCAAGCAATTTCAGAGGGCTGTAGGAAACTGGAATCTATCC
TGTACTTTTGCCAGAATATGACCAATGGAGCTGTGACAGCCATGTCGGAGAACTG
CCCGCAGCTTACTGTGTTTAGACTTTGCATAATGGGTCGCCATAGGCCTGACCAC
GTGACAGGAAAGCCAATGGACGATGGATTTGGTGCCATTGTTAAAAACTGCAAG
AAGCTAACCCGACTTGCAGTATCAGGGTTACTAACAGATGAAGCTTTTAGCTATA
TAGGAGAATATGGGAAATTGATCCGTACGCTATCTGTAGCGTTTGCTGGGAACAG
TGACAAGGCTCTGAGATACGTTCTTGAGGGTTGTCCTAAACTACAAAGCTTGAG
ATCAGGGACAGTCCCTTTGGAGATGTTGGATTGCGCTCTGGTATGCATCGGTATT
CCAATATGAGGTTTGTTTGGTTGTCGTCATGTCTCATATCCCGTGGAGGCTGCAG

FIG. 3I (AFB4)

GGGTGTTTCTCATGCTCTGCCTAATGTAGTCGTGGAAGTATTTGGAGCCGATGGT
GATGATGACGAAGACACTGTCACTGGGGATTATGTTGAGACATTGTACTTGTATC
GATCCCTTGATGGCCCAAGGAAGGATGCTCCAAAGTTTGTAACAATTTTATGA

FIG. 3J (AFB5)

(SEQ ID: 47)

ATGACACAAGATCGCTCAGAAATGTCTGAAGATGACGATGACCAACAATCTCCA
CCGTTGGATCTACCCTCTACCGCCATAGCTGATCCTTGCTCATCTTCCTCTTCACC
AAACAAATCTCGTAACTGTATCTCAAATTCTCAAACTTTCCCTGACCATGTTCTCG
AAAACGTACTTGAGAACGTTCTTCAGTTCCTAGATTCAAGATGTGACCGTAACGC
TGCTTCTCTAGTTTGCAAATCTTGGTGGCGTGTTGAAGCTTTGACTCGATCTGAGG
TTTTTATTGGTAACTGTTACGCTCTTTCTCCGGCGAGGTTGACTCAGAGATTCAAG
CGTGTTAGGTCTCTTGTGCTGAAAGGGAAACCTAGGTTTGCTGATTTCAATCTCA
TGCCTCCTGATTGGGGTGCTAATTTTGCTCCTTGGGTTTCTACTATGGCTCAAGCT
TATCCTTGTCTTGAGAAAGTTGATTTGAAGAGGATGTTTGTTACTGATGATGATTT
AGCTCTTCTTGCTGACTCTTTTCCTGGGTTTAAAGAGCTTATCTTGGTTTGTTGTG
AAGGTTTTGGTACTAGTGGTATCTCTATTGTTGCCAACAAGTGCAGAAAGCTGAA
AGTGCTTGATTTGATTGAGTCTGAGGTCACGGATGATGAAGTGGATTGGATCTCT
TGTTTCCCTGAGGATGTAACTTGTTTGGAGTCTTTAGCTTTTGACTGTGTGGAAGC
TCCTATCAATTTTAAGGCGCTTGAGGGTCTTGTTGCTAGGTCACCGTTCTTGAAGA
AACTTAGGCTAAACAGGTTTGTGTCTCTTGTGGAGCTACATCGTCTGCTACTTGG
AGCTCCACAGCTTACTAGTCTTGGGACTGGTTCATTTAGCCATGATGAGGAACCT
CAGAGTGAGCAAGAACCAGATTATGCTGCTGCATTTCGTGCTTGTAAATCTGTAG
TTTGCTTGTCAGGGTTTAGAGAGTTGATGCCGGAGTATCTTCCAGCTATCTTTCCG
GTGTGCGCTAATCTCACCTCCCTGAACTTCAGTTATGCTAACATTTCTCCTGACAT
GTTCAAGCCCATCATACTCAATTGCCACAAACTCCAGGTGTTCTGGGCCCTTGAT
TCAATATGTGATGAAGGACTACAGGCAGTTGCAGCCACTTGCAAGGAACTCCGT
GAACTCAGGATCTTCCCTTTTGATCCTCGGGAAGACAGTGAAGGTCCTGTCTCTG
AATTAGGCCTCCAAGCAATCTCCGAGGGTTGTAGGAAACTAGAATCTATTCTCTA
CTTTTGCCAGCGCATGACTAATGCCGCTGTGATAGCCATGTCAGAGAACTGTCCA
GAGCTTACTGTGTTTAGGCTGTGCATAATGGGTCGACATAGGCCTGACCATGTAA
CAGGAAAGCCTATGGACGAGGGATTTGGTGCCATTGTTAAAAACTGCAAGAAGC
TAACTCGCCTTGCAGTGTCGGGATTGCTGACAGATCAAGCTTTTAGGTATATGGG
TGAGTATGGGAAATTGGTCCGTACGCTTTCAGTAGCTTTTGCAGGGGACAGTGAC
ATGGCTCTGAGACATGTCCTAGAAGGTTGCCCTAGACTGCAGAAACTTGAGATA
AGGGACAGTCCCTTTGGAGATGTTGCATTACGGTCTGGTATGCATCGCTATTACA
ACATGAGGTTTGTTTGGATGTCAGCATGTAGCTTGTCTAAGGGATGCTGCAAGGA

FIG. 3K (AFB5)

TATTGCACGAGCAATGCCGAATCTAGTTGTGGAAGTAATTGGATCGGATGATGAT
GATGACAATAGGGATTATGTCGAGACTTTATACATGTATCGGTCTCTTGATGGTC
CAAGGAATGATGCACCAAAGTTCGTCACGATTTTATAG

FIG. 4A (ARF 10)

(SEQ ID: 48)

ATGGAGCAAGAGAAAAGCTTGGATCCACAACTATGGCATGCTTGTGCAGGATCA
ATGGTTCAAATCCCTTCACTGAATTCAACGGTTTTTACTTCGCTCAAGGCCACAC
AGAGCACGCTCACGCGCCTCCTGATTTTCACGCGCCGCGCGTTCCACCTCTTATC
CTCTGTCGTGTCGTCTCCGTGAAGTTCCTCGCCGACGCTGAAACAGACGAAGTTT
TTGCTAAAATTACGCTTTTGCCACTTCCGGGAAACGACTTGGATCTAGAAAACGA
CGCCGTTTTGGGTCTAACTCCTCCTTCTTCTGACGGTAACGGTAACGGTAAAGAG
AAACCGGCGTCTTTCGCTAAAACGTTAACGCAGTCTGACGCTAATAACGGCGGTG
GTTTCTCCGTTCCACGTTATTGCGCCGAGACGATTTTCCCGCGGCTTGATTACTCG
GCGGAGCCACCGGTTCAAACCGTGATTGCTAAAGACATCCACGGCGAGACTTGG
AAATTCCGGCATATTTACAGAGGAACACCTCGCCGTCATCTCCTAACCACCGGTT
GGAGCACTTTCGTTAACCAGAAGAAACTAATCGCCGGAGACTCAATCGTCTTCCT
CCGTTCTGAATCCGGTGACCTCTGCGTCGGAATCCGCCGCGCTAAACGCGGCGGT
CTCGGATCTAACGCAGGATCCGACAATCCTTACCCTGGATTCTCCGGTTTCCTCC
GTGACGACGAGTCAACAACAACAACATCGAAGCTAATGATGATGAAACGCAACG
GAAACAACGACGGAAACGCCGCGGCTACAGGGAGGGTTAGAGTAGAAGCAGTA
GCGGAAGCGGTGGCGCGTGCAGCGTGTGGACAAGCGTTTGAGGTTGTTTATTATC
CACGCGCTAGTACACCGGAGTTTTGCGTAAAAGCAGCTGATGTTAGATCAGCAAT
GAGGATAAGATGGTGTAGTGGTATGCGTTTTAAAATGGCGTTTGAAACAGAGGA
TTCTTCTAGAATCAGTTGGTTTATGGGTACTGTCTCCGCCGTTCAAGTCGCTGATC
CAATTCGTTGGCCTAATTCACCATGGCGTCTCCTTCAGGTAGCTTGGGACGAACC
GGATTTGTTACAAAACGTTAAGCGGGTTAGTCCGTGGTTAGTCGAATTGGTATCG
AACATGCCTACAATACATTTATCTCCATTCTCTCCGAGGAAGAAGATTAGGATTC
CGCAGCCATTTGAGTTTCCATTCCACGGTACTAAATTCCCGATTTTCTCCCCGGGA
TTCGCCAACAATGGCGGTGGCGAGTCCATGTGTTATCTGTCAAACGACAACAATA
ATGCTCCTGCAGGAATACAGGGAGCCAGGCAAGCTCAACAACTCTTCGGATCAC
CATCTCCGTCTTTGTTGTCTGATCTCAATCTTAGTAGTTACACCGGTAACAACAAG
TTACATTCTCCGGCGATGTTTCTATCGAGTTTCAACCCGAGGCATCATCATTATCA
GGCTAGGGATAGTGAGAATAGTAATAACATTTCGTGTTCTTTAACTATGGGGAAT
CCTGCTATGGTTCAGGATAAGAAGAAGTCTGTTGGTTCGGTTAAGACTCATCAGT
TCGTGTTGTTCGGTCAACCGATTTTAACCGAACAGCAAGTTATGAACCGAAAACG
GTTTTTGGAAGAAGAGGCGGAAGCGGAGGAGGAGAAAGGTTTAGTGGCTCGTGG

FIG. 4B (ARF 10)

GTTAACATGGAATTATAGTTTGCAAGGACTTGAGACGGGTCATTGTAAAGTTTTC
ATGGAATCTGAGGATGTTGGACGCACACTCGATCTCTCGGTTATTGGCTCGTACC
AAGAATTGTACCGGAAATTGGCTGAGATGTTTCATATAGAAGAGAGGTCGGATT
TGTTGACTCATGTTGTGTACCGGGATGCAAATGGTGTTATCAAACGTATTGGAGA
CGAACCTTTCAGTGATTTCATGAAAGCAACTAAACGGCTAACAATCAAGATGGA
TATTGGTGGCGACAACGTGAGAAAGACGTGGATAACCGGAATCAGGACTGGTGA
AAATGGTATAGACGCTTCTACGAAGACTGGTCCGCTCAGCATCTTCGCTTGA

FIG. 4C (ARF 16)

(SEQ ID: 49)

ATGATAAATGTGATGAATCCAATGAAAGGTGGAACAGAGAAAGGTTTAGATCCT
CAGCTATGGCATGCATGTGCTGGTGGTATGGTTCGTATGCCTCCTATGAACTCTA
AAGTCTTTTACTTTCCTCAAGGTCACGCCGAAAACGCTTACGATTGTGTCGATTTC
GGTAATCTCCCTATTCCTCCCATGGTTTTGTGTCGTGTTTTAGCCATTAAGTATAT
GGCTGATGCTGAATCTGACGAGGTTTTCGCTAAACTGAGATTGATTCCTTTGAAA
GATGATGAGTATGTTGATCACGAGTATGGTGATGGTGAAGATAGTAACGGTTTCG
AGAGTAATAGTGAGAAACGCCTTCGTTTGCTAAGACTTTGACTCAGTCTGATGC
TAATAACGGTGGGGGTTTCTCTGTTCCTCGTTATTGCGCTGAGACGATTTTCCCGA
GGTTGGATTATAACGCCGAGCCGCCGGTTCAGACCATTCTTGCTAAGGATGTTCA
TGGTGATGTTTGGAAGTTCAGACATATTTATAGAGGGACGCCTCGGCGTCACCTT
CTTACAACCGGATGGAGTAATTTTGTAAACCAGAAGAAGCTTGTGGCGGGAGAT
TCGATTGTCTTCATGAGAGCGGAGAATGGAGATCTTTGTGTAGGTATTAGGAGGG
CTAAGAGAGGAGGGATAGGTAATGGACCCGAATATTCAGCGGGTTGGAATCCGA
TCGGTGGAAGTTGCGGCTACTCTTCTCTGTTAAGGGAAGATGAAAGCAATAGTTT
GAGGAGAAGTAATTGTTCCCTTGCGGATAGGAAGGGGAAAGTGACGGCTGAATC
TGTTATAGAAGCAGCCACTCTTGCTATTAGCGGAAGACCGTTTGAGGTTGTGTAC
TATCCGAGAGCTAGCACTTCAGAGTTTTGTGTCAAGGCATTAGATGCTCGAGCTG
CCATGCGGATTCCGTGGTGCTCAGGTATGAGGTTTAAGATGGCTTTTGAGACAGA
GGATTCGTCTCGGATAAGTTGGTTTATGGGGACTGTTTCAGCTGTTAATGTCTCTG
ATCCTATCCGTTGGCCTAACTCTCCTTGGCGGCTTCTACAGGTGGCGTGGGATGA
GCCAGATTTACTCCAAAACGTGAAGCGAGTTAACCCGTGGTTGGTGGAATTGGTA
TCAAACGTACATCCGATCCCGCTTACTTCGTTTTCGCCACCGAGGAAAAAGATGC
GGCTACCTCAGCATCCAGATTACAACAATCTGATCAATTCGATTCCAGTACCTTC
ATTCCCAAGCAATCCCCTTATTAGATCAAGCCCGTTAAGCTCTGTTCTGGACAAT
GTTCCCGTGGGTTTACAGGGAGCCAGGCATAATGCTCATCAGTACTACGGGTTAT
CATCTTCGGATCTTCACCATTACTACTTGAATAGACCACCTCCTCCTCCTCCTCCA
TCCTCTCTCCAACTTTCTCCTTCTCTCGGTCTCCGAAACATCGATACCAAAAACGA
AAAAGGATTTTGCTTTTTGACAATGGGAACAACACCATGCAATGATACCAAATCT
AAAAAGTCCCATATTGTATTGTTCGGCAAGCTTATACTACCCGAGGAACAGCTAT
CAGAAAAAGGCTCAACGGATACCGCAAACATAGAGAAAACGCAGATTTCATCAG
GCGGGTCGAACCAAAACGGCGTTGCGGGAAGGGAGTTTTCTTCGTCAGATGAAG

FIG. 4D (ARF 16)

GATCACCTTGCTCTAAGAAAGTTCATGATGCATCAGGTTTGGAAACAGGGCATTG
TAAAGTGTTTATGGAGTCAGACGATGTAGGTCGAACCTTAGACCTATCGGTTCTT
GGTTCATACGAAGAATTGAGTCGGAAACTCTCTGACATGTTTGGAATCAAAAAGT
CTGAGATGTTAAGCTCTGTTCTCTATAGGGATGCATCAGGAGCCATCAAATACGC
AGGAAACGAACCTTTCAGTGAGTTCTTGAAGACAGCTCGAAGATTGACAATTCTG
ACGGAACAAGGAAGTGAGAGCGTTGTAGTATAA

FIG. 5A (Scarecrow promoter)

(SEQ ID: 50)

TAGATTGTGATCCTCTGCAACAAAGCGGATTTTGCTGGTGTTGAATGGATAAGGG
ATAGAGGAAGAGGACTTTGTTTATCAGAAACCTTTTGATGGGCCTTAATGGGCCT
ATAAACTGTAACTCTGTAGCGCTTTGCCAACAAGAGACTTTTTAAGGTTTTTGTTG
CCAAACAGATATTTGCATTTGGGCTATGTAATGTTAGAATTATTTTATAATGTATG
CTATTGCTAGATATTGTTTAAGTGCATTTGTGATTTACAAACATTTCATTTTTATTT
TGGTTTTAATGAGCATTTCTATTATAGAGACTTTGATGTTAATAAATGGTGTTCTA
AGATATATTAAAATATTTTATATACTTTCTTAAAATTGGATAAATTTTGGGAAAA
TCCTTAATATCAGTTAAATTGAAGATAAAGAGTATTAAAAAAAACTATGTAGTAA
AATACATTTCACATTTTTTGTGTATAATAGTACATGGTATTCGTTAAGATCACTCA
AAAATTAACAAATTAAGTCTAAAAGGGCAGAAAAGACTATTCAAATATGGACTT
GGAGAAAGACATTCAGCTTTTTACGCTGAGAAACTTTCATATTGAGCCGTGTGTT
TGTGTTGTGAAGAGAAGTAATAAAAAATAATTTGAAGTGAAAAAGGAGAAGAA
AAAATAAGATCGTAGAAAGCGTGGATGGTTTCTTCTTGGGTTCACTGCCATGCGA
TTATTAAATTGGCCATGGGGCTAGTGTTTGACGTACAAAAGTCTAAAAATTGTCA
GTCAAACAGGTCCAAAACTTTGTAAGAAAAATAATATAATAATAGCAAATTTTCT
AAAAATTGTTAAAAAAAGAACAAAAGGGAAAAGATGAGGATGCAGATGAAAGC
AAAATGTCAAACACTAGTTTCAGATTTTATCGGGAACTGGGGTTTGACAGTTGGT
GTATGTATGTAATGGCCTCTCATCAAAACATGTGCATCTTTTTCCTTTTTGTTATT
TACTGTTTTAGCTCTACGTCTTGTCCAATTCCTCTCAAGTAAAATGCCTTTAATAT
GATACTAATATACAAGGGGACTAATGCTTTTTCCCTTTTCTTATCCTTGTTTTGTC
TAAATCTTTACTTGGATTCCTTTATTTTTCTCCTCTCTTTAGATTAGTACGGTTTAA
GGAATACCATCTTTCTAATTTTAGCACAAAATTGCAAGTTGGTGCCCCATCTTAG
TAAGCACATCGTACCACACTTTGATTGTGTGAGAGACTTCTTCATCCCATCTCTCA
TACCAAACCTAAATCAAATGACTAGTGGTGCAACCTGCTGACTCCATATGACCAT
AACTAATAAATCGGTTTATGAATCCAACTCATGTAGCTCTATAGAATAGAAACCC
ATTCATTTCACATAATGAACTGAATCTGACATTTTATTTACATCATTTACTACTCA
ATTTTGTAATTAGCAAGATCATCTTTTTCATTATTCAACAATTTTGATATTCCATA
ATTTATTAACTTTGTCATACATCATAATATTCTGAAATTTTGTTATATATTGTACC
GGTTCCACGAAATAGAGCTCTATTATTATAGACCAAACAAACAAAATATTATCTT
CTTGTGGTTAGTTCGAGAGAGAGGTCAAGAAGAAACGAAATGGATCGGCAAACG
GAAGACGTCAAACACACAACGACGAACATTTTCCGATCACCCACCTAATCTCTTC

FIG. 5B (Scarecrow promoter)

CCATTTTTATTATTTTTCAAAACTCAAATTAATTAAGAAGAAAAAAACAGAAACA
GAGAGAGAAAGAGTTAAGATGAATAGAGATAGAAAGAGTCATTAAATGTACGA
AGCGACATTCACAATAATTCGAAAGGTGGAAGACGACTTAGATACGGCCAGGCT
TCACTGTCCTCCTCGTCCTCCTCAATTACCCCTAACCCCTTTTTCCGGGATTCATCT
CCAACCCACATCCTTCCAAATTCTCACCCCCTCACTGAGTTTTTGCTTTTTCTCCTC
ATCGGAGATCGTGAAGACGATCAAGTAATTTAAGAATCCCACCATTGATAAAAG
AGTCTAGCTTTTCTACTACCAAACCTTTTTCTGTTTGGAAATTTTCGATTTTGGATT
TAACCCTTTTCTTACCTTATTTATAACCATGCAATCTCACGACCAACAACCCTTCA
ATCTCC

FIG. 6A (*ARL2* promoter)

(SEQ ID: 51)

TTGTTCTCGACAGACCTCAAGATTTTTTTGTTTTAAACTGATTACAAAAATCTTAT
ATACACATGCACATAGTAAAGTCTAAACCAAAGCAATATAATAGATATAAATGT
TCAGTCAGAGTTTCTATTATCAATCTTGCAAAGAAATGAAAATATCTTTCGATAG
ATGAAGATTAAGATTCAGACAATAACATGCAACCTTTTCTTTCCCCCCAAAAAC
ACATCGATCACCCACCATCAATCCATCATGGATCGATCATCCATTTAGGGACCTA
TTTACGTTTGATTTTTTTTTCCTATAACTTTCTTTAATAAGGACAACAAGGCCAA
GATCTTCATCGTGTGTTTCGTGTGTCTCAAAATCCCTCTAAACTTTTTATTGTAGT
TTGGTGAGACTTGTTTGGTGGTGCTGATGATGATGAGAGAGAGAGAGAGAGAGA
GCGCGCGAGGAAATCATGGCTGGTAAACAGAAGAAGAGACATGATGATTACTGA
TTGAAATATTATATATGTACACCATTGAAATAAGTTATAAAAGTGTCGTAAATCG
TCAAAAGAATCAGTAGTATATATCTACTCTATATGATCTATATACACCATTCATA
TATAAAAGAATCACAAGTATGTTATTGAGGATGTGTGTCAATGAAGCCCTACGA
GAAAGGTCTGTGCACTACCAAAAAAGAGACACATAGTTTGTTTGAGTTTTTTTAT
TGGGTTCATTTGTTAAATTTATATCCATAAATACCTCCTTGAGGTATAGCCGTACA
GGGTTTTTTTGCAGTTCAAGATATGGCATTTGTATGAAACTTATATACCCGCCAA
AAAAAACATACCTAGGTCACCCGTGGGTATTTTTTGATTGGGACAAACTGGCTGT
AGGGAAAGAAAAAACAGACAACGTTAGGTGCCTTGTCTCTCAAATCACTTATCA
GGACTCAGGAGCAATAATTTGTTCGAACCAATTGTACGTTGTAACATCTAAATGG
GTCCATAACAATCAGATAATAAAATTTTATCATCTTTCTTAATTTATTTATTTCCA
AATAACTTTCTTTATCATGTTTCTTAATTACGTTGATGCATGTTTAGATAGCCGAA
ACAAATCACTATTACTTTGATTCTTATTATTTATTTATCAATTTCTGGATTCATGA
CATTTGAAAAACTAAATGATGTATTACTGTGCATTTGCAATTCAATCGATCTTAA
AGTCTTAAAATCAACTAGACGATAAAACGGTCTATTTCCCTATAGAACTAGATAT
ATATACTATGCATTGTGATATAGAATTAAGAGATTACTGTTTCTTTGGATGTATG
ATCTTTTATCAGAATAAACTTCTTATTTTGTCTTCAGAAATAATCTTGACTTCGAT
CAATCATTATTTCGTAAGCGATAAAAACTTCTGATTATCTACCAAAAAATGATTT
CAATATATTGTGACATTGTTGCAATACGATAACCACAAACTCATATTCATAGGGA
AATGTTTTAACAAACTTTGTTACAAATTCATCTACTTACAACGTGATGCTCAATCA
TTGATATACATTATAAAAGAATTATTATCTTAAAATAGTATCAACATAAGACAA
CATGCTCGATCGAGATAATACATGTGCCAGCGCAGTCCATAGTCGTCAGAAAAA
GATCAACATCAAATACTTTTTAGGCTTATCGCGCACTTTTCACTTTAAGAGGTTAT

FIG. 6B (ARL2 promoter)

TGTGATTACACTTTACGTATTGAACCTAAATATCAATTTCACAGTTGGAAGTTTAC
AAAAATAATGCCAGTGTCGATCCTAGGATGATGCGAAACCAAAAGATGATGTTA
CATATATATACACATGCACATTTAGTATTCTGGTTATCAAGATAAGGATGAAAAG
ACTAATTAAACCAAAGCAGTGTCTATGACATTGCAAGCATTCTCCAACCCATAAG
ACAAAATTGATTCTACAAACTTTCATATCATCAGAATCTATGAAATGAATCAACA
ACTATCACATCTCAGCAGCAAAGTTAAAGGACTTTCCACATGATCTATATTTATA
AGGGTATCGTTAAGATCTTCTCACATGTGTGGCACGTGACATATTTAATATTCTTG
ATGGGCTTTTCTGTTTTTATGGGCCTTTTCGAATTTCAGGGTTTTAAATAAGTTA
GAAATTAGATAAATAAAAAACAAATTAGCAAAAAATAACGAAGTGTCTCGTCTC
TTCTCTCTTGTCTTCTCCAGATCAGTGTTTGTGGGGTTTTCCCAATGGAGCTTCTTC
TCTCATTGTCTCTCCTCCTGGGGTTTTGGTGTAACAACAATCCTCAATTCACGAGG
CATGAATCATTATTCTCCCCATTTGCTTATTCTCTGGCTAGAATCCCCAGATTTTA
CTGTATCGACTTTGGGAATTTAACTGGAGAACCATTTCCACTCAAACTGGGAAAC
AAAAACCTGTTATTGAAC

FIG. 7

|       | ARF5  | ARF7  | ARF19 | ARF6  | ARF8  |
|-------|-------|-------|-------|-------|-------|
| ARF5  | 100   | 41.80 | 41.83 | 39.88 | 39.44 |
| ARF7  | 41.80 | 100   | 63.32 | 45.87 | 44.90 |
| ARF19 | 41.83 | 63.32 | 100   | 46.66 | 44.89 |
| ARF6  | 39.88 | 45.87 | 46.66 | 100   | 61.69 |
| ARF8  | 39.44 | 44.90 | 44.89 | 61.69 | 100   |

FIG. 8

|      | AFB4  | AFB5  | AFB2  | AFB3  | AFB1  | TIR1  |
|------|-------|-------|-------|-------|-------|-------|
| AFB4 | 100   | 79.16 | 50.09 | 49.74 | 47.54 | 47.83 |
| AFB5 | 79.16 | 100   | 52.03 | 51.50 | 50.00 | 49.39 |
| AFB2 | 50.09 | 52.03 | 100   | 86.43 | 55.71 | 60.88 |
| AFB3 | 49.74 | 51.50 | 86.43 | 100   | 55.26 | 59.72 |
| AFB1 | 47.54 | 50.00 | 55.71 | 55.26 | 100   | 69.40 |
| TIR1 | 47.83 | 49.39 | 60.88 | 59.72 | 69.40 | 100   |

FIG. 11C
*arf10-3 arf16-2*  *nph4-1 arf19-1*
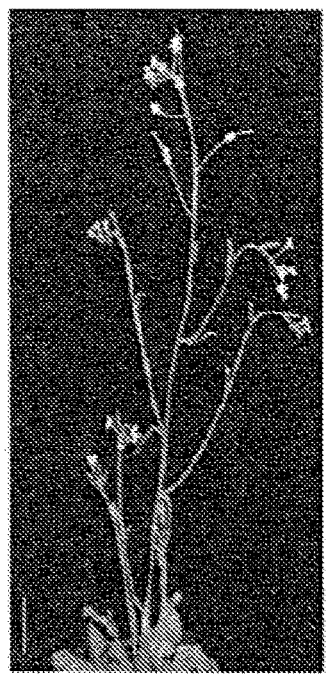
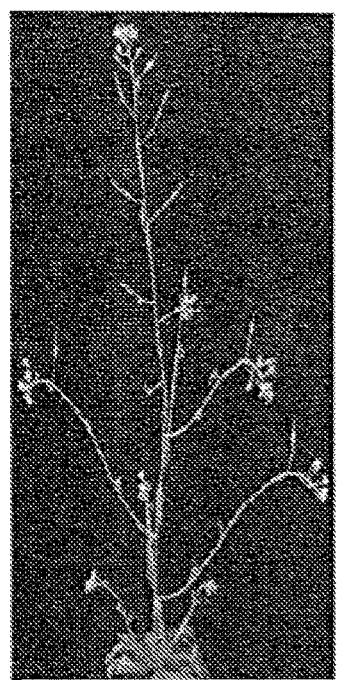
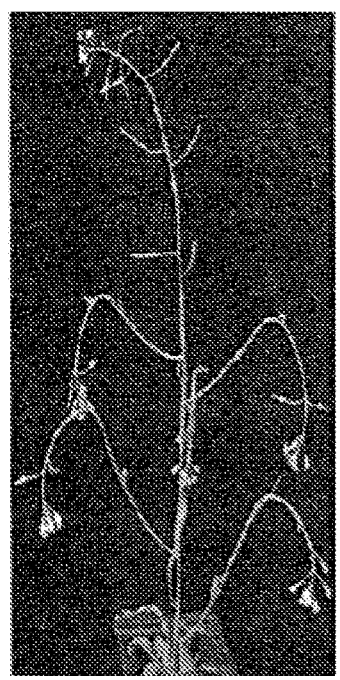

SCR::AtLGR
(DEX treated 9 days, untreated 3 days)

SCR::TIR1:GR (mock treated)   SCR::TIR1:GR (DEX treated)

SEQUENCE LISTING

```
<160> NUMBER OF SEQ ID NOS: 65

<210> SEQ ID NO 1
<211> LENGTH: 2376
<212> TYPE: DNA
<213> ORGANISM: Arabidopsis thaliana

<400> SEQUENCE: 1
atgatggctt cattgtcttg tgttgaagac aagatgaaaa caagttgttt ggttaatggt      60
ggaggaacta taacaacaac aacatctcaa tctaccttgc ttgaagagat gaagctgttg     120
aaagaccagt caggtacaag aaagccggta ataaactcgg agctatggca cgcttgtgca     180 ggcccttttgg tgtgtctccc tcaagttggg agcttagtgt attacttctc acaaggtcat    240
```

```
agcgagcagg ttgctgtttc aaccagaaga tcagcaacaa cacaagttcc taattatccg      300
aaccttccat ctcagttgat gtgtcaagtc cataatgtta ctcttcatgc tgacaaagac      360
agtgacgaaa tctatgctca gatgagtctt caacctgttc actctgagag agatgtgttc      420
cctgtaccag actttggaat gctgagagga agtaagcacc cgactgagtt tttctgcaaa      480
acacttactg caagtgacac aagcacacat ggaggtttct cagtgccacg tagagctgca      540
gagaagctat ttccaccatt ggactactca gcacagccgc caacgcaaga gcttgtagtt      600
cgagatcttc atgagaatac ttggacattt cgccatatct accgagggca accaaagaga      660
catctcctaa ctacaggatg gagtttgttc gttggatcga agagattgag agctggggat      720
tctgttttgt tcatcaggga tgagaagtca caacttatgg tcggtgttag gcgtgccaat      780
cgccaacaaa cagcacttcc ttcatcagtt ctctcagcgg atagtatgca catcggtgtt      840
cttgctgctg ctgctcacgc aaccgccaac cgtactcctt ttttgatatt ctataatcca      900
agagcttgtc cagcagagtt cgtgatccct ctagctaagt accgtaaggc gatatgcggg      960
tctcagctct cagttggtat gagatttgga atgatgtttg aaactgaaga ttccgggaaa     1020
cgaaggtaca tgggaactat tgttggaatc agcgatttgg atccgttgag atggcctggt     1080
tctaagtggc gtaaccttca ggtagaatgg gatgagcctg gatgtaatga taaacctact     1140
cgggtcagtc catgggatat cgaaacacct gaaagtctct tcattttttcc ttctctgacc     1200
tcaggactca aacgtcagct ccatccatct tactttgctg gtgaaactga atggggtagc     1260
ttgataaaac ggccacttat acgtgttcct gattccgcga atgggattat gccatatgca     1320
tctttcccta gtatggcttc ggagcagctt atgaaaatga tgatgaggcc tcacaacaac     1380
caaaatgtac catcttttcat gtctgagatg cagcagaata ttgtaatggg gaatggaggt     1440
ttgctaggag atatgaagat gcagcaaccc ctgatgatga accagaaatc tgagatggtg     1500
cagccacaaa acaagctaac agtgaaccca tctgcttcta atacgagtgg ccaagaacag     1560
aatctttcac agagtatgag tgctcctgct aaacctgaga actctacact ctctggttgc     1620
agctctggta gagtccaaca tggacttgag cagtcaatgg aacaggcaag ccaggttact     1680
acatccacag tgtgtaatga ggaaaaggtt aatcagctac ttcagaaacc gggtgcttcg     1740
tcgcctgtac aagctgatca atgtcttgac attactcatc agatttacca accacagtct     1800
gatccaataa atggattctc tttcctggaa actgatgagc tgcatcaca agtctcttcc      1860
ttccagtctc ttgccggatc atacaagcaa ccattcattc tatcctccca ggattcttca     1920
gctgttgtgt taccggattc cacaaactca ccgctgtttc atgatgtgtg ggacactcag     1980
ttgaacggtc tcaagtttga ccagttcagt cccttgatgc agcaggacct ttatgctagt     2040
cagaatatct gtatgagtaa tagcacaacc agtaacattc tagatcctcc actctcaaac     2100
acagtccttg atgacttctg tgccatcaaa gacactgatt tccagaacca cccttctggt     2160
tgtttggttg gaaacaacaa cactagcttt gctcaagatg tccagtcgca gatcacatca     2220
gctagctttg cagactcaca ggccttctct cgccaagatt ttccagataa ttctggaggc     2280
actggtacat cttcaagcaa tgttgatttt gatgattgta gtctgcggca aaatagtaaa     2340
ggctcatcat ggcagaaaat tgcgacaccc cgctaa                                2376

<210> SEQ ID NO 2
<211> LENGTH: 2385
<212> TYPE: DNA
<213> ORGANISM: Arabidopsis thaliana
```

```
<400> SEQUENCE: 2
atgagattat cttcagctgg gtttaatcct caacctcatg aagttacagg agagaaaaga    60
gttcttaatt ctgagctctg gcatgcttgt gctggtcctc ttgtctcact acctcctgtt   120
ggaagcagag ttgtgtattt tcctcaaggt cacagtgaac aggttgctgc ttcgaccaac   180
aaagaagtag atgctcatat accaaattat ccgagcttgc atccgcagct tatctgtcag   240
cttcataatg ttacaatgca tgctgatgtg gagactgatg aagtctatgc acagatgact   300
ttgcaaccgt gaatgcgca agagcaaaaa gatccttacc ttcccgcgga attaggtgtc   360
ccaagtagac agcctacaaa ctatttctgt aaaactctga ctgctagtga tacaagcact   420
cacggaggtt tttctgtacc tcgccgagct gctgagaaag ttttccctcc cttggattac   480
tcgcagcagc caccagctca agagttaatg gcgagggatc tgcatgataa tgaatggaag   540
ttcaggcata ttttccgagg ccaaccaaag agacatctcc ttaccacggg ttggagcgta   600
tttgtgagtg ctaaaaggct tgttgctggt gactctgttc ttttcatctg gaacgataag   660
aatcaattac ttcttggtat aagacgagcc aaccgaccac aaactgtcat gccttcatct   720
gttttgtcaa gtgacagtat gcatttaggc cttcttgctg cagcagctca tgctgccgct   780
acaaacagcc gattcaccat cttctataac ccgagggcga gtccatcaga gtttgttata   840
cccctggcta gtatgtgaa gcggtttat cacactcgcg tctctgttgg tatgcggttt   900
aggatgctgt ttgaaactga agaatctagt gttcgtcggt acatgggtac aataactggc   960
atttgtgatc tagatcctac tcgttgggct aattcgcatt ggcgatctgt caaggttggg  1020
tgggacgaat ctactgcagg agagagacag ccaagggttt cattgtggga gattgagcct  1080
ttaacaacat tccctatgta tccatctcct tttcctctca ggcttaaacg gccgtggcct  1140
cctggtctcc catcttttcca tggccttaaa gaagatgata tgggtatgag tatgagttca  1200
ccgcttatgt gggatcgagg actccaatct ctaaactttc aaggtatggg agtaaacccg  1260
tggatgcagc cgagacttga tacgtcgggc ttgcttggta tgcaaaatga tgtgtaccaa  1320
gcaatggctg cagctgccct tcaagacatg agaggcattg atcctgcaaa agctgctgct  1380
tcacttcttc agttccaaaa ttcgccgggg ttctcaatgc aatctccgtc cttagtgcag  1440
ccgcagatgc tgcagcagca actctctcag cagcagcaac aactctctca gcagcagcag  1500
cagcagcaac agctctccca acagcagcag caacagctct ctcaacagca gcagcagcag  1560
ctctctcaac agcagcagca caactctct cagcagcagc agcaacaggc gtatcttggc  1620
gttcctgaaa cccaccagcc tcagtctcag gctcaatcac agtcaaacaa tcatctttct  1680
cagcagcagc agcaagtagt ggataatcat aatccgtctg cgtccagtgc tgctgttgtt  1740
tccgctatgt ctcaatttgg ttctgcttct cagcccaaca cgtcaccact ccagtccatg  1800
acctctctgt gtcatcagca aagcttctcc gataccaacg gaggaaacaa tcctatttct  1860
ccacttcaca ctcttctcag taacttctct caagacgaat cttctcaact gctccacctc  1920
actagaacaa actctgcaat gacttcatcc ggttggccat caaagcgtcc tgcagttgat  1980
tcatcgttcc agcactctgg agccggtaat aataacactc aatccgtatt ggagcaactg  2040
ggacagtccc acacaagcaa cgttcctcca acgctgtct cgttgcctcc atttcccggt  2100
ggtagagagt gctcgatcga gcaagaagga agcgcctcag acccgcatag ccatcttctc  2160
tttggagtca atatagattc atcttctctt ttgatgccga acggaatgtc aaaccttaga  2220
agcattggta ttgaaggtgg tgactccacg actttaccct tcacatcatc taattttcaac  2280
aatgatttct cgggtaatct tgcaatgaca acaccttcta gttgcataga tgaatcgggt  2340
```
tttctacaat cctcagaaaa cctcggttcc gagaacccac aataa         2385

<210> SEQ ID NO 3
<211> LENGTH: 3111
<212> TYPE: DNA
<213> ORGANISM: Arabidopsis thaliana

<400> SEQUENCE: 3

| | | | | |
|---|---|---|---|---|
| atgaaagctc | cttcatcaaa | tggagtttct | cctaatcctg | ttgaaggaga | aaggagaaat |   60 |
| ataaactcag | agctatggca | cgcttgtgct | gggccattga | tttcgttgcc | tccagcagga |  120 |
| agtcttgttg | tttacttccc | tcaaggtcac | agtgagcaag | tcgcggcttc | aatgcagaag |  180 |
| cagactgatt | tcataccaag | ttacccgaat | cttccttcca | agctcatatg | catgctccac |  240 |
| aatgttacac | tgaatgctga | tcctgagacg | gatgaggtct | atgcgcagat | gactcttcag |  300 |
| ccagtaaaca | aatatgacag | agatgcattg | cttgcttctg | acatgggtct | taagctaaac |  360 |
| agacaaccta | tgaattttt  | ctgcaaaacc | ctcacggcga | gtgacacaag | tactcacggt |  420 |
| ggattttctg | taccccgacg | agctgctgag | aaaatctttc | ctgctctgga | tttctcgatg |  480 |
| caaccacctt | gtcaggagct | tgttgctaag | gatattcatg | acaacacatg | gactttcaga |  540 |
| catatttatc | gaggtcaacc | aaaaaggcac | ttgctaacta | caggctggag | tgtgtttgtc |  600 |
| agcacgaaaa | ggctctttgc | tggagactct | gttcttttta | taagagatgg | aaaggcgcaa |  660 |
| cttctgttgg | ggataagacg | tgcaaataga | caacagcctg | cactttcttc | atctgtaata |  720 |
| tcaagtgata | gcatgcacat | cggagttctt | gcagctgcag | ctcatgctaa | tgctaataac |  780 |
| agtcctttca | ccatttctca | caacccgagg | tgggctgctc | ctgctgagtt | tgtggttcct |  840 |
| ttagccaagt | ataccaaagc | gatgtacgct | caagtttccc | tcggtatgcg | gtttagaatg |  900 |
| atatttgaga | ctgaagaatg | tggagttcgt | cggtatatgg | gtacagttac | cggtatcagt |  960 |
| gatcttgatc | cagtgagatg | gaaaaactct | cagtggcgga | atcttcagat | tggatgggat | 1020 |
| gagtcagctg | ctggtgatag | gcccagtcga | gtttcagttt | gggacattga | accggtttta | 1080 |
| actcctttct | acatatgtcc | tcctccattt | ttccgacctc | gcttttctgg | acaacctgga | 1140 |
| atgccagatg | atgagactga | catggagtct | gcactgaaga | gagcaatgcc | atggcttgat | 1200 |
| aatagcttag | agatgaaaga | cccttcgagt | actatctttc | ctggtctgag | tttagttcag | 1260 |
| tggatgaata | tgcagcagca | gaacggccag | ctaccctctg | ctgctgcaca | gccaggtttc | 1320 |
| ttcccatcaa | tgctttcgcc | aaccgcggcg | ctgcacaaca | atcttggcgg | cactgatgat | 1380 |
| ccctccaagt | tactgagctt | tcagacgccg | cacgggggga | tttcctcctc | aaatctccaa | 1440 |
| tttaacaaac | agaatcagca | agccccaatg | tctcagttgc | ctcagccacc | aactacgttg | 1500 |
| tcccaacaac | agcagctgca | gcaattgttg | cactcctctt | tgaaccatca | acaacagcaa | 1560 |
| tcgcagtctc | aacaacagca | acaacaacaa | cagttgctgc | agcagcaaca | acaattgcag | 1620 |
| tctcaacaac | acagcaacaa | caatcaatcg | cagtctcagc | aacaacaaca | attgctccag | 1680 |
| cagcaacaac | aacaacaact | gcagcaacaa | catcaacaac | cgttacagca | acagactcag | 1740 |
| cagcagcagc | taagaacaca | gccattgcaa | tctcactcgc | atccacagcc | acaacagtta | 1800 |
| caacaacata | agttgcagca | acttcaggtt | ccacagaatc | agctttacaa | tggtcaacaa | 1860 |
| gcagcgcagc | agcatcagtc | gcaacaagca | tctacacatc | atttgcaacc | acaattagtt | 1920 |
| tcgggatcaa | tggcaagcag | tgtcatcacg | cctccgtcca | gctcccttaa | tcaaagcttt | 1980 |
| caacagcaac | aacaacagtc | taagcaactt | caacaagcac | atcaccattt | aggtgctagc | 2040 |

-continued

| | |
|---|---|
| actagccaga gtagtgtaat tgaaaccagc aagtcttcat ccaatctgat gtccgcaccg | 2100 |
| ccgcaagaga cacagttttc acgacaagta aacagcagc agcctcctgg tctcaacggg | 2160 |
| cagaatcagc aaacactttt gcagcagaaa gctcaccagg cacaggccca acagatattc | 2220 |
| cagcagagtc tcttggaaca gccgcatata cagtttcagc tgttacagag attacaacag | 2280 |
| caacagcagc agcaatttct ttcgccgcag tctcagttac cacaccatca attgcaaagc | 2340 |
| cagcagttgc aacagctgcc tactctctct caaggtcatc agtttccgtc atcttgcact | 2400 |
| aacaatggct tatcgacgtt gcaaccacct caaatgctgg tgagccgacc tcaggaaaaa | 2460 |
| caaaacccac cggttggggg aggggtcaaa gcttattcag gcatcacaga tggaggagat | 2520 |
| gcaccttcct cttcaacgtc gccttccacc aacaactgtc agatctcttc ttcaggcttt | 2580 |
| ctcaacagaa gccaaagcgg gccagcgatc ttgatacctg atgcagcgat tgatatgtct | 2640 |
| ggtaatcttg ttcaggatct ttacagcaaa tccgatatgc ggctaaaaca agaactcgtg | 2700 |
| ggtcagcaaa agtccaaagc tagtttaaca gatcatcaac tagaagcatc tgcctctgga | 2760 |
| acttcttacg gtttagatgg aggcgaaaac aacagacaac aaaatttctt ggctccaact | 2820 |
| tttggccttg acggtgattc caggaacagc ttgctcggtg gagctaatgt tgataatggc | 2880 |
| tttgtgcctg acacgctact ctcgagggga tatgactccc agaaagatct tcagaacatg | 2940 |
| ctttcaaaact atggaggagt gacaaatgac attggtacag atgtctac ttcagctgta | 3000 |
| agaactcaat cttttggtgt ccccaatgtg cccgccattt cgaacgatct agctgtcaac | 3060 |
| gatgctggag ttcttggtgg tggattgtgg ccagctcaga ctcagcgata a | 3111 |

<210> SEQ ID NO 4
<211> LENGTH: 2112
<212> TYPE: DNA
<213> ORGANISM: Arabidopsis thaliana

<400> SEQUENCE: 4

| | |
|---|---|
| atgaagctgt caacatctgg attgggtcaa cagggtcatg aaggagagaa gtgtctgaat | 60 |
| tctgagctat ggcatgcttg tgctggacca ttagtctctc ttccatcatc tggtagtcga | 120 |
| gttgtttact ttccacaggg tcacagtgaa caggtagctg ctacaactaa taaggaagtt | 180 |
| gatggtcaca tacccaatta cccaagccta ccaccacaat tgatatgcca gctccataat | 240 |
| gttacaatgc atgcagatgt tgagacggat gaagtctatg ctcaaatgac acttcaacca | 300 |
| ttgacaccgg aggagcagaa ggaaacattt gtaccgattg agttggggat accgagtaag | 360 |
| caacctagta attatttttg taagactctc acagctagtg ataccagtac acatggaggg | 420 |
| ttttctgttc ctagacgtgc tgctgagaaa gtgtttcctc cattggatta cacactgcag | 480 |
| ccaccagctc aagaactgat tgcaagggat ctccatgatg ttgaatggaa gtttaggcat | 540 |
| atcttttcggg gacagcccaa acggcatctc ctaactactg gatggagtgt ctttgtcagt | 600 |
| gccaagcgac tagtagctgg agattctgtc attttcatca ggaatgaaaa gaatcaactc | 660 |
| ttttggggaa ttcgtcatgc cactcggccg cagactattg taccatcatc tgttttatct | 720 |
| agtgatagca tgcatattgg actccttgct gctgctgcac atgcttctgc aactaatagc | 780 |
| tgtttcactg ttttctttca tccaagggct agccaatctg agtttgtgat acaacttttcc | 840 |
| aagtacatta agccgttttt tcacacgcgt atttcagttg ggatgcgctt tcgcatgctc | 900 |
| ttcgagacag aagagtcgag tgtccgcagg tacatgggta ctataactgg tattagtgat | 960 |
| ctagattctg ttcgttggcc aaactctcat tggcgatctg tgaaggttgg ttgggatgaa | 1020 |
| tcgactgcag gggagagaca gccaaggggtt tcttttatggg agattgagcc tctgactacc | 1080 |

```
tttcctatgt atccatctct ttttcctctc agactaaaac gtccatggca tgctggcaca    1140
tcatctttgc ctgatggaag gggtgatttg ggaagtggtc taacatggct aagaggggga    1200
ggtggagagc agcaaggttt gcttcctcta aattatccat ctgttggttt gtttccatgg    1260
atgcaacaaa ggctggatct cagtcaaatg gggactgata taatcagca ataccaagca     1320 atgttagctg ctgggttgca gaacatcggc ggtggagatc ctttaagaca gcagtttgta    1380
cagctgcaag agcctcacca ccaatatctt caacaatcag cttcccataa ttctgatttg    1440
atgcttcagc agcaacagca gcaacaagcg tcacgccatc tcatgcatgc tcaaacacag    1500
attatgagtg agaatcttcc gcagcagaat atgcgacaag aagttagtaa ccaaccagct    1560
ggacagcagc aacagctaca gcaaccggac caaaatgcat atcttaatgc tttcaaaatg    1620
caaaatggcc atcttcaaca gtggcagcag caatcagaga tgccatctcc ctcgttcatg    1680
aagtcagatt ttactgactc aagcaacaaa tttgcaacaa ctgctagtcc ggcttctgga    1740
gatggcaatc ttttgaattt ttctataacc ggtcagtctg tactccctga gcagttaaca    1800
acagagggct ggtctccaaa agcatccaac acttttctg aaccgttgtc acttccacaa     1860
gcctatcctg ggaagagtct tgctctagaa cccggaaatc cgcagaatcc ctctcttttc    1920
ggtgttgatc ccgactctgg actcttcctc cccagtacgg ttccccgctt tgcttcttca    1980
tcaggagatg ctgaagcttc ccctatgtca ctaacagatt caggatttca gaattcctta    2040
tatagctgca tgcaagacac aactcatgag ttattgcatg gagctggaca gattaactcg    2100
tccaaccaat aa                                                        2112

<210> SEQ ID NO 5
<211> LENGTH: 2871
<212> TYPE: DNA
<213> ORGANISM: Arabidopsis thaliana

<400> SEQUENCE: 5
atgaaagctc catcaaatgg atttcttcca gttccaacg aaggagagaa gaagccaatc      60
aattctcaac tatggcacgc ttgtgcaggg cctttagttt cattacctcc tgtgggaagt    120
cttgtggttt acttccctca aggacacagc gagcaagttg cagcatcgat gcagaagcaa    180 acagattta taccaaatta cccaaatctt ccttctaagc tgatttgctt gcttcacagt     240
gttacattac atgctgatac cgaaacagat gaagtctatg cacaaatgac tcttcaacct    300
gtgaataagt atgatagaga agcattgcta gcttctgata tgggcttgaa gctaaacaga    360
caacctactg agtttttttg caagactctt actgcaagtg acacaagcac tcatggtgga    420
ttctctgtac cgcgtcgtgc agctgagaaa atattccctc tcttgatttt ctcgatgcaa    480
ccgcctgcgc aagagattgt agctaaagat ttacatgata ctacatggac tttcagacat    540
atctatcgag gccaaccaaa aagacacttg cttaccacag gttggagcgt ttttgttagc    600
acaaagagac tatttgcggg tgattcagtt ttgtttgtaa gagatgagaa atcacagctg    660
atgttgggta agacgtgca aaatagacaa actccgactc tttcctcatc ggtcatatcc     720
agcgacagta tgcacattgg gatacttgca gctgcagctc atgctaatgc caatagtagc    780
ccttttacca tcttcttcaa tccaagggca agtccttcag agtttgtagt tcctttagcc    840
aaatacaaca aagccttata cgctcaagta tctctaggaa tgagattccg gatgatgttt    900
gagactgagg attgtggggt tcgtagatat atgggtacag tcacaggtat tagtgatctt    960
gaccctgtaa gatggaaagg ctcacaatgg cgtaatcttc aggtaggatg ggatgaatca   1020
```

| | |
|---|---|
| acagctggag ataggccaag ccgagtatcc atatgggaaa tcgaacccgt cataactcct | 1080 |
| ttttacatat gtcctcctcc attttttcaga cctaagtacc cgaggcaacc cgggatgcca | 1140 |
| gatgatgagt tagacatgga aaatgctttc aaaagagcaa tgccttggat gggagaagac | 1200 |
| tttgggatga aggacgcaca gagttcgatg ttccctggtt taagtctagt tcaatggatg | 1260 |
| agtatgcagc aaaacaatcc attgtcaggt tctgctactc ctcagctccc gtccgcgctc | 1320 |
| tcatcttttta acctaccaaa caattttgct tccaacgacc cttccaagct gttgaacttc | 1380 |
| caatccccaa acctctcttc cgcaaattcc caattcaaca aaccgaacac ggttaaccat | 1440 |
| atcagccaac agatgcaagc acaaccagcc atggtgaaat ctcaacaaca caacaacaa | 1500 |
| caacaacaac aacaccaaca ccaacaacaa caactgcaac aacaacaaca actacagatg | 1560 |
| tcacagcaac aggtgcagca acaagggatt ataacaatg gtacgattgc tgttgctaac | 1620 |
| caagtctctt gtcaaagtcc aaaccaacct actggattct ctcagtctca gcttcagcag | 1680 |
| cagtcaatgc tccctactgg tgctaaaatg acacaccaga acataaattc tatggggaat | 1740 |
| aaaggcttgt ctcaaatgac atcgtttgcg caagaaatgc agtttcagca gcaactggaa | 1800 |
| atgcataaca gtagccagtt attaagaaac cagcaagaac agtcctctct ccattcatta | 1860 |
| caacaaaatc tgtcccaaaa tcctcagcaa ctccaaatgc aacaacaatc atcaaaacca | 1920 |
| agtccttcac aacagcttca gttgcagcta ctgcagaagc tacagcagca gcaacagcag | 1980 |
| cagtcgattc ctccagtaag ctcatcctta cagccacaat tatcagcgtt gcagcagaca | 2040 |
| caaagccatc aattgcaaca acttctgtcg tctcaaaatc aacagccctt ggcacatggt | 2100 |
| aataacagct tccagcttc aactttcatg cagcctccac agattcaggt gagtcctcag | 2160 |
| cagcaaggac agatgagtaa caaaaatctt gtagccgctg aagatcaca ttctggccac | 2220 |
| acagatggag aagctccttc ttgttcaacc tcaccttccg ccaataacac gggacatgat | 2280 |
| aatgtttcac cgacaaattt cctgagcaga atcaacagc aaggacaagc tgcatctgta | 2340 |
| tctgcatctg attcagtctt tgagcgcgca agcaatccgg tccaagagct ttatacaaaa | 2400 |
| actgagagcc ggatcagtca aggcatgatg aatatgaaga gtgctggtga acatttcaga | 2460 |
| tttaaaagcg cggtaacaga tcaaatcgat gtatccacag cgggaacgac gtactgtcct | 2520 |
| gatgttgttg ccctgtaca gcagcaacaa actttcccac taccatcatt tggttttgat | 2580 |
| ggagactgcc aatctcatca tccaagaaac aacttagctt tccctggtaa tctcgaagcc | 2640 |
| gtaacttctg atccactcta ttctcaaaag gactttcaaa acttggttcc caactatggc | 2700 |
| aacacaccaa gagacattga gacggagctg tccagtgctg caatcagttc tcagtcattt | 2760 |
| ggtattccca gcattcccttt taagcccgga tgttcaaatg aggttggcgg catcaatgat | 2820 |
| tcaggaatca tgaatggtgg aggactgtgg cccaatcaga ctcaacgata a | 2871 |

<210> SEQ ID NO 6
<211> LENGTH: 2709
<212> TYPE: DNA
<213> ORGANISM: Arabidopsis thaliana

<400> SEQUENCE: 6

| | |
|---|---|
| atgatggctt cattgtcttg tgttgaagac aagatgaaaa caagttgttt ggttaatggt | 60 |
| ggaggaacta taacaacaac aacatctcaa tctaccttgc ttgaagagat gaagctgttg | 120 |
| aaagaccagt caggtacaag aaagccggta taaaactcgg agctatggca cgcttgtgca | 180 |
| ggcccctttgg tgtgtctccc tcaagttggg agcttagtgt attacttctc acaaggtcat | 240 |
| agcgagcagg ttgctgtttc aaccagaaga tcagcaacaa cacaagttcc taattatccg | 300 |

```
aaccttccat ctcagttgat gtgtcaagtc cataatgtta ctcttcatgc tgacaaagac    360
agtgacgaaa tctatgctca gatgagtctt caacctgttc actctgagag agatgtgttc    420
cctgtaccag actttggaat gctgagagga agtaagcacc cgactgagtt tttctgcaaa    480
acacttactg caagtgacac aagcacacat ggaggtttct cagtgccacg tagagctgca    540
gagaagctat ttccaccatt ggactactca gcacagccgc caacgcaaga gcttgtagtt    600
cgagatcttc atgagaatac ttggacattt cgccatatct accgagggca accaaagaga    660
catctcctaa ctacaggatg gagtttgttc gttggatcga agagattgag agctggggat    720
tctgttttgt tcatcaggga tgagaagtca caacttatgg tcggtgttag gcgtgccaat    780
cgccaacaaa cagcacttcc ttcatcagtt ctctcagcgg atagtatgca catcggtgtt    840
cttgctgctg ctgctcacgc aaccgccaac cgtactcctt ttttgatatt ctataatcca    900
agagcttgtc cagcagagtt cgtgatccct ctagctaagt accgtaaggc gatatgcggg    960
tctcagctct cagttggtat gagatttgga atgatgtttg aaactgaaga ttccgggaaa   1020
cgaaggtaca tgggaactat tgttggaatc agcgatttgg atccgttgag atggcctggt   1080
tctaagtggc gtaaccttca ggtagaatgg gatgagcctg gatgtaatga taaacctact   1140
cgggtcagtc catgggatat cgaaacacct gaaagtctct tcatttttcc ttctctgacc   1200
tcaggactca aacgtcagct ccatccatct tactttgctg gtgaaactga atggggtagc   1260
ttgataaaac ggccacttat acgtgttcct gattccgcga atggattat gccatatgca   1320 tctttcccta gtatggcttc ggagcagctt atgaaaatga tgatgaggcc tcacaacaac   1380
caaaatgtac catctttcat gtctgagatg cagcagaata ttgtaatggg gaatggaggt   1440
ttgctaggag atatgaagat gcagcaaccc ctgatgatga accagaaatc tgagatggtg   1500
cagccacaaa acaagctaac agtgaaccca tctgcttcta atacgagtgg ccaagaacag   1560
aatctttcac agagtatgag tgctcctgct aaacctgaga actctacact ctctggttgc   1620
agctctggta gagtccaaca tggacttgag cagtcaatgg aacaggcaag ccaggttact   1680
acatccacag tgtgtaatga ggaaaaggtt aatcagctac ttcagaaacc gggtgcttcg   1740
tcgcctgtac aagctgatca atgtcttgac attactcatc agatttacca accacagtct   1800
gatccaataa atggattctc tttcctggaa actgatgagc tgacatcaca agtctcttcc   1860
ttccagtctc ttgccggatc atacaagcaa ccattcattc tatcctccca ggattcttca   1920
gctgttgtgt taccggattc cacaaactca ccgctgtttc atgatgtgtg ggacactcag   1980
ttgaacggtc tcaagtttga ccagttcagt cccttgatgc agcaggacct ttatgctagt   2040
cagaatatct gtatgagtaa tagcacaacc agtaacattc tagatcctcc actctcaaac   2100
acagtccttg atgacttctg tgccatcaaa gacactgatt ccagaaccca ccttctggt    2160 tgtttggttg aaacaacaa cactagcttt gctcaagatg tccagtcgca gatcacatca    2220
gctagctttg cagactcaca ggccttctct cgccaagatt ttccagataa ttctggaggc   2280
actggtacat cttcaagcaa tgttgatttt gatgattgta gtctgcggca aaatagtaaa   2340
ggctcatcat ggcagaaaat tgcgacaccc cgcgtccgaa cctacactaa ggttcaaaaa    2400
accgggtcag tcgggagatc aattgatgtc acaagcttta aagactacga ggagctaaaa    2460
tctgctatcg aatgcatgtt tggattggaa ggactactaa ctcacccaca aagctcgggt   2520
tggaagcttg tatatgttga ttatgagagt gatgttctgc ttgtaggaga tgatccatgg   2580
gaagagtttg tgggatgcgt aaggtgcata aggatattgt cgccaactga ggtccagcag   2640
```

-continued

```
atgagtgaag aagggatgaa gcttttgaac agcgcaggca ttaacgatct taagacttct    2700
gtttcataa                                                             2709

<210> SEQ ID NO 7
<211> LENGTH: 3827
<212> TYPE: DNA
<213> ORGANISM: Arabidopsis thaliana

<400> SEQUENCE: 7
cttcttcttc tgattctcat ttcaaataag agagagagag agagaagtaa gtaaaacttt      60
agcagagaga agaataaaca aataattata gcaccgtcac gtcgccgccg tatttcgtta     120
ccggaaaaaa aaaatcattc ttcaacataa aaataaaaac agtctctttc tttctatctt     180
tgtctatctt tgattattct ctgtgtaccc atgttctgca acagttgagc aagtgcatgc     240
cccatatctc tctgtttctc atttcccgat ctttgcatta atcatatact tcgcctgaga     300
tctcgattaa gccagcttat agaagaagaa acggcaccag cttctgtcgt tttagttagc     360
tcgagatctg tgtttctttt tttcttggct tctgagcttt tggcggtggt gggttttct     420 ggagaaaccc aaacgactat caaagttttg tttttttacaa ttttaagtgg gagttatgag     480
tggggtggat taagtaagtt acaagtatga aggagttgaa gattcgaaga agcgggtttt     540
tagatttggt tggtgaatgg gtgggaggtg gagggaaaca gttaaaaaag ttatgctttt     600
agtgtctctt cttcataatt acatttgggc atcttgaaat ctttggatct ttgaagaaac     660
aaagttgtgt ttttttttttt gttctttgtt gtttgctttt taagttagaa taaaaaatga     720
gattatcttc agctgggttt aatcctcaac ctcatgaagt tacaggagag aaaagagttc     780
ttaattctga gctctggcat gcttgtgctg gtcctcttgt ctcactacct cctgttggaa     840
gcagagttgt gtatttttcct caaggtcaca gtgaacaggt tgctgcttcg accaacaaag     900
aagtagatgc tcatatacca aattatccga gcttgcatcc gcagcttatc tgtcagcttc     960
ataatgttac aatgcatgct gatgtggaga ctgatgaagt ctatgcacag atgactttgc    1020
aaccgttgaa tgcgcaagag caaaaagatc cttaccttcc cgcggaatta ggtgtcccaa    1080
gtagacagcc tacaaactat ttctgtaaaa ctctgactgc tagtgataca agcactcacg    1140 gaggttttc tgtacctcgc cgagctgctg agaaagtttt ccctccctttg gattactcgc    1200 agcagccacc agctcaagag ttaatggcga gggatctgca tgataatgaa tggaagttca    1260
ggcatatttt ccgaggccaa ccaaagagac atctccttac cacgggttgg agcgtatttg    1320
tgagtgctaa aaggcttgtt gctggtgact ctgttctttt catctggaac gataagaatc    1380
aattacttct tggtataaga cgagccaacc gaccacaaac tgtcatgcct tcatctgttt    1440
tgtcaagtga cagtatgcat ttaggccttc ttgctgcagc agctcatgct gccgctacaa    1500
acagccgatt caccatcttc tataacccga gggcgagtcc atcagagttt gttataccc    1560 tggctaagta tgtgaaagcg gtttatcaca ctcgcgtctc tgttggtatg cggtttagga    1620
tgctgtttga aactgaagaa tctagtgttc gtcggtacat gggtacaata actggcattt    1680
gtgatctaga tcctactcgt tgggctaatt cgcattggcg atctgtcaag gttgggtggg    1740
acgaatctac tgcaggagag agacagccaa gggtttcatt gtgggagatt gagccttaa    1800 caacattccc tatgtatcca tctccttttc ctctcaggct taaacggccg tggcctcctg    1860
gtctcccatc tttccatggc cttaaagaag atgatatggg tatgagtatg agttcaccgc    1920
ttatgtggga tcgaggactc caatctctaa actttcaagg tatgggagta aacccgtgga    1980
tgcagccgag acttgatacg tcgggcttgc ttggtatgca aaatgatgtg taccaagcaa    2040
```

```
tggctgcagc tgcccttcaa gacatgagag gcattgatcc tgcaaaagct gctgcttcac      2100
ttcttcagtt ccaaaattcg ccggggttct caatgcaatc tccgtcctta gtgcagccgc      2160
agatgctgca gcagcaactc tctcagcagc agcaacaact ctctcagcag cagcagcagc      2220
agcaacagct ctcccaacag cagcagcaac agctctctca acagcagcag cagcagctct      2280
ctcaacagca gcagcaacaa ctctctcagc agcagcagca acaggcgtat cttggcgttc      2340
ctgaaaccca ccagcctcag tctcaggctc aatcacagtc aaacaatcat ctttctcagc      2400
agcagcagca agtagtggat aatcataatc cgtctgcgtc cagtgctgct gttgtttccg      2460
ctatgtctca atttggttct gcttctcagc ccaacacgtc accactccag tccatgacct      2520
ctctgtgtca tcagcaaagc ttctccgata ccaacggagg aaacaatcct atttctccac      2580
ttcacactct tctcagtaac ttctctcaag acgaatcttc tcaactgctc cacctcacta      2640
gaacaaactc tgcaatgact tcatccggtt ggccatcaaa gcgtcctgca gttgattcat      2700
cgttccagca ctctggagcc ggtaataata acactcaatc cgtattggag caactgggac      2760
agtcccacac aagcaacgtt cctccaaacg ctgtctcgtt gcctccattt cccggtggta      2820
gagagtgctc gatcgagcaa gaaggaagcg cctcagaccc gcatagccat cttctctttg      2880
gagtcaatat agattcatct tctcttttga tgccgaacgg aatgtcaaac cttagaagca      2940
ttggtattga aggtggtgac tccacgactt taccctcac atcatctaat ttcaacaatg      3000
atttctcggg taatcttgca atgacaacac cttctagttg catagatgaa tcgggttttc      3060
tacaatcctc agaaaacctc ggttccgaga acccacaatc taacaccttt gtgaaggtgt      3120
acaagtcagg gtcttttgga agatcgttag atatatcaaa gtttagcagc taccacgagc      3180
tgcgaagcga gcttgctcgc atgtttggcc tcgaaggcca attagaagac cctgtgagat      3240
caggctggca gcttgtattt gttgaccgag agaacgacgt tcttctcctc ggcgatgacc      3300
cttggccgga gtttgtgagc agcgtgtggt gcattaagat actgtcacca caagaagtgc      3360
aacaaatggg aaaaagaggc cttgagcttc tcaactccgc gccatcttcc aacaatgtcg      3420
ataagctccc gagcaacggg aactgtgacg actttgggaa ccggtcagac ccgaggaatc      3480
tcggtaacgg tatcgcatca gttggggggtt cattcaacta ctagaagtag atggaaacct      3540
ccctttttat tcaagttaag tttcaatctt ataaattagt agtgagatca tcttagttta      3600
attactagca aaaatctctc tttattactt ataaaaagg gagatttgcc tttgcctttg      3660
atggaaacaa aaactatata atccctctgt cgactcgtaa tactgtaatt ataagatctt      3720
ttggtctttt tcttatatga atattttac tgaactctat atatgtcact ttccttactc      3780
atttcttcaa tcaatatgat agtgaagggt tattttggag ttacatt                   3827
```

<210> SEQ ID NO 8
<211> LENGTH: 3498
<212> TYPE: DNA
<213> ORGANISM: Arabidopsis thaliana

<400> SEQUENCE: 8

```
atgaaagctc cttcatcaaa tggagtttct cctaatcctg ttgaaggaga aaggagaaat       60
ataaactcag agctatggca cgcttgtgct gggccattga tttcgttgcc tccagcagga     120
agtcttgttg tttacttccc tcaaggtcac agtgagcaag tcgcggcttc aatgcagaag     180
cagactgatt tcataccaag ttacccgaat cttccttcca agctcatatg catgctccac     240
aatgttacac tgaatgctga tcctgagacg gatgaggtct atgcgcagat gactcttcag     300
```

```
ccagtaaaca aatatgacag agatgcattg cttgcttctg acatgggtct taagctaaac    360
agacaaccta atgaattttt ctgcaaaacc ctcacggcga gtgacacaag tactcacggt    420
ggattttctg taccccgacg agctgctgag aaaatctttc ctgctctgga tttctcgatg    480
caaccacctt gtcaggagct tgttgctaag gatattcatg acaacacatg gactttcaga    540
catatttatc gaggtcaacc aaaaaggcac ttgctaacta caggctggag tgtgtttgtc    600
agcacgaaaa ggctctttgc tggagactct gttctttta taagagatgg aaaggcgcaa     660
cttctgttgg ggataagacg tgcaaataga caacagcctg cactttcttc atctgtaata    720
tcaagtgata gcatgcacat cggagttctt gcagctgcag ctcatgctaa tgctaataac    780
agtcctttca ccatttttcta caacccgagg tgggctgctc ctgctgagtt tgtggttcct    840
ttagccaagt ataccaaagc gatgtacgct caagtttccc tcggtatgcg gtttagaatg    900
atatttgaga ctgaagaatg tggagttcgt cggtatatgg gtacagttac cggtatcagt    960
gatcttgatc cagtgagatg gaaaaactct cagtggcgga atcttcagat tggatgggat   1020
gagtcagctg ctggtgatag gcccagtcga gtttcagttt gggacattga accggtttta   1080 actccttttct acatatgtcc tcctccattt ttccgacctc gcttttctgg acaacctgga   1140
atgccagatg atgagactga catggagtct gcactgaaga gagcaatgcc atggcttgat   1200
aatagcttag agatgaaaga cccttcgagt actatctttc ctggtctgag tttagttcag   1260
tggatgaata tgcagcagca gaacggccag ctaccctctg ctgctgcaca gccaggtttc   1320
ttcccatcaa tgctttcgcc aaccgcggcg ctgcacaaca atcttggcgg cactgatgat   1380
ccctccaagt tactgagctt tcagacgccg cacggggga tttcctcctc aaatctccaa    1440
tttaacaaac agaatcagca agccccaatg tctcagttgc ctcagccacc aactacgttg   1500
tcccaacaac agcagctgca gcaattgttg cactcctctt tgaaccatca acaacagcaa   1560
tcgcagtctc aacaacagca acaacaacaa cagttgctgc agcagcaaca caattgcag    1620 tctcaacaac acagcaacaa caatcaatcg cagtctcagc aacaacaaca attgctccag   1680
cagcaacaac aacaacaact gcagcaacaa catcaacaac cgttacagca acagactcag   1740
cagcagcagc taagaacaca gccattgcaa tctcactcgc atccacagcc acaacagtta   1800
caacaacata agttgcagca acttcaggtt ccacagaatc agctttacaa tggtcaacaa   1860
gcagcgcagc agcatcagtc gcaacaagca tctacacatc atttgcaacc acaattagtt   1920
tcgggatcaa tggcaagcag tgtcatcacg cctccgtcca gctcccttaa tcaaagcttt   1980
caacagcaac aacaacagtc taagcaactt caacaagcac atcaccattt aggtgctagc   2040
actagccaga gtagtgtaat tgaaaccagc aagtcttcat ccaatctgat gtccgcaccg   2100
ccgcaagaga cacagttttc acgacaagta aacagcagc agcctcctgg tctcaacggg    2160
cagaatcagc aaacactttt gcagcagaaa gctcaccagg cacaggccca acagatattc   2220
cagcagagtc tcttggaaca gccgcatata cagtttcagc tgttacagag attacaacag   2280
caacagcagc agcaatttct ttcgccgcag tctcagttac acaccatca attgcaaagc    2340 cagcagttgc aacagctgcc tactctctct caaggtcatc agtttccgtc atcttgcact   2400
aacaatggct tatcgacgtt gcaaccacct caaatgctgg tgagccgacc tcaggaaaaa   2460
caaaacccac cggttggggg aggggtcaaa gcttattcag gcatcacaga tggaggagat   2520
gcaccttcct cttcaacgtc gccttccacc aacaactgtc agatctcttc ttcaggcttt   2580
ctcaacagaa gccaaagcgg gccagcgatc ttgatacctg atgcagcgat tgatatgtct   2640
ggtaatcttg ttcaggatct ttacagcaaa tccgatatgc ggctaaaaca agaactcgtg   2700
```

-continued

```
ggtcagcaaa agtccaaagc tagtttaaca gatcatcaac tagaagcatc tgcctctgga    2760
acttcttacg gtttagatgg aggcgaaaac aacagacaac aaaatttctt ggctccaact    2820
tttggccttg acggtgattc caggaacagc ttgctcggtg gagctaatgt tgataatggc    2880
tttgtgcctg acacgctact ctcgagggga tatgactccc agaaagatct tcagaacatg    2940
ctttcaaact atggaggagt gacaaatgac attggtacag agatgtctac ttcagctgta    3000
agaactcaat cttttggtgt ccccaatgtg cccgccattt cgaacgatct agctgtcaac    3060
gatgctggag ttcttggtgg tggattgtgg ccagctcaga ctcagcgaat gcgaacttat    3120
acaaaggtgc aaaaacgagg ctcagtgggg agatcaatag acgtcaaccg ttacagaggt    3180
tacgatgagc tgaggcatga tctagcgcgc atgtttggga tcgaaggaca gctcgaagat    3240
cctcaaacat ctgactggaa acttgtttat gtcgatcatg aaaatgacat cctcctcgtc    3300
ggcgatgatc catgggaaga attcgtaaac tgtgttcaga gcattaagat cctttcatca    3360
gctgaggttc agcagatgag cttagacggg aactttgccg gtgtaccagt tactaatcaa    3420
gcttgtagtg gcggtgacag tggcaatgct tggagaggtc attatgatga taactcagcc    3480
acttcgttta accggtga                                                  3498
```

<210> SEQ ID NO 9
<211> LENGTH: 2436
<212> TYPE: DNA
<213> ORGANISM: Arabidopsis thaliana

<400> SEQUENCE: 9

```
atgaagctgt caacatctgg attgggtcaa cagggtcatg aaggagagaa gtgtctgaat      60
tctgagctat ggcatgcttg tgctggacca ttagtctctc ttccatcatc tggtagtcga     120
gttgtttact ttccacaggg tcacagtgaa caggtagctg ctacaactaa taaggaagtt     180
gatggtcaca tacccaatta cccaagccta ccaccacaat tgatatgcca gctccataat     240
gttacaatgc atgcagatgt tgagacggat gaagtctatg ctcaaatgac acttcaacca     300
ttgacaccgg aggagcagaa ggaaacattt gtaccgattg agttggggat accgagtaag     360
caacctagta attattttg taagactctc acagctagta ataccagtac acatggaggg     420
ttttctgttc ctagacgtgc tgctgagaaa gtgtttcctc cattggatta cacactgcag     480
ccaccagctc aagaactgat gcaagggat ctccatgatg ttgaatgaa gtttaggcat      540
atctttcggg acagcccaa acggcatctc ctaactactg atggagtgt ctttgtcagt      600
gccaagcgac tagtagctgg agattctgtc attttcatca ggaatgaaaa gaatcaactc     660
tttttgggaa ttcgtcatgc cactcggccg cagactattg taccatcatc tgttttatct     720
agtgatagca tgcatattgg actccttgct gctgctgcac atgcttctgc aactaatagc     780
tgtttcactg tttctcttca tccaagggct agccaatctg agtttgtgat acaactttcc     840
aagtacatta agccgttttt tcacacgcgt atttcagttg ggatgcgctt tcgcatgctc     900
ttcgagacag aagagtcgag tgtccgcagg tacatgggta ctataactgg tattagtgat     960
ctagattctg ttcgttggcc aaactctcat tggcgatctg tgaaggttgg ttgggatgaa    1020
tcgactgcag gggagagaca gccaagggtt tctttatggg agattgagcc tctgactacc    1080
tttcctatgt atccatctct ttttcctctc agactaaaac gtccatggca tgctggcaca    1140
tcatctttgc ctgatggaag gggtgatttg gaagtggtc taacatggct aagagggga    1200
ggtggagagc agcaaggttt gcttcctcta aattatccat ctgttggttt gtttccatgg    1260
```

| | |
|---|---|
| atgcaacaaa ggctggatct cagtcaaatg gggactgata taatcagca ataccaagca | 1320 |
| atgttagctg ctgggttgca gaacatcggc ggtggagatc ctttaagaca gcagtttgta | 1380 |
| cagctgcaag agcctcacca ccaatatctt caacaatcag cttcccataa ttctgatttg | 1440 |
| atgcttcagc agcaacagca gcaacaagcg tcacgccatc tcatgcatgc tcaaacacag | 1500 |
| attatgagtg agaatcttcc gcagcagaat atgcgacaag aagttagtaa ccaaccagct | 1560 |
| ggacagcagc aacagctaca gcaaccggac caaaatgcat atcttaatgc tttcaaaatg | 1620 |
| caaaatggcc atcttcaaca gtggcagcag caatcagaga tgccatctcc ctcgttcatg | 1680 |
| aagtcagatt ttactgactc aagcaacaaa tttgcaacaa ctgctagtcc ggcttctgga | 1740 |
| gatggcaatc ttttgaattt ttctataacc ggtcagtctg tactccctga gcagttaaca | 1800 |
| acagagggct ggtctccaaa agcatccaac acttttctg aaccgttgtc acttccacaa | 1860 |
| gcctatcctg ggaagagtct tgctctagaa cccggaaatc gcagaatcc ctctcttttc | 1920 |
| ggtgttgatc ccgactctgg actcttcctc cccagtacgg ttccccgctt tgcttcttca | 1980 |
| tcaggagatg ctgaagcttc ccctatgtca ctaacagatt caggatttca gaattcctta | 2040 |
| tatagctgca tgcaagacac aactcatgag ttattgcatg gagctggaca gattaactcg | 2100 |
| tccaaccaaa ccaagaactt tgtaaaggtt ataaatctg gttcggttgg gcgttcatta | 2160 |
| gacatctccc gattcagcag ctaccacgag ctgcgagaag agttagggaa gatgtttgct | 2220 |
| atcgaagggt gttggaaga ccccttaga tcaggctggc agcttgtatt cgttgacaag | 2280 |
| gaaaatgata ttcttctcct tggtgatgac ccatgggagt catttgtgaa taacgtttgg | 2340 |
| tacataaaga tactatcacc agaagatgtg catcaaatgg gagatcatgg agaaggcagt | 2400 |
| ggtgggttat tcccgcaaaa cccgacccat ctctag | 2436 |

<210> SEQ ID NO 10
<211> LENGTH: 3261
<212> TYPE: DNA
<213> ORGANISM: Arabidopsis thaliana

<400> SEQUENCE: 10

| | |
|---|---|
| atgaaagctc catcaaatgg atttcttcca agttccaacg aaggagagaa gaagccaatc | 60 |
| aattctcaac tatggcacgc ttgtgcaggg cctttagttt cattacctcc tgtgggaagt | 120 |
| cttgtggttt acttccctca aggacacagc gagcaagttg cagcatcgat gcagaagcaa | 180 |
| acagatttta taccaaatta cccaaatctt ccttctaagc tgatttgctt gcttcacagt | 240 |
| gttacattac atgctgatac cgaaacagat gaagtctatg cacaaatgac tcttcaacct | 300 |
| gtgaataagt atgatagaga agcattgcta gcttctgata tgggcttgaa gctaaacaga | 360 |
| caacctactg agttttttg caagactctt actgcaagtg acacaagcac tcatggtgga | 420 |
| ttctctgtac cgcgtcgtgc agctgagaaa atattccctc ctcttgattt ctcgatgcaa | 480 |
| ccgcctgcgc aagagattgt agctaaagat ttacatgata ctacatggac tttcagacat | 540 |
| atctatcgag gccaaccaaa aagacacttg cttaccacag gttggagcgt ttttgttagc | 600 |
| acaaagagac tatttgcggg tgattcagtt ttgtttgtaa gagatgagaa atcacagctg | 660 |
| atgtgggta agacgtgc aaatagacaa actccgactc tttcctcatc ggtcatatcc | 720 |
| agcgacagta tgcacattgg gatacttgca gctgcagctc atgctaatgc caatagtagc | 780 |
| ccttttacca tcttcttcaa tccaagggca agtccttcag agtttgtagt tcctttagcc | 840 |
| aaatacaaca aagcccttata cgctcaagta tctctaggaa tgagattccg gatgatgttt | 900 |
| gagactgagg attgtggggt tcgtagatat atgggtacag tcacaggtat tagtgatctt | 960 |

```
gaccctgtaa gatggaaagg ctcacaatgg cgtaatcttc aggtaggatg ggatgaatca    1020
acagctggag ataggccaag ccgagtatcc atatgggaaa tcgaacccgt cataactcct    1080
ttttacatat gtcctcctcc attttttcaga cctaagtacc cgaggcaacc cgggatgcca   1140
gatgatgagt tagacatgga aaatgctttc aaaagagcaa tgccttggat gggagaagac    1200
tttgggatga aggacgcaca gagttcgatg ttccctggtt taagtctagt tcaatggatg    1260
agtatgcagc aaaacaatcc attgtcaggt tctgctactc ctcagctccc gtccgcgctc    1320
tcatctttta acctaccaaa caattttgct tccaacgacc cttccaagct gttgaacttc    1380
caatccccaa acctctcttc cgcaaattcc caattcaaca aaccgaacac ggttaaccat    1440
atcagccaac agatgcaagc acaaccagcc atggtgaaat ctcaacaaca acaacaacaa    1500
caacaacaac acaccaaca ccaacaacaa caactgcaac aacaacaaca actacagatg     1560
tcacagcaac aggtgcagca caagggatt tataacaatg gtacgattgc tgttgctaac     1620
caagtctctt gtcaaagtcc aaaccaacct actggattct ctcagtctca gcttcagcag    1680
cagtcaatgc tccctactgg tgctaaaatg acacaccaga acataaattc tatggggaat    1740
aaaggcttgt ctcaaaatgac atcgtttgcg caagaaatgc agtttcagca gcaactggaa   1800
atgcataaca gtagccagtt attaagaaac cagcaagaac agtcctctct ccattcatta    1860
caacaaaatc tgtcccaaaa tcctcagcaa ctccaaatgc aacaacaatc atcaaaacca    1920
agtccttcac aacagcttca gttgcagcta ctgcagaagc tacagcagca gcaacagcag    1980
cagtcgattc ctccagtaag ctcatcctta cagccacaat tatcagcgtt gcagcagaca    2040
caaagccatc aattgcaaca acttctgtcg tctcaaaatc aacagcccctt ggcacatggt   2100 aataacagct tccagcttc aactttcatg cagcctccac agattcaggt gagtcctcag     2160
cagcaaggac agatgagtaa caaaaatctt gtagccgctg aagatcaca ttctggccac     2220 acagatggag aagctccttc ttgttcaacc tcaccttccg ccaataacac gggacatgat    2280
aatgtttcac cgacaaattt cctgagcaga aatcaacagc aaggacaagc tgcatctgta    2340
tctgcatctg attcagtctt tgagcgcgca agcaatccgg tccaagagct ttatacaaaa    2400
actgagagcc ggatcagtca aggcatgatg aatatgaaga gtgctggtga acatttcaga    2460
tttaaaagcg cggtaacaga tcaaatcgat gtatccacag cgggaacgac gtactgtcct    2520
gatgttgttg gccctgtaca gcagcaacaa actttcccac taccatcatt tggttttgat    2580
ggagactgcc aatctcatca tccaagaaac aacttagctt ccctggtaa tctcgaagcc    2640 gtaacttctg atccactcta ttctcaaaag gactttcaaa acttggttcc caactatggc    2700
aacacaccaa gagacattga gacggagctg tccagtgctg caatcagttc tcagtcattt    2760
ggtattccca gcattcccctt taagcccgga tgttcaaatg aggttggcgg catcaatgat    2820
tcaggaatca tgaatggtgg aggactgtgg cccaatcaga ctcaacgaat gcgaacatat    2880
acaaaggttc aaaaacgagg gtcagtaggt agatcaatag atgttacccg ttatagcggc    2940
tatgatgaac ttaggcatga cttagcgaga atgtttggca tcgaaggaca gctcgaagat    3000
ccgctaacct ctgattggaa actcgtctac accgatcacg aaaacgatat tttactagtt    3060
ggtgatgatc cttgggaaga gttttgtgaac tgcgtgcaga acataaagat actatcatca   3120
gtagaagttc agcaaatgag cttagacgga gatcttgcag ctatcccaac cacaaaccaa    3180
gcctgcagcg aaacagacag cggaaatgct tggaaagtac actatgaaga cacttctgct    3240
gcagcttctt tcaacagata g                                              3261
```

<210> SEQ ID NO 11
<211> LENGTH: 507
<212> TYPE: DNA
<213> ORGANISM: Arabidopsis thaliana

<400> SEQUENCE: 11

| | | | | | |
|---|---|---|---|---|---|
| atggaagtca | ccaatgggct | taaccttaag | gacacagagc | ttcgtttggg | attacccgga | 60 |
| gcacaagaag | aacaacaact | agaactttct | tgcgtcagaa | gcaacaacaa | gcgcaagaac | 120 |
| aacgactcaa | cagaagaatc | tgctcctcct | cctgcaaaaa | cacaaatcgt | tggatggcct | 180 |
| ccagtgagat | ctaaccgtaa | gaacaacaac | aacaaaaacg | tgagttatgt | gaaagtgagt | 240 |
| atggacggag | ctccatatct | ccgtaagata | gatctcaaga | tgtacaaaaa | ctatccagag | 300 |
| cttctcaaag | cactagagaa | catgttcaag | ttcacagtag | gtgaatattc | cgagagagaa | 360 |
| ggctacaaag | gatctggatt | tgtacctact | tatgaagaca | aagatggaga | ttggatgttg | 420 |
| gtcggtgatg | ttccatggga | catgttctct | tcatcttgtc | aaaaactcag | aatcatgaaa | 480 |
| ggatccgaag | ctcctactgc | cttatga | | | | 507 |

<210> SEQ ID NO 12
<211> LENGTH: 525
<212> TYPE: DNA
<213> ORGANISM: Arabidopsis thaliana

<400> SEQUENCE: 12

| | | | | | |
|---|---|---|---|---|---|
| atggcgtacg | agaaagtcaa | cgagcttaac | cttaaggaca | cagagctatg | tcttggatta | 60 |
| cccggaagaa | cagagaagat | caagaagaa | caagaggttt | cttgcgttaa | aagtaacaac | 120 |
| aagcgtctat | ttgaggaaac | tcgtgatgaa | gaagaatcta | cacctcctac | caaaactcaa | 180 |
| atcgttggtt | ggccaccagt | gagatcttcc | cgtaagaaca | caacagtgt | gagctacgtg | 240 |
| aaagtgagta | tggacggagc | tccttacctt | cgcaagatcg | atctcaagac | atacaaaaac | 300 |
| taccccgagc | ttctcaaagc | gttagagaat | atgttcaaag | tcatgattgg | tgaatattgt | 360 |
| gagagagaag | gatacaaagg | atctggattt | gtaccaacat | acgaagataa | agatggtgac | 420 |
| tggatgttgg | ttggtgatgt | tccatgggac | atgttctctt | cttcttgtaa | gagactcaga | 480 |
| atcatgaagg | gatccgacgc | tcctgctcta | gactcttcct | tatga | | 525 |

<210> SEQ ID NO 13
<211> LENGTH: 570
<212> TYPE: DNA
<213> ORGANISM: Arabidopsis thaliana

<400> SEQUENCE: 13

| | | | | | |
|---|---|---|---|---|---|
| atggatgagt | tgttaacct | caaggaaaca | gagctgaggc | tgggattacc | gggaacagat | 60 |
| aatgtatgtg | aagcaaaaga | gagagtttct | tgctgtaata | caacaataa | gagagtacta | 120 |
| tcaactgata | ctgagaagga | gattgaatca | tcatcaagga | aaactgaaac | atcccctcct | 180 |
| cgaaaggctc | agattgttgg | atggccacca | gttagatctt | acaggaagaa | caacattcag | 240 |
| agtaagaaga | atgaatctga | gcatgagggt | caaggaatct | atgtgaaagt | aagtatggat | 300 |
| ggtgcaccat | acttgaggaa | aatagatctg | agttgttaca | aaggatactc | agagttgctt | 360 |
| aaagctttag | aagtgatgtt | caaattctct | gtgggagagt | actttgagag | agatggatat | 420 |
| aaaggttcag | actttgtgcc | tacttatgaa | gacaaagatg | gtgattggat | gctcattggt | 480 |
| gatgttccat | gggagatgtt | catatgtacg | tgcaagagac | taaggatcat | gaaaggatca | 540 |
| gaagccaaag | gtttaggctg | tggtgtatga | | | | 570 |

<210> SEQ ID NO 14
<211> LENGTH: 561
<212> TYPE: DNA
<213> ORGANISM: Arabidopsis thaliana

<400> SEQUENCE: 14

| | | | | | |
|---|---|---|---|---|---|
| atggaaaaag | ttgatgttta | tgatgagctt | gttaacctaa | aggcaacaga | gctgagattg | 60 |
| ggattaccag | ggacagaaga | aactgtttct | tgtggaaaaa | gcaacaaaag | agttttacct | 120 |
| gaagctactg | agaaagagat | tgaatccact | ggaaaaactg | aaaccgcttc | tcctccaaag | 180 |
| gctcagattg | ttgatggcc | accagttaga | tcttacagaa | gaacaatgt | tcagacaaag | 240 |
| aagagtgaat | ctgaaggtca | aggaaactat | gtgaaagtaa | gtatggatgg | tgctccatat | 300 |
| ctaaggaaga | tagatctaac | gatgtataaa | caatatccag | agttgatgaa | atcacttgaa | 360 |
| aacatgttta | aattctctgt | gggagaatat | tttgagagag | aaggatataa | aggctcagac | 420 |
| tttgtaccta | cttatgaaga | caaagatggt | gattggatgc | ttgttggtga | tgttccttgg | 480 |
| gagatgtttg | tttcgtcttg | taagaggcta | aggatcatga | aaggatctga | agttaaaggt | 540 |
| ttaggttgtg | gtggtctttta | a | | | | 561 |

<210> SEQ ID NO 15
<211> LENGTH: 492
<212> TYPE: DNA
<213> ORGANISM: Arabidopsis thaliana

<400> SEQUENCE: 15

| | | | | | |
|---|---|---|---|---|---|
| atggcgaatg | agagtaataa | tcttggactc | gaaatcaccg | aactacggct | aggtcttccc | 60 |
| ggagatatcg | tcgtctccgg | tgagtccatc | tccgggaaga | gagggcttc | tccggaagta | 120 |
| gagattgatt | tgaaatgtga | accggcgaaa | aagagtcaag | ttgtggttg | gccaccggtt | 180 |
| tgttcgtacc | ggagaaagaa | cagtctcgaa | cggaccaaaa | gttcgtacgt | gaaagtgagt | 240 |
| gtagatggag | ctgcattttt | aaggaagatt | gatttggaaa | tgtacaaatg | ttaccaagat | 300 |
| cttgcttccg | ctctgcaaat | tctgttcgga | tgctatatca | attttgatga | tacgttgaag | 360 |
| gaaagtgaat | gtgtaccaat | atatgaagac | aaagatggag | attggatgct | tgctggagat | 420 |
| gttccttggg | aaatgttcct | tggatcgtgc | aagaggttaa | ggattatgaa | gagatcatgt | 480 |
| aacagaggat | ga | | | | | 492 |

<210> SEQ ID NO 16
<211> LENGTH: 570
<212> TYPE: DNA
<213> ORGANISM: Arabidopsis thaliana

<400> SEQUENCE: 16

| | | | | | |
|---|---|---|---|---|---|
| atggcaaagg | aaggtctagc | actcgagatc | acagagcttc | gattgggtct | tccaggagat | 60 |
| aattatagcg | aaatatcagt | atgcggatcg | agtaagaaga | gaagagggt | gctctcggat | 120 |
| atgatgacct | catcagcgtt | agatactgag | aatgaaaaca | gcgtcgtttc | atcagttgaa | 180 |
| gatgaatcac | tgccggttgt | gaagagtcaa | gcggtgggat | ggccacctgt | gtgttcttac | 240 |
| aggagaaaga | gaacaatga | ggaagcatcg | aaagctatag | gctacgtgaa | agtgagcatg | 300 |
| gatggtgtgc | catacatgag | gaagattgac | cttggttcga | gcaacagtta | tattaatcta | 360 |
| gtcacggttc | ttgagaatct | cttcggctgt | cttggcatag | gagtggcgaa | ggagggtaag | 420 |
| aagtgtgaat | acattattat | atacgaagac | aaggatagag | actggatgct | cgtcggagat | 480 |

| gtaccttggc agatgtttaa agaatcatgc aagaggctga ggatcgtgaa gagatcagat | 540 |
| gcaactggtt ttggtctcca gcaagattaa | 570 |

<210> SEQ ID NO 17
<211> LENGTH: 732
<212> TYPE: DNA
<213> ORGANISM: Arabidopsis thaliana

<400> SEQUENCE: 17

| atgatcggcc aacttatgaa cctcaaggcc acggagctct gtctcggcct ccccggcggc | 60 |
| gctgaagcag ttgagagtcc tgccaaatcg gcggtgggaa gcaagagagg cttctccgaa | 120 |
| accgttgatc tcatgctcaa tcttcaatct aacaaagaag ctccgttga tctcaaaaac | 180 |
| gtttctgctg ttcccaagga gaagactacc cttaaagatc cttctaagcc tcctgctaaa | 240 |
| gcacaagtgg tgggatggcc acctgtgagg aactacagga gaacatgat gactcagcag | 300 |
| aagaccagta gtggtgcgga ggaggccagc agtgagaagg ccgggaactt tggtggagga | 360 |
| gcagccggag ccggcttggt gaaggtctcc atggacggtg ctccatatct gaggaaagtt | 420 |
| gacctcaaga tgtacaaaag ctaccaggat cttttctgatg cattggccaa aatgttcagc | 480 |
| tcctttacta tgggaaacta tggagcacaa ggaatgatag attttcatgaa cgagagcaag | 540 |
| ctaatgaatc tgctgaatag ctctgagtat gtgccaagct acgaggacaa agatggtgac | 600 |
| tggatgctcg ttggcgatgt cccatgggaa atgtttgtcg agtcttgcaa acgttttgcgc | 660 |
| attatgaagg gatctgaagc agttggactt gctccgagag caatggagaa gtactgcaag | 720 |
| aacagatctt ga | 732 |

<210> SEQ ID NO 18
<211> LENGTH: 1017
<212> TYPE: DNA
<213> ORGANISM: Arabidopsis thaliana

<400> SEQUENCE: 18

| atgagttctg ggaacgataa gataaaacaa gtcctgcata ttgaagatct gatgtcttat | 60 |
| cgattgctaa gtgtggataa ggatgaactg gttacgtcac cttgtttgaa agaacgtaac | 120 |
| tacttgggtc tctctgattg ttcctctgtt gatagctcaa ctattcccaa tgttgttggg | 180 |
| aagagcaatc tcaatttcaa agctactgaa ctgaggctag tcttcctga gtctcaatct | 240 |
| cctgagagag agactgattt cggtttgctg agtccgagaa cacccgatga aagcttctc | 300 |
| ttcccgttgc taccttctaa agacaatggt tctgctacta cagggcataa gaatgttgtt | 360 |
| tctggtaaca agagaggatt tgctgacact tgggatgagt ttttcgggtgt gaaaggatct | 420 |
| gttagacctg gaggaggaat caacatgatg ttgtcgccga agttaaggga tgtctcgaag | 480 |
| agtattcaag aagaaagatc tcatgctaag ggtggcttga caatgcacc agctgccaag | 540 |
| gcacaggttg ttggttggcc tccaatcaga tcataccgga gaatacaat ggcttcttct | 600 |
| acttcgaaga cactgatga ggttgatggg aaacctggtc ttggtgttct gtttgtgaag | 660 |
| gtgagcatgg atggtgctcc gtatctgaga aaggtcgact tgagaactta cacttcctat | 720 |
| caacagttgt cttctgcact tgagaaaatg ttcagctgct tcaccttgg tcaatgtggt | 780 |
| cttcatggtg ctcaagggag ggaaagaatg agcgagatta aactgaagga tcttcttcat | 840 |
| ggatcagaat ttgtgcttac ttatgaagat aaagacggtg attggatgct tgttggcgat | 900 |
| gttccatggg agatatttac tgaaacatgc cagaaactga gatcatgaa gggttctgat | 960 |
| tctattggct tagctccagg tgcagtggag aaatcgaaga acaaagagcg gtttga | 1017 |

<210> SEQ ID NO 19
<211> LENGTH: 1017
<212> TYPE: DNA
<213> ORGANISM: Arabidopsis thaliana

<400> SEQUENCE: 19

| | | | | | | |
|---|---|---|---|---|---|---|
| atgtccccgg | aagaggagct | acagagcaat | gtatcggtgg | ctagttcttc | acctactagc | 60 |
| aattgcatct | ccaggaacac | tctaggagga | cttaaagagc | ataactactt | gggtctctct | 120 |
| gattgttctt | ctgttggaag | ctctactctc | tctcccttg | ctgaagatga | caaagctact | 180 |
| atcagcctca | aggctacgga | gctgacactt | ggtcttcctg | atcacaatc | tcctgcgaga | 240 |
| gacacagagc | ttaaccttt | gagcccagca | agctagatg | agaagccatt | ctttcctttg | 300 |
| cttccttcta | aagatgagat | atgctcctcc | tcgcaaaaga | acaatgcatc | gggaaacaaa | 360 |
| agaggctttt | ctgacacaat | ggatcagttt | gctgaagcta | aaagttcagt | gtatactgag | 420 |
| aaaaactgga | tgttccctga | agcagcagcc | acccagtctg | taacaaagaa | agatgtgcca | 480 |
| caaaacatac | ccaaaggaca | gtctagcact | acaaacaata | gctctagtcc | acctgcagcc | 540 |
| aaggcacaaa | ttgtcggttg | gcctccagtg | agatcctaca | ggaagaacac | attggccact | 600 |
| acttgtaaga | acagtgacga | agttgatggg | aggccaggtt | ctgggctct | cttcgtgaag | 660 |
| gtcagtatgg | atggtgctcc | ttatctgagg | aaagttgacc | tgaggagcta | cactaactac | 720 |
| ggggagcttt | cttcagcctt | ggagaaaatg | ttcaccactt | tcactcttgg | tcaatgtgga | 780 |
| tctaatggag | ctgctgggaa | ggatatgctt | agtgagacca | agctcaagga | tcttttgaat | 840 |
| ggaaaagact | atgtgctcac | ttatgaggat | aaggatggtg | actggatgct | tgttggagat | 900 |
| gttccgtggg | agatgtttat | tgatgtctgc | aagaagctga | agataatgaa | agggtgtgat | 960 |
| gctattgggt | tagctgcagc | tccgagagca | atggagaaat | cgaagatgag | agcttaa | 1017 |

<210> SEQ ID NO 20
<211> LENGTH: 786
<212> TYPE: DNA
<213> ORGANISM: Arabidopsis thaliana

<400> SEQUENCE: 20

| | | | | | | |
|---|---|---|---|---|---|---|
| atgaatggtt | tgcaagaagt | ttgttcgtca | agtgggtcgg | tgatgatcgg | actaccagct | 60 |
| gaagaagacg | aaaacgccgc | acattcgtcg | gaggattcat | cttgccccga | cgagtcagtg | 120 |
| tcagagacag | agctcgacct | agctttgggt | cttagcattg | gtcgtcggaa | ggttcgatcg | 180 |
| tcttttgtctt | cctcgtcttc | ttctctgacc | agggaaagtg | ggaccaaacg | ctctgctgat | 240 |
| tcttctccgg | ctgccgcctc | aaacgcaacc | agacaagttg | ctgtaggttg | gccgcctcta | 300 |
| cggacttaca | gaatcaacag | tttggtcaat | caagcaaagt | ctttagctac | ggaaggcggc | 360 |
| ttgagttctg | gcattcaaaa | ggagactaca | aaaagtgtag | tggttgctgc | taagaacgat | 420 |
| gatgcttgct | ttatcaaatc | gtccaggact | tctatgcttg | tgaaggtgac | aatggacgga | 480 |
| gttataattg | gaaggaaggt | tgatctcaat | gctctggatt | cttatgcagc | cttagagaaa | 540 |
| actttggatc | taatgttttt | ccagattcct | tctcctgtaa | caagatccaa | cacacaagga | 600 |
| tacaagacaa | ttaaggaaac | atgtacttcg | aaattactgg | atggctcatc | ggaatatatc | 660 |
| ataacatatc | aagataaaga | cggagattgg | atgcttgtag | agatgttcc | ttggcagatg | 720 |
| ttcctcgggt | ctgtgacaag | actgagaatc | atgaagacat | caattggagc | tggagtaggt | 780 |
| aagtag | | | | | | 786 |

<210> SEQ ID NO 21
<211> LENGTH: 909
<212> TYPE: DNA
<213> ORGANISM: Arabidopsis thaliana

<400> SEQUENCE: 21

| atggaaggcg | gttccgctag | tggatcggct | tcggctttgt | caaacgatga | aaatctcgtc | 60 |
| gtttcttgtg | aggattcttc | ttctcctata | gggaatgagc | ttgagcttgg | tcttacgttg | 120 |
| agccttggtc | gcaaagggta | tcgagattgt | agggtttacg | ctgatgattc | ttcttcttct | 180 |
| tcatcatctt | cttctctgag | cagagctagc | gtaattgctg | ggatcaagag | gacagctgat | 240 |
| tccatggctg | caactagtgg | gcaagttgtg | ggatggccac | aataaggac | ttacagaatg | 300 |
| aacagtatgg | ttaaccaagc | taaggcttca | gccactgaag | atccgaactt | ggagataagt | 360 |
| caagccgtaa | acaagaatag | aagtgattca | acaaagatga | gaaattccat | gtttgttaag | 420 |
| gtgactatgg | atggcattcc | tattggaagg | aaaatcgatc | tgaatgctca | taaatgctat | 480 |
| gaatcattgt | caaacactct | agaggaaatg | tttctgaaac | ctaaattagg | ttcacgcaca | 540 |
| ctagaaaccg | atggtcacat | ggaaacaccg | gtcaagatac | taccagatgg | gtcttccgga | 600 |
| ttagtactaa | cgtatgaaga | caaggaagga | gattggatgc | ttgttggcga | tgttccgtgg | 660 |
| gggatgttta | ttggttcagt | gagaaggctc | cggataatga | aaacatcgga | ggctactggt | 720 |
| aaagatgata | ttatgaagca | aataataatc | tacgaagaac | cctttatgtt | tgaagcagta | 780 |
| ataagacaga | tcacagatca | aagagaagac | aaaaacattg | taagaagctt | cttcttcttc | 840 |
| tctccccttt | acagtttctt | ttttggctct | gccattttc | ttttagttag | ttatatgttc | 900 |
| tctttgtaa | | | | | | 909 |

<210> SEQ ID NO 22
<211> LENGTH: 720
<212> TYPE: DNA
<213> ORGANISM: Arabidopsis thaliana

<400> SEQUENCE: 22

| atgcgtggtg | tgtcagaatt | ggaggtgggg | aagagtaatc | ttccggcgga | gagtgagctg | 60 |
| gaattgggat | tagggctcag | cctcggtggt | ggcgcgtgga | aagagcgtgg | gaggattctt | 120 |
| actgctaagg | attttccttc | cgttgggtct | aaacgctctg | ctgaatcttc | ctctcaccaa | 180 |
| ggagcttctc | ctcctcgttc | aagtcaagtg | gtaggatggc | caccaattgg | gttacacagg | 240 |
| atgaacagtt | tggttaataa | ccaagctatg | aaggcagcaa | gagcggaaga | aggagacggg | 300 |
| gagaagaaag | ttgtgaagaa | tgatgagctc | aaagatgtgt | caatgaaggt | gaatccgaaa | 360 |
| gttcagggct | tagggtttgt | taaggtgaat | atggatggag | ttggtatagg | cagaaaagtg | 420 |
| gatatgagag | ctcattcgtc | ttacgaaaac | ttggctcaga | cgcttgagga | aatgttcttt | 480 |
| ggaatgacag | gtactacttg | tcgagaaaag | gttaaaccttt | aaggctttt | agatggatca | 540 |
| tcagactttg | tactcactta | tgaagataag | gaaggggatt | ggatgcttgt | tggagatgtt | 600 |
| ccatggagaa | tgtttatcaa | ctcggtgaaa | aggcttcgga | tcatgggaac | ctcagaagct | 660 |
| agtggactag | ctccaagacg | tcaagagcag | aaggatagac | aaagaaacaa | ccctgtttag | 720 |

<210> SEQ ID NO 23
<211> LENGTH: 744
<212> TYPE: DNA
<213> ORGANISM: Arabidopsis thaliana

<400> SEQUENCE: 23

```
atgattactg aacttgagat ggggaaaggt gagagtgagc ttgagcttgg tctagggctg      60
agtcttggcg gtggaacggc ggccaagatt ggtaaatcag gtggtggtgg cgcgtgggga     120
gagcgtggaa ggcttttgac ggctaaggat tttccttctg ttggttctaa acgtgctgct     180
gattctgctt ctcatgctgg ttcatctcct cctcgttcaa gcagtcaagt tgttggatgg     240
cctcctatag ggtcacacag gatgaacagt ttggttaata accaagctac aaagtcagca     300
agagaagaag aagaagctgg taagaagaaa gtgaaagatg atgaacctaa agatgtgaca     360
aagaaagtga atgggaaagt acaagttgga tttattaagg tgaacatgga tggagttgct     420
ataggaagaa aagtggattt gaatgctcat tcttcttacg agaatttggc gcaaacattg     480
gaagatatgt tctttcgcac taatccgggt actgtcgggt taaccagtca gttcactaaa     540
ccgttgaggc tttagatgg atcgtctgag tttgtactta cttatgaaga taggaagga      600 gattggatgc ttgttggtga tgttccatgg agaatgttca tcaactcggt gaaaaggcta     660
cgtgtgatga aaacctctga agctaatgga ctcgctgcac gaaatcaaga accaaacgag     720
agacagcgaa agcagccggt ttag                                            744

<210> SEQ ID NO 24
<211> LENGTH: 687
<212> TYPE: DNA
<213> ORGANISM: Arabidopsis thaliana

<400> SEQUENCE: 24
atgaacctta aggagacgga gctttgtctt ggcctccccg gaggcactga aaccgttgaa      60
agtccggcca agtcgggtgt tgggaacaag agaggcttct ccgagaccgt tgatctcaaa    120
cttaatcttc aatctaacaa acaaggacat gtggatctca cactaatgg agctcccaag     180 gagaagacct tccttaaaga cccttctaag cctcctgcta agcacaagt ggtgggttgg     240 ccaccggtga ggaactaccg gaaaaatgtt atggctaatc agaagagcgg cgaagcagag    300
gaggcaatga gtagtggtgg aggaaccgtc gcctttgtga aggtttccat ggatggagct    360
ccttatcttc ggaaggttga cctcaagatg tacaccagct acaaggatct ctctgatgcc    420
ttggccaaaa tgttcagctc ctttaccatg gggagttatg agcacaagg gatgatagat    480 ttcatgaacg agagtaaagt gatggatctg ttgaacagtt ctgagtatgt tccaagctac    540
gaggacaaag atggtgactg gatgctcgtt ggtgatgtcc cctggccgat gtttgtcgag    600
tcatgcaaac gtttgcgcat aatgaaagga tccgaagcaa ttggacttgc tccaagagca    660
atggagaagt tcaagaacag atcatga                                        687

<210> SEQ ID NO 25
<211> LENGTH: 540
<212> TYPE: DNA
<213> ORGANISM: Arabidopsis thaliana

<400> SEQUENCE: 25
atgtcaccgg aggaatacgt tagggtttgg ccggattccg gtgatcttgg aggaactgag     60
ctgaccctag ctttgcctgg cactccgaca aatgcatcgg aaggtccaaa aaagttcggg    120
aacaaacgta gattcctcga gaccgttgat ttaaaactcg gggaagcaca cgagaacaat    180
tatatctcaa gcatggtcac taatgaccag ttggtgggct ggccgccggt agcgacagcg    240
aggaaaacag tgaggcggaa atacgtgaaa gtggcgttgg atggtgcggc ctatctcaga    300
aaggttgatc ttgggatgta cgattgctat ggacagcttt tcaccgctct agaaaacatg    360
```

```
tttcagggga taataacaat atgtagagtg acagagttgg agaggaaggg agagtttgtt      420
gctacttacg aggataagga cggtgacttg atgttagtcg agatgtgcc gtggatgatg       480 tttgtggaat cttgcaaacg tatgaggtta atgaaaaccg agatgctat tggattatag      540
```

<210> SEQ ID NO 26
<211> LENGTH: 711
<212> TYPE: DNA
<213> ORGANISM: Arabidopsis thaliana

<400> SEQUENCE: 26

```
atgattaatt ttgaggccac ggagctgaga ttagggctac cgggtgggaa tcacggagga       60
gaaatggctg gaaaaaataa tggtaaaaga ggattttctg agactgttga tctcaaactg      120
aatctttcat cgacggctat ggattcagtt tccaaagtcg atttagaaga tatgaaggag      180
aaggtcgtaa aaccaccagc caaggcacaa gttgtgggat ggccaccggt acgatctttc      240
cgcaagaacg tcatgtccgg ccaaaaaccg accaccggag atgccaccga aggaaacgat      300
aagacttctg gcagcagtgg agccacctca tccgcctccg catgtgccac cgtggcttat      360
gtgaaggtta gcatggacgg tgcaccgtac ctacggaaaa ttgacttgaa actctacaaa      420
acttaccaag atctctccaa cgccttaagc aaaatgttta gctctttttac cataggcaac     480 tatggaccac aaggaatgaa agatttcatg aatgagagta aattgatcga tcttctaaac      540
ggatcagatt atgttccaac atatgaagat aaagatggcg actggatgct tgtaggagac      600
gtaccgtggg agatgtttgt tgattcatgc aaacgtatac gaataatgaa gggatcagaa      660
gcaatcggac ttgctccaag ggcattagaa aagtgcaaga acagaagttg a               711
```

<210> SEQ ID NO 27
<211> LENGTH: 690
<212> TYPE: DNA
<213> ORGANISM: Arabidopsis thaliana

<400> SEQUENCE: 27

```
atgatgggca gtgtcgagct gaatctgagg gagactgagc tgtgtcttgg tcttcccggt       60
ggagatacag tggctccggt aaccggaaac aagagagggt tctcagagac ggttgatctg      120
aagctaaatc tgaataatga gcctgcaaac aaggaaggat ctacgactca tgacgtcgtg      180
acttttgatt ccaaggagaa gagtgcttgt cctaaagatc cagccaaacc tccggccaag      240
gcacaagttg tgggatggcc accggtgaga tcataccgga agaacgtgat ggtttcctgc      300
caaaaatcaa gcggtggccc ggaggcgcg gcgttcgtga aggtatcaat ggacggagca       360
ccgtacttga ggaaaatcga tttgaggatg tataaaagct acgatgagct ttctaatgct      420
ttgtccaaca tgttcagctc ttttaccatg ggcaaacatg gaggagaaga aggaatgata      480
gacttcatga atgagaggaa attgatggat ttggtgaata gctgggacta tgttccctct      540
tatgaagaca aagacggtga ttggatgctc gtcggcgacg ttccttggcc aatgttcgtc      600
gatacatgca agcgtttacg tctcatgaaa ggatcggatg ccattggtct cgctccgagg      660
gcgatggaga agtgcaagag cagagcttga                                       690
```

<210> SEQ ID NO 28
<211> LENGTH: 804
<212> TYPE: DNA
<213> ORGANISM: Arabidopsis thaliana

<400> SEQUENCE: 28

```
atggagggtt attcaagaaa cggtgaaatc tctccgaagc tgcttgactt gatgattcca       60
```

```
caagagagaa gaaattggtt tcacgatgag aaaaactctg ttttcaaaac agaggagaag      120
aagcttgagc taaagcttgg accacctggt gaagaagatg atgatgaatc gatgataaga      180
cacatgaaga aagaaccaaa agacaaatct atcctctctc tcgctggcaa atacttctct      240
ccttcttcca ccaaaaccac atcccataaa gaaactgctc ctggtccagt ggtgggatgg      300
cctccggttc gatccttcag gaagaattta gctagtggaa gttcttcaaa gcttggaaat      360
gactcaacca cctccaatgg tgttaccctc aagaaccaaa agtgtgatgc tgctgctaag      420
acaacagaac caaagagaca aggaggcatg tttgtgaaga tcaacatgta tggtgttccc      480
attggtcgta aagttgatct cagtgctcat aatagctatg agcagttatc tttcacagtt      540
gacaagctct tcagaggtct tcttgcagct caaagagact ttccatcatc catagaagat      600
gaaaaaccaa tcactggatt attagatggg aatggagaat atactcttac atatgaagac      660
aatgaaggag acaagatgct tgtaggagat gttccatggc aaatgtttgt gtcttcggtg      720
aagaggctgc gtgtgattaa aacttctgag atttcttcag cattaacata tggaaatggt      780
aagcaagaga aaatgagaag atga                                            804

<210> SEQ ID NO 29
<211> LENGTH: 968
<212> TYPE: DNA
<213> ORGANISM: Arabidopsis thaliana

<400> SEQUENCE: 29
aagagaagtg taggagaaga aagttctcat ttcataattg tatcaaattg tgagaggaaa       60
aaaagaagtt caagaaatgg agaaggaagg actcgggctt gagataacgg agctgagatt      120
ggggcttccg gggagagatg tggcagagaa gatgatgaag aagagagctt tcacggagat      180
gaatatgacg tcgtcgggta gtaatagtga tcaatgtgaa agcggcgtcg tttcatctgg      240
tggtgacgct gagaaggtta atgattcgcc ggcggcgaaa agccaggtgg tggggtggcc      300
accggtttgt tcttaccgga agaaaaacag ctgtaaggaa gcttcgacca cgaaagtggg      360
gttagggtat gtgaaagtga gcatggatgg tgtgccttat ttgaggaaga tggatcttgg      420
ttcgagccaa ggctatgatg atctagcctt tgctcttgat aagctcttcg gtttccgtgg      480
catcggtgtg gccttgaaag atggtgacaa ctgcgaatac gttaccatat acgaagacaa      540
agatggagac tggatgctcg ccggtgatgt accttggggg atgttctag agtcatgcaa      600
gaggttgaga ataatgaaaa gatcggatgc taccgggttt gggctgcagc ctagaggagt      660
agacgagtga tgatgacttg aacaagaagc aaggagctgg ttcattaatt taatcttaaa      720
cttgatcatc aagatccttt agaacatttt tcctattcat gttatataaa tatatatgtt      780
atagtatatt attttgcaac aaaatttcat gttatggttt tgcataatta tcttcagaaa      840
gacagctata tatatataca ctacttgttt cttgagtgtt gagttaaaac attaatctgt      900
ttcaaaattt attgttattt cggatctata tatgtgtgta gaaacatatg taataagtat      960
ccattatt                                                              968

<210> SEQ ID NO 30
<211> LENGTH: 528
<212> TYPE: DNA
<213> ORGANISM: Arabidopsis thaliana

<400> SEQUENCE: 30
atgggaagag ggagaagttc atcgtcttct tcaatagaga gtagcagcaa gagcaaccca       60
```

```
ttcggtgctt cgtcaagtac tcgaaaccta agcacggacc tgagactcgg actcagcttc    120
gggacatcct cagggactca atatttcaac ggtggctatg ggtactccgt tgcagctccg    180
gcggtagagg atgcggaata tgtggcggct gtggaggagg aagaagagaa tgagtgtaac    240
agtgtaggga gcttttacgt gaaagtgaac atggaaggag ttccaattgg aagaaagatc    300
gatctaatgt ctcttaatgg ctaccgcgac ttgatcagaa cccttgattt catgttcaac    360
gcatccattc tctgggctga agaagaagac atgtgcaatg agaagagtca cgtgctaacg    420
tacgcagata aggaaggtga ctggatgatg gttggagatg ttccttggga gatgttcttg    480
tctactgtga agactgaa gatttcaaga gctaattacc actactga                    528
```

```
<210> SEQ ID NO 31
<211> LENGTH: 810
<212> TYPE: DNA
<213> ORGANISM: Arabidopsis thaliana

<400> SEQUENCE: 31
atggaaggtt gtccaagaaa cagagaaatc ggtccaaaac ttcttgattt gattccacaa     60
ggaaggaaat ggtaccaaga agacaagaac aacacagatc aggagaagaa acttgagcta    120
aggcttggac cacccggtgg tgatgaagaa gatcattcag caatcaagaa gaagaacaca    180
gagataagaa acatcaagaa ggaaacagaa gacaaatctt tccactgttt taatggcaat    240
cacttctctc cttccaacaa aaccacttct gttcctcaca tctcacagaa aagaactgct    300
cctggtccag tggtggggttg gcctccggtt cgttcgttca gaaagaatct agcgagcaca    360
agctcttcaa agctaggtaa cgaatcctct catggaggtc aaatcaacaa gagtgatgat    420
ggtgaaaaac aagttgaaac caagaaggaa ggaatgtttg tcaagatcaa catggatggt    480
gttcctattg tcgtaaagt tgatctcaat gcttacaaca gctacgaaca gctctctttt    540
gtcgttgaca aactcttcag aggtctactc gcagctcaaa gagatatctc tgatggtcaa    600
ggagaagaga aacctatcat tggattatta atgggaaag gagaatttac tttaacctat    660
gaagacaatg aaggggacaa gatgcttgtt ggggatgttc catggcaaat gtttgtttca    720
tctgtgaaga gactgcgtgt gattaaaagc tctgagattt catctgcctt gacatttgga    780
tgcagtaagc aagagaagat gatgcactga                                     810
```

```
<210> SEQ ID NO 32
<211> LENGTH: 918
<212> TYPE: DNA
<213> ORGANISM: Arabidopsis thaliana

<400> SEQUENCE: 32
atgtctgtat ctgtagcagc agagcatgat tacataggtt tgtcagagtt tccaaccatg     60
gaagcaacaa caatgtctga caaaaccaaa accagagaca taacaacgg tctcaatttc    120 aaggctaccg agttaagact cggttttaccc ggttctgagt cgccggagcg agtcgactca    180
agattcttgg ctctcaacaa gagtagctgt cccgtgtcag gtgccaaaag ggtgttctcc    240
gacgctatta acgactctaa caaatgggtc ttctctcctg gatccactac tgctactggt    300
gatgtcggct cgggtctgg tccccgtacc tccgtcgtta agatggaaa gtcgacaact    360 ttcactaaac cggctgttcc ggttaaggag aagaagagct ctgctacagc tccagcttca    420
aaagcacaag tggtgggatg gccaccaata agatcattca ggaagaactc aatggcttct    480
tctcaatctc agaaacctgg taataactca gagactgaag aagcagaagc taagtctgga    540
ccagaacaac cttgcttgta tgtcaaagtg agtatggaag gtgctcctta cttgaggaaa    600
```

```
atcgatctca agacttacaa aagctacctt gagctctctt ctgctcttga gaagatgttc    660
agttgcttca ccattggtca gtttggttct catggagggt gtggcagaga tgggttaaac    720
gagagtcgct tgactgatct cttgcgtggt tctgagtatg ttgtaaccta tgaagataaa    780
gacagtgact ggatgctggt cggagatgtc ccttgggaaa tgtttatatg ctcctgcaag    840
aagctgagaa tcatgaagag ctctgaggct atcggcttag ctccaagggt gatggagaag    900
tgcagaagca ggaactag                                                 918

<210> SEQ ID NO 33
<211> LENGTH: 528
<212> TYPE: DNA
<213> ORGANISM: Arabidopsis thaliana

<400> SEQUENCE: 33
atggaagaag aaaagagatt ggagctaagg ctagctcctc cttgtcacca attcacttcc     60
aacaacaaca tcaatggatc taaacaaaaa agctcgacca agaaacatc attcctttcc    120 aataacaggg ttgaggtagc tccagtggtg ggatggccgc cggtgagatc atcccggaga    180
aacctaacgg cacaactaaa ggaggagatg aagaagaagg agagtgatga agagaaggaa    240
ttgtacgtta agatcaacat ggaaggagtt ccaataggaa gaaaagtcaa cctttcagct    300
tataacaact accaacagct ttcacatgcc gttgaccaac tcttctctaa gaaagattcg    360
tgggatctaa acagacaata cactttggtc tacgaagaca ctgaaggaga taaagttctg    420
gtcggggatg ttccttggga gatgtttgta tctactgtaa agaggttgca tgttttaaag    480
acctcccacg ccttctcact ctcacctaga aaacatggca aggaatag                528

<210> SEQ ID NO 34
<211> LENGTH: 756
<212> TYPE: DNA
<213> ORGANISM: Arabidopsis thaliana

<400> SEQUENCE: 34
atggagttgg atcttggtct atctctttca cctcataaat cttccaagtt agggtttaac     60
tttgacctca acaagcattg tgcgatcgag ggtgctgcgt cttgtttggg taccgaaaaa    120
ctgcgttttg aggcgacgtt tgggttaggg aatgtggagg aaaattgtta tatgccaaaa    180 cagcgttttgt ttgccttgaa tggccagccc aacgaggaag acgaagatcc tctggaatcc    240
gagtcttcaa tagtttacga tgatgaggag gaaaatagcg aagttgttgg atggccacca    300
gtaaaaacat gtatgataaa gtatggtagt tatcatcatc gtcatattcg taatcaccat    360
cattgcccgt atcatcatcg tggtaggagg atcacggcga tgaacaacaa catatctaat    420
ccaacaacgg ctactgtggg atcatcatct tcttcgtcaa tatcatcaag atcatcaatg    480
tatgttaagg ttaagatgga tggtgtggca atagcaagaa aagtggatat caagcttttt    540
aactcttacg agtccctcac taactccttg atcactatgt ttaccgaata tgaagattgc    600
gacagagaag atacaaatta tacattcacc ttccaaggga agagggtga ctggctactt    660 cgaggggatg ttcatggaa gatctttgcg gaatctgttc atcggatatc aataattaga    720
gatcgaccgt gtgcatatac aagatgtttg ttttaa                             756

<210> SEQ ID NO 35
<211> LENGTH: 519
<212> TYPE: DNA
<213> ORGANISM: Arabidopsis thaliana
```

<400> SEQUENCE: 35

```
atgggaagag ggagaagctc atcgtcttca tcgatagaga gcagctgcaa aagcaaccca      60
tttggtgtgt cttcgagtaa tactcggaac ctaagcacgg acctgagact cgggctcagc     120
ttcggatcat cttccggaca atattacaac ggtggagata accatgaata tgatggagtc     180
ggtgcggcag aggaaatgat gatcatggaa gaagaagagc aaaacgagtg taatagtgtc     240
ggaagcttct acgtgaaagt gaacatggaa ggagttccta ttgggagaaa gatcgatctt     300
ttatctctta atggatatca tgatttgatc acaactctcg actacatgtt caatgcttca     360
atcctttggg ctgaagaaga agatatgtgt agtgagaaga gtcacgtgct aacgtacgca     420
gacaaagaag gtgactggat gatggttgga gatgttcctt gggagatgtt cttgtctagc     480
gtgagaagac taaagatctc aagagcttat cactactga                            519
```

<210> SEQ ID NO 36
<211> LENGTH: 477
<212> TYPE: DNA
<213> ORGANISM: Arabidopsis thaliana

<400> SEQUENCE: 36

```
atggaggtct ctaactcttg ttcttcattt tcttcatcct ctgtcgacag tactaaacct      60
tctccttctg aatcttctgt taatctctcc cttagtctca catttccttc tacttctcca     120
caaagagaag caagacaaga ttggccaccg ataaagtcta gattaagaga tacactaaag     180
ggtcgtcgtc ttcttcgtcg tggtgatgac acttctctct tgttaaggt ttatatggaa      240
ggtgttccca ttggaagaaa actcgacctt tgcgtattct caggctacga gagtctatta     300
gaaaatctct ctcacatgtt cgatacttca atcatctgcg gtaatcgaga tcgaaaacat     360
catgttttga catatgaaga caaggatgga gattggatga tggtcggaga tattccatgg     420
gatatgtttc ttgaaaccgt gagaagacta agatcacga gaccggagag gtattaa         477
```

<210> SEQ ID NO 37
<211> LENGTH: 576
<212> TYPE: DNA
<213> ORGANISM: Arabidopsis thaliana

<400> SEQUENCE: 37

```
atggacccaa acacacctgc agacttcttc aaaggttctt ccaagtttca tacatattac      60
tcacagacca aaaagggtgg tggggtaatc gatctaggcc tcagccttag gaccatacaa     120
catgaaactt acctcccacc ggcgcgaatg ataggtctcg acgggtatgg agagctcata     180
gactggtcgc agcccagcta taacagcatt acacagttga agagtgagga cactggacac     240
caaagacttg cccaaggata ttacaataat gaaggagaga gcagaggaaa atatgcttac     300
gtaaaggtaa atctggatgg cctagtggta gggcgcaagg tttgccttgt tgatcaagga     360
gcttacgcaa ctcttgctct tcagctcaat gatatgtttg gatgcagac cgtgtcggga     420
ttgaggttgt tccagactga gtctgagttc tctttggtct acagagacag agaaggcatt     480
tggaggaatg ttggggatgt tccatggaag gagtttgtcg aaagcgtgga tcggatgcga     540
atcgcaagaa gaaacgatgc tcttcttccc ttttaa                              576
```

<210> SEQ ID NO 38
<211> LENGTH: 516
<212> TYPE: DNA
<213> ORGANISM: Arabidopsis thaliana

<400> SEQUENCE: 38

```
atgaatagtt tcgagccaca aagccaagac tctttgcaaa gaaggtttca tcaagacaac    60
agcaccacac aacaacctcg tgacaccacg acacctttca tacccaaacc ggcttccaaa   120
aaccataata atagcaactc cagctctgga gcggccggga gatcattcca aggctttggg   180
cttaacgtag aggacgatct tgtttcatcg gtggttcctc cggttacggt tgtgctagag   240
ggacgttcta tatgtcaacg cataagccta gacaagcatg ggagttatca gagcttggct   300
tcggctctaa ggcaaatgtt tgtcgatgga gctgattcaa cggacgatct tgatctgtca   360
aacgccattc ctggccatct tattgcttat gaagacatgg agaacgatct ccttcttgcc   420
ggagatctta cttggaagga ctttgttcgt gtagcgaaga gaattcgaat cttgccggtc   480
aagggaaaca caagacaagt taaaagaaac gagtga                             516
```

```
<210> SEQ ID NO 39
<211> LENGTH: 558
<212> TYPE: DNA
<213> ORGANISM: Arabidopsis thaliana

<400> SEQUENCE: 39
atgtattgca gcgatcctcc ccatcccttg cacttagtgg catcagacaa acaacaaaaa    60
gaccacaaac tgatcctttc ctggaagaaa ccaacaatgg actcagaccc actcggtgtt   120
ttcccaaatt ctcccaagta tcatccatat tactcgcaga ccacggagtt tggtggcgta   180
atcgatttag gtctcagcct gagaaccata acacatgaga tttaccactc atctggccaa   240
agatattgta gtaatgaagg atacagacgg aagtgggggtt atgtaaaggt caccatggat   300
ggtttggtgg taggtcgcaa ggtctgtgtt cttgatcatg gaagctattc aactcttgct   360
catcaactcg aggacatgtt tgggatgcag agtgtgtcgg gattgaggtt gttccagatg   420
gagtctgagt tctgtttggt ctacagagac gaagaaggtc tgtggagaaa tgctggggat   480
gttccatgga atgagttcat agaaagcgtg gagcggctga gaatcacaag aagaaacgat   540
gctgtacttc cctttttaa                                                558
```

```
<210> SEQ ID NO 40
<211> LENGTH: 720
<212> TYPE: DNA
<213> ORGANISM: Arabidopsis thaliana

<400> SEQUENCE: 40
atgcgtggtg tgtcagaatt ggaggtgggg aagagtaatc ttccggcgga gagtgagctg    60
gaattgggat tagggctcag cctcggtggt ggcgcgtgga aagagcgtgg gaggattctt   120
actgctaagg attttccttc cgttgggtct aaacgctctg ctgaatcttc ctctcaccaa   180
ggagcttctc ctcctcgttc aagtcaagtg gtaggatggc caccaattgg gttacacagg   240
atgaacagtt tggttaataa ccaagctatg aaggcagcaa gagcggaaga aggagacggg   300
gagaagaaag ttgtgaagaa tgatgagctc aaagatgtgt caatgaaggt gaatccgaaa   360
gttcagggct tagggtttgt taaggtgaat atggatggag ttggtatagg cagaaaagtg   420
gatatgagag ctcattcgtc ttacgaaaac ttggctcaga cgcttgagga aatgttcttt   480
ggaatgacag gtactacttg tcgagaaaag gttaaacctt taaggctttt agatggatca   540
tcagactttg tactcactta tgaagataag gaagggggatt ggatgcttgt tggagatgtt   600
ccatggagaa tgtttatcaa ctcggtgaaa aggcttcgga tcatgggaac ctcagaagct   660
agtggactag ctccaagacg tcaagagcag aaggatagac aaagaaacaa ccctgtttag   720
```

```
<210> SEQ ID NO 41
<211> LENGTH: 690
<212> TYPE: DNA
<213> ORGANISM: Arabidopsis thaliana

<400> SEQUENCE: 41
atgatgggca gtgtcgagct gaatctgagg gagactgagc tgtgtcttgg tcttcccggt        60
ggagatacag tggctccggt aaccggaaac aagagagggt tctcagagac ggttgatctg       120
aagctaaatc tgaataatga gcctgcaaac aaggaaggat ctacgactca tgacgtcgtg       180
acttttgatt ccaaggagaa gagtgcttgt cctaaagatc cagccaaacc tccggccaag       240
gcacaagttg tgggatggcc accggtgaga tcataccgga agaacgtgat ggtttcctgc       300
caaaaatcaa gcgtggcccc ggaggcggcg gcgttcgtga aggtatcaat ggacggagca       360
ccgtacttga ggaaaatcga tttgaggatg tataaaagct acgatgagct ttctaatgct       420
ttgtccaaca tgttcagctc ttttaccatg ggcaaacatg gaggagaaga aggaatgata       480
gacttcatga atgagaggaa attgatggat ttggtgaata gctgggacta tgttccctct       540
tatgaagaca agacggtgat tggatgctc gtcggcgacg ttccttggcc aatgttcgtc       600
gatacatgca agcgtttacg tctcatgaaa ggatcggatg ccattggtct cgctccgagg       660
gcgatggaga agtgcaagag cagagcttga                                        690

<210> SEQ ID NO 42
<211> LENGTH: 1785
<212> TYPE: DNA
<213> ORGANISM: Arabidopsis thaliana

<400> SEQUENCE: 42
atgcagaagc gaatagcctt gtcgtttcca gaagaggtac tagagcatgt gttctcgttt        60
attcagctgg ataaggatag gaactcagtc tctctggtgt gcaagtcatg gtacgagatc       120
gagcggtggt gcaggaggaa agtcttcatc gggaactgct acgccgtgag tccagcgacg       180
gtgattagga ggttcccgaa agtgagatcc gtggagctta aggaaaaacc tcactttgct       240
gactttaatt tggtacctga cggatgggga ggttacgtgt atccatggat tgaggccatg       300
tcttcgtctt acacgtggct tgaagagata aggctgaaga ggatggtggt caccgacgat       360
tgcttggagc tcatagccaa gtcttttaag aattttaagg ttcttgtgct ttcttcctgc       420
gaaggcttct ccaccgatgg tctcgctgct atcgctgcca cttgcaggaa tctgaaagag       480
cttgacttac gagagagtga tgttgacgac gttagtggcc actggcttag ccatttccca       540
gatacataca cttctttggt atcactcaat atatcttgct tagcatctga ggtcagtttc       600
tctgctctgg aaaggctggt gactaggtgt cccaatctca gtctctcaa gcttaaccga       660 gctgttccac ttgaaaaatt ggctacttta cttcaaagag cacctcaatt ggaggaattg       720
ggcactggtg gtacactgc agaagtgcga ccagatgttt actctggttt atctgtagcg       780
ctctctgggt gcaaggaatt gaggtgctta tctggatttt gggatgctgt tcctgcctat       840
cttccagcag tttattcggt ttgcagtcgg cttacaactt tgaatctgag ttatgcaaca       900
gtccagagct atgatcttgt caagcttctt tgtcaatgcc ctaaactgca gcgcctctgg       960
gtgcttgact acatcgagga tgctggtctt gaggtgcttg cttcaacctg caaggaccta      1020
cgcgagctga gagtgtttcc gtccgagcct tttgtcatgg aaccaaatgt ggcattgacg      1080
gaacaggggc ttgtctccgt ctccatgggc tgtccaaaac tcgagtcggt tctctacttc      1140
tgccgtcaaa tgaccaatgc tgcattgata accattgcta ggaaccgtcc caacatgact      1200
```

```
cgcttccgtt tgtgcatcat tgagccaaaa gccccagact atctgactct agagccactg    1260
gatattggat ttggagccat agtagagcac tgcaaggatc tccgtcgcct ctctctatct    1320
ggcctcttga ccgacaaggt ttttgaatac attgggacat atgccaagaa gatggaaatg    1380
ctctcagtgg catttgcagg agacagtgac ttaggcatgc atcatgtttt gtccgggtgc    1440
gatagcttga ggaaactaga gataagggac tgcccgtttg agacaaggc gcttttggcc     1500 aatgcttcaa agctggagac aatgcgatcc ctttggatgc cttcttgttc cgtgagtttt    1560
ggagcctgca agttactagg acagaagatg ccaaagctga atgtggaagt catcgatgaa    1620
cggggtgcac cggactcgag accagagagc tgccctgttg agagagtctt catataccga    1680
acagtggctg gtcctcgatt tgacatgcct ggcttcgtct ggaacatgga ccaagactca    1740
acaatgaggt tttccaggca aatcattact actaacggat tataa                    1785
```

<210> SEQ ID NO 43
<211> LENGTH: 1758
<212> TYPE: DNA
<213> ORGANISM: Arabidopsis thaliana

<400> SEQUENCE: 43

```
atgggtctcc gattcccacc taaggtgttg aacatatcc tctccttcat tgattccaac      60
gaggaccgga actctgtttc tctggtctgc aagtcatggt ttgagacaga acggaagact    120
aggaagcgag tctttgtcgg aaactgttac gcggtcagtc ctgctgcggt tacacgacgg    180
ttcccggaga tgagatcttt gactttgaag gggaagccac acttcgctga ctataatctc    240
gttcctgatg gttggggtgg ttatgcttgg ccgtggattg aagctatggc ggcgaaaagt    300
tcgtctcttg aagagatcag aatgaagagg atggtggtga ctgatgagtg cttagagaaa    360
attgctgctt cgtttaagga ttttaaagtc cttgtgttga cttcttgtga aggtttctct    420
actgatggta tcgctgctat tgcagctact tgcaggaact tgagagtgtt ggaactacga    480
gagtgtattg ttgaagattt aggaggagat tggcttagct attttccaga gagttcaact    540 tcttggtct ctcttgactt ctcttgttta gattctgagg ttaaaatctc ggatttagag    600
cgtcttgtga gcagatctcc aaacttgaag tctttgaagt tgaatccagc tgtgactcta    660
gatggactcg ttagcttact tcgttgtgct ccacaactga ctgagctcgg cacaggttct    720
ttcgcagctc aattgaaacc tgaagcgttt tcaaagttat cagaagcttt ttcaaactgt    780
aagcaacttc agagcttatc tggtctctgg gatgtcctcc ctgaatatct tccagctctt    840
tattctgtct gtcctggtct tacctcgttg aacttgagct acgctactgt ccgaatgcct    900
gatcttgttg agcttcttag gcgatgctcg aaactgcaga agctatgggt gatggacttg    960
attgaggaca aaggtcttga agctgttgcc tcatattgca aggaactgcg agaactgagg   1020
gtgtttccat ctgagccaga tcttgatgca accaacatac ctctgacgga caaggcctg    1080 gtctttgtgt ctaaaggctg tcgaaagctt gagtctgttc tctacttctg tgtccagttc   1140
acaaacgcag ctttgtttac catagcaaga aaacgtccga atctcaagtg cttccgtctc   1200
tgtgtgatag agccatttgc tcctgattac aaaacaaatg agccactga taaaggattc    1260 aaagccatag ctgagggatg cagggatctt cgacggctc ccgtctctgg tcttctctct    1320
gacaaggcct tcaaatacat tgggaaacat gccaagaagg ttaggatgct atcaatagca   1380
tttgctgggg acagtgattt gatgcttcat cacttgttgt cggctgtga gagtttaaag   1440 aagcttgaga tacgagactg ccctttgga gacactgcac tactggagca cgctgccaag    1500
```

| | |
|---|---|
| ctagagacca tgcgatccct ttggatgtca tcttgctttg taagttttgg tgcttgcaag | 1560 |
| cttctaagtc agaaaatgcc aaggctcaat gtcgaagtca ttgatgaaca tcctccagag | 1620 |
| tcaagacctg agagctctcc agttgagagg atatacatat acagaacagt cgcaggaccg | 1680 |
| agaatggata cgcctgaatt tgtgtggacg atacacaaga atcctgagaa tggagtttca | 1740 |
| catctagcca taaagtaa | 1758 |

<210> SEQ ID NO 44
<211> LENGTH: 1728
<212> TYPE: DNA
<213> ORGANISM: Arabidopsis thaliana

<400> SEQUENCE: 44

| | |
|---|---|
| atgaattatt tcccagatga agtaatagag catgtattcg actttgtaac atctcacaaa | 60 |
| gacaggaatg ctatatctct tgtatgcaaa tcatggtaca agattgaaag atacagtagg | 120 |
| caaaaggttt tcattggaaa ctgttatgcc attaatccag agaggttgct tcggagattc | 180 |
| ccatgtctaa agtctttgac tttgaaagga aaacctcatt ttgcggattt caatttggtt | 240 |
| cctcatgaat ggggaggttt tgtgctacct tggattgagg ctttggctag aagccgtgta | 300 |
| ggacttgaag agcttaggtt gaagaggatg gttgttactg atgagagtct tgagctgctt | 360 |
| tctcgttctt ttgtcaattt taagtctttg gtccttgtta gctgtgaagg tttttaccact | 420 |
| gatggtcttg cctctattgc cgctaattgc aggcatcttc gggatcttga tttgcaagag | 480 |
| aatgaaatcg atgatcatag aggtcaatgg ttaagttgtt tcccagacac ttgcacgact | 540 |
| cttgtcacgc taaactttgc gtgcctcgaa ggagaaacta atctggttgc tctagagagg | 600 |
| cttgttgcta ggtctccaaa cctaaagagt ctgaagctaa atcgtgcagt accgttagat | 660 |
| gcactcgcaa ggttaatggc gtgtgcgccg cagatagttg acttaggagt agggtcttat | 720 |
| gagaatgacc cagattccga gtcttacttg aaactcatgg ctgtcataaa gaaatgcacc | 780 |
| tcgttgagga gtttgtcggg ttttctagag gctgctcctc actgtctctc agcttttcca | 840 |
| ccaatatgtc ataacctcac ctccttgaat cttagttacg cagctgagat tcatggtagc | 900 |
| caccttatta agcttattca gcattgcaag aaacttcagc ggttatggat tttggatagt | 960 |
| ataggtgaca aagggcttga agttgtagct tctacatgta agagttaca agagcttagg | 1020 |
| gttttttccat ctgatttact cggtggaggc aacacagctg tgaccgaaga aggtctagtt | 1080 |
| gccatctcgg caggctgccc taagctccac tctatactct acttctgcca acaaatgaca | 1140 |
| aacgcagctc tcgtaaccgt tgccaagaac tgtccaaatt tcatccgttt ccgactctgc | 1200 |
| atcctcgagc caaacaaacc cgatcacgtc acatctcaac ctctagacga aggctttgga | 1260 |
| gcaatcgtca aagcctgcaa gagcctgaga aggcttttctc tctcaggtct ccttacagac | 1320 |
| caagtcttcc tctacatcgg aatgtacgcg aatcagctcg agatgctctc catagccttt | 1380 |
| gcaggagata cagacaaagg catgctatat gtgttgaatg gttgcaaaaa gatgaagaaa | 1440 |
| ctagagataa gggatagtcc gtttggggac acggcgcttc ttgctgatgt gagcaagtat | 1500 |
| gaaacaatgc gatcccttg gatgtcttca tgtgaagtca cactcagtgg atgcaaaagg | 1560 |
| ctcgcagaga aagcgccatg gctcaatgta gagatcataa acgagaatga taataaccgg | 1620 |
| atggaagaaa acggacacga ggggaggcag aaagtggata agttgtatct gtaccggact | 1680 |
| gtggttggga caagaatgga tgcgccgcca tttgtgtgga ttctctaa | 1728 |

<210> SEQ ID NO 45
<211> LENGTH: 1675

```
<212> TYPE: DNA
<213> ORGANISM: Arabidopsis thaliana

<400> SEQUENCE: 45
atgaattatt tcccagacga ggttatagag cacgtgtttg acttcgtagc ttctcacaaa      60
gacaggaact cgatatctct ggtctgcaaa tcatggcaca agatcgagag gtttagtagg     120
aaggaagtgt tcatcggaaa ctgctacgcg attaacccgg agaggttgat caggaggttt     180
ccatgtctca aatccttaac tttaaaaggg aagcctcatt ttgcagactt caacttggtt     240
cctcatgaat ggggaggttt cgtgcatcct tggattgaag ctttggctag aagccgtgtg     300
ggacttgagg agctgaggtt gaagcggatg gttgtaacag atgaaagctt ggaccttctt     360
tcacgttctt ttgcaaattt caagtctttg gttcttgtta gctgtgaagg gtttaccact     420
gatggcttag cttccattgc cgctaattgc aggcatcttc gtgagctgga cttgcaagag     480
aatgagattg atgatcatag aggtcaatgg ctgaactgtt ttccagatag ctgcactact     540
cttatgtcgt tgaatttcgc ttgccttaaa ggagagacca atgttgctgc tttagaaagg     600
cttgttgcta ggtcaccaaa cctgaagagc ttgaagttaa accgtgcagt accgcttgac     660
gcactcgcaa ggtaatgag ttgtgcgccg cagctagtgg acttaggagt agggtcttat     720
gagaatgagc cagatcctga atcttttgca aaactcatga ctgccattaa gaaatacaca     780
tcgttaagga gcttgtctgg cttttttagag gttgctccac tctgcctccc agcgttctac     840
ccaatttgcc aaaaccttat ctctttgaac ctcagctatg cagctgaaat ccaaggcaac     900
cacctcatta agcttattca gctttgcaag agacttcaac gattatggat attggatagt     960
attggtgaca aaggacttgc ggttgtcgct gccacatgta aagagttaca agagcttaga    1020 gttttttccct ctgatgtaca tggtgaagaa gataacaacg catctgtgac tgaggttgga    1080
ctagtcgcca tttccgcagg ttgccctaaa cttcattcga ttctgtactt ctgcaaacag    1140
atgacaaacg cagcgctcat agccgtggcc aaaaactgtc caaacttcat ccggttcagg    1200
ctatgcattc tcgagccaca caaacctgac cacattacat ttcaatcact ggacgagggc    1260
tttggtgcaa tcgtacaagc ttgcaagggg ctaagacggc tctctgtctc cggtctctta    1320
accgatcaag tctttctcta catcggtatg tacgcggaac agctcgagat gctttcgata    1380
gcttttgcgg gggacactga caaggaatg ctctatgtgt tgaatggatg caaaaaaatg    1440
aggaagctgg agataaggga cagtcctttt gggaacgctg cgcttcttgc tgacgtgggt    1500
aggtacgaaa caatgcgatc cctttggatg tcgtcttgtg aagtaacact cggtggctgc    1560
aagaggctcg cgcagaattc gccacggctt aacgtagaga tcatcaacga gaatgagaat    1620
aatgggatgg aacagaatga agaagatgaa agagagaagg ttgataaact ttacc         1675

<210> SEQ ID NO 46
<211> LENGTH: 1872
<212> TYPE: DNA
<213> ORGANISM: Arabidopsis thaliana

<400> SEQUENCE: 46
atgacagaag aagatagctc agctaaaatg tcagaggatg ttgagaaata tctcaactta      60
aatccacctt gctcctcctc ctcctcttct tcctccgccg ctacattcac gaacaagtct     120
cgaaatttca atcttctctc cccgccgtgt ccagatcatg tccttgagaa cgttttagag     180
aacgtgcttc agttcctcac ttccagatgc gatcgcaacg cagtctcatt ggtctgcaga     240
tcgtggtatc gcgtcgaggc tcagactcga ttagaggttt ttattggaaa ctgttactcg     300
```

```
ctctctcctg ctcggcttat tcaccggttc aagcgtgtta ggtctcttgt gcttaaaggg      360
aaacctaggt ttgctgattt taatctcatg cctcctaatt ggggagctca attctctcct      420
tgggttgctg ctacagctaa ggcttatcct tggctcgaga aggttcattt gaagcgtatg      480
tttgttacgg atgatgattt ggctcttctt gctgagtcgt ttcctgggtt caaagagctt      540
actttggtct gctgtgaagg ttttgggact agtggtattg ctattgttgc taacaaatgc      600
aggcagctaa aggtccttga tttgatggag tcagaagtca cagatgatga gttggattgg      660
atttcttgtt ttcctgaggg tgaaactcat ctggagtctt tgtcttttga ctgtgttgaa      720 tccctatca atttcaaggc attggaggag ctcgtggtta ggtcaccatt cttgaagaaa      780
cttagaacga acaggtttgt ttcccttgaa gagctgcatc gactaatggt tcgagcgccg      840
cagttaacga gtcttgggac ggggtcattt agtccagaca atgtgcctca gggagaacaa      900
caaccggatt atgcagctgc ttttcgtgct tgtaaatcca tagtttgtct ctcaggattc      960
agggaattta gaccggaata cctcctagcc atctcttcag tttgtgctaa tctcacctct     1020
cttaacttca gttatgctaa catttctcct cacatgctca agcccatcat aagcaactgt     1080
cacaatatcc gagtcttctg ggctcttgac tcgatacgtg atgaaggact acaggcagtg     1140
gctgccacat gcaaggagct ccgtgagctt cggattttcc cttttgatcc tcgtgaagac     1200
agtgaaggtc ctgtctcggg agtaggcctc caagcaattt cagagggctg taggaaactg     1260
gaatctatcc tgtactttg ccagaatatg accaatggag ctgtgacagc catgtcggag     1320
aactgcccgc agcttactgt gtttagactt tgcataatgg tcgccatag gcctgaccac     1380 gtgacaggaa agccaatgga cgatggattt ggtgccattg ttaaaaactg caagaagcta     1440
acccgacttg cagtatcagg gttactaaca gatgaagctt ttagctatat aggagaatat     1500
gggaaattga tccgtacgct atctgtagcg tttgctggga acagtgacaa ggctctgaga     1560
tacgttcttg agggttgtcc taaactacaa aagcttgaga tcagggacag tccctttgga     1620
gatgttggat tgcgctctgg tatgcatcgg tattccaata tgaggtttgt ttggttgtcg     1680
tcatgtctca tatcccgtgg aggctgcagg ggtgtttctc atgctctgcc taatgtagtc     1740
gtggaagtat ttggagccga tggtgatgat gacgaagaca ctgtcactgg ggattatgtt     1800
gagacattgt acttgtatcg atcccttgat ggcccaagga aggatgctcc aaagtttgta     1860
acaattttat ga                                                         1872
```

<210> SEQ ID NO 47
<211> LENGTH: 1860
<212> TYPE: DNA
<213> ORGANISM: Arabidopsis thaliana

<400> SEQUENCE: 47

```
atgacacaag atcgctcaga aatgtctgaa gatgacgatg accaacaatc tccaccgttg       60
gatctaccct ctaccgccat agctgatcct tgctcatctt cctcttcacc aaacaaatct      120
cgtaactgta tctcaaattc tcaaactttc cctgaccatg ttctcgaaaa cgtacttgag      180
aacgttcttc agttcctaga ttcaagatgt gaccgtaacg ctgcttctct agtttgcaaa      240
tcttggtggc gtgttgaagc tttgactcga tctgaggttt ttattggtaa ctgttacgct      300 cttttctccgg cgaggttgac tcagagattc aagcgtgtta ggtctcttgt gctgaaaggg      360
aaacctaggt ttgctgattt caatctcatg cctcctgatt ggggtgctaa ttttgctcct      420
tgggtttcta ctatggctca agcttatcct tgtcttgaga agttgatttt gaagaggatg      480
tttgttactg atgatgattt agctcttctt gctgactctt ttcctgggtt taaagagctt      540
```

```
atcttggttt gttgtgaagg ttttggtact agtggtatct ctattgttgc caacaagtgc     600
agaaagctga aagtgcttga tttgattgag tctgaggtca cggatgatga agtggattgg     660
atctcttgtt tccctgagga tgtaacttgt ttggagtctt tagcttttga ctgtgtggaa     720
gctcctatca attttaaggc gcttgagggt cttgttgcta ggtcaccgtt cttgaagaaa     780
cttaggctaa acaggtttgt gtctcttgtg gagctacatc gtctgctact ggagctcca      840 cagcttacta gtcttgggac tggttcattt agccatgatg aggaacctca gagtgagcaa     900
gaaccagatt atgctgctgc atttcgtgct tgtaaatctg tagtttgctt gtcagggttt     960
agagagttga tgccggagta tcttccagct atctttccgg tgtgcgctaa tctcacctcc    1020
ctgaacttca gttatgctaa catttctcct gacatgttca agcccatcat actcaattgc    1080
cacaaactcc aggtgttctg ggcccttgat tcaatatgtg atgaaggact acaggcagtt    1140
gcagccactt gcaaggaact ccgtgaactc aggatcttcc cttttgatcc tcgggaagac    1200
agtgaaggtc ctgtctctga attaggcctc caagcaatct ccgagggttg taggaaacta    1260
gaatctattc tctacttttg ccagcgcatg actaatgccg ctgtgatagc catgtcagag    1320
aactgtccag agcttactgt gtttaggctg tgcataatgg gtcgacatag gcctgaccat    1380
gtaacaggaa agcctatgga cgagggattt ggtgccattg ttaaaaactg caagaagcta    1440
actcgccttg cagtgtcggg attgctgaca gatcaagctt ttaggtatat gggtgagtat    1500
gggaaattgg tccgtacgct ttcagtagct tttgcagggg acagtgacat ggctctgaga    1560
catgtcctag aaggttgccc tagactgcag aaacttgaga taaggggacag tccctttgga   1620 gatgttgcat acggtctgg tatgcatcgc tattacaaca tgaggtttgt ttggatgtca    1680
gcatgtagct tgtctaaggg atgctgcaag gatattgcac gagcaatgcc gaatctagtt    1740
gtggaagtaa ttggatcgga tgatgatgat gacaataggg attatgtcga gactttatac    1800
atgtatcggt ctcttgatgg tccaaggaat gatgcaccaa agttcgtcac gattttatag   1860
```

<210> SEQ ID NO 48
<211> LENGTH: 2082
<212> TYPE: DNA
<213> ORGANISM: Arabidopsis thaliana

<400> SEQUENCE: 48

```
atggagcaag agaaaagctt ggatccacaa ctatggcatg cttgtgcagg atcaatggtt      60
caaatccctt cactgaattc aacggttttt tacttcgctc aaggccacac agagcacgct     120
cacgcgcctc ctgattttca cgcgccgcgc gttccacctc ttatcctctg tcgtgtcgtc     180
tccgtgaagt tcctcgccga cgctgaaaca gacgaagttt ttgctaaaat tacgcttttg     240
ccacttccgg gaaacgactt ggatctagaa acgacgccgt tttgggtct aactcctcct     300 tcttctgacg gtaacggtaa cggtaaagag aaaccggcgt cttttcgctaa acgttaacg     360 cagtctgacg ctaataacgg cggtggtttc tccgttccac gttattgcgc cgagacgatt     420
ttcccgcggc ttgattactc ggcggagcca ccggttcaaa ccgtgattgc taaagacatc     480
cacggcgaga cttggaaatt ccggcatatt tacagaggaa cacctcgccg tcatctccta     540
accaccggtt ggagcacttt cgttaaccag aagaaactaa tcgccggaga ctcaatcgtc     600
ttcctccgtt ctgaatccgg tgacctctgc gtcggaatcc gccgcgctaa acgcggcggt     660
ctcggatcta acgcaggatc cgacaatcct taccctggat tctccggttt cctccgtgac    720
gacgagtcaa caacaacaac atcgaagcta atgatgatga aacgcaacgg aaacaacgac    780
```

| | |
|---|---|
| ggaaacgccg cggctacagg gagggttaga gtagaagcag tagcggaagc ggtggcgcgt | 840 |
| gcagcgtgtg gacaagcgtt tgaggttgtt tattatccac gcgctagtac accggagttt | 900 |
| tgcgtaaaag cagctgatgt tagatcagca atgaggataa gatggtgtag tggtatgcgt | 960 |
| tttaaaatgg cgtttgaaac agaggattct tctagaatca gttggtttat gggtactgtc | 1020 |
| tccgccgttc aagtcgctga tccaattcgt tggcctaatt caccatggcg tctccttcag | 1080 |
| gtagcttggg acgaaccgga tttgttacaa aacgttaagc gggttagtcc gtggttagtc | 1140 |
| gaattggtat cgaacatgcc tacaatacat ttatctccat tctctccgag gaagaagatt | 1200 |
| aggattccgc agccatttga gtttccattc cacggtacta aattcccgat tttctccccg | 1260 |
| ggattcgcca acaatggcgg tggcgagtcc atgtgttatc tgtcaaacga caacaataat | 1320 |
| gctcctgcag gaatacaggg agccaggcaa gctcaacaac tcttcggatc accatctccg | 1380 |
| tctttgttgt ctgatctcaa tcttagtagt tacaccggta acaacaagtt acattctccg | 1440 |
| gcgatgtttc tatcgagttt caacccgagg catcatcatt atcaggctag ggatagtgag | 1500 |
| aatagtaata acatttcgtg ttctttaact atggggaatc ctgctatggt tcaggataag | 1560 |
| aagaagtctg ttggttcggt taagactcat cagttcgtgt tgttcggtca accgatttta | 1620 |
| accgaacagc aagttatgaa ccgaaaacgg tttttggaag aagaggcgga agcggaggag | 1680 |
| gagaaaggtt tagtggctcg tgggttaaca tggaattata gtttgcaagg acttgagacg | 1740 |
| ggtcattgta aagttttcat ggaatctgag gatgttggac gcacactcga tctctcggtt | 1800 |
| attggctcgt accaagaatt gtaccggaaa ttggctgaga tgtttcatat agaagagagg | 1860 |
| tcggatttgt tgactcatgt tgtgtaccgg gatgcaaatg gtgttatcaa acgtattgga | 1920 |
| gacgaacctt tcagtgattt catgaaagca actaaacggc taacaatcaa gatggatatt | 1980 |
| ggtggcgaca acgtgagaaa gacgtggata accggaatca ggactggtga aaatggtata | 2040 |
| gacgcttcta cgaagactgg tccgctcagc atcttcgctt ga | 2082 |

<210> SEQ ID NO 49
<211> LENGTH: 2013
<212> TYPE: DNA
<213> ORGANISM: Arabidopsis thaliana

<400> SEQUENCE: 49

| | |
|---|---|
| atgataaatg tgatgaatcc aatgaaaggt ggaacagaga aaggtttaga tcctcagcta | 60 |
| tggcatgcat gtgctggtgg tatggttcgt atgcctccta tgaactctaa agtctttttac | 120 |
| tttcctcaag gtcacgccga aaacgcttac gattgtgtcg atttcggtaa tctcccatt | 180 |
| cctcccatgg ttttgtgtcg tgttttagcc attaagtata tggctgatgc tgaatctgac | 240 |
| gaggttttcg ctaaactgag attgattcct ttgaaagatg atgagtatgt tgatcacgag | 300 |
| tatggtgatg gtgaagatag taacggtttc gagagtaata gtgagaaaac gccttcgttt | 360 |
| gctaagactt tgactcagtc tgatgctaat aacggtgggg gtttctctgt tcctcgttat | 420 |
| tgcgctgaga cgatttttccc gaggttggat tataacgccg agccgccggt tcagaccatt | 480 |
| cttgctaagg atgttcatgg tgatgtttgg aagttcagac atatttatag agggacgcct | 540 |
| cggcgtcacc ttcttacaac cggatggagt aattttgtaa accagaagaa gcttgtggcg | 600 |
| ggagattcga ttgtcttcat gagagcggag aatggagatc tttgtgtagg tattaggagg | 660 |
| gctaagagag gagggatagg taatggaccc gaatattcag cgggttggaa tccgatcggt | 720 |
| ggaagttgcg gctactcttc tctgttaagg gaagatgaaa gcaatagttt gaggagaagt | 780 |
| aattgttccc ttgcggatag gaagggggaaa gtgacggctg aatctgttat agaagcagcc | 840 |

```
actcttgcta ttagcggaag accgtttgag gttgtgtact atccgagagc tagcacttca    900
gagttttgtg tcaaggcatt agatgctcga gctgccatgc ggattccgtg gtgctcaggt    960
atgaggttta agatggcttt tgagacagag gattcgtctc ggataagttg gtttatgggg   1020
actgtttcag ctgttaatgt ctctgatcct atccgttggc ctaactctcc ttggcggctt   1080
ctacaggtgg cgtgggatga gccagattta ctccaaaacg tgaagcgagt aacccgtgg    1140
ttggtggaat tggtatcaaa cgtacatccg atcccgctta cttcgttttc gccaccgagg   1200
aaaaagatgc ggctacctca gcatccagat tacaacaatc tgatcaattc gattccagta   1260
ccttcattcc caagcaatcc ccttattaga tcaagcccgt taagtctgt tctggacaat    1320
gttcccgtgg gtttacaggg agccaggcat aatgctcatc agtactacgg ttatcatct    1380
tcggatcttc accattacta cttgaataga ccacctcctc ctcctcctcc atcctctctc   1440
caactttctc cttctctcgg tctccgaaac atcgatacca aaacgaaaa aggattttgc    1500
ttttgacaa tgggaacaac accatgcaat gataccaaat ctaaaaagtc ccatattgta    1560
ttgttcggca agcttatact acccgaggaa cagctatcag aaaaaggctc aacggatacc   1620
gcaaacatag agaaaacgca gatttcatca ggcgggtcga accaaaacgg cgttgcggga   1680
agggagtttt cttcgtcaga tgaaggatca ccttgctcta agaaagttca tgatgcatca   1740
ggtttggaaa cagggcattg taaagtgttt atggagtcag acgatgtagg tcgaaccta    1800
gacctatcgg ttcttggttc atacgaagaa ttgagtcgga aactctctga catgtttgga   1860
atcaaaaagt ctgagatgtt aagctctgtt ctctataggg atgcatcagg agccatcaaa   1920
tacgcaggaa acgaaccttt cagtgagttc ttgaagacag ctcgaagatt gacaattctg   1980
acggaacaag gaagtgagag cgttgtagta taa                                2013

<210> SEQ ID NO 50
<211> LENGTH: 2164
<212> TYPE: DNA
<213> ORGANISM: Arabidopsis thaliana

<400> SEQUENCE: 50
tagattgtga tcctctgcaa caaagcggat tttgctggtg ttgaatggat aagggataga    60
ggaagaggac tttgtttatc agaaaccttt tgatgggcct taatgggcct ataaactgta   120
actctgtagc gctttgccaa caagagactt tttaaggttt ttgttgccaa acagatattt   180
gcatttgggc tatgtaatgt tagaattatt ttataatgta tgctattgct agatattgtt   240
taagtgcatt tgtgatttac aaacatttca ttttttatttt ggttttaatg agcatttcta   300
ttatagagac tttgatgtta ataaatggtg ttctaagata tattaaaata ttttatatac   360
tttcttaaaa ttggataaat tttgggaaaa tccttaatat cagttaaatt gaagataaag    420
agtattaaaa aaaactatgt agtaaaatac atttcacatt ttttgtgtat aatagtacat    480
ggtattcgtt aagatcactc aaaaattaac aaattaagtc taaagggca gaaaagacta     540
ttcaaatatg gacttggaga aagacattca gcttttacg ctgagaaact ttcatattga     600
gccgtgtgtt tgtgttgtga agagaagtaa taaaaaataa tttgaagtga aaaaggagaa    660
gaaaaaataa gatcgtagaa agcgtggatg gtttcttctt gggttcactg ccatgcgatt    720
attaaattgg ccatggggct agtgtttgac gtacaaaagt ctaaaaattg tcagtcaaac    780
aggtccaaaa ctttgtaaga aaataatat aataatagca aattttctaa aaattgttaa     840
aaaaagaaca aagggaaaa gatgaggatg cagatgaaag caaaatgtca aacactagtt     900
```

```
tcagattttta tcgggaactg gggtttgaca gttggtgtat gtatgtaatg gcctctcatc    960
aaaacatgtg catcttttc ctttttgtt atttactgtt ttagctctac gtcttgtcca     1020
attcctctca agtaaaatgc ctttaatatg atactaatat acaaggggac taatgctttt   1080 tccctttct tatccttgtt ttgtctaaat ctttacttgg attcctttat ttttctcctc    1140
tctttagatt agtacggttt aaggaatacc atctttctaa ttttagcaca aaattgcaag   1200
ttggtgcccc atcttagtaa gcacatcgta ccacactttg attgtgtgag agacttcttc   1260
atcccatctc tcataccaaa cctaaatcaa atgactagtg gtgcaacctg ctgactccat   1320
atgaccataa ctaataaatc ggtttatgaa tccaactcat gtagctctat agaatagaaa   1380
cccattcatt tcacataatg aactgaatct gacattttat ttacatcatt tactactcaa   1440
ttttgtaatt agcaagatca tcttttcat tattcaacaa ttttgatatt ccataattta    1500
ttaactttgt catacatcat aatattctga aattttgtta tatattgtac cggttccacg   1560
aaatagagct ctattattat agaccaaaca acaaaatat tatcttcttg tggttagttc     1620
gagagagagg tcaagaagaa acgaaatgga tcggcaaacg gaagacgtca aacacacaac   1680
gacgaacatt ttccgatcac ccacctaatc tcttcccatt tttattattt ttcaaaactc   1740
aaattaatta agaagaaaaa aacagaaaca gagagagaaa gagttaagat gaatagagat   1800
agaaagagtc attaaatgta cgaagcgaca ttcacaataa ttcgaaaggt ggaagacgac   1860
ttagatacgg ccaggcttca ctgtcctcct cgtcctcctc aattacccct aaccccttt    1920 tccgggattc atctccaacc cacatccttc caaattctca cccctcact gagttttgc     1980 tttttctcct catcggagat cgtgaagacg atcaagtaat ttaagaatcc caccattgat   2040
aaaagagtct agcttttcta ctaccaaacc ttttctgtt tggaaatttt cgatttggga    2100 tttaacccctt tccttacctt atttataacc atgcaatctc acgaccaaca acccttcaat   2160
ctcc                                                                 2164
```

<210> SEQ ID NO 51  
<211> LENGTH: 2447  
<212> TYPE: DNA  
<213> ORGANISM: Arabidopsis thaliana

<400> SEQUENCE: 51

```
ttgttctcga cagacctcaa gattttttg ttttaaactg attacaaaaa tcttatatac     60
acatgcacat agtaaagtct aaaccaaagc aatataatag atataaatgt tcagtcagag   120
tttctattat caatcttgca aagaaatgaa aatatcttc gatagatgaa gattaagatt    180
cagacaataa catgcaacct ttttctttcc ccccaaaaac acatcgatca cccaccatca   240
atccatcatg gatcgatcat ccatttaggg acctatttac gtttgatttt ttttttccta   300
taactttctt taataaggac aacaaggcca agatcttcat cgtgtgtttc gtgtgtctca   360
aaatccctct aaacttttta ttgtagtttg gtgagacttg tttggtggtg ctgatgatga   420
tgagagagag agagagagag agcgcgcgag gaaatcatgg ctggtaaaca gaagaagaga   480
catgatgatt actgattgaa atattatata tgtacaccat tgaaataagt tataaaagtg   540
tcgtaaatcg tcaaaagaat cagtagtata tatctactct atatgatcta tatacaccat   600
tcatatataa aagaatcaca agtatgttat tgaggatgtg tgtcaatgaa gccctacgag   660
aaaggtctgt gcactaccaa aaagagaca catagtttgt ttgagttttt ttattgggtt    720
catttgttaa atttatatcc ataaatacct ccttgaggta tagccgtaca gggttttttt   780
gcagttcaag atatggcatt tgtatgaaac ttatataccc gccaaaaaaa acatacctag   840
```

```
gtcacccgtg ggtattttt gattgggaca aactggctgt agggaaagaa aaaacagaca      900
acgttaggtg ccttgtctct caaatcactt atcaggactc aggagcaata atttgttcga      960
accaattgta cgttgtaaca tctaaatggg tccataacaa tcagataata aaattttatc     1020
atctttctta atttatttat ttccaaataa ctttctttat catgtttctt aattacgttg     1080
atgcatgttt agatagccga acaaatcac tattactttg attcttatta tttatttatc      1140
aatttctgga ttcatgacat ttgaaaaact aaatgatgta ttactgtgca tttgcaattc     1200
aatcgatctt aaagtcttaa atcaactag acgataaaac ggtctatttc cctatagaac      1260
tagatatata tactatgcat tgtgatatag aattaagaga ttactgtttc tttggatgta     1320
tgatctttta tcagaataaa cttcttattt tgtcttcaga ataatcttg acttcgatca      1380 atcattattt cgtaagcgat aaaaacttct gattatctac caaaaaatga tttcaatata    1440
ttgtgacatt gttgcaatac gataaccaca aactcatatt catagggaaa tgttttaaca    1500
aactttgtta caaattcatc tacttacaac gtgatgctca atcattgata tacattataa    1560
aaagaattat tatcttaaaa tagtatcaac ataagacaac atgctcgatc gagataatac    1620
atgtgccagc gcagtccata gtcgtcagaa aaagatcaac atcaaatact ttttaggctt    1680
atcgcgcact tttcacttta agaggttatt gtgattacac tttacgtatt gaacctaaat    1740
atcaatttca cagttggaag tttacaaaaa taatgccagt gtcgatccta ggatgatgcg    1800
aaaccaaaag atgatgttac atatatatac acatgcacat ttagtattct ggttatcaag    1860
ataaggatga aaagactaat taaaccaaag cagtgtctat gacattgcaa gcattctcca    1920
acccataaga caaaattgat tctacaaact ttcatatcat cagaatctat gaaatgaatc    1980
aacaactatc acatctcagc agcaaagtta aggactttc cacatgatct atatttataa     2040
gggtatcgtt aagatcttct cacatgtgtg gcacgtgaca tatttaatat tcttgatggg    2100
cttttctgtt ttttatgggc cttttcgaat tcagggtttt aaataagtt agaaattaga     2160 taaataaaaa acaaattagc aaaaaataac gaagtgtctc gtctcttctc tcttgtcttc    2220
tccagatcag tgtttgtggg gttttcccaa tggagcttct tctctcattg tctctcctcc    2280 tgggtttg gtgtaacaac aatcctcaat tcacgaggca tgaatcatta ttctccccat      2340
ttgcttattc tctggctaga atccccagat tttactgtat cgactttggg aatttaactg    2400
gagaaccatt tccactcaaa ctgggaaaca aaacctgtt attgaac                   2447
```

<210> SEQ ID NO 52
<211> LENGTH: 13
<212> TYPE: PRT
<213> ORGANISM: Arabidopsis thaliana

<400> SEQUENCE: 52

Gln Val Val Gly Trp Pro Pro Val Arg Ser Tyr Arg Lys
1               5                   10

<210> SEQ ID NO 53
<211> LENGTH: 57
<212> TYPE: DNA
<213> ORGANISM: Arabidopsis thaliana

<400> SEQUENCE: 53
ggggacaagt ttgtacaaaa aagcaggcta attttgaatc cattctcaaa gctttgc       57

<210> SEQ ID NO 54
<211> LENGTH: 52

<212> TYPE: DNA
<213> ORGANISM: Arabidopsis thaliana

<400> SEQUENCE: 54
ggggacaact ttgtataca aagttgtgga gattgaaggg ttgttggtcg tg    52

<210> SEQ ID NO 55
<211> LENGTH: 53
<212> TYPE: DNA
<213> ORGANISM: Arabidopsis thaliana

<400> SEQUENCE: 55
ggggacaact tgtatacaa aagttgaaca atgaaagctc cttcatcaaa tgg    53

<210> SEQ ID NO 56
<211> LENGTH: 50
<212> TYPE: DNA
<213> ORGANISM: Arabidopsis thaliana

<400> SEQUENCE: 56
ggggaccact ttgtacaaga aagctgggtc ccggttaaac gaagtggctg    50

<210> SEQ ID NO 57
<211> LENGTH: 55
<212> TYPE: DNA
<213> ORGANISM: Arabidopsis thaliana

<400> SEQUENCE: 57
ggggacaact ttgtatacaa aagttgaaca atgcgtggtg tgtcagaatt ggagg    55

<210> SEQ ID NO 58
<211> LENGTH: 61
<212> TYPE: DNA
<213> ORGANISM: Arabidopsis thaliana

<400> SEQUENCE: 58
ggggaccact ttgtacaaga aagctgggtc aacagggttg tttctttgtc tatccttctg    60
c    61

<210> SEQ ID NO 59
<211> LENGTH: 8
<212> TYPE: PRT
<213> ORGANISM: Arabidopsis thaliana
<220> FEATURE:
<221> NAME/KEY: MISC_FEATURE
<222> LOCATION: (4)..(4)
<223> OTHER INFORMATION: Xaa is proline or lysine
<220> FEATURE:
<221> NAME/KEY: MISC_FEATURE
<222> LOCATION: (7)..(7)
<223> OTHER INFORMATION: Xaa is isoleucine or valine

<400> SEQUENCE: 59

Arg Val Ser Xaa Trp Glu Xaa Glu
1               5

<210> SEQ ID NO 60
<211> LENGTH: 6
<212> TYPE: PRT
<213> ORGANISM: Arabidopsis thaliana
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE

```
<222> LOCATION: (3)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is glutamine, tyrosine or histidine

<400> SEQUENCE: 60

Thr Xaa Xaa Lys Val Xaa
1               5

<210> SEQ ID NO 61
<211> LENGTH: 5
<212> TYPE: PRT
<213> ORGANISM: Arabidopsis thaliana

<400> SEQUENCE: 61

Val Gly Trp Pro Pro
1               5

<210> SEQ ID NO 62
<211> LENGTH: 13
<212> TYPE: PRT
<213> ORGANISM: Arabidopsis thaliana

<400> SEQUENCE: 62

Gln Val Val Gly Trp Pro Pro Val Arg Ser Tyr Arg Lys
1               5                   10

<210> SEQ ID NO 63
<211> LENGTH: 8
<212> TYPE: PRT
<213> ORGANISM: Arabidopsis thaliana
<220> FEATURE:
<221> NAME/KEY: MISC_FEATURE
<222> LOCATION: (4)..(4)
<223> OTHER INFORMATION: X is proline or leucine
<220> FEATURE:
<221> NAME/KEY: MISC_FEATURE
<222> LOCATION: (7)..(7)
<223> OTHER INFORMATION: X is isoleucine or valine

<400> SEQUENCE: 63

Arg Val Ser Xaa Trp Glu Xaa Glu
1               5

<210> SEQ ID NO 64
<211> LENGTH: 7
<212> TYPE: PRT
<213> ORGANISM: Arabidopsis thaliana
<220> FEATURE:
<221> NAME/KEY: MISC_FEATURE
<222> LOCATION: (1)..(1)
<223> OTHER INFORMATION: X is argine or lysine
<220> FEATURE:
<221> NAME/KEY: MISC_FEATURE
<222> LOCATION: (5)..(5)
<223> OTHER INFORMATION: X is phenylalanine or valine or isoleucine
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: X is leucine or isoleucine or valine

<400> SEQUENCE: 64

Xaa Leu Phe Gly Xaa Xaa Xaa
1               5
```

```
<210> SEQ ID NO 65
<211> LENGTH: 8
<212> TYPE: PRT
<213> ORGANISM: Arabidopsis thaliana
<220> FEATURE:
<221> NAME/KEY: MISC_FEATURE
<222> LOCATION: (1)..(1)
<223> OTHER INFORMATION: X is phenylalanine or isoleucine or leucine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: X is glutamine or lysine or valine or alanine
<220> FEATURE:
<221> NAME/KEY: misc_feature
<222> LOCATION: (7)..(7)
<223> OTHER INFORMATION: Xaa can be any naturally occurring amino acid

<400> SEQUENCE: 65

Xaa Xaa Leu Phe Gly Xaa Xaa Ile
1               5
```

MODIFIED PLANT CELL

BACKGROUND OF THE INVENTION

In order to feed and fuel a growing world population against a backdrop of threats to harvests from climate change requires a dramatic leap in crop production of 40-50% by 2030 (IAASTD report (2009) Agriculture at a crossroads). Limitations of nutrient, light and water availability can have drastic detrimental effects on crop yield. In North America alone it is estimated that 40% of annual crop losses are due to low water availability (IAASTD report (2009) Agriculture at a crossroads; Lynch (2011). *Plant Physiol* 156:1041-9; Lynch (2013). *Annals of Botany* doi: 10.1093/aob/mcs293).

Similarly, sub-optimal levels of the essential nutrients phosphate and nitrogen require the application of fertilisers that are expensive to produce, have a significant carbon footprint, and can adversely affect natural habitats through run-off from farmland. The urgent need to improve crop performance while seeking to reduce fertiliser and irrigation inputs has brought renewed interest in the manipulation of structural traits to maximise nutrient-use efficiency, water-use efficiency and optimise the capture of solar energy. While the number and length of lateral branches produced by the plant have an important bearing on the extent of possible occupation of above and below ground space, it is the angle of growth of those branches that is the major determinant of the efficiency and effectiveness of resource capture both above and below ground (Lynch (2011) *Plant Physiol* 156:1041-9; Lynch (2013). *Annals of Botany* doi: 10.1093/aob/mcs293; Liao et al. (2001) *Plant and Soil* 232:69-79; Liao et al. (2004) *Functional Plant Biology* 31:959-70; Ouyang et al. (2011). *J. Integrative Agriculture* 1701-9). For example, shallow rooting genotypes in maize and bean display up to a 50% increase in yield low phosphate soils (Liao et al. (2001) *Plant and Soil* 232:69-79; Liao et al. (2004) *Functional Plant Biology* 31:959-70).

The approach of breeders and biotechnology companies to the optimisation of crop architecture via the manipulation of GSA in crops has been severely limited by the complete lack of knowledge of the mechanisms underlying the regulation of branch angle. Hence approaches have been restricted to conventional breeding practices that are time-consuming and lack the precision required to optimise growth angle without compromising other performance traits.

The most desirable growth angle habit for root and shoot varies according to the agricultural environment. For example, in dry soils it can be advantageous to have steeper, more vertical lateral roots while, as noted above, in low phosphorous soils, a shallower, less vertical lateral root system can increase phosphate uptake thereby reducing or eliminating the need for additional inputs. Importantly, there are also crop-specific ideals for branch angle. For example, in oilseed rape a more vertical branch angle in the shoot canopy is desired because it improves light penetration during the crucial pod-filling phase prior to harvest.

The overall architecture of higher plants is determined by the number and arrangement of lateral branches around the main root-shoot axis. The principal function of these shoot and root branches is to hold leaves and other organs to the sun, and below ground, to facilitate the uptake of nutrients and water, and provide secure anchorage for the plant. Most commonly, these lateral root and shoot branches are set and maintained at specific angles with respect to gravity, a quantity known as the gravitropic setpoint angle (GSA). While the GSA of the primary root and shoot is typically approximately vertical, the GSA values of lateral shoots and roots are most often non-vertical, allowing the plant to optimise the capture of resources both above- and below-ground. Despite the importance of branch angle as a fundamental parameter of plant form, until recently the mechanism underlying the setting and maintenance of non-vertical GSAs was not known. A defining characteristic of the GSA concept is that upon being displaced from its GSA, an organ will rapidly undergo a gravitropic response to return to its original angle of growth with respect to gravity (Digby R D and Firn J. (1995). *Plant Cell Environ.* 12:1434-40; Cline M G (1996). *Ann Bot (Lond)* 78: 255-266). For the primary axis, in which vertically growing roots and shoots have a GSA of 0° and 180° respectively, this is readily accounted for by the well-supported model for gravitropism proposed by Cholodny and Went (Mullen J P and Hangarter R, (2003). *Advances in Space Research.* 31:2229-2236; Morita M T (2010). *Annu. Rev. Plant Biol.* 61:705-20; Blancaflor E. B., Masson P. H. (2003). *Plant Physiol.* 133: 1677-1690): the orientation of shoots and roots is monitored in specialised gravity-sensing cells called statocytes within which starch-rich bodies called statoliths sediment according to the gravity vector. As such statoliths provide a biophysical sensor of statocyte orientation within the gravity field and displacement from the vertical leads to the PIN auxin efflux carrier-mediated movement of auxin to the lower side in both root and shoot tissue. This auxin redistribution generates an asymmetry in auxin-regulated gene expression between upper and lower tissues that drives organ-level bending growth (Morita M T (2010). *Annu. Rev. Plant Biol.* 61:705-20; Blancaflor E. B., Masson P. H. (2003). *Plant Physiol.* 133: 1677-1690). In the shoot, auxin promotes cell elongation, causing upward bending, while in the root auxin inhibits cell elongation, causing downward anisotropic growth (Morita M T (2010). *Annu. Rev. Plant Biol.* 61:705-20; Blancaflor E. B., Masson P. H. (2003). *Plant Physiol.* 133: 1677-1690). The magnitude of this gravitropic response can in many cases be described by sine law, formulated by von Sachs in 1882, which states that the strength of the gravitropic response is dependent on the sine of the initial displacement angle (Sachs J (1882). Arb Bot Inst Würzburg 2:226-284. While there are species-specific differences in the range of displacement angles over which the sine law applies (Sachs J (1882). Arb Bot Inst Würzburg 2:226-284; Galland P. (2002) Planta 215: 779-784), as a general principle it is the case that the greater an organ is tilted away from its GSA, the greater the magnitude of the gravitropic response (Sachs J (1882). Arb Bot Inst Würzburg 2:226-284; Galland P. (2002) Planta 215: 779-784).

In contrast to the primary axis, the robust maintenance of growth at non-vertical GSAs in lateral organs cannot be explained by standard model Cholodny-Went-based gravitropism as described above. We recently established the existence of a mechanism, the anti-gravitropic offset (AGO), that counteracts gravitropic response specifically in the gravity-sensing cells of lateral branches but not in those of the primary root-shoot axis. Our key findings can be summarised as follows:

i. Gravity-dependent non-vertical growth of lateral root and shoot branches is sustained by an anti-gravitropic offset (AGO) mechanism that operates in tension with gravitropic response to generate net non-vertical growth.

ii. The activity of the AGO requires auxin transport.

iii. The angle of growth of lateral root and shoot branches is dependent on the magnitude of this anti-gravitropic offset component; a stronger AGO induces less vertical growth and vice versa.

iv. Auxin regulates the magnitude of the AGO and hence the GSA of lateral branches, separately from driving the anti-gravitropic growth itself.

v. Auxin's regulation of the AGO is effected, via TIR1/AFB-mediated transcriptional control, specifically in the gravity sensing cells of the root and shoot.

We have elucidated the means by which the growth angle of lateral root and shoots can be made either more or less vertical. The invention is therefore based on the finding that expressing regulators of auxin signalling in the gravity-sensing cells of the shoot and the root in higher plants is sufficient to alter the angles of lateral root and shoot branches in these species. For example, this may lead to plants having more vertical or less vertical lateral root and shoot branches. The targeted manipulation of branch angle traits may play a significant role in enhancing water and nutrient acquisition and photosynthetic efficiency in plants (including crops) grown in a range of agricultural conditions.

BRIEF DESCRIPTION OF THE DRAWINGS

FIG. 1A-FIG. 1J are the truncated nucleic acid sequences of ARF 5 (FIG. 1A-FIG. 1B ), ARF 6 (FIG. 1C-FIG. 1D), ARF 7 (FIG. 1E-FIG. 1F), ARF 8 (FIG. 1G-FIG. 1H) and ARF 19 (FIG. 1I-FIG. 1J) (SEQ ID NO: 1-5 respectively); truncations are as shown in Table 1;

FIG. 1K-FIG. 1V are the nucleic acid sequences of full length ARF 5 (FIG. 1K-FIG. 1L), ARF 6 (FIG. 1M-FIG. 1O), ARF 7 (FIG. 1P-FIG. 1R), ARF 8 (FIG. 1S-FIG. 1T) and ARF 19 (FIG. 1U-FIG. 1V) (SEQ ID NO: 6-10 respectively);

FIG. 2A-FIG. 2CC list the nucleic acid sequences of IAA 1 to 20 and 26 to 34 respectively (SEQ ID NO: 11-39 respectively); FIG. 2DD is the nucleic acid sequence of IAA12/BDL (SEQ ID NO: 40) which contains a stabilising mutation at position 74 within the conserved domain II; FIG. 2EE the nucleic acid sequence of IAA17/AXR3 (SEQ ID NO: 41) which contains a stabilising mutation at position 88 within the conserved domain II;

FIG. 3A-FIG. 3B is the nucleic acid sequence of TIR1 (SEQ ID NO: 42);

FIG. 3C-FIG. 3K are the nucleic acid sequences of AFB1 (FIG. 3C-FIG. 3D), AFB2 (FIG. 3D-FIG. 3F), AFB3 (FIG. 3G), AFB4 (FIG. 3H-FIG. 3I) and AFB5 (FIG. 3J-FIG. 3K) (SEQ ID NO: 43-47 respectively);

FIG. 4A-FIG. 4B is the nucleic acid sequence of ARF 10 (SEQ ID NO: 48);

FIG. 4C-FIG. 4D is the nucleic acid sequence of ARF 16 (SEQ ID NO: 49);

FIG. 5A-FIG. 5B is the nucleic acid sequence of the promoter of the SCARECROW gene (SEQ ID NO: 50);

FIG. 6A-FIG. 6B is the nucleic acid sequence of the promoter of the ARL2 gene (SEQ ID NO: 51);

FIG. 7 is a table showing the alignment of the ARF sequences in *Arabidopsis*; percentage identity matrix for the activating ARF (ARF$^A$) protein family in *Arabidopsis thaliana*. Values range from 39.44% to 63.32% (amino acid identity);

FIG. 8 is a table showing the alignment of the ARF sequences in *Arabidopsis*; percentage identity matrix for the TIR1/AFB protein family in *Arabidopsis thaliana*. Values range from 47.54% to 86.43%;

FIG. 9A-FIG. 9J Gravitropic Setpoint Angle (GSA) and the anti-gravitropic offset; (FIG. 9A) Typical GSA profiles of *A. thaliana* (Col. 0) shoot and root branches with diagram of GSA designations.

(FIG. 9B and FIG. 9C) Changes in the GSA of *Arabidopsis* and pea subapical branches after removal of the shoot apex and application of 1 mM IAA or mock treatment to the apical stump (white arrowheads, decapitated apices; grey arrowheads, subapical lateral branches) (FIG. 9B). Quantitative analysis of branch GSA is shown ($p<0.05$; error bars indicate the SEM) (FIG. 9C).

(FIG. 9D, FIG. 9E, FIG. 9G, and FIG. 9H) Effect of horizontal clinorotation on lateral shoot (FIG. 9D and FIG. 9E) and lateral root (FIG. 9G and FIG. 9H) GSA. Note: for clinorotated plants, a nominal GSA was derived by measurement of the growth angle of the final 5 mm of cauline branches and 2 mm of lateral roots with respect to the vertical in upright plants. White and grey lines represent the action of gravitropic and antigravitropic growth components, respectively. Lateral shoot GSA (FIG. 9E) and lateral root GSA (FIG. 9H) in wild-type and ein2-1 mutant plants are shown.

(FIG. 9F and FIG. 9I) Effect of local application of the auxin transport inhibitor NPA and subsequent clinorotation on lateral shoot (FIG. 9F) and lateral root GSA (FIG. 9I).

Figure 9A:
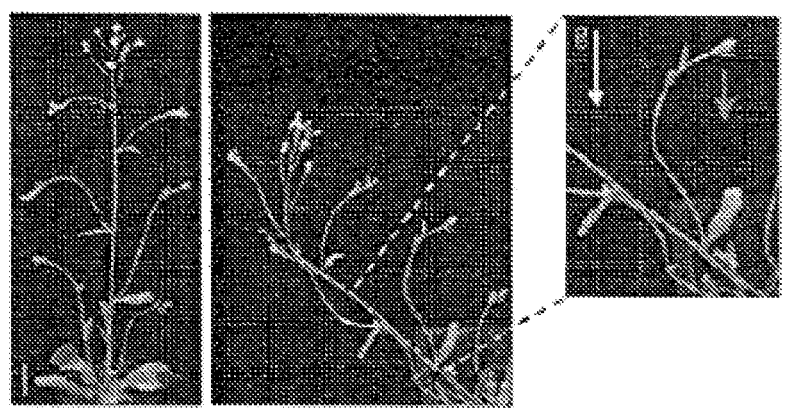
Figure 9B:
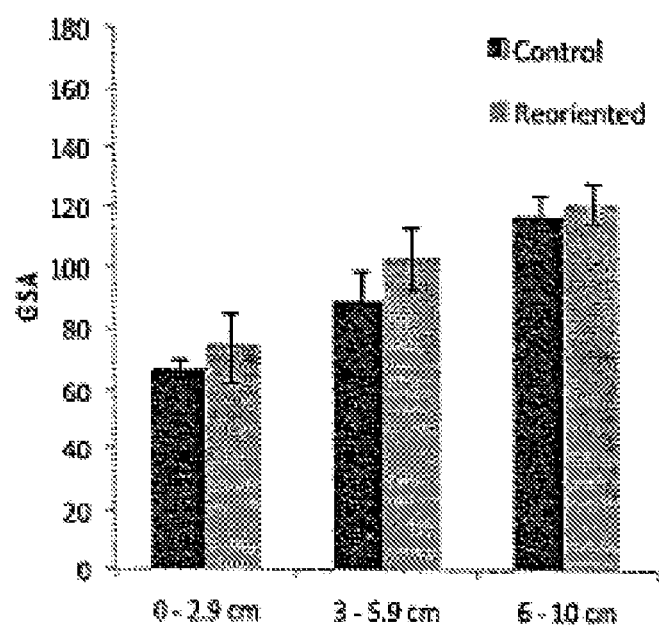
Figure 9C:
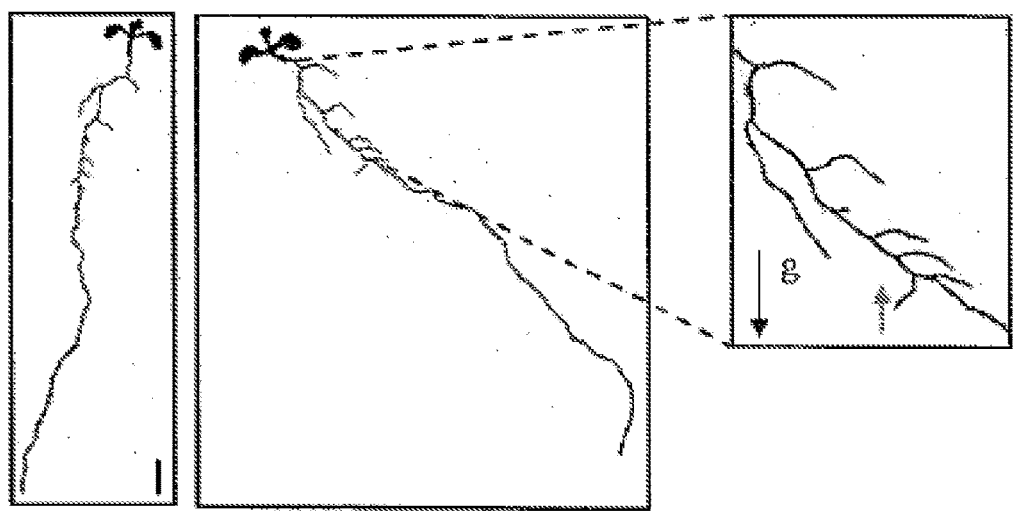
Figure 9D:
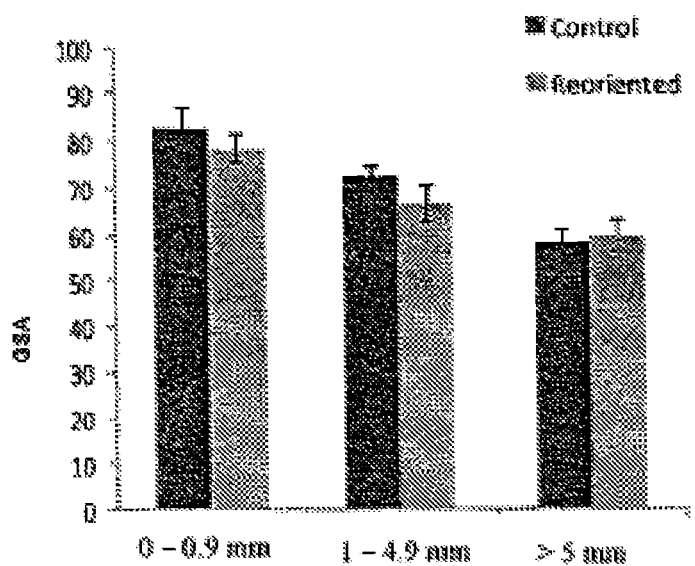
Figure 9E:
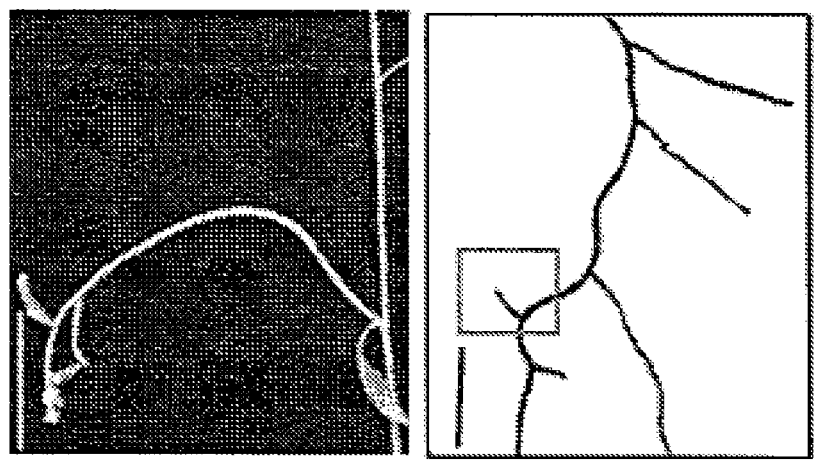
Figure 9F:
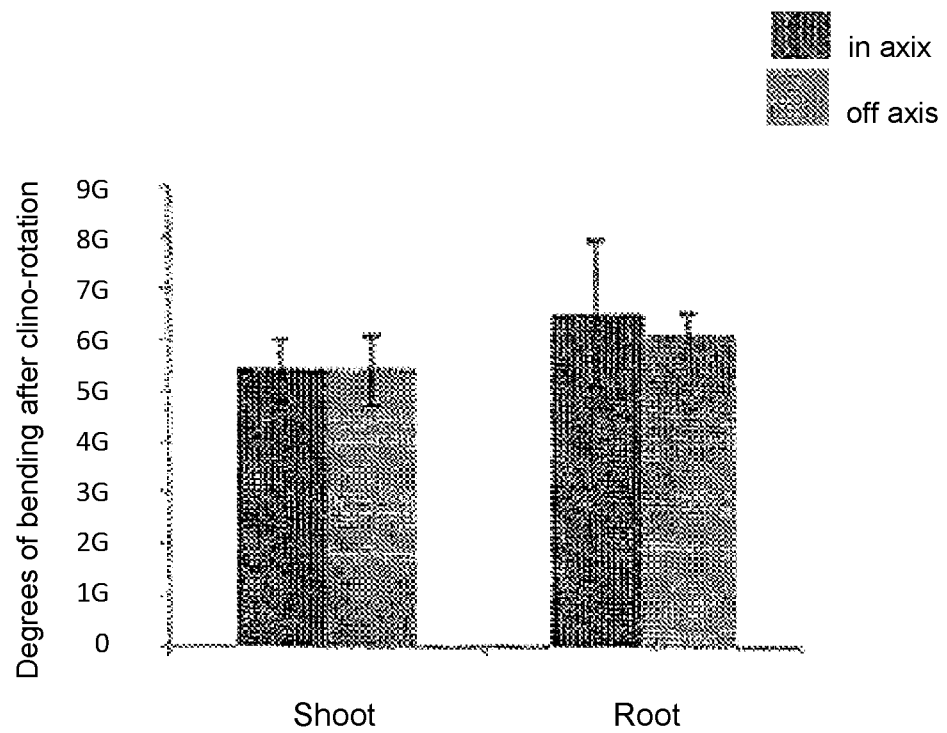
Figure 9G:
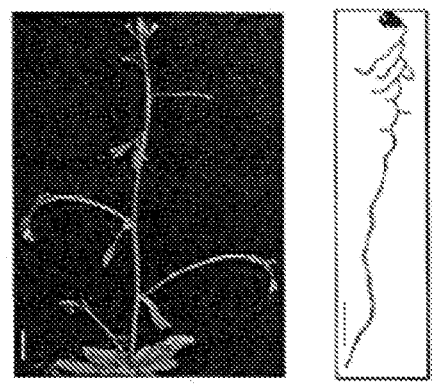
Figure 9H:
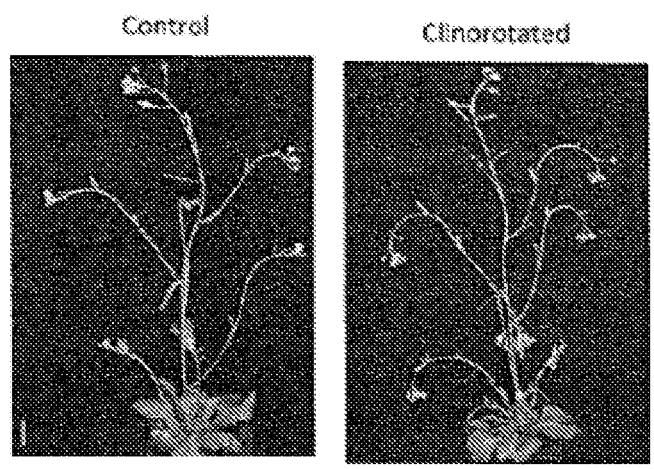
Figure 9I:
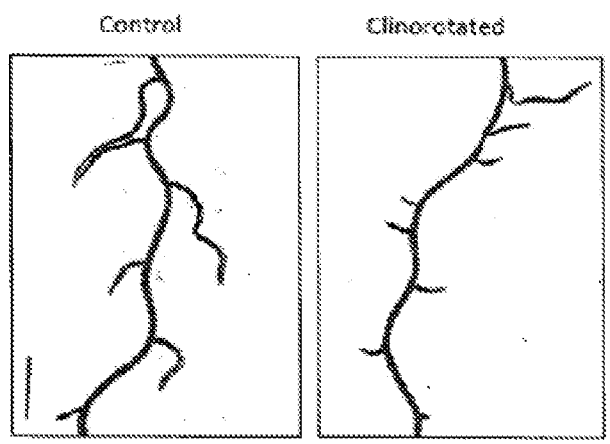

Clinorotation at 4 rph (FIG. 9D-FIG. 9F) and 1 rpm (FIG. 9G-FIG. 9I). Scale bars represent 1 cm (FIG. 9D) and 0.5 cm (FIG. 9G). Error bars indicate the SEM.

Figure 10A:
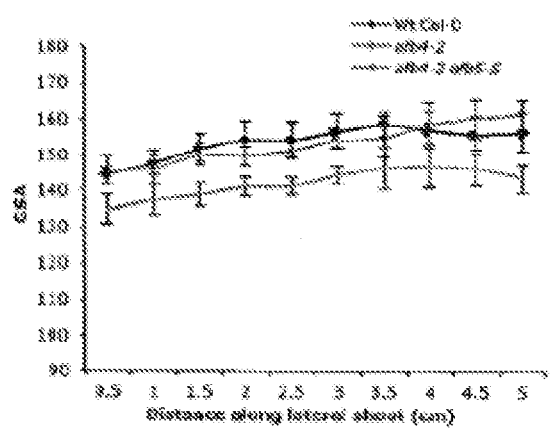
Figure 10B:
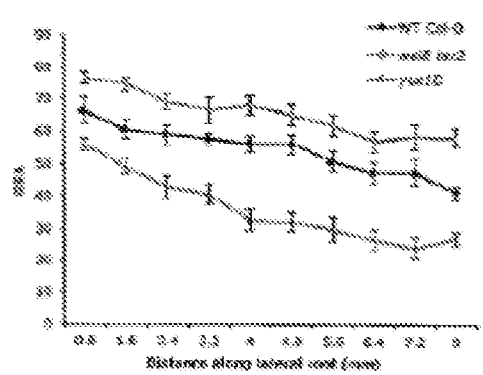
Figure 10C:
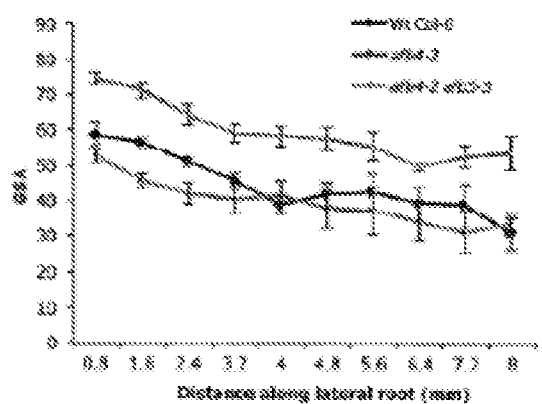
Figure 10D:
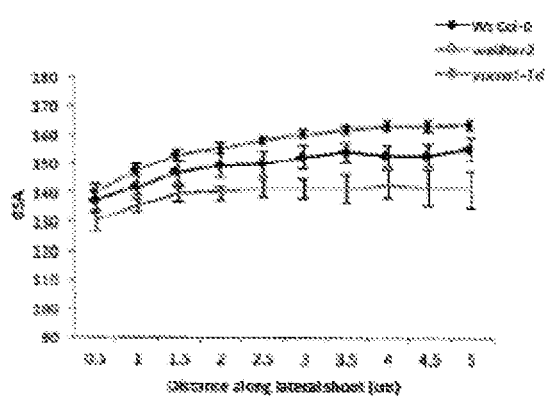
Figure 10E:
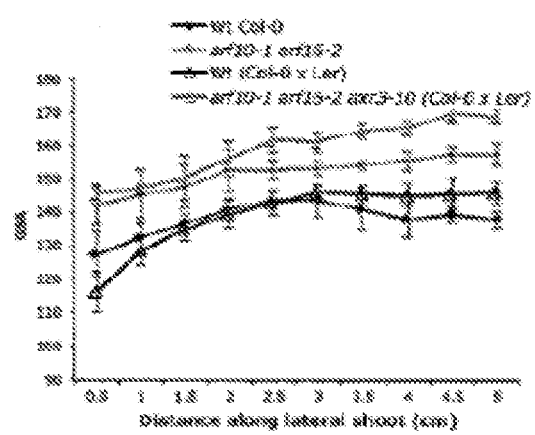
Figure 10F:
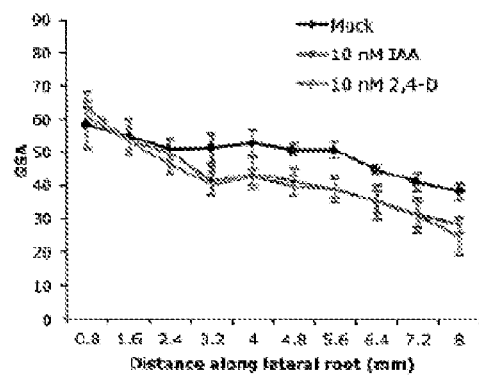
Figure 10G:
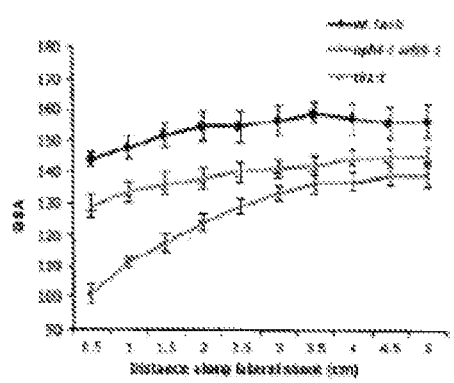
Figure 10H:
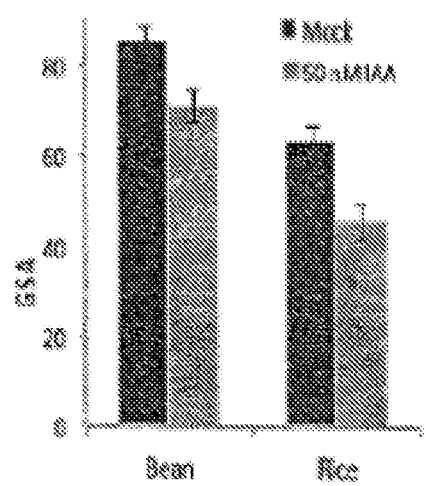
Figure 10I:
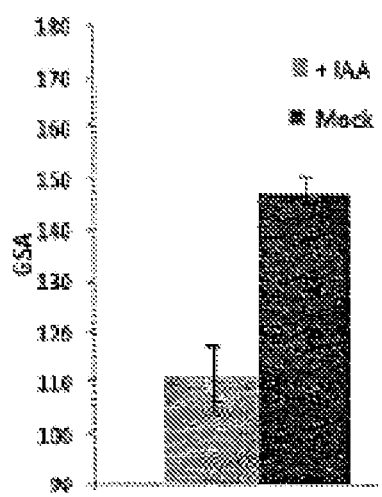
Figure 10J:
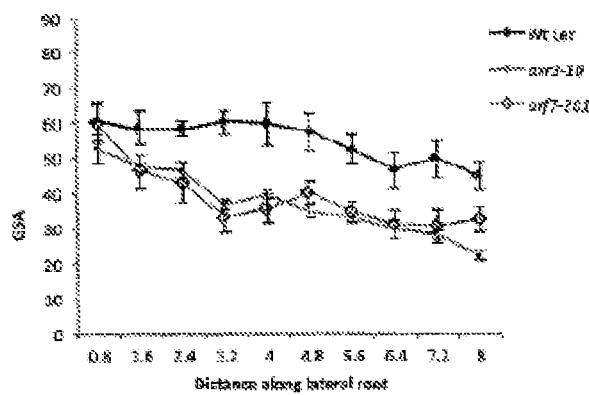
Figure 10K:
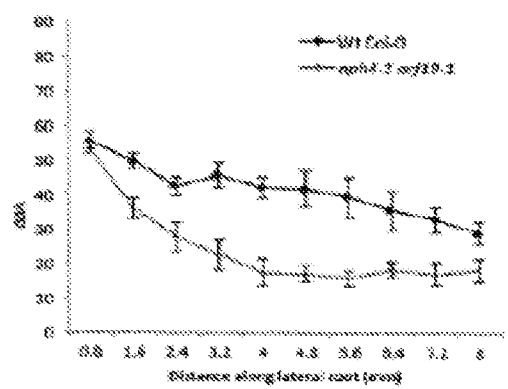

FIG. 10A-FIG. 10K Lateral branch GSA phenotypes of auxin signalling mutants; Changes in (FIG. 10A) lateral shoot GSA and (FIG. 10B) lateral root GSA induced by loss-of-function mutations affecting the AFB4 and AFB5 auxin receptors: afb4-2 and afb4-2 afb5-5 double mutant. The afb4-2 afb5-5 double mutant [26] has a significantly less vertical cauline branch and lateral root GSA, while afb4-2 single mutants are not significantly different from wild-type. Although we cannot rule out possible redundancy between AFB4 and AFB5 in this analysis, these data suggest that at the very least, AFB5 does contribute to GSA control (FIG. 10C and FIG. 10D) GSA phenotypes of mutants with altered auxin levels (wild-type Col-0, yucca1-1d and yuc1D auxin overproducing mutants and wei8 tar2 auxin deficient biosynthesis mutants). Lateral shoot GSA (FIG. 10C) and lateral root GSA (FIG. 10D). GSA recorded for successive 0.8 mm segments in the root and 0.5 cm segments in the shoot (mean of 12-15 lateral roots or shoots, one way ANOVA, $p<0.05$ for FIG. 10C and data points 5-10 in FIG. 10D). (FIG. 10E) Comparison of changes in lateral shoot GSA between wild-type plants and the arf10-3 arf16-2 and the arf10-3 arf16-2 axr3-10 double and triple mutants (mean of 12-15 roots, one-way ANOVA, $p<0.05$). (FIG. 10F) Effects on lateral root GSA of growth on media containing 10 nM IAA or 10 nM 2,4-D (mean of 12-15 lateral roots, one-way ANOVA, $p<0.05$, data points 6-10). (FIG. 10G) Comparison of changes in lateral shoot GSA in the tir1-1 and nph4-1 arf19-1 mutants (mean of 12-15 lateral roots, one-way ANOVA, $p<0.05$). (FIG. 10H) The effect of auxin treatment on lateral root GSA in bean and crown root GSA in rice ($p<0.05$, Student's t-test, n=15-20). (FIG. 10I) Changes in the GSA of nph4-1 arf19-1 sub-apical branches after removal of the shoot apex and application of 1 mM IAA or mock treatment to the apical stump (12-15 lateral shoots, Student's t-test, $p<0.05$). (FIG. 10J and FIG. 10K)

Comparison of changes in lateral root GSA between wild-type plants and the axr3-10, arf7-201 (FIG. 10J) and nph4-1 arf19-1 (FIG. 10K) mutants (mean of 12-15 lateral roots, one way ANOVA (FIG. 10J), Student's t-test (FIG. 10K), p<0.05, data points 2-10). Error bars: s.e.m. Scale bar=1 cm.

Figure 11A:
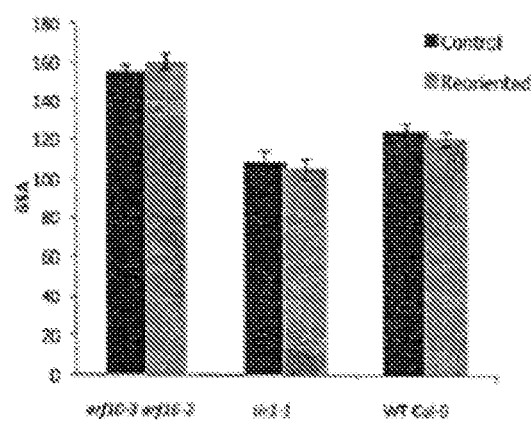
Figure 11B:
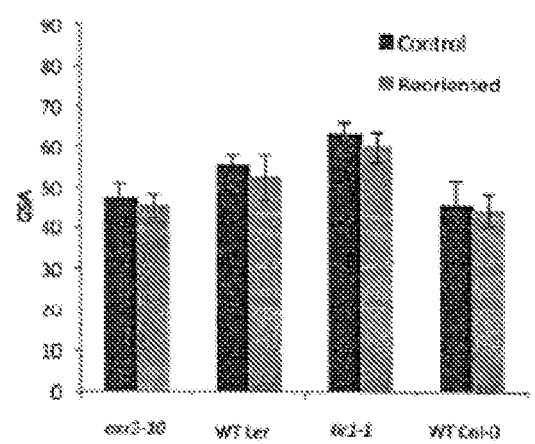
Figure 11D:
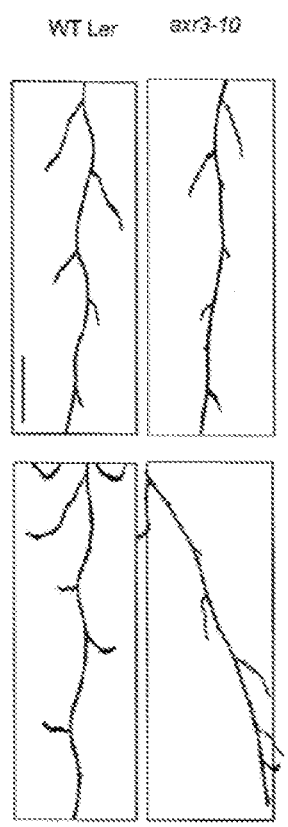

FIG. 11A-FIG. 11D Auxin specifies shoot and root branch GSA by regulating the magnitude of the anti-gravitropic offset component. Auxin specifies shoot and root branch GSA by regulating the magnitude of the anti-gravitropic offset component. (FIG. 11A and FIG. 11B) Lateral branch GSA before and after re-orientation by 45° in wild-type and auxin response mutants. (FIG. 11A) Lateral shoot GSA measured using the final 0.5 mm segment of 5-6 cm long lateral shoots or (FIG. 11B) the final 0.2 mm segment of 2-4 mm long lateral roots. (FIG. 11C and FIG. 11D) Comparison of the changes in lateral shoot GSA (FIG. 11C) and lateral root GSA (FIG. 11D) following clinorotation (4 rph shoots/1 rpm roots, 8 hours) in the auxin response mutants: (FIG. 11C) nph4-1 arf19-1 and arf10-3 arf16-2 (wild-type Col. 0 in main FIG. 3A); (FIG. 11D) wild-type Ler and axr3-10 plants. Error bars: s.e.m. Scale bars=1 cm (FIG. 11C) and 0.5 cm (FIG. 11D).

Figure 12A:
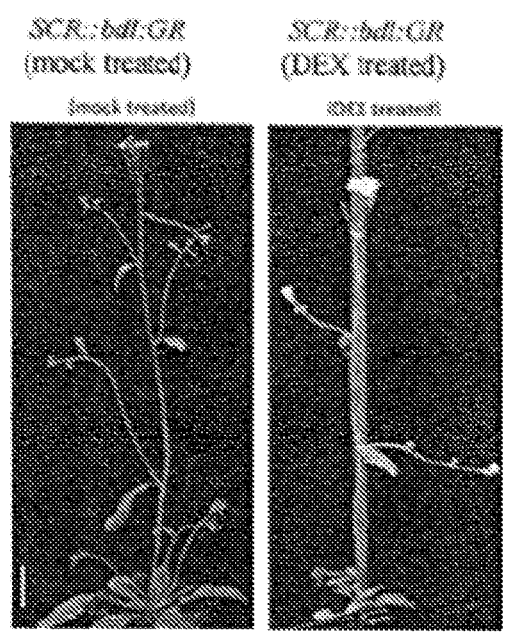
Figure 12B:

FIG. 12A and FIG. 12B: Auxin specifies GSA within the gravity-sensing cells of the root and shoot; Induction of a mutated, stabilised form of IAA12/BDL in the gravity-sensing cells of the shoot (SCR::bdl:GR) causes branches to grow at an extreme non-vertical GSA. This phenotype is lost 72 hours after the cessation of dexamethasone treatment. (FIG. 12B) Reversion of the lateral shoot GSA phenotype three days after the last DEX treatment. Scale bar=1 cm.

Figure 13A:
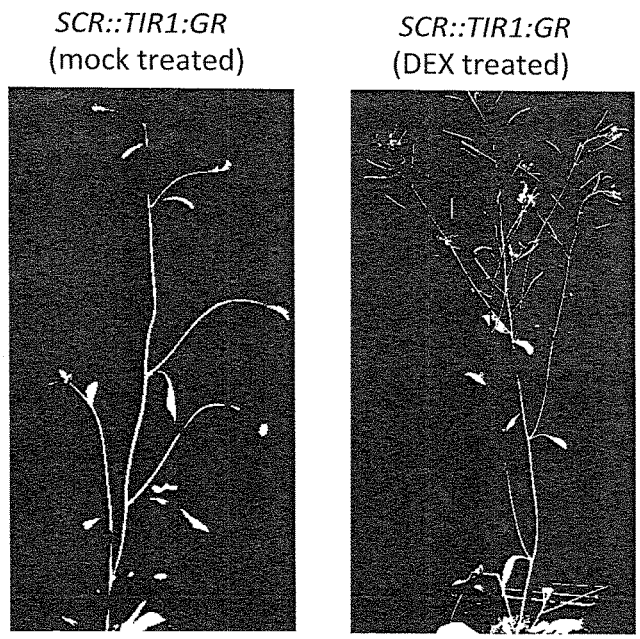
Figure 13B:
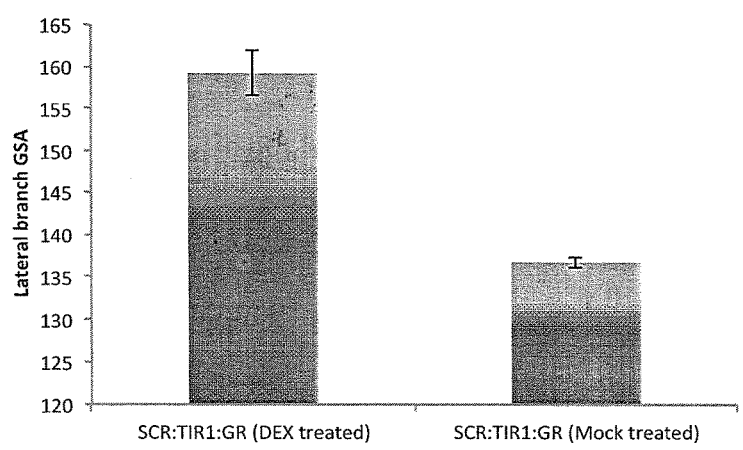

FIG. 13A Representative mock and DEX treated SCR::TIR1:GR plants. (FIG. 13B) Quantification of GSA from an average of 10 lateral branches showing a more vertical GSA phenotype in DEX treated plants. Bars represent standard error.

SUMMARY OF THE INVENTION

The disclosure relates to the manipulation of auxin signalling within the gravity-sensing cells of the root and shoot.

According to the invention there is provided a plant cell the genome of which is modified by the inclusion of a nucleic acid molecule adapted for expression in a gravity sensing cell wherein the nucleic acid molecule encodes a regulator of auxin signalling.

Preferably the plant cell is a transgenic plant cell.

As used herein a "gravity sensing cell" may be used interchangeably with statocyte to mean a cell which is responsive to gravitational forces. Statocytes contain starch-rich bodies called statoliths sediment according to the gravity vector.

As used herein a "regulator of auxin signalling" includes the protein families: F-box proteins called TRANSPORT INHIBITOR RESPONSE-1 (TIR1), or one of a small family of related F-box proteins called Auxin signalling F-box Proteins (AFBs), auxin response factors (ARFs) and modified auxin/indole-3-acetic acid (Aux/IAA) transcriptional regulators (repressors).

ARF proteins have DNA binding domains and can bind promoter regions of genes and activate or repress gene expression. AUX/IAA proteins can bind ARF proteins sitting on gene promoters and prevent them from doing their job. TIR1/AFB proteins are F-box proteins that have distinct domains giving them the ability to bind to three different ligands: a SKP1 protein (via the F-box domain) that tethers the F-box proteins to the other subunits of the SCF$^{TIR1/AFB}$ ubiquitin ligase complex, auxin (so TIR1/AFB proteins are auxin receptors), and AUX/IAA proteins (auxin and AUX/IAA proteins bind to a common pocket in TIR1 formed from adjacent leucine-rich repeats). Upon binding of auxin, a TIR1/AFB protein's auxin/AUX/IAA binding pocket has increased affinity for AUX/IAA repressor proteins, which when bound to TIR1/AFB and its SCF complex undergo ubiquitination and subsequent degradation by a proteasome. The degradation of AUX/IAA proteins frees ARF proteins to activate or repress genes at whose promoters they are bound.

In a preferred embodiment of the invention, the regulator of auxin signalling is an ARF which can be either transcriptional Activators (ARF$^A$) or repressors (ARF$^R$).

Whether an ARF is an ARF$^A$ or ARF$^R$ depends on the make-up of a variable region between the defined amino- and carboxy-terminal domains known as the middle region (MR). The middle region (MR) of ARF proteins is flanked at its amino-terminal end by the conserved ARF DNA binding domain (DBD) and at its carboxy-terminal end by the conserved protein interaction domains III and IV (that also occur in Aux/IAA proteins). For reference, a highly conserved RVSP/LWEI/VE (SEQ ID NO: 63) motif occurs close to the end of the DBD and similarly, a TXXKVQ/Y/H (SEQ ID NO: 60) motif (where X can be any amino acid) occurs close to the start of domain III. Thus the MR occurs between these motifs. A small number of ARFs lack the carboxy-terminal domains III and IV and in these cases the MR can be considered to run from the end of the DBD to the carboxy-terminus of the protein.

ARF$^A$s have a MR that is glutamine/Q-rich and promote transcription (Ulmasov, T et al (1997b). *Proc Natl Acad Sci USA* 96: 5844-5849; Tiwari et al. (2003). *Plant Cell* 15(2): 533-543). As used herein "glutamate rich" is intended to include those MRs having about 13 to 18% glutamate residues. This is in contrast to ARF$^R$s that have an MR which is not glutamate rich (generally has between 5 and 8% glutamate residues). MRs rich in proline/serine/threonine (P/S/T) residues act as repressors of transcription (Ulmasov et al. (1997). *Proc Natl Acad Sci USA* 96: 5844-5849; Tiwari et al. (2003). *Plant Cell* 15(2): 533-543. Of the 23 ARFs in *arabidopsis*, only 5 (ARFs 5, 6, 7, 8, 19) fall into the activating class while the remainder are repressors (Ulmasov, T et al (1997b). *Proc Natl Acad Sci USA* 96: 5844-5849; Tiwari et al. (2003). *Plant Cell* 15(2): 533-543). The MR of ARF$^R$ proteins also contain other features that distinguish them from the ARF$^A$ subclade. These include a so-called B3 repression domain (BRD) corresponding to the well conserved R/KLFGF/V/IXL/I/V (SEQ ID NO: 64) sequence (Ikeda and Ohme-Takadi, (2009) *Plant Cell Physiol.* 50(5):970-975) or the less well characterised but related F/I/LXLFGQ/KN/AXI (SEQ ID NO: 65) sequence. Many ARF$^R$ MRs also contain additional LxLxL EAR-type repression domains (Hiratsu et al. (2004) *Biochem Biophys Res Commun* 321:172-178). There is a broad agreement that both BRD and EAR domains represent the interaction domains with the TPL/TPR family of co-repressor proteins (Causier et al. (2012) *Plant Physiol.* 158:423-438). In summary, the MRs of ARF$^R$ are distinguished from those of ARF$^A$ by their lower relative glutamine content and by the presence of at least one BRD or related repression domain, and often the additional presence of typical EAR domain.

The regulator of auxin signalling may be an ARF$^A$ which may be selected from ARF5, ARF6, ARF7, ARF8 and ARF19.

The regulator of auxin signalling may be an ARF$^R$ which may be selected from ARF1, ARF2, ARF3, ARF4, ARF9, ARF10, ARF11, ARF12, ARF13, ARF14, ARF15, ARF16, ARF17, ARF18, ARF20, ARF21, ARF22, ARF23.

The regulator of auxin signalling may be a modified version of an Aux/IAA transcriptional repressor. The term "Aux/IAA" encompasses any Aux/IAA that is capable of interaction with an ARF, especially an $ARF^A$, and has repressor activity, the latter which is mediated sequences in domain I of the protein (Tiwari et al., *Plant Cell*, 16: 533-543 (2004)). Aux/IAAs interact with $ARF^A$ via carboxyl terminal domains II and IV within the Aux-IAA (Kim et al., *PNAS*, 94:11786-11791 (1997); Tiwari et al., Plant cell, 15:533-543 (2003. In *Arabidopsis thaliana*, the AUX/IAA may be selected from IAA1 to IAA29 (note that in the nomenclature of the *Arabidopsis thaliana* AUX/IAA family the names IAA21, IAA22, IAA23, IAA24, IAA25 are not used).

Examples of modified versions of Aux/IAA falling within the present invention include auxin resistant3-1 (axr3-1), axr3-3, and bodenlos (bdl) (Rouse et al., (1998) *Science* 279:1371-1373; Hamann et al. (2002) *Genes Devel.* 16:1610-1615).

The regulator of auxin signalling may be TIR1 (transport inhibitor response 1) protein or AFB, for example AFB1, AFB2, AFB3, AFB4 or AFB5.

According to an aspect of the invention there is provided a plant cell the genome of which is modified by the inclusion of a nucleic acid molecule adapted for expression in a gravity sensing cell wherein the nucleic acid molecule is selected from:
  i) a nucleic acid molecule encoding a polypeptide, or part thereof, with ARF activity;
  ii) a nucleic acid molecule encoding a modified polypeptide, or part thereof, with Aux/IAA activity which modification is by the addition, deletion or substitution of at least one nucleotide characterized in that said modification provides an Aux/IAA which has increased activity when compared to a non-transgenic reference cell of the same plant species; and
  iii) a nucleic acid molecule encoding a polypeptide, or part thereof, with TIR1 or AFB activity.

As used herein "part thereof" is intended to encompass truncated versions of proteins which retain transcription activator activity or auxin receptor activity.

In a preferred embodiment of the invention the nucleic acid molecule in (i) encodes an activating ARF, for example selected from ARF5, ARF6, ARF7, ARF8 and ARF19. Preferably, the ARF is ARF7.

In a preferred embodiment of the invention the nucleic acid molecule in (ii) is modified by the addition, deletion or substitution of at least one nucleotide characterized in that said modification provides an Aux/IAA which has increased activity when compared to a non-transgenic reference cell of the same plant species.

According to an aspect of the invention there is provided a transgenic plant cell the genome of which is modified by the inclusion of a nucleic acid molecule adapted for expression in a gravity sensing cell wherein the nucleic acid molecule is selected from:
  i) a nucleic acid molecule comprising a nucleic acid sequence as represented in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5);
  ii) a nucleic acid molecule that hybridizes under stringent hybridization conditions to the nucleic acid sequence in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5); and encodes a polypeptide with ARF activity;
  iii) nucleic acid sequence represented in FIG. 2 (SEQ ID NO: 11-41) wherein said nucleic acid molecule is modified by the addition, deletion or substitution of at least one nucleotide characterized in that said modification provides a transcription regulator which has increased activity when compared to a non-transgenic reference cell of the same plant species;
  iv) a nucleic acid molecule that hybridizes under stringent hybridization conditions to the nucleic acid sequence in FIG. 2 (SEQ ID NO: 11-41) and encodes a polypeptide with Aux/IAA activity;
  v) a nucleic acid molecule comprising a nucleic acid sequence as represented in FIG. 3*a* (TIR1) (SEQ ID NO: 42), FIG. 3*b* (AFB1) (SEQ ID NO: 43), FIG. 3*c* (AFB2) (SEQ ID NO: 44), FIG. 3*d* (AFB3) (SEQ ID NO: 45), FIG. 3*e* (AFB4) (SEQ ID NO: 46) or FIG. 3*f* (AFB5) (SEQ ID NO: 47); and
  vi) a nucleic acid molecule that hybridizes under stringent hybridization conditions to the nucleic acid sequence in FIG. 3*a* (SEQ ID NO: 42), 3*b* (SEQ ID NO: 43), 3*c* (SEQ ID NO: 44), 3*d* (SEQ ID NO: 45), 3*e* (SEQ ID NO: 46) or 3*f* (SEQ ID NO: 47) and encodes a polypeptide with auxin receptor activity.

As used herein "repressor activity" refers to the effect of the Aux/IAA proteins in preventing the transcriptional activity of ARFs. By modifying the Aux/IAA polypeptides to introduce a stabilising mutation, the Aux/IAAs have no or reduced binding to ARFs thereby allowing the ARFs to resume transcriptional activity.

In a preferred aspect of the invention there is provided a transgenic plant cell the genome of which is modified by the inclusion of a nucleic acid molecule adapted for expression in a gravity sensing cell wherein the nucleic acid molecule comprises a nucleic acid sequence selected from:
  i) a nucleic acid molecule comprising a nucleic acid sequence as represented in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5); and
  ii) a nucleic acid molecule that hybridizes under stringent hybridization conditions to the nucleic acid sequence in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5) and encodes a polypeptide with (ARF) transcription factor activity.

In a preferred embodiment of the invention said nucleic acid molecule comprises a nucleic acid sequence as represented in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5).

In a preferred embodiment of the invention said nucleic acid molecule comprises a nucleic acid sequence as represented in FIG. 1*c* (SEQ ID NO: 3) or 1*e* (SEQ ID NO: 5).

In a preferred embodiment of the invention said nucleic acid molecule comprises or consists of a nucleic acid sequence as represented in FIG. 1*c* (SEQ ID NO: 3).

In a preferred embodiment of the invention said nucleic acid molecule comprises a nucleic acid sequence as represented in FIG. 1*f* (SEQ ID NO: 6), 1*g* (SEQ ID NO: 7), 1*h* (SEQ ID NO: 8), 1*i* (SEQ ID NO: 9) or 1*j* (SEQ ID NO: 10).

In a preferred aspect of the invention there is provided a plant cell the genome of which is modified by the inclusion of a nucleic acid molecule adapted for expression in a gravity sensing cell wherein the nucleic acid molecule comprises a nucleic acid sequence selected from:
  i) a nucleic acid molecule comprising a nucleic acid sequence encoding a polypeptide with $ARF^R$ activity; and ii) a nucleic acid molecule that hybridizes under stringent hybridization conditions to the nucleic acid sequence in (ii) and encodes a polypeptide with ARF$^R$ activity.

In a preferred embodiment of the invention said nucleic acid molecule comprises a nucleic acid sequence as represented in FIG. 4*a* (SEQ ID NO: 48) or 4*b* (SEQ ID NO: 49).

In a preferred aspect of the invention there is provided a transgenic plant cell the genome of which is modified by the inclusion of a nucleic acid molecule adapted for expression in a gravity sensing cell wherein the nucleic acid molecule comprises a nucleic acid sequence selected from:

i) a nucleic acid molecule comprising a nucleic acid sequence as represented in FIG. 3*a* (TIR1) (SEQ ID NO: 42), FIG. 3*b* (AFB1) (SEQ ID NO: 43), FIG. 3*c* (AFB2) (SEQ ID NO: 44), FIG. 3*d* (AFB3) (SEQ ID NO: 45), FIG. 3*e* (AFB4) (SEQ ID NO: 46) or FIG. 3*f* (AFB5) (SEQ ID NO: 47); and ii) a nucleic acid molecule that hybridizes under stringent hybridization conditions to the nucleic acid sequence in FIG. 3*a* (TIR1) (SEQ ID NO: 42), FIG. 3*b* (AFB1) (SEQ ID NO: 43), FIG. 3*c* (AFB2) (SEQ ID NO: 44), FIG. 3*d* (AFB3) (SEQ ID NO: 45), FIG. 3*e* (AFB4) (SEQ ID NO: 46) or FIG. 3*f* (AFB5) (SEQ ID NO: 47) and encodes a polypeptide with auxin receptor activity.

In a preferred embodiment of the invention said nucleic acid molecule comprises a nucleic acid sequence as represented in FIG. 3*a* (SEQ ID NO: 42).

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbour Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (allows sequences that share at least 90% identity to hybridize)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (allows sequences that share at least 80% identity to hybridize)

Hybridization: 5×-6×SSC at 65° C.–70° C. for 16-20 hours

Wash twice: 2×SSC at RT for 5-20 minutes each

Wash twice: 1×SSC at 55° C.–70° C. for 30 minutes each

Low Stringency (allows sequences that share at least 50% identity to hybridize)

Hybridization: 6×SSC at RT to 55° C. for 16-20 hours

Wash at least twice: 2×-3×SSC at RT to 55° C. for 20-30 minutes each.

The present invention also includes nucleic acid molecules that share at least 30% homology with a nucleic acid molecule of the invention. In particular, the nucleic acid molecule may have 40%, 50%, 60%, 70%, 80%, 90%, 95%, 96% 97%, 98% or 99% homology to a nucleic acid molecule of the invention.

In a preferred embodiment of the invention said transcription factor, preferably ARF, or auxin receptor, activity is increased when compared to a non-transgenic reference plant of the same species. Preferably said activity is increased by at least about 2-fold above a basal level of activity. More preferably said activity is increased by at least about 5 fold; 10 fold; 20 fold, 30 fold, 40 fold, 50 fold. Preferably said activity is increased by between at least 50 fold and 100 fold. Preferably said increase is greater than 100-fold.

In a preferred embodiment of the invention said Aux/IAA activity is increased when compared to a non-transgenic reference plant of the same species. Preferably said activity is increased by at least about 2-fold above a basal level of activity. More preferably said activity is increased by at least about 5 fold; 10 fold; 20 fold, 30 fold, 40 fold, 50 fold. Preferably said activity is increased by between at least 50 fold and 100 fold. Preferably said increase is greater than 100-fold.

It will be apparent that means to increase the activity of a polypeptide encoded by a nucleic acid molecule are known to the skilled artisan. For example, and not by limitation, increasing the gene dosage by providing a cell with multiple copies of said gene. Alternatively or in addition, a gene(s) may be placed under the control of a powerful promoter sequence or an inducible promoter sequence to elevate expression of mRNA encoded by said gene. The modulation of mRNA stability is also a mechanism used to alter the steady state levels of an mRNA molecule, typically via alteration to the 5' or 3' untranslated regions of the mRNA.

In a preferred aspect of the invention there is provided a transgenic plant cell the genome of which is modified by the inclusion of a nucleic acid molecule adapted for expression in a gravity sensing cell wherein the nucleic acid molecule comprises a nucleic acid sequence as represented in FIG. 2*a* (SEQ ID NO: 40) or FIG. 2*b* (SEQ ID NO: 41), or a nucleic acid sequence with homology to the sequence represented in FIG. 2*a* (SEQ ID NO: 40) or FIG. 2*b* (SEQ ID NO: 41) and which encodes a protein with Aux/IAA activity, wherein said nucleic acid molecule is modified by the addition, deletion or substitution of at least one nucleotide characterized in that said modification provides an Aux/IAA which has increased activity when compared to a non-transgenic reference cell of the same plant species.

Preferably the modification (or mutation) is within domain II of nucleic acid sequence encoding an Aux/IAA. Domain II is highly conserved in all plant species studied to date. The domain consists of 13 amino acids with an almost invariant VGWPP (SEQ ID NO: 61) motif (for positions 3-7 in this sequence). In *Arabidopsis thaliana* the consensus Aux/IAA domain II sequence is QVVGWPPVRSYRK (SEQ ID NO: 62). For reference, the 13 amino acid domain II of IAA17/AXR3 lies between amino acids 82-94 of the protein (nucleic acid residues 248-287 in the coding sequence (FIG. 2*b* (SEQ ID NO: 41))). For IAA12/BDL the 13 amino acid domain II lies between amino acids 69-81 of the protein (nucleic acid residues 208-247 in the coding sequence FIG. 2*a* (SEQ ID NO: 40)). The mutation may involve substitution within the VGWPP (SEQ ID NO: 61) motif of a proline residue with a non-proline residue (such as serine or leucine).

In a preferred embodiment of the invention said nucleic acid molecule is a vector adapted for transformation of said plant cell. Preferably said vector is adapted for the over expression of said nucleic acid molecule.

Suitable vectors can be constructed, containing appropriate regulatory sequences, including promoter sequences, terminator fragments, polyadenylation sequences, enhancer sequences, marker genes and other sequences as appropriate. For further details see, for example, Molecular Cloning: Laboratory Manual: $2^{nd}$ edition, Sambrook et al. 1989, Cold Spring Habor Laboratory Press or Current Protocols in Molecular Biology, Second Edition, Ausubel et al. Eds., John Wiley & Sons, 1992.

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, (e.g. bacterial), or plant cell. The vector may be a bi-functional expression vector which functions in multiple hosts. In the case of GTase genomic DNA this may contain its own promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

In a preferred embodiment of the invention the promoter is that of a gene that is expressed specifically in the gravity-sensing cells of the shoot (e.g. SCARECROW [SCR, AT3G54220; GENBANK: NM_115282 and FIG. 5 (SEQ ID NO: 50)] or related genes, the contents of which are incorporated by reference in their entirety, consisting of 2500 bp upstream of the start of the SCR gene in *Arabidopsis*.

In a preferred embodiment of the invention the promoter is that of a gene that is expressed specifically in the gravity-sensing cells of the root (e.g. the ARL2 gene [AT1G59980; GENBANK: NM_104690 and FIG. 6 (SEQ ID NO: 51)] or related genes, the contents of which are incorporated by reference in their entirety, consisting of 2441 bp upstream of the start of the ARL2 gene in *Arabidopsis*).

The invention further provides an isolated nucleic acid molecule adapted for expression in a gravity sensing cell wherein the nucleic acid molecule comprises a nucleic acid sequence encoding a protein involved in auxin signalling and a promoter that confers expression of said nucleic acid sequence in a gravity sensing cell wherein the nucleic acid sequence is selected from:

i) a nucleic acid molecule encoding an ARF;
ii) a nucleic acid sequence encoding an Aux/IAA wherein said nucleic acid molecule is modified by the addition, deletion or substitution of at least one nucleotide characterized in that said modification provides an Aux/IAA which has increased activity when compared to a non-transgenic reference cell of the same plant species; and
iii) a nucleic acid molecule encoding a TIR1 or AFB.

In one embodiment, the invention further provides an isolated nucleic acid molecule adapted for expression in a gravity sensing cell wherein the nucleic acid molecule comprises a nucleic acid sequence encoding a protein involved in auxin signalling and a promoter that confers expression of said nucleic acid sequence in a gravity sensing cell wherein the nucleic acid sequence is selected from:

i) a nucleic acid molecule comprising a nucleic acid sequence as represented in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5);
ii) a nucleic acid molecule that hybridizes under stringent hybridization conditions to the nucleic acid sequence in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5) and encodes a polypeptide with (ARF) transcription factor activity;
iii) a nucleic acid sequence represented in FIG. 2 (SEQ ID NO: 11 to 41) wherein said nucleic acid molecule is modified by the addition, deletion or substitution of at least one nucleotide characterized in that said modification provides an Aux/IAA which has increased activity when compared to a non-transgenic reference cell of the same plant species;
iv) a nucleic acid molecule that hybridizes under stringent hybridization conditions to the nucleic acid sequence in FIG. 2 (SEQ ID NO: 11 to 41) and encodes a polypeptide with Aux/IAA activity;
v) a nucleic acid molecule comprising a nucleic acid sequence as represented in FIG. 3*a* (TIR1) (SEQ ID NO: 42), FIG. 3*b* (AFB1) (SEQ ID NO: 43), FIG. 3*c* (AFB2) (SEQ ID NO: 44), FIG. 3*d* (AFB3) (SEQ ID NO: 45), FIG. 3e (AFB4) (SEQ ID NO: 46) or FIG. 3f (AFB5) (SEQ ID NO: 47); and vi) a nucleic acid molecule that hybridizes under stringent hybridization conditions to the nucleic acid sequence in FIG. 3a (TIR1) (SEQ ID NO: 42), FIG. 3b (AFB1) (SEQ ID NO: 43), FIG. 3c (AFB2) (SEQ ID NO: 44), FIG. 3d (AFB3) (SEQ ID NO: 45), FIG. 3e (AFB4) (SEQ ID NO: 46) or FIG. 3f (AFB5) (SEQ ID NO: 47) and encodes a polypeptide with auxin receptor activity.

In a preferred aspect of the invention there is provided a nucleic acid molecule comprising a transcription cassette wherein said cassette includes a nucleotide sequence designed with reference to any one of FIG. 1 (FIG. 1a (SEQ ID NO: 1), 1b (SEQ ID NO: 2), 1c (SEQ ID NO: 3), 1d (SEQ ID NO: 4) or 1e (SEQ ID NO: 5)), FIG. 2 (SEQ ID NO: 11 to 41) or FIG. 3 (FIG. 3a (TIR1) (SEQ ID NO: 42), FIG. 3b (AFB1) (SEQ ID NO: 43), FIG. 3c (AFB2) (SEQ ID NO: 44), FIG. 3d (AFB3) (SEQ ID NO: 45), FIG. 3e (AFB4) (SEQ ID NO: 46) or FIG. 3f (AFB5) (SEQ ID NO: 47)) and is adapted for expression in a gravity sensing cell by provision of at least one promoter operably linked to said nucleotide sequence such that said nucleotide sequence is expressed in a gravity sensing cell. Preferably the promoter is suited to drive expression of a nucleotide sequence in the gravity sensing cells. The promoter may comprise all or part of the nucleic acid sequence represented in FIG. 5 (SEQ ID NO: 50) or FIG. 6 (SEQ ID NO: 51).

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is an inducible promoter.

Particular of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP-A-194809).

If desired, selectable genetic markers may be included in the construct, such as those that confer selectable phenotypes such as resistance to antibodies or herbicides (e.g. kanamycin, hygromycin, phosphinotricin, chlorsulfuron, methotrexate, gentamycin, spectinomycin, imidazolinones and glyphosate).

Plants transformed with a DNA construct of the invention may be produced by standard techniques known in the art for the genetic manipulation of plants. DNA can be introduced into plant cells using any suitable technology, such as a disarmed Ti-plasmid vector carried by *Agrobacterium* exploiting its natural gene transferability (EP-A-270355, EP-A-0116718, NAR 12(22):8711-87215 (1984), Townsend et al., U.S. Pat. No. 5,563,055); particle or microprojectile bombardment (U.S. Pat. No. 5,100,792, EP-A-444882, EP-A-434616; Sanford et al, U.S. Pat. No. 4,945,050; Tomes et al. (1995) "Direct DNA Transfer into Intact Plant Cells via Microprojectile Bombardment", in Plant Cell, Tissue and Organ Culture: Fundamental Methods, ed. Gamborg and Phillips (Springer-Verlag, Berlin); and McCabe et al. (1988) Biotechnology 6: 923-926); microinjection (WO 92/09696, WO 94/00583, EP 331083, EP 175966, Green et al. 91987) Plant Tissue and Cell Culture, Academic Press, Crossway et al. (1986) Biotechniques 4:320-334); electroporation (EP 290395, WO 8706614, Riggs et al. (1986) Proc. Natl. Acad. Sci. USA 83:5602-5606; D'Halluin et al. 91992). Plant Cell 4:1495-1505 other forms of direct DNA uptake (DE 4005152, WO 9012096, U.S. Pat. No. 4,684,611, Paszkowski et al. (1984) EMBO J. 3:2717-2722); liposome-mediated DNA uptake (e.g. Freeman et al (1984) Plant Cell Physiol, 29:1353); or the vortexing method (e.g. Kindle (1990) Proc. Nat. Acad. Sci. USA 87:1228). Physical methods for the transformation of plant cells are reviewed in Oard (1991) Biotech. Adv. 9:1-11. See generally, Weissinger et al. (1988) Ann. Rev. Genet. 22:421-477; Sanford et al. (1987) Particulate Sciences and Technology 5:27-37; Christou et al. (1988) Plant Physiol. 87:671-674; McCabe et al. (1988) Bio/Technology 6:923-926; Finer and McMullen (1991) In Vitro Cell Dev. Biol. 27P:175-182; Singh et al. (1988) Theor. Appl. Genet. 96:319-324; Datta et al. (1990) Biotechnology 8:736-740; Klein et al. (1988) Proc. Natl. Acad. Sci. USA 85: 4305-4309; Klein et al. (1988) Biotechnology 6:559-563; Tomes, U.S. Pat. No. 5,240,855; Buising et al. U.S. Pat. Nos. 5,322,783 and 5,324,646; Klein et al. (1988) Plant Physiol 91: 440-444; Fromm et al (1990) Biotechnology 8:833-839; Hooykaas-Von Slogteren et al. 91984). Nature (London) 311:763-764; Bytebier et al. (1987) Proc. Natl. Acad. Sci. USA 84:5345-5349; De Wet et al. (1985) in The Experimental Manipulation of Ovule Tissues ed. Chapman et al. (Longman, New York), pp. 197-209; Kaeppler et al. (1990) Plant Cell Reports 9:415-418 and Kaeppler et al. (1992) Theor. Appl. Genet. 84:560-566; Li et al. (1993) Plant Cell Reports 12: 250-255 and Christou and Ford (1995) Annals of Botany 75: 407-413; Osjoda et al. (1996) Nature Biotechnology 14:745-750, all of which are herein incorporated by reference.

*Agrobacterium* transformation is widely used by those skilled in the art to transform dicotyledonous species. Recently, there has been substantial progress towards the routine production of stable, fertile transgenic plants in almost all economically relevant monocot plants (Toriyama et al. (1988) Bio/Technology 6: 1072-1074; Zhang et al. (1988) Plant Cell rep. 7379-384; Zhang et al. (1988) Theor. Appl. Genet. 76:835-840; Shimamoto et al. (1989) Nature 338:274-276; Datta et al. (1990) Bio/Technology 8: 736-740; Christou et al. (1991) Bio/Technology 9:957-962; Peng et al (1991) International Rice Research Institute, Manila, Philippines, pp. 563-574; Cao et al. (1992) Plant Cell Rep. 11: 585-591; Li et al. (1993) Plant Cell Rep. 12: 250-255; Rathore et al. (1993) Plant Mol. Biol. 21:871-884; Fromm et al (1990) Bio/Technology 8:833-839; Gordon Kamm et al. (1990) Plant Cell 2:603-618; D'Halluin et al. (1992) Plant Cell 4:1495-1505; Walters et al. (1992) Plant Mol. Biol. 18:189-200; Koziel et al. (1993). Biotechnology 11194-200; Vasil, I. K. (1994) Plant Mol. Biol. 25:925-937; Weeks et al (1993) Plant Physiol. 102:1077-1084; Somers et al. (1992) Bio/Technology 10:1589-1594; WO 92/14828). In particular, *Agrobacterium* mediated transformation is now emerging also as a highly efficient transformation method in monocots. (Hiei, et al. (1994) The Plant Journal 6:271-282). See also, Shimamoto, K. (1994) Current Opinion in Biotechnology 5:158-162; Vasil, et al. (1992) Bio/Technology 10:667-674; Vain, et al. (1995) Biotechnology Advances 13(4):653-671; Vasil, et al. (1996) Nature Biotechnology 14: 702).

Microprojectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium*-coated microparticles (EP-A-486234) or microprojectile bombardment to induce wounding followed by co-cultivation with *Agrobacterium* (EP-A-486233).

According to a further aspect of the invention there is provided a plant comprising a plant cell according to the invention. Preferably the plant is a transgenic plant comprising a transgenic plant cell according to the invention.

In a preferred embodiment of the invention said plant is selected from the group consisting of: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolor, Sorghum vulgare*), squash (*Curcurbita* spp.), tomato (*Solanum lycopersicum*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Iopmoea batatus*), cassava (*Manihot esculenta*), coffee (*Cofea* spp.), switchgrass (*Panicum virgatum*), elephant grass (*Miscanthus giganteus*), coconut (*Cocos nucifera*), pineapple (*Anana comosus*), citris tree (*Citrus* spp.) cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats (*Avena sativa*), barley (*Hordeum vulgare*), vegetables.

Grain plants that provide seeds of interest include oil-seed plants and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava been, lentils, chickpea, etc.

Important crops are oil-seed rape (canola), wheat, rice, maize, soybean and cotton. Preferably said crop is oil seed rape (canola).

According to a yet further aspect of the invention there is provided a seed obtained from a plant according to the invention.

According to a further aspect of the invention there is provided a method to manipulate the angle of growth of a plant root and/or shoot comprising:
i) providing a plant cell a the genome of which is modified by the inclusion of a nucleic acid molecule adapted for expression in a gravity sensing cell wherein the nucleic acid molecule comprises a nucleic acid sequence selected from:
  i) a nucleic acid molecule encoding an ARF;
  ii) a nucleic acid sequence encoding a modified Aux/IAA wherein said nucleic acid molecule is modified by the addition, deletion or substitution of at least one nucleotide characterized in that said modification provides an Aux/IAA which has increased activity when compared to a non-transgenic reference cell of the same plant species; and
  iii) a nucleic acid molecule encoding a TIR1 or AFB;
ii) cultivating said cell to produce a plant; and optionally
iii) harvesting said plant or part thereof In an embodiment of the invention there is provided a method to manipulate the angle of growth of a plant root and/or shoot comprising:
i) providing a plant cell the genome of which is modified by the inclusion of a nucleic acid molecule adapted for expression in a gravity sensing cell wherein the nucleic acid molecule comprises a nucleic acid sequence selected from:
  i) a nucleic acid molecule comprising a nucleic acid sequence as represented in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5);
  ii) a nucleic acid molecule that hybridizes under stringent hybridization conditions to the nucleic acid sequence in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5) and encodes a polypeptide with ARF activity;
  iii) a nucleic acid sequence represented in FIG. 2 (SEQ ID NO: 11 to 41) wherein said nucleic acid molecule is modified by the addition, deletion or substitution of at least one nucleotide characterized in that said modification provides an Aux/IAA which has increased activity when compared to a non-transgenic reference cell of the same plant species;
  iv) a nucleic acid molecule that hybridizes under stringent hybridization conditions to the nucleic acid sequence in FIG. 2 (SEQ ID NO: 11 to 41) and encodes a polypeptide with Aux/IAA activity;
  v) a nucleic acid molecule comprising a nucleic acid sequence as represented in
    FIG. 3*a* (TIR1) (SEQ ID NO: 42), FIG. 3*b* (AFB1) (SEQ ID NO: 43), FIG. 3*c* (AFB2) (SEQ ID NO: 44), FIG. 3*d* (AFB3) (SEQ ID NO: 45), FIG. 3*e* (AFB4) (SEQ ID NO: 46) or FIG. 3*f* (AFB5) (SEQ ID NO: 47); and
  vi) a nucleic acid molecule that hybridizes under stringent hybridization conditions to the nucleic acid sequence in FIG. 3*a* (TIR1) (SEQ ID NO: 42), FIG. 3*b* (AFB1) (SEQ ID NO: 43), FIG. 3*c* (AFB2) (SEQ ID NO: 44), FIG. 3*d* (AFB3) (SEQ ID NO: 45), FIG. 3*e* (AFB4) (SEQ ID NO: 46) or FIG. 3*f* (AFB5) (SEQ ID NO: 47) and encodes a polypeptide with auxin receptor activity;
ii) cultivating said cell to produce a plant; and optionally
iii) harvesting said plant or part thereof.

In a preferred embodiment of the invention there is provided a method for increasing the vertical growth of a plant shoot when compared to the shoot of a non-modified reference plant of the same species comprising providing a plant cell the genome of which is modified by the inclusion of a nucleic acid molecule adapted for expression in a gravity sensing cell wherein the nucleic acid molecule comprises a nucleic acid molecule comprising a nucleic acid sequence as represented in FIG. 1*c* (SEQ ID NO: 3), or a nucleic acid sequence with homology to the sequence represented in FIG. 1*c* (SEQ ID NO: 3) and which encodes a protein with ARF activity.

In a preferred embodiment of the invention there is provided a method for reducing the vertical growth of a plant shoot when compared to the shoot of a non-modified reference plant of the same species comprising providing a plant cell the genome of which is modified by the inclusion of a nucleic acid molecule adapted for expression in a gravity sensing cell wherein said nucleic acid molecule comprises a nucleic acid sequence represented in FIG. 2 (SEQ ID NO: 11 to 41), or a nucleic acid sequence with homology to the sequence represented in FIG. 2 (SEQ ID NO: 11 to 41), for example FIG. 2*a* (SEQ ID NO: 40), and which encodes a protein with Aux/IAA activity, and wherein said nucleic acid molecule is modified by the addition, deletion or substitution of at least one nucleotide characterized in that said modification provides an Aux/IAA which has increased activity when compared to a non-transgenic reference cell of the same plant species.

In a preferred embodiment of the invention there is provided a method for increasing the vertical growth of a plant root when compared to the root of a non-modified reference plant of the same species comprising providing a plant cell the genome of which is modified by the inclusion of a nucleic acid molecule adapted for expression in a gravity sensing cell wherein said nucleic acid molecule comprises a nucleic acid sequence represented in FIG. 2 (SEQ ID NO: 11 to 41), or a nucleic acid sequence with homology to the sequence represented in FIG. 2 (SEQ ID NO: 11 to 41), for example FIG. 2*b* (SEQ ID NO: 41), which encodes a protein with Aux/IAA activity, and wherein said nucleic acid molecule is modified by the addition, deletion or substitution of at least one nucleotide characterized in that said modification provides an Aux/IAA which has increased activity when compared to a non-transgenic reference cell of the same plant species.

In a preferred embodiment of the invention there is provided a method for reducing the vertical growth of a plant root when compared to the root of a non-modified reference plant of the same species comprising providing a plant cell the genome of which is modified by the inclusion of a nucleic acid molecule adapted for expression in a gravity sensing cell wherein the nucleic acid molecule comprises a nucleic acid molecule comprising a nucleic acid sequence as represented in FIG. 1*c* (SEQ ID NO: 3) or a nucleic acid sequence with homology to the sequence represented in FIG. 1*c* (SEQ ID NO: 3) and which encodes a protein with ARF activity.

Mutagenesis as a means in induce phenotypic changes in organisms is well known in the art and includes but is not limited to the use of mutagenic agents such as chemical mutagens [e.g. base analogues, deaminating agents, DNA intercalating agents, alkylating agents, transposons, bromine, sodium azide] and physical mutagens [e.g. ionizing radiation, psoralen exposure combined with UV irradiation].

According to a further aspect of the invention there is provided a method to produce a plant variety that has increased expression of an ARF comprising the steps of:
  i) mutagenesis of wild-type seed from a plant that does express said ARF;
  ii) cultivation of the seed in i) to produce first and subsequent generations of plants;
  iii) obtaining seed from the first generation plant subsequent generations of plants;
  iv) determining if the seed from said first and subsequent generations of plants has increased expression of said ARF;
  v) obtaining a sample and analysing the nucleic acid sequence of a nucleic acid molecule selected from the group consisting of:
    a) a nucleic acid molecule comprising a nucleic acid sequence as represented in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5);
    b) a nucleic acid molecule that hybridises to the nucleic acid molecule in a) under stringent hybridisation conditions and that encodes a polypeptide with transcription factor activity; and optionally
  vi) comparing the sequence of the nucleic acid molecule in said sample to a nucleic acid sequence of a nucleic acid molecule of a plant that has increased expression of said ARF.

In a preferred method of the invention said nucleic acid molecule is analysed by a method comprising the steps of:
  i) extracting nucleic acid from said mutated plants;
  ii) amplification of a part of said nucleic acid molecule by a polymerase chain reaction;
  iii) forming a preparation comprising the amplified nucleic acid and nucleic acid extracted from wild-type seed to form heteroduplex nucleic acid;
  iv) incubating said preparation with a single stranded nuclease that cuts at a region of heteroduplex nucleic acid to identify the mismatch in said heteroduplex; and
  v) determining the site of the mismatch in said nucleic acid heteroduplex.

In a preferred method of the invention said plant variety has increased expression of ARF 7 and/or ARF19.

According to a further aspect of the invention there is provided a plant obtained by the method according to the invention wherein said plant is modified wherein said modification is transformation with a nucleic acid molecule encoding an ARF wherein said nucleic acid molecule is operably linked to a promoter that controls expression of said nucleic acid molecule in a gravity sensing cell.

According to an aspect of the invention there is provided an isolated nucleic acid molecule that encodes an ARF wherein said nucleic acid molecule comprises or consists of a nucleotide sequence selected from the group consisting of:
  i) a nucleotide sequence as represented by the sequence in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5);
  ii) a nucleotide sequence wherein said sequence is degenerate as a result of the genetic code to the nucleotide sequence defined in (i); and
  iii) a nucleic acid molecule the complementary strand of which hybridizes under stringent hybridization conditions to the sequence in FIG. 1*a* (SEQ ID NO: 1), 1*b* (SEQ ID NO: 2), 1*c* (SEQ ID NO: 3), 1*d* (SEQ ID NO: 4) or 1*e* (SEQ ID NO: 5) wherein said nucleic acid molecule encodes an ARF.

Preferably the nucleotide sequence is represented by the sequence in FIG. 1*c* (SEQ ID NO: 3) or 1*e* (SEQ ID NO: 5).

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIGS. 1*a* to *e* are the truncated nucleic acid sequences of ARF 5 (1*a*), 6 (1*b*), 7 (1*c*), 8 (1*d*) and 19 (1*e*); truncations are as shown in Table 1;

FIGS. 1*f* to *j* are the nucleic acid sequences of full length ARF 5 (1*f*), 6 (1*g*), 7 (1*h*), 8 (1*i*) and 19 (1*j*);

FIG. 2*i* to xxix list the nucleic acid sequences of IAA 1 to 20 and 26 to 34 respectively; (a) is the nucleic acid sequence of IAA12/BDL which contains a stabilising mutation at position 74 within the conserved domain II; (b) the nucleic acid sequence of IAA17/AXR3 which contains a stabilising mutation at position 88 within the conserved domain II;

FIG. 3*a* is the nucleic acid sequence of TIR1;

FIGS. 3b to f are the nucleic acid sequences of AFB1 (3b), AFB2 (3c), AFB3 (3d), AFB4 (3e) and AFB5 (3f);

FIG. 4a is the nucleic acid sequence of ARF 10;

FIG. 4b is the nucleic acid sequence of ARF 16;

FIG. 5 is the nucleic acid sequence of the promoter of the SCARECROW gene (SEQ ID NO: 50);

FIG. 6 is the nucleic acid sequence of the promoter of the ARL2 gene (SEQ ID NO: 51);

FIG. 7 is a table showing the alignment of the ARF sequences in Arabidopsis; percentage identity matrix for the activating ARF (ARF$^A$) protein family in Arabidopsis thaliana. Values range from 39.44% to 63.32% (amino acid identity);

FIG. 8 is a table showing the alignment of the ARF sequences in Arabidopsis; percentage identity matrix for the TIR1/AFB protein family in Arabidopsis thaliana. Values range from 47.54% to 86.43%;

FIG. 9A to I Gravitropic Setpoint Angle (GSA) and the anti-gravitropic offset; (A) Typical GSA profiles of A. thaliana (Col. 0) shoot and root branches with diagram of GSA designations.

(B and C) Changes in the GSA of Arabidopsis and pea subapical branches after removal of the shoot apex and application of 1 mM IAA or mock treatment to the apical stump (white arrowheads, decapitated apices; gray arrowheads, subapical lateral branches) (B). Quantitative analysis of branch GSA is shown ($p<0.05$; error bars indicate the SEM) (C).

(D, E, G, and H) Effect of horizontal clinorotation on lateral shoot (D and E) and lateral root (G and H) GSA. Note: for clinorotated plants, a nominal GSA was derived by measurement of the growth angle of the final 5 mm of cauline branches and 2 mm of lateral roots with respect to the vertical in upright plants. White and grey lines represent the action of gravitropic and antigravitropic growth components, respectively. Lateral shoot GSA (E) and lateral root GSA (H) in wild-type and ein2-1 mutant plants are shown.

(F and I) Effect of local application of the auxin transport inhibitor NPA and subsequent clinorotation on lateral shoot (F) and lateral root GSA (I).

Clinorotation at 4 rph (D-F) and 1 rpm (G-I). Scale bars represent 1 cm (D) and 0.5 cm (G). Error bars indicate the SEM.

FIG. 10A to K Lateral branch GSA phenotypes of auxin signalling mutants; Changes in (FIG. 10A) lateral shoot GSA and (FIG. 10B) lateral root GSA induced by loss-of-function mutations affecting the AFB4 and AFB5 auxin receptors: afb4-2 and afb4-2 afb5-5 double mutant. The afb4-2 afb5-5 double mutant [26] has a significantly less vertical cauline branch and lateral root GSA, while afb4-2 single mutants are not significantly different from wild-type. Although we cannot rule out possible redundancy between AFB4 and AFB5 in this analysis, these data suggest that at the very least, AFB5 does contribute to GSA control (FIG. 10C,D) GSA phenotypes of mutants with altered auxin levels (wild-type Col-0, yucca1-1d and yuc1D auxin overproducing mutants and wei8 tar2 auxin deficient biosynthesis mutants). Lateral shoot GSA (FIG. 10C) and lateral root GSA (FIG. 10D). GSA recorded for successive 0.8 mm segments in the root and 0.5 cm segments in the shoot (mean of 12-15 lateral roots or shoots, one way ANOVA, $p<0.05$ for FIG. 10C and data points 5-10 in FIG. 10D). (FIG. 10E) Comparison of changes in lateral shoot GSA between wild-type plants and the arf10-3 arf16-2 and the arf10-3 arf16-2 axr3-10 double and triple mutants (mean of 12-15 roots, one-way ANOVA, $p<0.05$). (FIG. 10F) Effects on lateral root GSA of growth on media containing 10 nM IAA or 10 nM 2,4-D (mean of 12-15 lateral roots, one-way ANOVA, $p<0.05$, data points 6-10). (FIG. 10G) Comparison of changes in lateral shoot GSA in the tir1-1 and nph4-1 arf19-1 mutants (mean of 12-15 lateral roots, one-way ANOVA, $p<0.05$). (FIG. 10H) The effect of auxin treatment on lateral root GSA in bean and crown root GSA in rice ($p<0.05$, Student's t-test, n=15-20). (FIG. 10I) Changes in the GSA of nph4-1 arf19-1 sub-apical branches after removal of the shoot apex and application of 1 mM IAA or mock treatment to the apical stump (12-15 lateral shoots, Student's t-test, $p<0.05$). (FIG. 10J,K) Comparison of changes in lateral root GSA between wild-type plants and the axr3-10, arf7-201 (FIG. 10J) and nph4-1 arf19-1 (FIG. 10K) mutants (mean of 12-15 lateral roots, one way ANOVA (FIG. 10J), Student's t-test (FIG. 10K), $p<0.05$, data points 2-10). Error bars: s.e.m. Scale bar=1 cm.

FIG. 11 A to D Auxin specifies shoot and root branch GSA by regulating the magnitude of the anti-gravitropic offset component. Auxin specifies shoot and root branch GSA by regulating the magnitude of the anti-gravitropic offset component. (FIG. 11A,B) Lateral branch GSA before and after re-orientation by 45° in wild-type and auxin response mutants. (A) Lateral shoot GSA measured using the final 0.5 mm segment of 5-6 cm long lateral shoots or (B) the final 0.2 mm segment of 2-4 mm long lateral roots. (C,D) Comparison of the changes in lateral shoot GSA (C) and lateral root GSA (D) following clinorotation (4 rph shoots/1 rpm roots, 8 hours) in the auxin response mutants: (C) nph4-1 arf19-1 and arf10-3 arf16-2 (wild-type Col. 0 in main FIG. 3A); (D) wild-type Ler and axr3-10 plants. Error bars: s.e.m. Scale bars=1 cm (C) and 0.5 cm (D).

FIGS. 12A and B: Auxin specifies GSA within the gravity-sensing cells of the root and shoot; Induction of a mutated, stabilised form of IAA12/BDL in the gravity-sensing cells of the shoot (SCR::bdl:GR) causes branches to grow at an extreme non-vertical GSA. This phenotype is lost 72 hours after the cessation of dexamethasone treatment. (B) Reversion of the lateral shoot GSA phenotype three days after the last DEX treatment. Scale bar=1 cm.

FIG. 13 (A) Representative mock and DEX treated SCR::TIR1:GR plants (B) Quantification of GSA from an average of 10 lateral branches showing a more vertical GSA phenotype in DEX treated plants. Bars represent standard error.

DETAILED DESCRIPTION

Analysis of Gravitropic Setpoint Angle (GSA) and the Anti-Gravitropic Offset

Materials and Methods

Plant Material and Tissue Culture Growth Conditions.

Arabidopsis thaliana ecotypes Col-0 and Ler were used in this study. The mutant lines yucca1-1d, yuc1D, wei8 tart, tir1-1, afb4-2, afb4-2 afb5-5, arf7-201, nph4-1 arf19-1, arf10-3 arf16-2, axr3-10, ein2-1 and SCR::bdl have been described previously. Because of the critical importance of the ethylene insensitivity to the interpretation of clinostat studies, ein2-1 was verified as ethylene resistant by assaying growth on 1 μM ACC (data not shown). The arf10-3 arf16-2 axr3-10 triple mutant was generated by crossing, while the SCR::bdl:GR and SCR::ARF7:GR transgenic lines were constructed for this study (see below). The enhancer trap lines J1092 and M0013 were obtained from the Nottingham Arabidopsis Stock Centre. The seeds were surface sterilised using chlorine gas (produced by a mixture of 100 ml bleach and 3 ml conc. HCl) for three hours in a desiccator. Seeds were placed on round 9 cm petri dishes containing sterile ATS medium (5 mM $KNO_3$, 2.5 mM $KH_2PO_4$ (pH 5.5), 2 mM MgSO$_4$, 2 mM Ca(NO$_3$)$_2$, 50 µM Fe-EDTA, 70 µM H$_3$BO$_3$, 14 µM MnCl$_2$, 0.5 µM CuSO$_4$, 1 µM ZnSO$_4$, 0.2 µM NaMoO$_4$, 10 µM NaCl, 0.01 µM CoCl$_2$, 1% sucrose, 0.8% agar) and stratified for three days. The plates were then incubated vertically in a plant growth room (20-22° C., 16 h day). Five days post-germination, seedlings were transferred to 120 mm square petri plates containing 50 ml of ATS medium. These plates were incubated vertically in a plant growth room with growth conditions as described above for a further seven days.

Hormone and Auxin Transport Inhibitor Treatments

For hormone treatments, five day old seedlings growing on ATS medium in 9 cm petri dishes were transferred to 120 mm square petri dishes containing 50 ml sterile ATS medium with 50 nM IAA, 50 nM 2,4-D or no auxin. 100 µM hormone stock solutions were made up in 70% ethanol. The plates were incubated vertically and seedlings were allowed to grow for a further 12 days prior to analysis. For root NPA treatments, ten day old Wt Col-0 seedlings growing on ATS medium on 9 cm petri dishes were transferred to fresh ATS medium containing either 0.2 or 1 µM NPA. The seedlings were left to grow on the NPA plates for 4 hours and scanned just before being clinorotated at 1 rpm for 8 hours. The plates were then scanned again and changes in GSA were measured using imageJ. For shoot NPA treatments, NPA was mixed with lanolin to a final concentration of 10 µM and applied along the length of the lateral branch of intact plants using a fine needle. The plants were left in the glasshouse for 2 hours and photographed before being clinorotated for 8 hours at 4 rph. For rice and bean auxin treatments, seeds were germinated on moist filter paper in petri dishes and transferred to 'Cyg' seed germination pouches (Minnesota, USA) containing 50 ml of liquid medium [S1] with/without 50 nM IAA. Plants were allowed to grow for seven days before being photographed.

Image Analysis and Lateral Root GSA Measurements

For root and angle measurements, 12 day old seedlings growing on 120 mm square petri plates were scanned using an HP Scanjet G4050 photo scanner and the images obtained were analysed using ImageJ. Each lateral root analysed was divided into 0.8 mm segments and the GSA of each segment was measured with reference to the gravity vector. For clinorotation and reorientation experiments the angle of growth with respect to the vertical of the final 2 mm section of lateral root was recorded. The data were statistically evaluated using the Wilkes-Shapiro and Kolmogorov-Shapiro tests for normality followed by a paired t-test or one-way ANOVA. A p value of <0.05 was used in all statistical tests.

Analysis of Shoot GSA

To analyse lateral shoot GSA, seeds of WT Col-0, yucca1-1D, wei8 tar2, tir1-1, nph4-1 arf19-1, arf10-3 arf16-2 axr3-10, SCR::bdl and SCR::bdl:GR lines were sown in small 5 cm pots containing compost which were stratified for 48 hours to promote uniform germination. After germination, seedlings were transplanted to individual square pots and allowed to grow for 28 days in the greenhouse at a photoperiod of 16 h day and 8 h darkness at 20+2° C. Photographs of individual branches were taken using a digital camera and the GSA of individual lateral branches was measured using ImageJ. Each shoot was divided into 0.5 cm segments and the GSA of each segment was measured with reference to the gravity vector. For clinorotation and reorientation experiments the angle of growth with respect to the vertical of the final 0.5 cm section of cauline branch was recorded. The data were evaluated using the statistical tests described above.

Decapitation Experiments

For measuring changes in GSA in response to decapitation, the apical branch was decapitated in 28-day-old plants. For auxin treatments, IAA was mixed with lanolin to a final concentration of 1 mM and was applied carefully to the tip of decapitated shoots using a fine needle. The decapitated plants were left to grow for a further five days prior to being photographed and analysed as described above. For pea experiments, seeds were sown in individual pots and stratified for 24 hours. 21-day-old plants were then decapitated and treated with auxin as described above.

Clinostat Experiments

For clinorotation studies in lateral roots and shoots, either 10 day old seedlings growing on 9 cm round petri dishes or 28-day-old intact or decapitated plants growing individually in square pots were placed on a 1-D clinostat in an orientation parallel to the axis of rotation. For clinorotation at 4 rph a Mikrops Electric Clinostat (Flatters & Garnett, Manchester, UK) was used. For clinorotation at speeds between 0.5 and 5 rpm clinostats were constructed using geared, variable speed electric motors. In order to minimise effects of plant movement during clinorotation (i.e. flopping), thin stakes were inserted to support the primary shoot along the axis of rotation. The plates or plants were subjected to horizontal or vertical clinorotation gravistimulation for 8 hours at a speed of 1 rpm or 4 rph. For lateral roots, the plates were scanned while lateral shoots were photographed prior to analysis using ImageJ. The final GSA of each lateral organ was measured with reference to the gravity vector.

Generation of SCR::ARF7:GR and SCR::Bdl:GR Transgenic Plants

The SCR::ARF7:GR and SCR::bdl:GR constructs were generated using 2-fragments MultiSite Gateway Pro technology (Invitrogen). A 2.5 Kb SCR promoter fragment was amplified from *arabidopsis* genomic DNA using Gateway primers with B1 and B5r extensions (B1pSCR: 5'-GGGGA-CAAGTTTGTACAAAAAAGCAGGCTAAT TTTGAATC-CATTCTCAAAG CTTTGC-3' (SEQ ID NO: 53) and pSCRB5r: 5'-GGGGACAACTTTTGTA TACAAAGTTG TGGAGATTGAAGGGTTGTTGGTCGTG-3' (SEQ ID NO: 54)). The NPH4/ARF7 and bdl mutant genes were amplified respectively from *arabidopsis* WT and bdl mutant cDNA using primers with B5 and B2 extensions. (B5KARF7: 5'-GGGGACAACTTTG TATACAAAAGTT-GAACAATGAAAGCT CCTTCATCAAATGG-3' (SEQ ID NO: 55), and ARF7B2: 5'-GGGG ACCACTTTGTA-CAAGAAAGCTGGGTCCCGGTTAAACGAAGTG-
GCTG-3' (SEQ ID NO: 56), B5Kbdl: 5'-GGGGA-CAACTTTGTATACAAAAAGTTGAACAATGCGTG-
GTGTGTC AGAATTG GAGG-3' (SEQ ID NO. 57) and bdlB2: 5'-GGGGACCACTTTGTACAAGAAAGCTGGG TCAACAGGGTTGTTTCTTTGTCT ATCCTTCTGC-3' (SEQ ID NO 58)). Following BP reactions the SCR promoter was cloned into pDONR 221 P1-P5r, while ARF7 and bdl were cloned into pDONR 221 P5-P2. The final binary vectors were assembled using 2-fragments LR reactions into a modified pFP100 vector containing the GR fragment and the NOS terminator. Constructs were transformed into *Agrobacterium* strain GV3101. WT Col-0 plants were transformed using the *Agrobacterium* floral dipping method.

Results:

*Arabidopsis* lateral branches are actively maintained at specific angles with respect to gravity (their GSA). To study the regulation of lateral branch GSA we used *arabidopsis* cauline branches and first-order lateral roots as model lateral shoot and root organs. In the ecotypes we examined (Col. 0 and Ler), newly emerged cauline branches begin growth at a very shallow GSA)(120°-130°) that becomes increasingly, although never entirely, vertical (FIG. 9A). Similarly, newly emerged lateral roots (<0.5 mm) have a very shallow GSA) (60°-70°) that becomes progressively more vertical as the lateral root grows out (FIG. 9A). Following reorientation, lateral roots and lateral shoots of a range of lengths undergo anisotropic growth to return to, or close to, their original GSA. In the root this bending growth is confined to the short elongation zone just behind the root apex while in the shoot branches, anisotropic growth along the youngest 2.5-3.5 cm of the branch can contribute to the reorientation of the organ. In these experiments the angle of the final 0.5 cm section of cauline branches and the final 2 mm section of lateral roots was recorded. In these experiments, lateral organs were displaced both above and below their GSA by 45° meaning that some lateral roots must grow up, and some cauline branches move down to reacquire their GSA (FIG. 9 A,C insets). Because in most cases this reorientation would not cause major displacements of statoliths to the opposite face of the statocyte, this indicates the existence of a mechanism to drive growth in the opposite direction to gravitropic response (white and black arrows: gravity vector; grey arrow: direction of GSA reorientation). It also confirms that the observed non-vertical GSAs of lateral branches cannot be attributed to partial or reduced gravitropic capacity compared to the primary axis. These data form an important baseline for the work presented here and confirm that at all points in the development of the lateral branches upon which the study is based, the angle of growth with respect to gravity is being monitored and maintained. The mean lateral shoot GSA (FIG. 9B) and lateral root GSA (FIG. 9D) for branches of increasing ages (defined as branch length size classes) before and after 45° plant re-orientation. (FIG. 9E,F) Quantitative changes in lateral shoot GSA and lateral root GSA following clinorotation of branches either on or off the axis of rotation. (FIG. 9G) Placing primary shoots and roots at an angle to the axis of rotation does not alter their direction of growth under horizontal clinorotation at the speeds used for the experiments here (4 rph-1 rpm for shoots, 0.5-1 rpm for roots); at higher rpm (5-60 rpm) random changes in the direction of growth of the primary root can sometimes be observed and hence were avoided for our experiments (data not shown). N.B. Vertical clinorotation at speeds from 4 rph to 5 rpm does not affect GSA in *arabidopsis* cauline branches and lateral roots (data not shown) (FIG. 9H,I). The ethylene insensitive mutant ein2-1 shows similar responses to wild-type plants upon horizontal clinorotation: lateral shoot GSA (4 rph, 8 hours) (FIG. 9H), lateral root GSA (1 rpm, 8 hours) (FIG. 9I) Error bars: s.e.m. (FIG. 9B,D). Scale bars=1 cm (FIG. 9A,E, G left panel, H) and 0.5 cm (FIG. 9B,F, G right panel, I).

See also Figure legends to FIGS. 10 to 12.

Manipulation of Lateral Branch Growth Angles

The Methodology

The invention is implemented in the chosen target plant species using a common, generic methodology: wild-type or modified versions of auxin signalling components from the ARF, Aux/IAA, and TIR1/AFB protein families are incorporated into plant expression vectors such that they are placed downstream of a gene promoter that drives expression in the gravity-sensing cells of the root or shoot. These constructs are then used, with a suitable plant transformation protocol, to generate stable, homozygous transgenic plants. Specific changes to either more vertical or less vertical growth angles are determined by the nature of the auxin signalling effector whose expression is targeted to the gravity-sensing cells. For example:

the expression of the *Arabidopsis thaliana* gene ARF7 (*Arabidopsis* Genome Initiative number: AT5g20730; GEN-BANK: NM_122080) or related genes in the gravity-sensing cells of the shoot induces more vertical growth.

the expression of a mutated, stabilised version of the *Arabidopsis thaliana* gene BDL/IAA12 (bdl; AT1G04550;) or mutated versions of related genes in the gravity-sensing cells of the shoot induces less vertical growth.

the expression of a mutated, stabilised version of the *Arabidopsis thaliana* gene AXR3/IAA17 (axr3-1 or axr3-3; AT1G04250; GENBANK: NM_100306) or mutated versions of related genes in the gravity-sensing cells of the root induces more vertical growth.

the expression of the *Arabidopsis thaliana* gene ARF7 (AT5g20730; GENBANK: NM_122080) or related genes in the gravity-sensing cells of the root induces less vertical growth.

Further details are set out below with specific examples of the implementation:

Modulation of Lateral Root and Shoot Branching Angles Using Activating ARF$^A$ Polypeptide and Related Sequences:

Modulation of Shoot Angle:

A method of inducing a more vertical root GSA phenotype in shoot lateral branches comprises the incorporation of a heterologous nucleic acid sequence that alters the expression levels of an activating ARF or related gene in the gravity-sensing cells by means of transformation and regenerating the plant from one or more transformed cells.

The full (or truncated/ARF-DCA* [see FIG. 1 and Table 1 below for gene sequences of truncated/ARF-DCA genes]) gene sequence coding for activating ARFs (sequences shown in FIG. 1) and related polypeptides may be amplified from genomic or cDNA of a plant species using appropriate primer sequences. The promoter sequence of a gene that is expressed specifically in the gravity-sensing cells of the shoot (e.g. SCARECROW [SCR, AT3G54220; GENBANK: NM_115282] (FIG. 5) (SEQ ID NO: 50) or related genes, consisting of 2500 bp upstream of the start of the SCR gene in *Arabidopsis*) is similarly amplified from the genomic or cDNA of the target plant species. Using conventional or GATEWAY cloning techniques the SCR or related promoter is placed upstream of the activating ARF sequence in a suitable binary plant transformation vector. Using a plant transformation technique appropriate for the desired species such as floral dipping, *Agrobacterium* mediated co-cultivation, microprojectile or particle bombardment the binary vector containing the SCR and activating ARF gene sequences are introduced into the plant cell(s). Plants or cells used for transformation preferably lack mutations in activating ARF gene sequences and may for example, be wild type. Following transformation the transgenic plants are regenerated e.g. from seed, single cells, callus tissue or leaf discs as is standard for the said species. The angle of shoot branches is compared to control plants in which the expression of the activating ARF related polypeptide is not increased in the shoot gravity-sensing cells.

Note on the use of truncated ARF$^4$/ARF-DCA (DCA=dominant constitutive activation) genes. Because Aux/IAA repressor proteins interact with ARF$^A$ proteins via the carboxyl-terminal domains III and IV common to both protein families, the truncation of domains III and IV from the ARF$^A$ increases its capacity for transcriptional activation (see 35S::ARF7-DCA supporting data). Thus, ARF-DCA is deployed in place of the cognate full-length ARF gene in the approaches described here in order to enhance the effects on root and shoot branch growth angle.

Induced expression or activity of an activating ARF related polypeptide at a specific stage of plant development is achieved by the addition of an additional regulatory or inducible element such as the glucocorticoid receptor (GR) sequence upstream or downstream of the activating ARF related polypeptide sequence within the plant binary vector used for transformation.

Modulation of Root Angle:

The full (or truncated) gene sequence coding for activating ARFs and related polypeptides is amplified from genomic or cDNA of a plant species using appropriate primer sequences. The promoter sequence of a gene that is expressed specifically in the gravity-sensing cells of the root (e.g. the ARL2 gene [AT1G59980; GENBANK: NM_104690] (FIG. 6) (SEQ ID NO: 51) or related genes, consisting of 2441 bp upstream of the start of the ARL2 gene in *Arabidopsis*) is similarly amplified from the genomic or cDNA of the appropriate plant species. Using conventional or GATEWAY cloning techniques the ARL2 or related promoter is placed upstream of the activating ARF sequence in a suitable binary plant transformation vector. Using a plant transformation technique appropriate for the desired species such as floral dipping, *Agrobacterium* mediated co-cultivation, microprojectile or particle bombardment, the binary vector containing the ARL2 or related promoter and activating ARF gene sequences is introduced into the plant cell(s). Plants or cells used for transformation preferably lack mutations in activating ARF gene sequences and are for example, be wild type. Following transformation the transgenic plants are regenerated e.g. from seed, single cells, callus tissue or leaf discs as is standard for the said species. The angle of root branches are compared to control plants in which the expression of the activating ARF related polypeptide is not increased in the root gravity-sensing cells.

An alternative method of expressing a gene sequence coding for activating ARFs and related polypeptides in the root gravity-sensing cells consists of amplifying its full (or truncated) gene coding sequence from genomic or cDNA and cloning this sequence downstream of a 3XUAS cassette (Field and Song (1989). *Nature* 340:245-246) in a suitably plant binary vector. Using a plant transformation technique appropriate for the desired species such as floral dipping, *Agrobacterium* mediated co-cultivation, microprojectile or particle bombardment the binary vector containing the UAS cassette and activating ARF gene sequences may be introduced into the plant cell(s). Plants or cells used for transformation preferably lack mutations in activating ARF related gene sequences and may for example, be wild type. Following transformation the transgenic plants may be regenerated e.g. from seed, single cells, callus tissue or leaf discs as is standard for the said species. Such regenerated plants may then be crossed with plants from an enhancer trap line, which is able to drive the expression of any gene downstream of a UAS cassette in a specific cell type, in this case the columella gravity-sensing cells of the root. The expression of the activating ARF related polypeptide may then be determined in the progeny plants and progeny plants in which the expression of the activating ARF related polypeptide is increased relative to control plants may be identified. The angle of root branches may be compared to control plants in which the expression of the activating ARF related polypeptide is not increased in the root gravity-sensing cells.

TABLE 1

Structure of truncated ARFA genes:

| Gene | Size of C-terminal deletion | Start nucluotide | End nucleotide | Start amino acid | End amino acid |
| --- | --- | --- | --- | --- | --- |
| ARF7 | 390 by | 1 | 3108 | M1 | R1036 |
| ARF19 | 393 by | 1 | 2868 | M1 | R956 |
| ARF8 | 327 by | 1 | 2109 | M1 | Q703 |
| ARF6 | 426 by | 1 | 2382 | M1 | Q793 |
| ARF5 | 336 by | 1 | 2373 | M1 | R791 |

Modulation of Lateral Root and Shoot Branching Angles Using Stabilised Aux/IAA Transcriptional Repressor Polypeptide Related Sequences:

Modulation of Shoot Angle:

A method of inducing a more vertical root GSA phenotype in shoot lateral branches comprises incorporating a heterologous nucleic acid sequence which alters the expression levels of an Aux/IAA and related genes containing a stabilizing mutation in the conserved domain II region of the proteins in the gravity-sensing cells by means of transformation and regenerating the plant from one or more transformed cells.

The full Aux/IAA gene coding sequence (with the stabilising mutation in the conserved domain II region) is amplified from genomic or cDNA of a plant species using appropriate primer sequences. The promoter sequence of a gene that is expressed specifically in the gravity-sensing cells of the shoot (e.g. SCARECROW [SCR, AT3G54220; GENBANK: NM_115282] (SEQ ID NO: 50) or related genes, consisting of 2500 bp upstream of the start of the SCR gene in *Arabidopsis*) is similarly amplified from the genomic or cDNA of the target plant species. Using conventional or GATEWAY cloning techniques the SCR or related promoter may be placed upstream of the Aux/IAA related sequence in a suitable binary plant transformation vector. Using a plant transformation technique appropriate for the desired species such as floral dipping, *Agrobacterium* mediated co-cultivation, microprojectile or particle bombardment the binary vector containing the SCR and activating ARF gene sequences may be introduced into the plant cell(s). Plants or cells used for transformation preferably lack mutations in Aux/IAA related gene sequences and may for example, be wild type. Following transformation the transgenic plants may be regenerated e.g. from seed, single cells, callus tissue or leaf discs as is standard for the said species. The angle of shoot branches may be compared to control plants in which the expression of the Aux/IAA related polypeptide is not increased in the shoot gravity-sensing cells.

Modulation of Root Angle:

The full Aux/IAA gene coding sequence (with the stabilising mutation in the conserved domain II region) is amplified from genomic or cDNA of a plant species using appropriate primer sequences. The promoter sequence of a gene that is expressed specifically in the gravity-sensing cells of the root (e.g. the ARL2 gene [AT1G59980; GENBANK: NM_104690] (SEQ ID NO: 51) or related genes, consisting of 2441 bp upstream of the start of the ARL2 gene in *Arabidopsis*) is similarly amplified from the genomic or cDNA of the appropriate plant species. Using conventional or GATEWAY cloning techniques the ARL2 or related promoter is placed upstream of the Aux/IAA related sequence in a suitable binary plant transformation vector. Using a plant transformation technique appropriate for the desired species such as floral dipping, *Agrobacterium* mediated co-cultivation, microprojectile or particle bombardment the binary vector containing the ARL2 or related promoter and activating ARF gene sequences is introduced into the plant cell(s). Plants or cells used for transformation preferably lack mutations in activating ARF gene sequences and may for example, be wild type. Following transformation the transgenic plants are regenerated e.g. from seed, single cells, callus tissue or leaf discs as is standard for the said species. The angles of root branches are compared to control plants in which the expression of the Aux/IAA related polypeptide is not increased in the root gravity-sensing cells.

An alternative method of expressing an activating Aux/IAA related polypeptide in the root gravity-sensing cells consists of amplifying its full gene coding sequence from genomic or cDNA and cloning this sequence downstream of a 3XUAS cassette (Fischer et al. (1988) Nature 322:853-856) in a suitable plant binary vector using GATEWAY or conventional cloning techniques. Using a plant transformation technique appropriate for the desired species such as floral dipping, Agrobacterium mediated co-cultivation, microprojectile or particle bombardment the binary vector containing the UAS cassette and Aux/IAA related polypeptide sequences are introduced into the plant cell(s). Plants or cells used for transformation preferably lack mutations in Aux/IAA related gene sequences and are for example, be wild type. Following transformation the transgenic plants are regenerated e.g. from seed, single cells, callus tissue or leaf discs as is standard for the said species. Such regenerated plants are then crossed with plants from an enhancer trap line, which is able to drive the expression of any gene downstream of a UAS cassette in a specific cell type, in this case the columella gravity-sensing cells of the root. The expression of the Aux/IAA related polypeptide is then determined in the progeny plants and progeny plants in which the expression of the Aux/IAA related polypeptide is increased relative to control plants may be identified. The angle of lateral roots is compared to control plants in which the expression of the Aux/IAA related polypeptide is not increased in the root gravity-sensing cells.

Modulation of Lateral Root and Shoot Branching Angles Using TIR1/AFB Auxin Receptor Related Polypeptide Sequences:

Modulation of Shoot Angle:

A method of inducing a more vertical root GSA phenotype in shoot lateral branches comprises incorporating a heterologous nucleic acid sequence which alters the expression levels of a TIR1/AFB auxin receptor or related gene in gravity-sensing cells by means of transformation and regenerating the plant from one or more transformed cells.

The full length TIR1/AFB auxin receptor or related coding sequence is amplified from genomic or cDNA of a plant species using appropriate primer sequences. The promoter sequence of a gene that is expressed specifically in the gravity-sensing cells of the shoot (e.g. SCARECROW [SCR, AT3G54220; GENBANK: NM_115282] (SEQ ID NO: 50) or related genes, consisting of 2500 bp upstream of the start of the SCR gene in Arabidopsis) is similarly amplified from the genomic or cDNA of the appropriate plant species. Using conventional or GATEWAY cloning techniques the SCR or related promoter is placed upstream of the TIR1/AFB polypeptide related sequence in a suitable binary plant transformation vector. Using a plant transformation technique appropriate for the desired species such as floral dipping, Agrobacterium mediated co-cultivation, microprojectile or particle bombardment the binary vector containing the SCR and TIR1/AFB auxin receptor or related gene sequences is introduced into the plant cell(s). Plants or cells used for transformation preferably lack mutations in the TIR1/AFB auxin receptor related gene sequences and are for example, be wild type. Following transformation the transgenic plants are regenerated e.g. from seed, single cells, callus tissue or leaf discs as is standard for the said species. The angle of shoot branches is compared to control plants in which the expression of the TIR1/AFB auxin receptor related polypeptide is not increased in the shoot gravity-sensing cells.

Modulation of Root Angle:

The full length TIR1/AFB auxin receptor or related coding sequence is amplified from genomic or cDNA of a plant species using appropriate primer sequences. The promoter sequence of a gene that is expressed specifically in the gravity-sensing cells of the root (e.g. the ARL2 gene [AT1G59980; GENBANK: NM_104690] (SEQ ID NO: 51) or related genes, consisting of 2441 bp upstream of the start of the ARL2 gene in Arabidopsis) is similarly amplified from the genomic or cDNA of the appropriate plant species. Using conventional or GATEWAY cloning techniques the ARL2 or related promoter is placed upstream of the TIR1/AFB auxin receptor-related gene sequence in a suitable binary plant transformation vector. Using a plant transformation technique appropriate for the desired species such as floral dipping, Agrobacterium mediated co-cultivation, microprojectile or particle bombardment the binary vector containing the ARL2 or related promoter and TIR1/AFB auxin receptor related gene sequences is introduced into the plant cell(s). Plants or cells used for transformation preferably lack mutations in activating TIR1/AFB auxin receptor related sequences and are for example, wild type. Following transformation the transgenic plants are regenerated e.g. from seed, single cells, callus tissue or leaf discs as is standard for the said species. The angle of lateral roots is compared to control plants in which the expression of the TIR1/AFB auxin receptor related polypeptide is not increased in the root gravity-sensing cells.

An alternative method of expressing a TIR1/AFB auxin receptor or related polypeptide in the root gravity-sensing cells consists of amplifying its full gene coding sequence from genomic or cDNA and cloning this sequence downstream of a 3XUAS cassette (Field and Song (1989). Nature 340:245-246) in a suitable plant binary vector using GATEWAY or conventional cloning techniques. Using a plant transformation technique appropriate for the desired species such as floral dipping, Agrobacterium mediated co-cultivation, microprojectile or particle bombardment the binary vector containing the UAS cassette and TIR1/AFB auxin receptor related polypeptide sequences are introduced into the plant cell(s). Plants or cells used for transformation preferably lack mutations in Aux/IAA gene sequences and are for example, be wild type. Following transformation the transgenic plants are regenerated e.g. from seed, single cells, callus tissue or leaf discs as is standard for the said species. Such regenerated plants are then crossed with plants from an enhancer trap line, which is able to drive the expression of any gene downstream of a UAS cassette in a specific cell type, in this case the columella gravity-sensing cells of the root. The expression of the TIR1/AFB auxin receptor related polypeptide is then determined in the progeny plants and progeny plants may be identified in which the expression of the Aux/IAA related polypeptide is increased relative to control plants. The angles of lateral roots are compared to control plants in which the expression of the TIR1/AFB auxin receptor related polypeptide is not increased in the root gravity-sensing cells.

EXAMPLES

Example 1

In this example, transgenic *Arabidopsis* plants having more vertical shoot branching angles were generated by inducing the expression of the activating ARF7 in the gravity-sensing cells of the shoot.

Unless stated otherwise, standard techniques were used as follows:

*Arabidopsis* Growth Conditions:

*Arabidopsis thaliana* (Col-0) plants were grown individually in pots containing compost in the greenhouse with 20 h light and 8 h darkness at a temperature range of 20+2° C.

Generation of Transgenic SCR:ARF7:GR Plants:

The genomic construct SCR::ARF7:GR contains the SCARECROW promoter upstream of the coding sequence of ARF7 (AT5g20730; GENBANK: NM_122080) fused in to the GR protein coding sequence (the GR motif allows the nuclear localisation of the ARF7:GR protein to be induced upon treatment with dexamethasone). This construct was generated using the GATEWAY system (Invitrogen). 2.5 Kb of the SCR promoter and the full length ARF7 coding sequence were amplified with PCR primers containing recombination sequences and cloned into pDONR P1P5r and pDONR P5P2 Gateway entry vectors. A multisite LR reaction was then performed with the two pDONR entry plasmids and a modified pFP100 destination vector containing a GR fragment and a Nos terminator. The SCR::ARF7:GR construct was transformed into Col-0 *Arabidopsis* plants by floral dipping and transformants were selected on the basis of seed coat fluorescence. Eight independent transgenic lines were selected using seed coat fluorescence as a marker and grown in soil for two weeks. These plants (along with untransformed sister controls) were sprayed with a solution of 30 uM Dexamethasone (in distilled water) for a period of ten days. All transgenic lines displayed varying strengths of the more vertical lateral shoot branch phenotype as compared to control plants.

Primer Sequences:

```
SCR promoter:
B1pSCR:
                                        (SEQ ID NO: 53)
5'-GGGGACAAGTTTGTACAAAAAAGCAGGCTAATTTTGAA

TCCATTCTCAAAGCTTTGC-3 pSCRB5r:
                                        (SEQ ID NO: 54)
5'-GGGGACAACTTTTGTATACAAAGTTGTGGAGATTGAA

GGGTTGTT GGTCGTG-3

ARF7:
B5KARF7:_
                                        (SEQ ID NO: 55)
5'-GGGGACAACTTTGTATACAAAAGTTGAACAATGAAAGC

TCCTTCATC AAATGG-3'

ARF7B2:
                                        (SEQ ID NO: 56)
5'-GGGG ACCACTTTGTACAAGAAAGCTGGGTCCCGGTTA

AACGAA GTGGCTG-3',
```

Example 2

In this example, transgenic *Arabidopsis* plants having more vertical lateral root angles through the expression of a stabilized form of IAA17/AXR3 (axr3-1) in the root columella gravity-sensing cells were generated.

*Arabidopsis* Growth Conditions:

*Arabidopsis thaliana* (Col-0) plants were grown individually in pots containing compost in the greenhouse with 20 h light and 8 h darkness at a temperature range of 20+2° C.

For lateral root angle analysis, transgenic plants along with suitable controls were grown on ATS medium on 120 cm square petri dishes with 20 h light and 8 h darkness at a temperature range of 20±2° C.

Construction of UAS::Axr3-1:

The genomic construct UAS::axr3-1 contains the GAL4 recognition sequence UAS upstream of the coding sequence of AXR3/IAA17 (AT1G04250; GENBANK: NM 100306) containing a stabilising proline to leucine mutation at position 88 within the conserved domain II of this protein (axr3-1). The UAS and axr3-1 sequences were subcloned into a BIN19 based plant transformation binary vector and transformed into wild-type Col-0 *Arabidopsis* plants using floral dipping. Transformants were selected using kanamycin resistance as a marker.

Generation of Transgenic UAS::Axr3-1×11092 Transgenic Plants:

UAS:axr3-1 plants were crossed into the J1092 enhancer trap GAL4-GFP driver line which drives expression of axr3-1 in the columella and lateral root cap cells of the root. Seven independent transgenic lines were obtained displayed varying strengths of the more vertical lateral root branch phenotype as compared to control plants.

---

What is claimed is:

1. A root columella and/or root cap cell the genome of which is modified by the inclusion of a nucleic acid molecule adapted for expression in a gravity sensing cell of the root wherein the nucleic acid molecule encodes a regulator of auxin signalling and wherein the regulator of auxin signalling includes a protein selected from a TRANSPORTER INHIBITOR RESPONSE-1 (TIR1), Auxin signalling F-box Proteins (AFBs), auxin response factors (ARFs), and auxin/indole-3-acetic acid (Aux/Iaa) transcriptional regulators (repressors).

2. The root columella and/or root cap cell as claimed in claim 1 wherein the regulator of auxin signalling is an ARF.

3. The root columella and/or root cap cell as claimed in claim 2 wherein the ARF is a transcriptional Activator (ARFA).

4. The root columella and/or root cap cell as claimed in claim 3 wherein the ARFA is selected from ARF5, ARF6, ARF7, ARF8 and ARF19.

5. The root columella and/or root cap cell as claimed in claim 1 wherein the regulator of auxin signalling is a modified version of an Aux/IAA.

6. The root columella and/or root cap cell as claimed in claim 5 wherein the modified version of an Aux/IAA is selected from auxin resistant3-1 (axr3-1), axr3-3, and bodenlos (bdl).

7. The root columella and/or root cap cell as claimed in claim 1 wherein the regulator of auxin signalling is TIR1 or an AFB.

8. The root columella and/or root cap cell as claimed in claim 1 wherein the nucleic acid molecule is selected from:
   i) a nucleic acid molecule encoding a polypeptide, or part thereof, with ARF activity;
   ii) a nucleic acid molecule encoding a modified or unmodified polypeptide, or part thereof, with Aux/IAA activity; and
   iii) a nucleic acid molecule encoding a polypeptide, or part thereof, with TIR1 or AFB activity.

9. The root columella and/or root cap cell as claimed in claim 8 wherein the nucleic acid molecule in (ii) is modified by the addition, deletion or substitution of at least one nucleotide characterized in that said modification provides an Aux/IAA polypeptide which has increased transcription repressor activity when compared to a non-transgenic reference cell of the same plant species.

10. The root columella and/or root cap cell as claimed in claim 9 wherein the modification is within domain II of the nucleic acid sequence encoding an Aux/IAA.

11. The root columella and/or root cap cell as claimed in claim 10 wherein the modification is within the nucleic acid sequence encoding the VGWPP (SEQ ID NO: 61) motif.

12. The root columella and/or root cap cell as claimed in claim 1 wherein said nucleic acid molecule is a vector adapted for transformation of said plant cell.

13. The root columella and/or root cap cell as claimed in claim 12 wherein said vector is adapted for the over expression of said nucleic acid molecule.

14. The root columella and/or root cap cell as claimed in claim 12 wherein said nucleic acid molecule in said vector is operably linked to a promoter wherein the promoter is that of a gene that is expressed specifically in the gravity-sensing cells of the shoot.

15. The root columella and/or root cap cell as claimed in claim 12 wherein said nucleic acid molecule in said vector is operably linked to a promoter wherein the promoter is that of a gene that is expressed specifically in the gravity-sensing cells of the root.

16. The root columella and/or root cap cell as claimed in claim 15 wherein the promoter is that of the ARL2 gene [AT1G59980; GENBANK: NM_104690] (SEQ ID NO: 51).

* * * * *